(12) United States Patent
Nuñez et al.

(10) Patent No.: US 7,176,019 B2
(45) Date of Patent: Feb. 13, 2007

(54) RICK3 NUCLEIC ACIDS AND PROTEINS

(75) Inventors: Gabriel Nuñez, Ann Arbor, MI (US);
Naohiro Inohara, Ann Arbor, MI (US);
Akihiro Muto, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/317,329

(22) Filed: Dec. 22, 2005

(65) Prior Publication Data
US 2006/0105413 A1 May 18, 2006

Related U.S. Application Data

(62) Division of application No. 10/128,174, filed on Apr. 23, 2002, now abandoned.

(51) Int. Cl.
*C12N 15/00* (2006.01)
*C12N 1/20* (2006.01)
*C07H 21/04* (2006.01)

(52) U.S. Cl. .............................. 435/320.1; 536/232.2; 435/252.3

(58) Field of Classification Search ............... 536/23.2; 435/252.3, 320.1
See application file for complete search history.

(56) References Cited

U.S. PATENT DOCUMENTS

2004/0048310 A1* 3/2004 Plowman et al. ............ 435/7.1

FOREIGN PATENT DOCUMENTS

WO    WO 01/55356 A2    8/2001

OTHER PUBLICATIONS

Inohara et al., J. Biol. Chem. 274, 14560-14568 [1998].
Ogura et al., J. Biol. Chem. 276:4812-4818 [2001].
Kelliher et al., Immunity 8:297-303 [1998].
Lin et al., Mol. Cell. Biol. 20:6638-6645 [2000].
Bertin et al., J. Biol. Chem. 274:12955-12958 [1999].
Inohara et al., J. Biol. Chem. 275:27823-27831 [2001].
Inohara et al., J. Biol. Chem. 273:12296-12300 [1998].
McCarthy et al., J. Biol. Chem. 273:16968-16975 [1998].
Thome et al., Curr. Biol. 8:885-888 [1998].
Stanger et al., Cell 81:513-523 [1995].
Mercurio et al., Mol. Cell. Biol. 19:1526 [1999].
Chen et al., J Biol Chem. 276:21737 [2001].
Bähr et al., J. Biol. Chem. 275:36350 [2000].
Krappmann et al., Mol. Cell. Biol. 21, 6640 [2001].
Yu et al., Curr. Biol. 9:539-542 [1999].
Sun et al., J. Biol. Chem. 274:16871-16875 [1999].
Pazdernik et al., Mol. Cell. Biol. 19:6500-6508 [1999].
Karin and Ben-Neriah, Annu. Rev. Immunol. 18:621 [2000].
Xu et al., Proc. Natl. Acad. Sci. USA. 93:5291 [1996].
Li et al., Proc. Natl. Acad. Sci. USA. 96;1042 [1999].
Hsu et al., Immunity 4:387-396 [1996].
Ruland et al., Cell. 104:33 [2001].
Rothwarf et al., Nature 395:297 [1998].
Wesche et al., Immunity 7:837 [1997].

* cited by examiner

*Primary Examiner*—Maryam Monshipouri
(74) *Attorney, Agent, or Firm*—Medlen & Carroll, LLP

(57) ABSTRACT

The present invention related to methods and compositions for modulating cellular signaling. In particular, the present invention relates to PKK and RICK3 proteins. The present invention further relates the to use of PKK and RICK3 proteins in modulating NF-κB signaling. The present invention thus provides novel targets for drug screening and therapeutics.

4 Claims, 52 Drawing Sheets

FIG. 1

Figure 6
SEQ ID NO: 1

```
   1    ATGGAGGGCGACGGCGGGACCCCATGGGCCCTGGCGCTGCTGCGCACCTTCGACGCGGGCGA
  63    GTTCACGGGCTGGGAGAAGGTGGGCTCGGGCGGCTTCGGGCAGGTGTACAAGGTGCGCCATG
 125    TCCACTGGAAGACCTGGCTGGCCATCAAGTGCTCGCCCAGCCTGCACGTCGACGACAGGGAG
 187    CGCATGGAGCTTTTGGAAGAAGCCAAGAAGATGGAGATGGCCAAGTTTCGCTACATCCTGCC
 249    TGTGTATGGCATCTGCCGCGAACCTGTCGGCCTGGTCATGGAGTACATGGAGACGGGCTCCC
 311    TGGAAAAGCTGCTGGCTTCGGAGCCATTGCCATGGGATCTCCGGTTCCGAATCATCCACGAG
 373    ACGGCGGTGGGCATGAACTTCCTGCACTGCATGGCCCCGCCACTCCTGCACCTGGACCTCAA
 435    GCCCGCGAACATCCTGCTGGATGCCCACTACCACGTCAAGATTTCTGATTTTGGTCTGGCCA
 497    AGTGCAACGGGCTGTCCCACTCGCATGACCTCAGCATGGATGGCCTGTTTGGCACAATCGCC
 559    TACCTCCCTCCAGAGCGCATCAGGGAGAAGAGCCGGCTCTTCGACACCAAGCACGATGTATA
 621    CAGCTTTGCGATCGTCATCTGGGGCGTGCTCACACAGAAGAAGCCGTTTGCAGATGAGAAGA
 683    ACATCCTGCACATCATGGTGAAGGTGGTGAAGGGCCACCGCCCCGAGCTGCCGCCCGTGTGC
 745    AGAGCCCGGCCGCGCGCCTGCAGCCACCTGATACGCCTCATGCAGCGGTGCTGGCAGGGGGA
 807    TCCGCGAGTTAGGCCCACCTTCCAAGAAATTACTTCTGAAACCGAGGACCTGTGTGAAAAGC
 869    CTGATGACGAAGTGAAAGAAACTGCTCATGATCTGGACGTGAAAAGCCCCCCGGAGCCCAGG
 931    AGCGAGGTGGTGCCTGCGAGGCTCAAGCGGGCCTCTGCCCCCACCTTCGATAACGACTACAG
 993    CCTCTCCGAGCTGCTCTCACAGCTGGACTCTGGAGTTTCCCAGGCTGTCGAGGGCCCCGAGG
1055    AGCTCAGCCGCAGCTCCTCTGAGTCCAAGCTGCCATCGTCCGGCAGTGGGAAGAGGCTCTCG
1117    GGGGTGTCCTCGGTGGACTCCGCCTTCTCTTCCAGAGGATCACTGTCGCTGTCCTTTGAGCG
1179    GGAACCTTCAACCAGCGATCTGGGCACCACAGACGTCCAGAAGAAGAAGCTTGTGGATGCCA
1241    TCGTGTCCGGGGACACCAGCAAACTGATGAAGATCCTGCAGCCGCAGGACGTGGACCTGGCA
1303    CTGGACAGCGGTGCCAGCCTGCTGCACCTGGCGGTGGAGGCCGGGCAAGAGGAGTGCGCCAA
1365    GTGGCTGCTGCTCAACAATGCCAACCCCAACCTGAGCAACCGTAGGGGCTCCACCCCGTTGC
1427    ACATGGCCGTGGAGAGGAGGGTGCGGGGTGTCGTGGAGCTCCTGCTGGCGCGGAAGATCAGT
1489    GTCAACGCCAAGGATGAGGACCAGTGGACAGCCCTCCACTTTGCAGCCCAGAACGGGGACGA
1551    GTCTAGCACACGGCTGCTGTTGGAGAAGAACGCCTCGGTCAACGAGGTGGACTTTGAGGGCC
1613    GGACGCCCATGCACGTGGCCTGCCAGCACGGGCAGGAGAATATCGTGCGCATCCTGCTGCGC
1675    CGAGGCGTGGACGTGAGCCTGCAGGGCAAGGATGCCTGGCTGCCACTGCACTACGCTGCCTG
1737    GCAGGGCCACCTGCCCATCGTCAAGCTGCTGGCCAAGCAGCCGGGGGTGAGTGTGAACGCCC
1799    AGACGCTGGATGGGAGGACGCCATTGCACCTGGCCGCACAGCGCGGGCACTACCGCGTGGCC
1861    CGCATCCTCATCGACCTGTGCTCCGACGTCAACGTCTGCAGCCTGCTGGCACAGACACCCCT
1923    GCACGTGGCCGCGGAGACGGGGCACACGAGCACTGCCAGGCTGCTCCTGCATCGGGGCGCTG
1985    GCAAGGAGGCCgTGACCTCAGACGGCTACACCGCTCTGCACCTGGCTGCCCGCAACGGACAC
2047    CTGGCCACTGTCAAGCTGCTTGTCGAGGAGAAGGCCGATGTGCTGGCCCGGGGACCCCTGAA
2109    CCAGACGGCGCTGCACCTGGCTGCCGCCCACGGGCACTCGGAGGTGGTGGAGGAGTTGGTCA
2171    GCGCCGATGTCATTGACCTGTTCGACGAGCAGGGGCTCAGCGCGCTGCACCTGGCCGCCCAG
2233    GGCCGGCACGCACAGACGGTGGAGACTCTGCTCAGGCATGGGGCCCACATCAACCTGCAGAG
2295    CCTCAAGTTCCAGGGCGGCCATGGCCCCGCCGCCACaCTCCTGCGGCGAAGCAAGACCTAG
```

Figure 7
SEQ ID NO:2 taaataaactggatccaacttctcaggctggacttcttccagcttcgggacaccttctcccagcatccctc
cctaggggaactggggaaaatcaaaggctgagacaggggaaatgcgagggcttcggagggacataccctc
ttccccaggcccaggtcgctccatccctgctggggcctcagggctcatgtctgggatttccccacctttgc
ggggcaggagcggctcctcttgggcggggaaggaggcagggccggctcgtctccccattccccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCCATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGGCAACATCCTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCCAGGGAGGTTAATGAGGACATCAG
CCAGGAACTGATGGACAGTGACTCAGGAAACTACCTGAAGCGGGCCCTTCAGCTCTCCGACCGTAAGAATT
TGGTCCCGAGAGATGAGGAACTGTGTATCTATGAGAACAAGGTCACCCCCCTCCAATTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGAGGATGGCTGGGCCCCACTGCACTTTGCAGCCCAGAATGGGGATGACCGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCGTG
AGGCTGAGGGCAAGACCCCCCTCCATGTGGCCGCCTACTTTGGCCATGTTAGCCTGGTCAAGCTGCTGACC
AGCCAGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTATG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc

Figure 8
SEQ ID NO:3

MAADPTELRLGSLPVFTRDDFEGDWRLVASGGFSQVFQARHRRWRTEYAIKCAPCLPPDAASSDVNYLIEE
AAKMKKIKFQHIVSIYGVCKQPLGIVMEFMANGSLEKVLSTHSLCWKLRFRIIHETSLAMNFLHSIKPPLL
HLDLKPGNILLDSNMHVKISDFGLSKWMEQSTRMQYIERSALRGMLSYIPPEMFLESNKAPGPKYDVYSFA
IVIWELLTQKKPYSGFNMMMIIIRVAAGMRPSLQPVSDQWPSEAQQMVDLMKRCWDQDPKKRPCFLDITIE
TDILLSLLQSRVAVPESKALARKVSCKLSLRQPREVNEDISQELMDSDSGNYLKRALQLSDRKNLVPRDEE
LCIYENKVTPLQFLVAQGSVEQVRLLLAHEVDVDCQTASGYTPLLIAAQDQQPDLCALLLAHGADANRVDE
DGWAPLHFAAQNGDDRTARLLLDHGACVDAQEREGWTPLHLAAQNNFENVARLLVSRQADPNLREAEGKTP
LHVAAYFGHVSLVKLLTSQGAELDAQQRNLRTPLHLAVERGKVRAIQHLLKSGAVPDALDQSGYGPLHTAA
ARGKYLICKMLLRYGASLELPTHQGWTPLHLAAYKGHLEIIHLLAESHANMGALGAVNWTPLHLAARHGEE
AVVSALLQCGADPNAAEQSGWTPLHLAVQRSTFLSVINLLEHHANVHARNKVGWTPAHLAALKGNTAILKV
LVEAGAQLDVQDGVSCTPLQLALRSRKQGIMSFLEGKEPSVATLGGSKPGAEMEI

Figure 9
SEQ ID NO:4

```
taaataaactggatccaacttctcaggctggacttcttccagcttcgggacaccttctcccagcatccctc
cctaggggggaactggggaaaatcaaaggctgagacaggggaaatgcgagggcttcggagggacataccctc
ttccccaggcccaggtcgctccatccctgctggggcctcagggctcatgtctgggatttcccccacctttgc
ggggcaggagcggctcctcttgggcggggaaggaggcagggccggctcgtctccccattccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCTATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGGCAACATCCTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCCAGGGAGGTTAATGAGGACATCAG
CCAGGAACTGATGGACAGTGACTCAGGAAACTACCTGAAGCGGGCCCTTCAGCTCTCCGACCGTAAGAATT
TGGTCCCGAGAGATGAGGAACTGTGTATCTATGAGAACAAGGTCACCCCCCTCCAATTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGAGGATGGCTGGGCCCCACTGCACTTTGCAGCCCAGAATGGGGATGACCGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCGTG
AGGCTGAGGGCAAGACCCCCCTCCATGTGGCCGCCTACTTTGGCCATGTTAGCCTGGTCAAGCTGCTGACC
AGCCAGGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTATG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc
```

Figure 10
SEQ ID NO:5

```
taaataaactggatccaacttctcaggctggacttcttccagcttcgggacaccttctcccagcatccctc
cctaggggaactggggaaaatcaaaggctgagacaggggaaatgcgagggcttcggagggacatacccte
ttccccaggcccaggtcgctccatccctgctggggcctcagggctcatgtctgggatttccccacctttgc
ggggcaggagcggctcctcttgggcggggaaggaggcagggccggctcgtctccccattccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCTATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGGCAACATACTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCCAGGGAGGTTAATGAGGACATCAG
CCAGGAACTGATGGACAGTGACTCAGGAAACTACCTGAAGCGGGCCCTTCAGCTCTCCGACCGTAAGAATT
TGGTCCCGAGAGATGAGGAACTGTGTATCTATGAGAACAAGGTCACCCCCCTCCAATTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGAGGATGGCTGGGCCCACTGCACTTTGCAGCCCAGAATGGGGATGACCGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCGTG
AGGCTGAGGGCAAGACCCCCCTCCATGTGGCCGCCTACTTTGGCCATGTTAGCCTGGTCAAGCTGCTGACC
AGCCAGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTATG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc
```

Figure 11
SEQ ID NO:6 taaataaactggatccaacttctcaggctggacttcttccagcttcgggacaccttctcccagcatccctc
cctaggggggaactggggaaaatcaaaggctgagacaggggaaatgcgagggcttcggagggacatacccct
ttccccaggcccaggtcgctccatccctgctggggcctcagggctcatgtctgggatttccccacctttgc
ggggcaggagcggctcctcttgggcggggaaggaggcagggccggctcgtctccccattccccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCTATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGGCAACATACTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCCGGGGAGGTTAATGAGGACATCAG
CCAGGAACTGATGGACAGTGACTCAGGAAACTACCTGAAGCGGGCCCTTCAGCTCTCCGACCGTAAGAATT
.TGGTCCCGAGAGATGAGGAACTGTGTATCTATGAGAACAAGGTCACCCCCCTCCAATTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGAGGATGGCTGGGCCCCACTGCACTTTGCAGCCCAGAATGGGGATGACCGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCGTG
AGGCTGAGGGCAAGACCCCCCTCCATGTGGCCGCCTACTTTGGCCATGTTAGCCTGGTCAAGCTGCTGACC
AGCCAGGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTATG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc

Figure 12
SEQ ID NO:7

```
taaataaactggatccaacttctcaggctggacttcttccagcttcgggacaccttctcccagcatccctc
cctaggggggaactgggggaaaatcaaaggctgagacaggggaaatgcgagggcttcggagggacataccctc
ttccccaggcccaggtcgctccatccctgctggggcctcagggctcatgtctgggatttccccacctttgc
ggggcaggagcggctcctcttgggcggggaaggaggcagggccggctcgtctccccattcccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCTATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGGCAACATACTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCCGGGGAGGTTAATGAGGACATCAG
CCAGGAACTGATGGACAGTGACTCAGGAAACTACCTGAAGCGGGCCCTTCAGCTCTCCGACCGTAAGAATT
TGGTCCCGAGAGATGAGGAACTGTGTATCTATGAGAACAAGGTCACCCCCCTCCACTTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGAGGATGGCTGGGCCCCACTGCACTTTGCAGCCCAGAATGGGGATGACCGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCGTG
AGGCTGAGGGCAAGACCCCCCTCCATGTGGCCGCCTACTTTGGCCATGTTAGCCTGGTCAAGCTGCTGACC
AGCCAGGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTATG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc
```

Figure 13
SEQ ID NO:8

```
taaataaactggatccaacttctcaggctggacttcttccagcttcgggacaccttctcccagcatccctc
cctaggggggaactggggaaaatcaaaggctgagacaggggaaatgcgagggcttcggagggacataccctc
ttccccaggcccaggtcgctccatccctgctggggcctcagggctcatgtctgggatttccccacctttgc
ggggcaggagcggctcctcttgggcggggaaggaggcagggccggctcgtctccccattcccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCTATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGCAACATACTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCCGGGGAGGTTAATGAGGACATCAG
CCAGGAACTGATGGACAGTGACTCAGGAAACTACCTGAAGCGGGCCCTTCAGCTCTCCGACCGTAAGAATT
TGGTCCCGAGAGATGAGGAACTGTGTATCTATGAGAACAAGGTCACCCCCCTCCACTTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGAGGATGGCTGGGCCCCACTGCACTTTGCAGCCCAGAATGGGGATGACGGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCGTG
AGGCTGAGGGCAAGACCCCCCTCCATGTGGCCGCCTACTTTGGCCATGTTAGCCTGGTCAAGCTGCTGACC
AGCCAGGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTATG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc
```

Figure 14
SEQ ID NO:9 taaataaactggatccaacttctcaggctggacttcttccagcttcgggacaccttctcccagcatccctc
cctaggggaactggggaaaatcaaaggctgagacaggggaaatgcgagggcttcggagggacataccctc
ttccccaggcccaggtcgctccatccctgctggggcctcagggctcatgtctgggatttccccacctttgc
ggggcaggagcggctcctcttgggcggggaaggaggcagggccggctcgtctccccattccccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCTATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGGCAACATACTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCCGGGGAGGTTAATGAGGACATCAG
CCAGGAACTGATGGACAGTGACTCAGGAAACTACCTGAAGCGGGCCCTTCAGCTCTCCGACCGTAAGAATT
TGGTCCCGAGAGATGAGGAACTGTGTATCTATGAGAACAAGGTCACCCCCCTCCACTTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGAGGATGGCTGGGCCCCACTGCACTTTGCAGCCCAGAATGGGGATGACGGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCATG
AGGCTGAGGGCAAGACCCCCCTCCATGTGGCCGCCTACTTTGGCCATGTTAGCCTGGTCAAGCTGCTGACC
AGCCAGGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTATG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc

Figure 15
SEQ ID NO:10

```
taaataaactggatccaacttctcaggctggacttcttccagcttcgggacaccttctcccagcatccctc
cctaggggggaactggggaaaatcaaaggctgagacaggggaaatgcgagggcttcggagggacataccctc
ttccccaggcccaggtcgctccatccctgctggggcctcagggctcatgtctgggatttccccacctttgc
ggggcaggagcggctcctcttgggcggggaaggaggcagggccggctcgtctccccattccctctcccgg
acccgaggagcaggaagcggcggctccttcggccacccaggcagcagccacagcggggagtgcgcggcgcg
gggacaggaagagaggggcaATGGCTGCCGACCCCACCGAGCTGCGGCTGGGCAGCCTCCCCGTCTTCACC
CGCGACGACTTCGAGGGCGACTGGCGCCTAGTGGCCAGCGGCGGCTTCAGCCAGGTGTTCCAGGCGCGGCA
CAGGCGCTGGCGGACGGAGTACGCCATCAAGTGCGCCCCCTGCCTTCCACCCGACGCCGCCAGCTCTGATG
TGAATTACCTCATTGAAGAAGCTGCCAAAATGAAGAAGATCAAGTTTCAGCACATCGTGTCTATCTACGGG
GTGTGCAAGCAGCCCCTGGGTATTGTGATGGAGTTTATGGCCAACGGCTCCCTGGAGAAGGTGCTGTCCAC
CCACAGCCTCTGCTGGAAGCTCAGGTTCCGCATCATCCATGAGACCAGCTTGGCCATGAACTTCCTGCACA
GCATTAAGCCGCCTCTGCTCCACCTGGACCTCAAGCCGGGCAACATACTCCTGGACAGCAACATGCATGTC
AAAATTTCAGACTTCGGCCTGTCCAAGTGGATGGAACAGTCCACCCGGATGCAGTACATCGAGAGGTCGGC
TCTGCGGGGCATGCTCAGCTACATCCCCCCTGAGATGTTCCTGGAGAGTAACAAGGCCCCAGGACCTAAAT
ATGATGTGTACAGCTTTGCAATTGTCATCTGGGAGCTACTCACTCAGAAGAAACCATACTCAGGGTTCAAC
ATGATGATGATTATTATCCGAGTGGCGGCAGGCATGCGGCCCTCCCTACAGCCTGTCTCTGACCAATGGCC
AAGCGAGGCCCAGCAGATGGTGGACCTGATGAAACGCTGCTGGGACCAGGACCCCAAGAAGAGGCCATGCT
TTCTAGACATTACCATCGAGACAGACATACTGCTGTCACTGCTGCAGAGTCGTGTGGCAGTCCCAGAGAGC
AAGGCCCTGGCCAGGAAGGTGTCCTGCAAGCTGTCGCTGCGCCAGCCGGGGAGGTTAATGAGGACATCAG
CCAGGAACTGATGGACAGTGACTCAGGAAACTACCTGAAGCGGGCCCTTCAGCTCTCCGACCGTAAGAATT
TGGTCCCGAGAGATGAGGAACTGTGTATCTATGAGAACAAGGTCACCCCCCTCCACTTCCTGGTGGCCCAG
GGCAGTGTGGAGCAGGTGAGGTTGCTGCTGGCCCACGAGGTAGACGTGGACTGCCAGACGGCCTCTGGATA
CACGCCCCTCCTGATCGCCGCCCAGGACCAGCAACCCGACCTCTGTGCCCTGCTTTTGGCACATGGTGCTG
ATGCCAACCGAGTGGATGGATGGCTGGGCCCCACTGCACTTTGCAGCCCAGAATGGGGATGACGGCACT
GCGCGCCTGCTCCTGGACCACGGGGCCTGTGTGGATGCCCAGGAACGTGAAGGGTGGACCCCTCTTCACCT
GGCTGCACAGAATAACTTTGAGAATGTGGCACGGCTTCTGGTCTCCCGTCAGGCTGACCCCAACCTGCATG
AGGCTGAGGGCAAGACCCCCCTCCATGTGGCCGCCTACTTTGGCCATGTTAGCCTGGTCAAGCTGCTGACC
AGCCAGGGGCTGAGTTGGATGCTCAGCAGAGAAACCTGAGAACACCACTGCACCTGGCAGTAGAGCGGGG
CAAAGTGAGGGCCATCCAACACCTGCTGAAGAGTGGAGCGGTCCCTGATGCCCTTGACCAGAGCGGCTACG
GCCCACTGCACACTGCAGCTGCCAGGGGCAAATACCTGATCTGCAAGATGCTGCTCAGGTACGGAGCCAGC
CTTGAGCTGCCCACCCACCAGGGCTGGACACCCCTGCATCTAGCAGCCTACAAGGGCCACCTGGAGATCAT
CCATCTGCTGGCAGAGAGCCACGCAAACATGGGTGCTCTTGGAGCTGTGAACTGGACTCCCCTGCACCTAG
CTGCACGCCACGGGGAGGAGGCGGTGGTGTCAGCACTGCTGCAGTGTGGGGCTGACCCCAATGCTGCAGAG
CAGTCAGGCTGGACACCCCTCCACCTGGCGGTCCAGAGGAGCACCTTCCTGAGTGTCATCAACCTCCTAGA
ACATCACGCAAATGTCCACGCCCGCAACAAGGTGGGCTGGACACCCGCCCACCTGGCCGCCCTCAAGGGCA
ACACAGCCATCCTCAAAGTGCTGGTCGAGGCAGGCGCCCAGCTGGACGTCCAGGATGGAGTGAGCTGCACA
CCCCTGCAACTGGCCCTCCGCAGCCGAAAGCAGGGCATCATGTCCTTCCTAGAGGGCAAGGAGCCGTCAGT
GGCCACTCTGGGTGGTTCTAAGCCAGGAGCCGAGATGGAAATTTAGacaacttggccagccgtggtggc
```

Figure 16
SEQ ID NO:11

ATGGAGGGCGAGGGCCGGGGCCGGTGGGCTCTGGGGCTGCTGCGCACCTTCGACGCCGGCGAATTCGCAGG
CTGGGAGAAGGTGGGCTCGGGCGGCTTCGGGCAGGTGTACAAGGTGCGCCATGTGCACTGGAAGACGTGGC
TCGCGATCAAGTGCTCGCCCAGTCTGCACGTCGACGACAGGGAACGAATGGAGCTCCTGGAGGAAGCTAAG
AAGATGGAGATGGCCAAGTTCCGATACATTCTACCTGTGTACGGCATATGCCAGGAACCTGTCGGCTTGGT
CATGGAGTACATGGAGACAGGCTCCCTGGAGAAGCTGCTGGCCTCAGAGCCATTGCCTTGGGACCTGCGCT
TTCGCATCGTGCACGAGACAGCCGTGGGCATGAACTTCCTGCATTGCATGTCTCCGCCACTGCTGCACCTA
GACCTGAAGCCAGCGAACATCCTGCTGGATGCCCACTACCATGTCAAGATTTCTGACTTTGGGCTGGCCAA
GTGCAATGGCATGTCCCACTCTCATGACCTCAGCATGGATGGCCTGTTTGGTACAATCGCTTACctCCCTC
CAGAGCGAATTCGTGAGAAGAGCCGCTTGTTTGACACCAAACATGATGTATACAGCTTCGCCATTGTGATC
TGGGGTGTGCTTACACAGAAGAAGCCATTTGCAGATGAAAAGAACATCCTACACATCATGATGAAAGTGGT
AAAGGGCCACCGCCCAGAGCTGCCACCCATCTGCAGACCCCGGCCGCGTGCCTGTGCCAGCCTGATAGGGC
TCATGCAACGGTGCTGGCATGCAGACCCACAGGTGCGGCCCACCTTCCAAGAAATTACCTCTGAAACAGAA
GACCTTTGTGAGAAGCCTGATGAGGAGGTGAAAGACCTGGCTCATGAGCCAGGCGAGAAAAGCTCTCTAGA
GTCCAAGAGTGAGGCCAGGCCCGAGTCCTCACGCCTCAAGCGCGCCTCTGCTCCCCCCTTCGATAACGACT
GCAGTCTCTCCGAGTTGCTGTCACAGTTGGACTCTGGGATCTCCCAGACTCTTGAAGGCCCCGAAGAGCTC
AGCCGAAGTTCCTCTGAATGCAAGCTCCCATCGTCCAGCAGTGGCAAGAGGCTCTCGGGGGTGTCCTCAGT
GGACTCAGCCTTTTCCTCCAGAGGATCGCTGTCACTGTCTTTTGAGCGGGAAGCTTCAACAGGCGACCTGG
GCCCCACAGACATCCAGAAGAAGAAGCTAGTGGATGCCATCaTATCAGGGGACACCAGCAGGCTGATGAAG
ATGCTACAGCCCCAAGATGTGGACTTGGTTCTAGACAGCAGTGCCAGCCTGCTGCACCTGGCTGTGGAGGC
CGGACAGgAGGAGTGTGTCAAGTGGCTGCTGCTTAACAATGCCAACCCCAACCTGACCAACAGGAAGGGCT
CTACACCACTGCATATGGCTGTGGAGCGGAAGGGACGTGGAATTGTGGAGCTACTGCTAGCCCGGAAGACC
AGTGTCAATGCCAAGGATGAAGACCAGTGGACTGCCCTGCACTTTGCAGCCCAGAATGGGGATGAGGCCAG
CACAAGGCTGCTGCTAGAGAAGAATGCTTCTGTCAATGAGGTGGACTTTGAGGGCCGAACACCCATGCATG
TAGCCTGCCAGCATGGACAGGAGAACATTGTGCGCACCCTGCTCCGCCGTGGTGTGGATGTGGGCCTGCAG
GGAAAGGATGCCTGGTTGCCTCTGCAcTATGCTGCCTGGCAGGGCCACCTTCCCATTGTTAAGCTGCTAGC
CAAGCAGCCTGGGGTGAGTGTGAATGCCCAGACACTAGACGGGAGGACACCCCTGCACCTGGCTGCTCAGA
GGGGGCATTACCGTGTGGCTCGCATTCTCATTGACCTGTGCTCTGATGTTAACATCTGCAGCCTACAGGCA
CAGACACCTCTGCATGTTGCTGCAGAGACTGGACACACTAGTACTGCCAGGCTACTCTTGCATCGTGGTGC
TGGCAAGGAGGCTTTGACCTCAGAGGGCTATACTGCCTTGCACCTGGCAGCCCAGAATGGACACCTGGCTA
CTGTCAAGCTGCTCATAGAGGAGAAGGCTGATGTGATGGCTCGGGGTCCCCTGAATCAGACAGCACTGCAC
CTGGCTGCTGCCCGTGGACACTCAGAGGTGGTAGAAGAGCTGGTCAGTGCTGACCTCATTGACCTGTCTGA
TGAGCAGGGCCTCAGCGCACTGCACCTaGCTGCTCAGGGCAGGCATTCACAGACTGTGGAGACACTGCTCA
AACATGGAGCACACATCAACTTGCAGAGTCTCAAGTTCCAAGGAGGCCAGAGCTCTGCTGCCACGTTGCTC
CGACGCAGCAAGACCTAG

Figure 17

SEQ ID NO:12

MEGDGGTPWALALLRTFDAGEFTGWEKVGSGGFGQVYKVRHVHWKTWLAIKCSPSLHVDDRERMELLEEAK
KMEMAKFRYILPVYGICREPVGLVMEYMETGSLEKLLASEPLPWDLRFRIIHETAVGMNFLHCMAPPLLHL
DLKPANILLDAHYHVKISDFGLAKCNGLSHSHDLSMDGLFGTIAYLPPERIREKSRLFDTKHDVYSFAIVI
WGVLTQKKPFADEKNILHIMVKVVKGHRPELPPVCRARPRACSHLIRLMQRCWQGDPRVRPTFQEITSETE
DLCEKPDDEVKETAHDLDVKSPPEPRSEVVPARLKRASAPTFDNDYSLSELLSQLDSGVSQAVEGPEELSR
SSSESKLPSSGSGKRLSGVSSVDSAFSSRGSLSLSFEREPSTSDLGTTDVQKKKLVDAIVSGDTSKLMKIL
QPQDVDLALDSGASLLHLAVEAGQEECAKWLLLNNANPNLSNRRGSTPLHMAVERRVRGVVELLLARKISV
NAKDEDQWTALHFAAQNGDESSTRLLLEKNASVNEVDFEGRTPMHVACQHGQENIVRILLRRGVDVSLQGK
DAWLPLHYAAWQGHLPIVKLLAKQPGVSVNAQTLDGRTPLHLAAQRGHYRVARILIDLCSDVNVCSLLAQT
PLHVAAETGHTSTARLLLHRGAGKEAVTSDGYTALHLAARNGHLATVKLLVEEKADVLARGPLNQTALHLA
AAHGHSEVVEELVSADVIDLFDEQGLSALHLAAQGRHAQTVETLLRHGAHINLQSLKFQGGHGPAATLLRR
SKT

Figure 18
SEQ ID NO: 13

MEGEGRGRWALGLLRTFDAGEFAGWEKVGSGGFGQVYKVRHVHWKTWLAIKCSPSLHVDDRERMELLEEAK
KMEMAKFRYILPVYGICQEPVGLVMEYMETGSLEKLLASEPLPWDLRFRIVHETAVGMNFLHCMSPPLLHL
DLKPANILLDAHYHVKISDFGLAKCNGMSHSHDLSMDGLFGTIAYLPPERIREKSRLFDTKHDVYSFAIVI
WGVLTQKKPFADEKNILHIMMKVVKGHRPELPPICRPRPRACASLIGLMQRCWHADPQVRPTFQEITSETE
DLCEKPDEEVKDLAHEPGEKSSLESKSEARPESSRLKRASAPPFDNDCSLSELLSQLDSGISQTLEGPEEL
SRSSSECKLPSSSSGKRLSGVSSVDSAFSSRGSLSLSFEREASTGDLGPTDIQKKKLVDAIISGDTSRLMK
ILQPQDVDLVLDSSASLLHLAVEAGQEECVKWLLLNNANPNLTNRKGSTPLHMAVERKGRGIVELLLARKT
SVNAKDEDQWTALHFAAQNGDEASTRLLLEKNASVNEVDFEGRTPMHVACQHGQENIVRTLLRRGVDVGLQ
GKDAWLPLHYAAWQGHLPIVKLLAKQPGVSVNAQTLDGRTPLHLAAQRGHYRVARILIDLCSDVNICSLQA
QTPLHVAAETGHTSTARLLLHRGAGKEALTSEGYTALHLAAQNGHLATVKLLIEEKADVMARGPLNQTALH
LAAARGHSEVVEELVSADLIDLSDEQGLSALHLAAQGRHSQTVETLLKHGAHINLQSLKFQGGQSSAATLL
RRSKT

Figure 23
SEQ ID NO:14

```
   1   ATGGAGGGCGACGGCGGGACCCCATGGGCCCTGGCGCTGCTGCGCACCTTCGACGCGGGCGA
  63   GTTCACGGGCTGGGAGAAGGTGGGCTCGGGCGGCTTCGGGCAGGTGTACAAGGTGCGCCATG
 125   TCCACTGGAAGACCTGGCTGGCCATCAAGTGCTCGCCCAGCCTGCACGTCGACGACAGGGAG
 187   CGCATGGAGCTTTTGGAAGAAGCCAAGAAGATGGAGATGGCCAAGTTTCGCTACATCCTGCC
 249   TGTGTATGGCATCTGCCGCGAACCTGTCGGCCTGGTCATGGAGTACATGGAGACGGGCTCCC
 311   TGGAAAAGCTGCTGGCTTCGGAGCCATTGCCATGGGATCTCCGGTTCCGAATCATCCACGAG
 373   ACGGCGGTGGGCATGAACTTCCTGCACTGCATGGCCCCGCCACTCCTGCACCTGGACCTCAA
 435   GCCCGCGAACATCCTGCTGGATGCCCACTACCACGTCAAGATTTCTGATTTTGGTCTGGCCA
 497   AGTGCAACGGGCTGTCCCACTCGCATGACCTCAGCATGGATGGCCTGTTTGGCACAATCGCC
 559   TACCTCCCTCCAGAGCGCATCAGGGAGAAGAGCCGGCTCTCCGACACCAAGCACGATGTATA
 621   CAGCTTTGCGATCGTCATCTGGGGCGTGCTCACACAGAAGAAGCCGTTTGCAGATGAGAAGA
 683   ACATCCTGCACATCATGGTGAAGGTGGTGAAGGGCCACCGCCCGAGCTGCCGCCCGTGTGC
 745   AGAGCCCGGCCGCGCGCCTGCAGCCACCTGATACGCCTCATGCAGCGGTGCTGGCAGGGGGA
 807   TCCGCGAGTTAGGCCCACCTTCCAAGAAATTACTTCTGAAACCGAGGACCTGTGTGAAAAGC
 869   CTGATGACGAAGTGAAAGAAACTGCTCATGATCTGGACGTGAAAAGCCCCCCGGAGCCCAGG
 931   AGCGAGGTGGTGCCTGCGAGGCTCAAGCGGGCCTCTGCCCCCACCTTCGATAACGACTACAG
 993   CCTCTCCGAGCTGCTCTCACAGCTGGACTCTGGAGTTTCCCAGGCTGTCGAGGGCCCCGAGG
1055   AGCTCAGCCGCAGCTCCTCTGAGTCCAAGCTGCCATCGTCCGGCAGTGGGAAGAGGCTCTCG
1117   GGGGTGTCCTCGGTGGACTCCGCCTTCTCTTCCAGAGGATCACTGTCGCTGTCCTTTGAGCG
1179   GGAACCTTCAACCAGCGATCTGGGCACCACAGACGTCCAGAAGAAGAAGCTTGTGGATGCCA
1241   TCGTGTCCGGGGACACCAGCAAACTGATGAAGATCCTGCAGCCGCAGGACGTGGACCTGGCA
1303   CTGGACAGCGGTGCCAGCCTGCTGCACCTGGCGGTGGAGGCCGGGCAAGAGGAGTGCGCCAA
1365   GTGGCTGCTGCTCAACAATGCCAACCCCAACCTGAGCAACCGTAGGGGCTCCACCCCGTTGC
1427   ACATGGCCGTGGAGAGGAGGGTGCGGGGTGTCGTGGAGCTCCTGCTGGCGCGGAAGATCAGT
1489   GTCAACGCCAAGGATGAGGACCAGTGGACAGCCCTCCACTTTGCAGCCCAGAACGGGGACGA
1551   GTCTAGCACACGGCTGCTGTTGGAGAAGAACGCCTCGGTCAACGAGGTGGACTTTGAGGGCC
1613   GGACGCCCATGCACGTGGCCTGCCAGCACGGGCAGGAGAATATCGTGCGCATCCTGCTGCGC
1675   CGAGGCGTGGACGTGAGCCTGCAGGGCAAGGATGCCTGGCTGCCACTGCACTACGCTGCCTG
1737   GCAGGGCCACCTGCCCATCGTCAAGCTGCTGGCCAAGCAGCCGGGGGTGAGTGTGAACGCCC
1799   AGACGCTGGATGGGAGGACGCCATTGCACCTGGCCGCACAGCGCGGGCACTACCGCGTGGCC
1861   CGCATCCTCATCGACCTGTGCTCCGACGTCAACGTCTGCAGCCTGCTGGCACAGACACCCCT
1923   GCACGTGGCCGCGGAGACGGGGCACACGAGCACTGCCAGGCTGCTCCTGCATCGGGGCGCTG
1985   GCAAGGAGGCCgTGACCTCAGACGGCTACACCGCTCTGCACCTGGCTGCCCGCAACGGACAC
2047   CTGGCCACTGTCAAGCTGCTTGTCGAGGAGAAGGCCGATGTGCTGGCCCGGGGACCCCTGAA
2109   CCAGACGGCGCTGCACCTGGCTGCCGCCCACGGGCACTCGGAGGTGGTGGAGGAGTTGGTCA
2171   GCGCCGATGTCATTGACCTGTTCGACGAGCAGGGGCTCAGCGCGCTGCACCTGGCCGCCCAG
2233   GGCCGGCACGCACAGACGGTGGAGACTCTGCTCAGGCATGGGGCCCACATCAACCTGCAGAG
2295   CCTCAAGTTCCAGGGCGGCCATGGCCCCGCCGCCACaCTCCTGCGGCGAAGCAAGACCTAG
```

Figure 24
SEQ ID NO: 15

```
1      ATGGAGGGCGACGGCGGGACCCCATGGGCCCTGGCGCTGCTGCGCACCTTCGACGCGGGCGA
63     GTTCACGGGCTGGGAGAAGGTGGGCTCGGGCGGCTTCGGGCAGGTGTACAAGGTGCGCCATG
125    TCCACTGGAAGACCTGGCTGGCCATCAAGTGCTCGCCCAGCCTGCACGTCGACGACAGGGAG
187    CGCATGGAGCTTTTGGAAGAAGCCAAGAAGATGGAGATGGCCAAGTTTCGCTACATCCTGCC
249    TGTGTATGGCATCTGCCGCGAACCTGTCGGCCTGGTCATGGAGTACATGGAGACGGGCTCCC
311    TGGAAAAGCTGCTGGCTTCGGAGCCATTGCCATGGGATCTCCGGTTCCGAATCATCCACGAG
373    ACGGCGGTGGGCATGAACTTCCTGCACTGCATGGCCCCGCCACTCCTGCACCTGGACCTCAA
435    GCCCGCGAACATCCTGCTGGATGCCCACTACCACGTCAAGATTTCTGATTTTGGTCTGGCCA
497    AGTGCAACGGGCTGTCCCACTCGCATGACCTCAGCATGGATGGCCTGTTTGGCACAATCGCC
559    TACCTCCCTCCAGAGCGCATCAGGGAGAAGAGCCGGCTCTTCGACACCAAGCACGATGTATA
621    CAGCTTTGCGATCGTCATCTGGGGCGTGCTCACACAGAAGAAGCCGTTTGCAGATGAGAAGA
683    ACATCCTGCACATCATGGTGAAGGTGGTGAAGGGCCACCGCCCCGAGCTGCCGCCCGTGTGC
745    AGAGCCCGGCCGCGCGCCTGCAGCCACCTGATACGCCTCATGCAGCGGTGCTGGCAGGGGGA
807    TCCGCGAGTTAGGCCCACCTTCCAAGAAATTACTTCTGAAACCGAGGACCTGTGTGAAAAGC
869    CTGATGACGAAGTGAAAGAAACTGCTCATGATCTGGACGTGAAAAGCCCCCCGGAGCCCAGG
931    AGCGAGGTGGTGCCTGCGAGGCTCAAGCGGGCCTCTGCCCCCACCTTCGATAACGACTACAG
993    CCTCTCCGAGCTTCTCTCACAGCTGGACTCTGGAGTTTCCCAGGCTGTCGAGGGCCCCGAGG
1055   AGCTCAGCCGCAGCTCCTCTGAGTCCAAGCTGCCATCGTCCGGCAGTGGGAAGAGGCTCTCG
1117   GGGGTGTCCTCGGTGGACTCCGCCTTCTCTTCCAGAGGATCACTGTCGCTGTCCTTTGAGCG
1179   GGAACCTTCAACCAGCGATCTGGGCACCACAGACGTCCAGAAGAAGAAGCTTGTGGATGCCA
1241   TCGTGTCCGGGGACACCAGCAAACTGATGAAGATCCTGCAGCCGCAGGACGTGGACCTGGCA
1303   CTGGACAGCGGTGCCAGCCTGCTGCACCTGGCGGTGGAGGCCGGGCAAGAGGAGTGCGCCAA
1365   GTGGCTGCTGCTCAACAATGCCAACCCCAACCTGAGCAACCGTAGGGGCTCCACCCCGTTGC
1427   ACATGGCCGTGGAGAGGAGGGTGCGGGGTGTCGTGGAGCTCCTGCTGGCGCGGAAGATCAGT
1489   GTCAACGCCAAGGATGAGGACCAGTGGACAGCCCTCCACTTTGCAGCCCAGAACGGGACGA
1551   GTCTAGCACACGGCTGCTGTTGGAGAAGAACGCCTCGGTCAACGAGGTGGACTTTGAGGGCC
1613   GGACGCCCATGCACGTGGCCTGCCAGCACGGGCAGGAGAATATCGTGCGCATCCTGCTGCGC
1675   CGAGGCGTGGACGTGAGCCTGCAGGGCAAGGATGCCTGGCTGCCACTGCACTACGCTGCCTG
1737   GCAGGGCCACCTGCCCATCGTCAAGCTGCTGGCCAAGCAGCCGGGGGTGAGTGTGAACGCCC
1799   AGACGCTGGATGGGAGGACGCCATTGCACCTGGCCGCACAGCGCGGGCACTACCGCGTGGCC
1861   CGCATCCTCATCGACCTGTGCTCCGACGTCAACGTCTGCAGCCTGCTGGCACAGACACCCCT
1923   GCACGTGGCCGCGGAGACGGGGCACACGAGCACTGCCAGGCTGCTCCTGCATCGGGGCGCTG
1985   GCAAGGAGGCCgTGACCTCAGACGGCTACACCGCTCTGCACCTGGCTGCCCGCAACGGACAC
2047   CTGGCCACTGTCAAGCTGCTTGTCGAGGAGAAGGCCGATGTGCTGGCCCGGGGACCCCTGAA
2109   CCAGACGGCGCTGCACCTGGCTGCCGCCCACGGGCACTCGGAGGTGGTGGAGGAGTTGGTCA
2171   GCGCCGATGTCATTGACCTGTTCGACGAGCAGGGGCTCAGCGCGCTGCACCTGGCCGCCCAG
2233   GGCCGGCACGCACAGACGGTGGAGACTCTGCTCAGGCATGGGGCCCACATCAACCTGCAGAG
2295   CCTCAAGTTCCAGGGCGGCCATGGCCCCGCCGCCACaCTCCTGCGGCGAAGCAAGACCTAG
```

Figure 25
SEQ ID NO: 16

| | |
|---|---|
| 1 | ATGGAGGGCGACGGCGGGACCCCATGGGCCCTGGCGCTGCTGCGCACCTTCGACGCGGGCGA |
| 63 | GTTCACGGGCTGGGAGAAGGTGGGCTCGGGCGGCTTCGGGCAGGTGTACAAGGTGCGCCATG |
| 125 | TCCACTGGAAGACCTGGCTGGCCATCAAGTGCTCGCCCAGCCTGCACGTCGACGACAGGGAG |
| 187 | CGCATGGAGCTTTTGGAAGAAGCCAAGAAGATGGAGATGGCCAAGTTTCGCTACATCCTGCC |
| 249 | TGTGTATGGCATCTGCCGCGAACCTGTCGGCCTGGTCATGGAGTACATGGAGACGGGCTCCC |
| 311 | TGGAAAAGCTGCTGGCTTCGGAGCCATTGCCATGGGATCTCCGGTTCCGAATCATCCACGAG |
| 373 | ACGGCGGTGGGCATGAACTTCCTGCACTGCATGGCCCCGCCACTCCTGCACCTGGACCTCAA |
| 435 | GCCCGCGAACATCCTGCTGGATGCCCACTACCACGTCAAGATTTCTGATTTTGGTCTGGCCA |
| 497 | AGTGCAACGGGCTGTCCCACTCGCATGACCTCAGCATGGATGGCCTGTTTGGCACAATCGCC |
| 559 | TACCTCCCTCCAGAGCGCATCAGGGAGAAGAGCCGGCTCTTCGACACCAAGCACGATGTATA |
| 621 | CAGCTTTGCGATCGTCATCTGGGGCGTGCTCACACAGAAGAAGCCGTTTGCAGATGAGAAGA |
| 683 | ACATCCTGCACATCATGGTGAAGGTGGTGAAGGGCCACCGCCCCGAGCTGCCGCCCGTGTGC |
| 745 | AGAGCCCGGCCGCGCGCCTGCAGCCACCTGATACGCCTCATGCAGCGGTGCTGGCAGGGGGA |
| 807 | TCCGCGAGTTAGGCCCACCTTCCAAGAAATTACTTCTGAAACCGAGGACCTGTGTGAAAAGC |
| 869 | CTGATGACGAAGTGAAAGAAACTGCTCATGATCTGGACGTGAAAAGCCCCCGGAGCCCAGG |
| 931 | AGCGAGGTGGTGCCTGCGAGGCTCAAGCGGGCCTCTGCCCCCACCTTCGATAACGACTACAG |
| 993 | CCTCTCCGAGCTGCTCTCACAGCTGGACTCTGGAGTTTCCCAGGCTGTCGAGGGCCCCGAGG |
| 1055 | AGCTCAGCCGCAGCTCCTCTGAGTCCAAGCTGCCATCGTCCGGCAGTGGGAAGAGGCTCTCG |
| 1117 | GGGGTGTCCTCGGTGGACTCCGCCTTCTCTTCCAGAGGATCACTGTCGCTGTCCTTTGAGCG |
| 1179 | GGAACCTTCAACCAGCGATCTGGGTACCACAGACGTCCAGAAGAAGAAGCTTGTGGATGCCA |
| 1241 | TCGTGTCCGGGGACACCAGCAAACTGATGAAGATCCTGCAGCCGCAGGACGTGGACCTGGCA |
| 1303 | CTGGACAGCGGTGCCAGCCTGCTGCACCTGGCGGTGGAGGCCGGGCAAGAGGAGTGCGCCAA |
| 1365 | GTGGCTGCTGCTCAACAATGCCAACCCCAACCTGAGCAACCGTAGGGGCTCCACCCCGTTGC |
| 1427 | ACATGGCCGTGGAGAGGAGGGTGCGGGGTGTCGTGGAGCTCCTGCTGGCGCGGAAGATCAGT |
| 1489 | GTCAACGCCAAGGATGAGGACCAGTGGACAGCCCTCCACTTTGCAGCCCAGAACGGGGACGA |
| 1551 | GTCTAGCACACGGCTGCTGTTGGAGAAGAACGCCTCGGTCAACGAGGTGGACTTTGAGGGCC |
| 1613 | GGACGCCCATGCACGTGGCCTGCCAGCACGGGCAGGAGAATATCGTGCGCATCCTGCTGCGC |
| 1675 | CGAGGCGTGGACGTGAGCCTGCAGGGCAAGGATGCCTGGCTGCCACTGCACTACGCTGCCTG |
| 1737 | GCAGGGCCACCTGCCCATCGTCAAGCTGCTGGCCAAGCAGCCGGGGGTGAGTGTGAACGCCC |
| 1799 | AGACGCTGGATGGGAGGACGCCATTGCACCTGGCCGCACAGCGCGGGCACTACCGCGTGGCC |
| 1861 | CGCATCCTCATCGACCTGTGCTCCGACGTCAACGTCTGCAGCCTGCTGGCACAGACACCCCT |
| 1923 | GCACGTGGCCGCGGAGACGGGGCACACGAGCACTGCCAGGCTGCTCCTGCATCGGGGCGCTG |
| 1985 | GCAAGGAGGCCgTGACCTCAGACGGCTACACCGCTCTGCACCTGGCTGCCCGCAACGGACAC |
| 2047 | CTGGCCACTGTCAAGCTGCTTGTCGAGGAGAAGGCCGATGTGCTGGCCCGGGGACCCCTGAA |
| 2109 | CCAGACGGCGCTGCACCTGGCTGCCGCCCACGGGCACTCGGAGGTGGTGGAGGAGTTGGTCA |
| 2171 | GCGCCGATGTCATTGACCTGTTCGACGAGCAGGGGCTCAGCGCGCTGCACCTGGCCGCCCAG |
| 2233 | GGCCGGCACGCACAGACGGTGGAGACTCTGCTCAGGCATGGGCCCACATCAACCTGCAGAG |
| 2295 | CCTCAAGTTCCAGGGCGGCCATGGCCCCGCCGCCACaCTCCTGCGGCGAAGCAAGACCTAG |

Figure 26
SEQ ID NO: 17

```
   1  ATGGAGGGCGACGGCGGGACCCCATGGGCCCTGGCGCTGCTGCGCACCTTCGACGCGGGCGA
  63  GTTCACGGGCTGGGAGAAGGTGGGCTCGGGCGGCTTCGGGCAGGTGTACAAGGTGCGCCATG
 125  TCCACTGGAAGACCTGGCTGGCCATCAAGTGCTCGCCCAGCCTGCACGTCGACGACAGGGAG
 187  CGCATGGAGCTTTTGGAAGAAGCCAAGAAGATGGAGATGGCCAAGTTTCGCTACATCCTGCC
 249  TGTGTATGGCATCTGCCGCGAACCTGTCGGCCTGGTCATGGAGTACATGGAGACGGGCTCCC
 311  TGGAAAAGCTGCTGGCTTCGGAGCCATTGCCATGGGATCTCCGGTTCCGAATCATCCACGAG
 373  ACGGCGGTGGGCATGAACTTCCTGCACTGCATGGCCCCGCCACTCCTGCACCTGGACCTCAA
 435  GCCCGCGAACATCCTGCTGGATGCCCACTACCACGTCAAGATTTCTGATTTTGGTCTGGCCA
 497  AGTGCAACGGGCTGTCCCACTCGCATGACCTCAGCATGGATGGCCTGTTTGGCACAATCGCC
 559  TACCTCCCTCCAGAGCGCATCAGGGAGAAGAGCCGGCTCTTCGACACCAAGCACGATGTATA
 621  CAGCTTTGCGATCGTCATCTGGGGCGTGCTCACACAGAAGAAGCCGTTTGCAGATGAGAAGA
 683  ACATCCTGCACATCATGGTGAAGGTGGTGAAGGGCCACCGCCCCGAGCTGCCGCCCGTGTGC
 745  AGAGCCCGGCCGCGCGCCTGCAGCCACCTGATACGCCTCATGCAGCGGTGCTGGCAGGGGGA
 807  TCCGCGAGTTAGGCCCACCTTCCAAGAAATTACTTCTGAAACCGAGGACCTGTGTGAAAAGC
 869  CTGATGACGAAGTGAAAGAAACTGCTCATGATCTGGACGTGAAAAGCCCCCGGAGCCCAGG
 931  AGCGAGGTGGTGCCTGCGAGGCTCAAGCGGGCCTCTGCCCCCACCTTCGATAACGACTACAG
 993  CCTCTCCGAGCTGCTCTCACAGCTGGACTCTGGAGTTTCCCAGGCTGTCGAGGGCCCCGAGG
1055  AGCTCAGCCGCGCAGCTCCTCTGAGTCCAAGCTGCCATCGTCCGGCAGTGGGAAGAGGCTCTCG
1117  GGGGTGTCCTCGGTGGACTCCGCCTTCTCTTCCAGAGGATCACTGTCGCTGTCCTTTGAGCG
1179  GGAACCTTCAACCAGCGATCTGGGCACCACAGACGTCAGAAGAAGAAGCTTGTGGATGCCA
1241  TCGTGTCCGGGGACACCAGCAAACTGATGAAGATCCTGCAGCCGCAGGACGTGGACCTGGCA
1303  CTGGACAGCGGTGCCAGCCTGCTGCACCTGGCGGTGGAGGCCGGGCAAGAGGAGTGCGCCAA
1365  GTGGCTGCTGCTCAACAATGCCAACCCCAACCTGAGCAACCGTAGGGGCTCCACCCCGTTGC
1427  ACATGGCCGTGGAGAGGAGGGTGCGGGGTGTCGTGGAGCGCCTGCTGGCGCGGAAGATCAGT
1489  GTCAACGCCAAGGATGAGGACCAGTGGACAGCCCTCCACTTTGCAGCCCAGAACGGGGACGA
1551  GTCTAGCACACGGCTGCTGTTGGAGAAGAACGCCTCGGTCAACGAGGTGGACTTTGAGGGCC
1613  GGACGCCCATGCACGTGGCCTGCCAGCACGGGCAGGAGAATATCGTGCGCATCCTGCTGCGC
1675  CGAGGCGTGGACGTGAGCCTGCAGGGCAAGGATGCCTGGCTGCCACTGCACTACGCTGCCTG
1737  GCAGGGCCACCTGCCCATCGTCAAGCTGCTGGCCAAGCAGCCGGGGGTGAGTGTGAACGCCC
1799  AGACGCTGGATGGGAGGACGCCATTGCACCTGGCCGCACAGCGCGGGCACTACCGCGTGGCC
1861  CGCATCCTCATCGACCTGTGCTCCGACGTCAACGTCTGCAGCCTGCTGGCACAGACACCCCT
1923  GCACGTGGCCGCGGAGACGGGGCACACGAGCACTGCCAGGCTGCTCCTGCATCGGGGCGCTG
1985  GCAAGGAGGCCgTGACCTCAGACGGCTACACCGCTCTGCACCTGGCTGCCCGCAACGGACAC
2047  CTGGCCACTGTCAAGCTGCTTGTCGAGGAGAAGGCCGATGTGCTGGCCCGGGGACCCCTGAA
2109  CCAGACGGCGCTGCACCTGGCTGCCGCCCACGGGCACTCGGAGGTGGTGAGGAGTTGGTCA
2171  GCGCCGATGTCATTGACCTGTTCGACGAGCAGGGGCTCAGCGCGCTGCACCTGGCCGCCCAG
2233  GGCCGGCACGCACAGACGGTGGAGACTCTGCTCAGGCATGGGGCCCACATCAACCTGCAGAG
2295  CCTCAAGTTCCAGGGCGGCCATGGCCCCGCCGCCAcTCCTGCGGCGAAGCAAGACCTAG
```

Figure 27
SEQ ID NO: 18

```
1     ATGGAGGGCGACGGCGGGACCCCATGGGCCCTGGCGCTGCTGCGCACCTTCGACGCGGGCGA
63    GTTCACGGGCTGGGAGAAGGTGGGCTCGGGCGGCTTCGGGCAGGTGTACAAGGTGCGCCATG
125   TCCACTGGAAGACCTGGCTGGCCATCAAGTGCTCGCCCAGCCTGCACGTCGACGACAGGGAG
187   CGCATGGAGCTTTTGGAAGAAGCCAAGAAGATGGAGATGGCCAAGTTTCGCTACATCCTGCC
249   TGTGTATGGCATCTGCCGCGAACCTGTCGGCCTGGTCATGGAGTACATGGAGACGGGCTCCC
311   TGGAAAAGCTGCTGGCTTCGGAGCCATTGCCATGGGATCTCCGGTTCCGAATCATCCACGAG
373   ACGGCGGTGGGCATGAACTTCCTGCACTGCATGGCCCCGCCACTCCTGCACCTGGACCTCAA
435   GCCCGCGAACATCCTGCTGGATGCCCACTACCACGTCAAGATTTCTGATTTTGGTCTGGCCA
497   AGTGCAACGGGCTGTCCCACTCGCATGACCTCAGCATGGATGGCCTGTTTGGCACAATCGCC
559   TACCTCCCTCCAGAGCGCATCAGGGAGAAGAGCCGGCTCTTCGACACCAAGCACGATGTATA
621   CAGCTTTGCGATCGTCATCGGGGCGTGCTCACACAGAAGAAGCCGTTTGCAGATGAGAAGA
683   ACATCCTGCACATCATGGTGAAGGTGGTGAAGGGCCACCGCCCCGAGCTGCCGCCCGTGTGC
745   AGAGCCCGGCCGCGCGCCTGCAGCCACCTGATACGCCTCATGCAGCGGTGCTGGCAGGGGGA
807   TCCGCGAGTTAGGCCCACCTTCCAAGAAATTACTTCTGAAACCGAGGACCTGTGTGAAAAGC
869   CTGATGACGAAGTGAAAGAAACTGCTCATGATCTGGACGTGAAAAGCCCCCCGGAGCCCAGG
931   AGCGAGGTGGTGCCTGCGAGGCTCAAGCGGGCCTCTGCCCCCACCTTCGATAACGACTACAG
993   CCTCTCCGAGCTGCTCTCACAGCTGGACTCTGGAGTTTCCCAGGCTGTCGAGGGCCCCGAGG
1055  AGCTCAGCCGCAGCTCCTCTGAGTCCAAGCTGCCATCGTCCGGCAGTGGGAAGAGGCTCTCG
1117  GGGGTGTCCTCGGTGGACTCCGCCTTCTCTTCCAGAGGATCACTGTCGCTGTCCTTTGAGCG
1179  GGAACCTTCAACCAGCGATCTGGGCACCACAGACGTCCAGAAGAAGAAGCTTGTGGATGCCA
1241  TCGTGTCCGGGGACACCAGCAAACTGATGAAGATCCTGCAGCCGCAGGACGTGGACCTGGCA
1303  CTGGACAGCGGTGCCAGCCTGCTGCACCTGGCGGTGGAGGCCGGGCAAGAGGAGTGCGCCAA
1365  GTGGCTGCTGCTCAACAATGCCAACCCCAACCTGAGCAACCGTAGGGGCTCCACCCCGTTGC
1427  ACATGGCCGTGGAGAGGAGGGTGCGGGGTGTCGTGGAGCTCCTGCTGGCACGGAAGATCAGT
1489  GTCAACGCCAAGGATGAGGACCAGTGGACAGCCCTCCACTTTGCAGCCCAGAACGGGGACGA
1551  GTCTAGCACACGGCTGCTGTTGGAGAAGAACGCCTCGGTCAACGAGGTGGACTTTGAGGGCC
1613  GGACGCCCATGCACGTGGCCTGCCAGCACGGGCAGGAGAATATCGTGCGCATCCTGCTGCGC
1675  CGAGGCGTGGACGTGAACCTGCAGGGCAAGGATGCCTGGCTGCCACTGCACTACGCTGCCTG
1737  GCAGGGCCACCTGCCCATCGTCAAGCTGCTGGCCAAGCAGCCGGGGGTGAGTGTGAACGCCC
1799  AGACGCTGGATGGAGGACGCCATTGCACCTGGCCGCACAGCGCGGGCACTACCGCGTGGCC
1861  CGCATCCTCATCGACCTGTGCTCCGACGTCAACGTCTGCAGCCTGCTGGCACAGACACCCCT
1923  GCACGTGGCCGCGGAGACGGGGCACACGAGCACTGCCAGGCTGCTCCTGCATCGGGGCGCTG
1985  GCAAGGAGGCCgTGACCTCAGACGGCTACACCGCTCTGCACCTGGCTGCCCGCAACGGACAC
2047  CTGGCCACTGTCAAGCTGCTTGTCGAGGAGAAGGCCGATGTGCTGGCCCGGGGACCCCTGAA
2109  CCAGACGGCGCTGCACCTGGCTGCCGCCCACGGGCACTCGGAGGTGGTGGAGGAGTTGGTCA
2171  GCGCCGATGTCATTGACCTGTTCGACGAGCAGGGGCTCAGCGCGCTGCACCTGGCCGCCCAG
2233  GGCCGGCACGCACAGACGGTGGAGACTCTGCTCAGGCATGGGCCCACATCAACCTGCAGAG
2295  CCTCAAGTTCCAGGGCGGCCATGGCCCCGCCGCCACaCTCCTGCGGCGAAGCAAGACCTAG
```

Figure 28
SEQ ID NO: 19

```
1       ATGGAGGGCGACGGCGGGACCCCATGGGCCCTGGCGCTGCTGCGCACCTTCGACGCGGGCGA
63      GTTCACGGGCTGGGAGAAGGTGGGCTCGGGCGGCTTCGGGCAGGTGTACAAGGTGCGCCATG
125     TCCACTGGAAGACCTGGCTGGCCATCAAGTGCTCGCCCAGCCTGCACGTCGACGACAGGGAG
187     CGCATGGAGCTTTTGGAAGAAGCCAAGAAGATGGAGATGGCCAAGTTTCGCTACATCCTGCC
249     TGTGTATGGCATCTGCCGCGAACCTGTCGGCCTGGTCATGGAGTACATGGAGACGGGCTCCC
311     TGGAAAAGCTGCTGGCTTCGGAGCCATTGCCATGGGATCTCCGGTTCCGAATCATCCACGAG
373     ACGGCGGTGGGCATGAACTTCCTGCACTGCATGGCCCCGCCACTCCTGCACCTGGACCTCAA
435     GCCCGCGAACATCCTGCTGGATGCCCACTACCACGTCAAGATTTCTGATTTTGGTCTGGCCA
497     AGTGCAACGGGCTGTCCCACTCGCATGACCTCAGCATGGATGGCCTGTTTGGCACAATCGCC
559     TACCTCCCTCCAGAGCGCATCAGGGAGAAGAGCCGGCTCTTCGACACCAAGCACGATGTATA
621     CAGCTTTGCGATCGTCATCTGGGGCGTGCTCACACAGAAGAAGCCGTTTGCAGATGAGAAGA
683     ACATCCTGCACATCATGGTGAAGGTGGTGAAGGGCCACCGCCCCGAGCTGCCGCCCGTGTGC
745     AGAGCCCGGCCGCGCGCCTGCAGCCACCTGATACGCCTCATGCAGCGGTGCTGGCAGGGGGA
807     TCCGCGAGTTAGGCCCACCTTCCAAGAAATTACTTCTGAAACCGAGGACCTGTGTGAAAAGC
869     CTGATGACGAAGTGAAAGAAACTGCTCATGATCTGGACGTGAAAAGCCCCCCGGAGCCCAGG
931     AGCGAGGTGGTGCCTGCGAGGCTCAAGCGGGCCTCTGCCCCACCTTCGATAACGACTACAG
993     CCTCTCCGAGCTGCTCTCACAGCTGGACTCTGGAGTTTCCCAGGCTGTCGAGGGCCCCGAGG
1055    AGCTCAGCCGCAGCTCCTCTGAGTCCAAGCTGCCATCGTCCGGCAGTGGGAAGAGGCTCTCG
1117    GGGGTGTCCTCGGTGGACTCCGCCTTCTCTTCCAGAGGATCACTGTCGCTGTCCTTTGAGCG
1179    GGAACCTTCAACCAGCGATCTGGGCACCACAGACGTCCAGAAGAAGAAGCTTGTGGATGCCA
1241    TCGTGTCCGGGGACACCAGCAAACTGATGAAGATCCTGCAGCCGCAGGACGTGGACCTGGCA
1303    CTGGACAGCGGTGCCAGCCTGCTGCACCTGGCGGTGGAGGCCGGGCAAGAGGAGTGCGCCAA
1365    GTGGCTGCTGCTCAACAATGCCAACCCCAACCTGAGCAACCGTAGGGGCTCCACCCCGTTGC
1427    ACATGGCCGTGGAGAGGAGGGTGCGGGGTGTCGTGGAGCTCCTGCTGGCGCGGAAGATCAGT
1489    GTCAACGCCAAGGATGAGGACCAGTGGACAGCCCTCCACTTTGCAGCCCAGAACGGGGATGA
1551    GTCTAGCACACGGCTGCTGTTGGAGAAGAACGCCTCGGTCAACGAGGTGGACTTTGAGGGCC
1613    GGACGCCCATGCACGTGGCCTGCCAGCACGGGCAGGAGAATATCGTGCGCATCCTGCTGCGC
1675    CGAGGCGTGGACGTGAGCCTGCAGGGCAAGGATGCCTGGCTGCCACTGCACTACGCTGCCTG
1737    GCAGGGCCACCTGCCCATCGTCAAGCTGCTGGCCAAGCAGCCGGGGGTGAGTGTGAACGCCC
1799    AGACGCTGGATGGGAGGACGCCATTGCACCTGGCCGCACAGCGCGGGCACTACCGCGTGGCC
1861    CGCATCCTCATCGACCTGTGCTCCGACGTCAACGTCTGCAGCCTGCTGGCACAGACACCCCT
1923    GCACGTGGCCGCGGAGACGGGGCACACGAGCACTGCCAGGCTGCTCCTGCATCGGGGCGCTG
1985    GCAAGGAGGCCgTGACCTCAGACGGCTACACCGCTCTGCACCTGGCTGCCCGCAACGGACAC
2047    CTGGCCACTGTCAAGCTGCTTGTCGAGGAGAAGGCCGATGTGCTGGCCCGGGGACCCCTGAA
2109    CCAGACGGCGCTGCACCTGGCTGCCGCCCACGGGCACTCGGAGGTGGTGGAGGAGTTGGTCA
2171    GCGCCGATGTCATTGACCTGTTCGACGAGCAGGGGCTCAGCGCGCTGCACCTGGCCGCCCAG
2233    GGCCGGCACGCACAGACGGTGGAGACTCTGCTCAGGCATGGGGCCCACATCAACCTGCAGAG
2295    CCTCAAGTTCCAGGGCGGCCATGGCCCCGCCGCCACaCTCCTGCGGCGAAGCAAGACCTAG
```

Figure 29
SEQ ID NO: 20

```
   1    ATGGAGGGCGACGGCGGGACCCCATGGGCCCTGGCGCTGCTGCGCACCTTCGACGCGGGCGA
  63    GTTCACGGGCTGGGAGAAGGTGGGCTCGGGCGGCTTCGGGCAGGTGTACAAGGTGCGCCATG
 125    TCCACTGGAAGACCTGGCTGGCCATCAAGTGCTCGCCCAGCCTGCACGTCGACGACAGGGAG
 187    CGCATGGAGCTTTTGGAAGAAGCCAAGAAGATGGAGATGGCCAAGTTTCGCTACATCCTGCC
 249    TGTGTATGGCATCTGCCGCGAACCTGTCGGCCTGGTCATGGAGTACATGGAGACGGGCTCCC
 311    TGGAAAAGCTGCTGGCTTCGGAGCCATTGCCATGGGATCTCCGGTTCCGAATCATCCACGAG
 373    ACGGCGGTGGGCATGAACTTCCTGCACTGCATGGCCCCGCCACTCCTGCACCTGGACCTCAA
 435    GCCCGCGAACATCCTGCTGGATGCCCACTACCACGTCAAGATTTCTGATTTTGGTCTGGCCA
 497    AGTGCAACGGGCTGTCCCACTCGCATGACCTCAGCATGGATGGCCTGTTTGGCACAATCGCC
 559    TACCTCCCTCCAGAGCGCATCAGGGAGAAGAGCCGGCTCTTCGACACCAAGCACGATGTATA
 621    CAGCTTTGCGATCGTCATCTGGGGCGTGCTCACACAGAAGAAGCCGTTTGCAGATGAGAAGA
 683    ACATCCTGCACATCATGGTGAAGGTGGTGAAGGGCCACCGCCCCGAGCTGCCGCCCGTGTGC
 745    AGAGCCCGGCCGCGCGCCTGCAGCCACCTGATACGCCTCATGCAGCGGTGCTGGCAGGGGGA
 807    TCCGCGAGTTAGGCCCACCTTCCAAGAAATTACTTCTGAAACCGAGGACCTGTGTGAAAAGC
 869    CTGATGACGAAGTGAAAGAAACTGCTCATGATCTGGACGTGAAAAGCCCCCCGGAGCCCAGG
 931    AGCGAGGTGGTGCCTGCGAGGCTCAAGCGGGCCTCTGCCCCCACCTTCGATAACGACTACAG
 993    CCTCTCCGAGCTGCTCTCACAGCTGGACTCTGGAGTTTCCCAGGCTGTCGAGGGCCCCGAGG
1055    AGCTCAGCCGCCAGCTCCTCTGAGTCCAAGCTGCCATCGTCCGGCAGTGGGAAGAGGCTCTCG
1117    GGGGTGTCCTCGGTGGACTCCGCCTTCTCTTCCAGAGGATCACTGTCGCTGTCCTTTGAGCG
1179    GGAACCTTCAACCAGCGATCTGGGCACCACAGACGTCCAGAAGAAGAAGCTTGTGGATGCCA
1241    TCGTGTCCGGGGACACCAGCAAACTGATGAAGATCCTGCAGCCGCAGGACGTGGACCTGGCA
1303    CTGGACAGCGGTGCCAGCCTGCTGCACCTGGCGGTGGAGGCCGGGCAAGAGGAGTGCGCCAA
1365    GTGGCTGCTGCTCAACAATGCCAACCCCAACCTGAGCAACCGTAGGGGCTCCACCCCGTTGC
1427    ACATGGCCGTGGAGAGGAGGGTGCGGGGTGTCGTGGAGCTCCTGCTGGCGCGGAAGATCAGT
1489    GTCAACGCCAAGGATGAGGACCAGTGGACAGCCCTCCACTTTGCAGCCCAGAACGGGGACGA
1551    GTCTAGCACACGGCTGCTGTTGGAGAAGAACGCCTCGGTCAACGAGGTGGACTTTGAGGGCC
1613    TGACGCCCATGCACGTGGCCTGCCAGCACGGGCAGGAGAATATCGTGCGCATCCTGCTGCGC
1675    CGAGGCGTGGACGTGAGCCTGCAGGGCAAGGATGCCTGGCTGCCACTGCACTACGCTGCCTG
1737    GCAGGGCCACCTGCCCATCGTCAAGCTGCTGGCCAAGCAGCCGGGGGTGAGTGTGAACGCCC
1799    AGACGCTGGATGGGAGGACGCCATTGCACCTGGCCGCACAGCGCGGGCACTACCGCGTGGCC
1861    CGCATCCTCATCGACCTGTGCTCCGACGTCAACGTCTGCAGCCTGCTGGCACAGACACCCCT
1923    GCACGTGGCCGCGGAGACGGGGCACACGAGCACTGCCAGGCTGCTCCTGCATCGGGGCGCTG
1985    GCAAGGAGGCCgTGACCTCAGACGGCTACACCGCTCTGCACCTGGCTGCCCGCAACGGACAC
2047    CTGGCCACTGTCAAGCTGCTTGTCGAGGAGAAGGCCGATGTGCTGGCCCGGGGACCCCTGAA
2109    CCAGACGGCGCTGCACCTGGCTGCCGCCCACGGGCACTCGGAGGTGGTGGAGGAGTTGGTCA
2171    GCGCCGATGTCATTGACCTGTTCGACGAGCAGGGGCTCAGCGCGCTGCACCTGGCCGCCCAG
2233    GGCCGGCACGCACAGACGGTGGAGACTCTGCTCAGGCATGGGGCCCACATCAACCTGCAGAG
2295    CCTCAAGTTCCAGGGCGGCCATGGCCCCGCCGCCACaCTCCTGCGGCGAAGCAAGACCTAG
```

Figure 30
SEQ ID NO: 21

| | |
|---|---|
| 1 | ATGGAGGGCGACGGCGGGACCCCATGGGCCCTGGCGCTGCTGCGCACCTTCGACGCGGGCGA |
| 63 | GTTCACGGGCTGGGAGAAGGTGGGCTCGGGCGGCTTCGGGCAGGTGTACAAGGTGCGCCATG |
| 125 | TCCACTGGAAGACCTGGCTGGCCATCAAGTGCTCGCCCAGCCTGCACGTCGACGACAGGGAG |
| 187 | CGCATGGAGCTTTTGGAAGAAGCCAAGAAGATGGAGATGGCCAAGTTTCGCTACATCCTGCC |
| 249 | TGTGTATGGCATCTGCCGCGAACCTGTCGGCCTGGTCATGGAGTACATGGAGACGGGCTCCC |
| 311 | TGGAAAAGCTGCTGGCTTCGGAGCCATTGCCATGGGATCTCCGGTTCCGAATCATCCACGAG |
| 373 | ACGGCGGTGGGCATGAACTTCCTGCACTGCATGGCCCCGCCACTCCTGCACCTGGACCTCAA |
| 435 | GCCCGCGAACATCCTGCTGGATGCCCACTACCACGTCAAGATTTCTGATTTTGGTCTGGCCA |
| 497 | AGTGCAACGGGCTGTCCCACTCGCATGACCTCAGCATGGATGGCCTGTTTGGCACAATCGCC |
| 559 | TACCTCCCTCCAGAGCGCATCAGGGAGAAGAGCCGGCTCTTCGACACCAAGCACGATGTATA |
| 621 | CAGCTTTGCGATCGTCATCTGGGGCGTGCTCACACAGAAGAAGCCGTTTGCAGATGAGAAGA |
| 683 | ACATCCTGCACATCATGGTGAAGGTGGTGAAGGGCCACCGCCCCGAGCTGCCGCCCGTGTGC |
| 745 | AGAGCCCGGCCGCGCGCCTGCAGCCACCTGATACGCCTCATGCAGCGGTGCTGGCAGGGGGA |
| 807 | TCCGCGAGTTAGGCCCACCTTCCAAGAAATTACTTCTGAAACCGAGGACCTGTGTGAAAAGC |
| 869 | CTGATGACGAAGTGAAAGAAACTGCTCATGATCTGGACGTGAAAAGCCCCCCGGAGCCCAGG |
| 931 | AGCGAGGTGGTGCCTGCGAGGCTCAAGCGGGCCTCTGCCCCCACCTTCGATAACGACTACAG |
| 993 | CCTCTCCGAGCTGCTCTCACAGCTGGACTCTGGAGTTTCCCAGGCTGTCGAGGGCCCCGAGG |
| 1055 | AGCTCAGCCGCAGCTCCTCTGAGTCCAAGCTGCCATCGTCCGGCAGTGGGAAGAGGCTCTCG |
| 1117 | GGGGTGTCCTCGGTGGACTCCGCCTTCTCTTCCAGAGGATCACTGTCGGTGTCCTTTGAGCG |
| 1179 | GGAACCTTCAACCAGCGATCTGGGCACCACAGACGTCCAGAAGAAGAAGCTTGTGGATGCCA |
| 1241 | TCGTGTCCGGGGACACCAGCAAACTGATGAAGATCCTGCAGCCGCAGGACGTGGACCTGGCA |
| 1303 | CTGGACAGCGGTGCCAGCCTGCTGCACCTGGCGGTGGAGGCCGGGCAAGAGGAGTGCGCCAA |
| 1365 | GTGGCTGCTGCTCAACAATGCCAACCCCAACCTGAGCAACCGTAGGGGCTCCACCCCGTTGC |
| 1427 | ACATGGCCGTGGAGAGGAGGGTGCGGGGTGTCGTGGAGCTCCTGCTGGCGCGGAAGATCAGT |
| 1489 | GTCAACGCCAAGGATGAGGACCAGTGGACAGCCCTCCACTTTGCAGCCCAGAACGGGGACGA |
| 1551 | GTCTAGCACACGGCTGCTGTTGGAGAAGAACGCCTCGGTCAACGAGGTGGACTTTGAGGGCC |
| 1613 | GGACGCCCATGCACGTGGCCTGCCAGCACGGGCAGGAGAATATCGTGCGCATCCTGCTGCGC |
| 1675 | CGAGGCGTGGACGTGAGCCTGCAGGGCAAGGATGCCTGGCTGCCACTGCACTACGCTGCCTG |
| 1737 | GCAGGGCCACCTGCCCATCGTCAAGCTGCTGGCCAAGCAGCCGGGGGTGAGTGTGAACGCCC |
| 1799 | AGACGCTGGATGGGAGGACGCCATTGCACCTGGCCGCACAGCGCGGGCACTACCGCGTGGCC |
| 1861 | CGCATCCTCATCGACCTGTGCTCCGACGTCAACGTCTGCAGCCTGCTGGCACAGACACCCCT |
| 1923 | GCACGTGGCCGCGGAGACGGGGCACACGAGCACTGCCAGGCTGCTCCTGCATCGGGGCGCTG |
| 1985 | GCAAGAAGGCCgTGACCTCAGACGGCTACACCGCTCTGCACCTGGCTGCCCGCAACGGACAC |
| 2047 | CTGGCCACTGTCAAGCTGCTTGTCGAGGAGAAGGCCGATGTGCTGGCCCGGGGACCCCTGAA |
| 2109 | CCAGACGGCGCTGCACCTGGCTGCCGCCCACGGGCACTCGGAGGTGGTGGAGGAGTTGGTCA |
| 2171 | GCGCCGATGTCATTGACCTGTTCGACGAGGCAGGGGCTCAGCGCGCTGCACCTGGCCGCCCAG |
| 2233 | GGCCGGCACGCACAGACGGTGGAGACTCTGCTCAGGCATGGGGCCCACATCAACCTGCAGAG |
| 2295 | CCTCAAGTTCCAGGGCGGCCATGGCCCCGCCGCCACaCTCCTGCGGCGAAGCAAGACCTAG |

Figure 31
SEQ ID NO: 22

```
   1   ATGGAGGGCGACGGCGGGACCCCATGGGCCCTGGCGCTGCTGCGCACCTTCGACGCGGGCGA
  63   GTTCACGGGCTGGGAGAAGGTGGGCTCGGGCGGCTTCGGGCAGGTGTACAAGGTGCGCCATG
 125   TCCACTGGAAGACCTGGCTGGCCATCAAGTGCTCGCCCAGCCTGCACGTCGACGACAGGGAG
 187   CGCATGGAGCTTTTGGAAGAAGCCAAGAAGATGGAGATGGCCAAGTTTCGCTACATCCTGCC
 249   TGTGTATGGCATCTGCCGCGAACCTGTCGGCCTGGTCATGGAGTACATGGAGACGGGCTCCC
 311   TGGAAAAGCTGCTGGCTTCGGAGCCATTGCCATGGGATCTCCGGTTCCGAATCATCCACGAG
 373   ACGGCGGTGGGCATGAACTTCCTGCACTGCATGGCCCCGCCACTCCTGCACCTGGACCTCAA
 435   GCCCGCGAACATCCTGCTGGATGCCCACTACCACGTCAAGATTTCTGATTTTGGTCTGGCCA
 497   AGTGCAACGGGCTGTCCCACTCGCATGACCTCAGCATGGATGGCCTGTTTGGCACAATCGCC
 559   TACCTCCCTCCAGAGCGCATCAGGGAGAAGAGCCGGCTCTTCGACACCAAGCACGATGTATA
 621   CAGCTTTGCGATCGTCATCTGGGGCGTGCTCACACAGAAGAAGCCGTTTGCAGATGAGAAGA
 683   ACATCCTGCACATCATGGTGAAGGTGGTGAAGGGCCACCGCCCCGAGCTGCCGCCCGTGTGC
 745   AGAGCCCGGCCGCGCGCCTGCAGCCACCTGATACGCCTCATGCAGCGGTGCTGGCAGGGGGA
 807   TCCGCGAGTTAGGCCCACCTTCCAAGAAATTACTTCTGAAACCGAGGACCTGTGTGAAAAGC
 869   CTGATGACGAAGTGAAAGAAACTGCTCATGATCTGGACGTGAAAAGCCCCCCGGAGCCCAGG
 931   AGCGAGGTGGTGCCTGCGAGGCTCAAGCGGGCCTCTGCCCCCACCTTCGATAACGACTACAG
 993   CCTCTCCGAGCTGCTCTCACAGCTGGACTCTGGAGTTTCCCAGGCTGTCGAGGGCCCCGAGG
1055   AGCTCAGCCGCAGCTCCTCTGAGTCCAAGCTGCCATCGTCCGGCAGTGGGAAGAGGCTCTCG
1117   GGGTGTCCTCGGTGGACTCCGCCTTCTCTTCCAGAGGATCACTGTCGCTGTCCTTTGAGCG
1179   GGAACCTTCAACCAGCGATCTGGGCACCACAGACGTCCAGAAGAAGAAGCTTGTGGATGCCA
1241   TCGTGTCCGGGGACACCAGCAAACTGATGAAGATCCTGCAGCCGCAGGACGTGGACCTGGCA
1303   CTGGACAGCGGTGCCAGCCTGCTGCACCTGGCGGTGGAGGCCGGGCAAGAGGAGTGCGCCAA
1365   GTGGCTGCTGCTCAACAATGCCAACCCCAACCTGAGCAACCGTAGGGGCTCCACCCCGTTGC
1427   ACATGGCCGTGGAGAGGAGGGTGCGGGGTGTCGTGGAGCTCCTGCTGGCGCGGAAGATCAGT
1489   GTCAACGCCAAGGATGAGGACCAGTGGACAGCCCTCCACTTTGCAGCCCAGAACGGGGACGA
1551   GTCTAGCACACGCTGCTGTTGGAGAAGAACGCCTCGGTCAACGAGGTGGACTTTGAGGGCC
1613   GGACGCCCATGCACGTGGCCTGCCAGCACGGGCAGGAGAATATCGTGCGCATCCTGCTGCGC
1675   CGAGGCGTGGACGTGAGCCTGCAGGGCAAGGATGCCTGGCTGCCACTGCACTACGCTGCCTG
1737   GCAGGGCCACCTGCCCATCGTCAAGCTGCTGGCCAAGCAGCCGGGGGTGAGTGTGAACGCCC
1799   AGACGCTGGATGGGAGGACGCCATTGCACCTGGCCGCACAGCGCGGGCACTACCGCGTGGCC
1861   CGCATCCTCATCGACCTGTGCTCCGACGTCAACGTCTGCAGCCTGCTGGCACAGACACCCCT
1923   GCACGTGGCCGCGGAGACGGGGCACACGAGCACTGCCAGGCTGCTCCTGCATCGGGGCGCTG
1985   GCAAGGAGGCCATGACCTCAGACGGCTACACCGCTCTGCACCTGGCTGCCCGCAACGGACAC
2047   CTGGCCACTGTCAAGCTGCTTGTCGAGGAGAAGGCCGATGTGCTGGCCCGGGGACCCCTGAA
2109   CCAGACGGCGCTGCACCTGGCTGCCGCCCACGGGCACTCGGAGGTGGTGGAGGAGTTGGTCA
2171   GCGCCGATGTCATTGACCTGTTCGACGAGCAGGGGCTCAGCGCGCTGCACCTGGCCGCCCAG
2233   GGCCGGCACGCACAGACGGTGGAGACTCTGCTCAGGCATGGGGCCCACATCAACCTGCAGAG
2295   CCTCAAGTTCCAGGGCGGCCATGGCCCCGCCGCCACaCTCCTGCGGCGAAGCAAGACCTAG
```

Figure 32
SEQ ID NO: 23

```
   1  ATGGAGGGCGACGGCGGGACCCCATGGGCCCTGGCGCTGCTGCGCACCTTCGACGCGGGCGA
  63  GTTCACGGGCTGGGAGAAGGTGGGCTCGGGCGGCTTCGGGCAGGTGTACAAGGTGCGCCATG
 125  TCCACTGGAAGACCTGGCTGGCCATCAAGTGCTCGCCCAGCCTGCACGTCGACGACAGGGAG
 187  CGCATGGAGCTTTTGGAAGAAGCCAAGAAGATGGAGATGGCCAAGTTTCGCTACATCCTGCC
 249  TGTGTATGGCATCTGCCGCGAACCTGTCGGCCTGGTCATGGAGTACATGGAGACGGGCTCCC
 311  TGGAAAAGCTGCTGGCTTCGGAGCCATTGCCATGGGATCTCCGGTTCCGAATCATCCACGAG
 373  ACGGCGGTGGGCATGAACTTCCTGCACTGCATGGCCCCGCCACTCCTGCACCTGGACCTCAA
 435  GCCCGCGAACATCCTGCTGGATGCCCACTACCACGTCAAGATTTCTGATTTTGGTCTGGCCA
 497  AGTGCAACGGGCTGTCCCACTCGCATGACCTCAGCATGGATGGCCTGTTTGGCACAATCGCC
 559  TACCTCCCTCCAGAGCGCATCAGGGAGAAGAGCCGGCTCTTCGACACCAAGCACGATGTATA
 621  CAGCTTTGCGATCGTCATCTGGGGCGTGCTCACACAGAAGAAGCCGTTTGCAGATGAGAAGA
 683  ACATCCTGCACATCATGGTGAAGGTGGTGAAGGGCCACCGCCCCGAGCTGCCGCCCGTGTGC
 745  AGAGCCCGGCCGCGCGCCTGCAGCCACCTGATACGCCTCATGCAGCGGTGCTGGCAGGGGGA
 807  TCCGCGAGTTAGGCCCACCTTCCAAGAAATTACTTCTGAAACCGAGGACCTGTGTGAAAAGC
 869  CTGATGACGAAGTGAAAGAAACTGCTCATGATCTGGACGTGAAAAGCCCCCGGAGCCCAGG
 931  AGCGAGGTGGTGCCTGCGAGGCTCAAGCGGGCCTCTGCCCCCACCTTCGATAACGACTACAG
 993  CCTCTCCGAGCTGCTCTCACAGCTGGACTCTGGAGTTTCCCAGGCTGTCGAGGGCCCCGAGG
1055  AGCTCAGCCGCAGCTCCTCTGAGTCCAAGCTGCCATCGTCCGGCAGTGGGAAGAGGCTCTCG
1117  GGGGTGTCCTCGGTGGACTCCGCCTTCTCTTCCAGAGGATCACTGTCGCTGTCCTTTGAGCG
1179  GGAACCTTCAACCAGCGATCTGGGCACCACAGACGTCCAGAAGAAGAAGCTTGTGGATGCCA
1241  TCGTGTCCGGGGACACCAGCAAACTGATGAAGATCCTGCAGCCGCAGGACGTGGACCTGGCA
1303  CTGGACAGCGGTGCCAGCCTGCTGCACCTGGCGGTGGAGGCCGGGCAAGAGGAGTGCGCCAA
1365  GTGGCTGCTGCTCAACAATGCCAACCCCAACCTGAGCAACCGTAGGGGCTCCACCCCGTTGC
1427  ACATGGCCGTGGAGAGGAGGGTGCGGGGTGTCGTGGAGCTCCTGCTGGCGCGGAAGATCAGT
1489  GTCAACGCCAAGGATGAGGACCAGTGGACAGCCCTCCACTTTGCAGCCCAGAACGGGGACGA
1551  GTCTAGCACACGGCTGCTGTTGGAGAAGAACGCCTCGGTCAACGAGGTGGACTTTGAGGGCC
1613  GGACGCCCATGCACGTGGCCTGCCAGCACGGGCAGGAGAATATCGTGCGCATCCTGCTGCGC
1675  CGAGGCGTGGACGTGAGCCTGCAGGGCAAGGATGCCTGGCTGCCACTGCACTACGCTGCCTG
1737  GCAGGGCACCTGCCCATCGTCAAGCTGCTGGCCAAGCAGCCGGGGGTGAGTGTGAACGCCC
1799  AGACGCTGGATGGGAGGACGCCATTGCACCTGGCCGCACAGCGCGGGCACTACCGCGTGGCC
1861  CGCATCCTCATCGACCTGTGCTCCGACGTCAACGTCTGCAGCCTGCTGGCACAGACACCCCT
1923  GCACGTGGCCGCGGAGACGGGGCACACGAGCACTGCCAGGCTGCTCCTGCATCGGGCGCTG
1985  GCAAGGAGGCCgTGACCTCAGACGGCTACACCGCTCTGCACCTGGCTGCCCGCAACGGACAC
2047  CTGGCCACTGTCAAGCTGCTTGTCGAGGAGAAGGCCGATGTGCTGGCCCGGGGACCCCTGAA
2109  CCAGACGGCGCTGCACCTGGCTGCCGCCCACGGGCACTCGGAGGTGGTGGAGGAGTTGGTCA
2171  GCGCCGATGTCATTGACCTGTTCGACGAGCAGGGGCTCAGCGCGCTGCACCTGGCCGCCCAG
2233  GGCCGGCACGCACAGACGGTGGAGACTCTGCTCAGGCATGGGGCCCACATCAACCTGCAGAG
2295  CCTCAAGTTCCAGGGCGGCCATGGCCCCGCCGCCACGCTCCTGCGGCGAAGCAAGACCTAG
```

FIG. 33A
SEQ ID NO: 27

Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
            20                  25                  30

Phe Gly Gln Val Tyr Lys Val Arg His Val His Trp Lys Thr Trp Leu
            35                  40                  45

Ala Ile Lys Cys Ser Pro Ser Leu His Val Asp Asp Arg Glu Arg Met
    50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
            115                 120                 125

Met Asn Phe Leu His Cys Met Ser Pro Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
            165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
    195                 200                 205

Phe Ala Ile Val Ile Trp Gly Val Leu Thr Gln Lys Lys Pro Phe Ala
    210                 215                 220

Asp Glu Lys Asn Ile Leu His Ile Met Met Lys Val Val Lys Gly His
225                 230                 235                 240

Arg Pro Glu Leu Pro Pro Ile Cys Arg Pro Arg Pro Arg Ala Cys Ala
            245                 250                 255

FIG. 33B

```
Ser Leu Ile Gly Leu Met Gln Arg Cys Trp His Ala Asp Pro Gln Val
            260                 265                 270

Arg Pro Thr Phe Gln Glu Ile Thr Ser Glu Thr Glu Asp Leu
```

FIG. 34A
SEQ ID NO: 28

Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
            20                  25                  30

Phe Gly Gln Val Tyr Lys Val Arg His Val His Trp Lys Thr Trp Leu
            35                  40                  45

Ala Ile Lys Cys Ser Pro Ser Leu His Val Asp Asp Arg Glu Arg Met
50                  55                  60

Glu Leu Leu Glu Glu Ala Lys Lys Met Glu Met Ala Lys Phe Arg Tyr
65              70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
        115                 120                 125

Met Asn Phe Leu His Cys Met Ser Pro Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
                165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

FIG. 34B

Phe Ala Ile Val Ile Trp Gly Val Leu Thr Gln Lys Lys Pro Phe Ala
    210             215             220

Asp Glu Lys Asn Ile Leu His Ile Met Met Lys Val Val Lys Gly His
225             230             235             240

Arg Pro Glu Leu Pro Pro Ile Cys Arg Pro Arg Pro Arg Ala Cys Ala
                245             250             255

Ser Leu Ile Gly Leu Met Gln Arg Cys Trp His Ala Asp Pro Gln Val
            260             265             270

Arg Pro Thr Phe Gln Glu Ile Thr Ser Glu Thr Glu Asp Leu Cys Glu
        275             280             285

Lys Pro Asp Glu Glu Val Lys Asp Leu Ala His Glu Pro Gly Glu Lys
    290             295             300

Ser Ser Leu Glu Ser Lys Ser Glu Ala Arg Pro Glu Ser Ser Arg Leu
305             310             315             320

Lys Arg Ala Ser Ala Pro Pro Phe Asp Asn Asp Cys Ser Leu Ser Glu
                325             330             335

Leu Leu Ser Gln Leu Asp Ser Gly Ile Ser Gln Thr Leu Glu Gly Pro
            340             345             350

Glu Glu Leu Ser Arg Ser Ser Ser Glu Cys Lys Leu Pro Ser Ser Ser
        355             360             365

Ser Gly Lys Arg Leu Ser Gly Val Ser Ser Val Asp Ser Ala Phe Ser
    370             375             380

Ser Arg Gly Ser Leu Ser Leu Ser Phe Glu Arg Glu Ala Ser Thr Gly
385             390             395             400

Asp Leu Gly Pro Thr Asp Ile Gln Lys Lys Lys Leu Val Asp Ala Ile
                405             410             415

Ile Ser Gly Asp Thr Ser Arg Leu Met Lys Ile Leu Gln Pro Gln Asp
            420             425             430

FIG. 34C

Val Asp Leu Val Leu Asp Ser

Figure 35
SEQ ID NO: 29

Cys Glu Lys Pro Asp Glu Glu Val Lys Asp Leu Ala His Glu Pro Gly

Glu Lys Ser Ser Leu Glu Ser Lys Ser Glu Ala Arg Pro Glu Ser Ser

Arg Leu Lys Arg Ala Ser Ala Pro Pro Phe Asp Asn Asp Cys Ser Leu

Ser Glu Leu Leu Ser Gln Leu Asp Ser Gly Ile Ser Gln Thr Leu Glu

Gly Pro Glu Glu Leu Ser Arg Ser Ser Ser Glu Cys Lys Leu Pro Ser

Ser Ser Ser Gly Lys Arg Leu Ser Gly Val Ser Ser Val Asp Ser Ala

Phe Ser Ser Arg Gly Ser Leu Ser Leu Ser Phe Glu Arg Glu Ala Ser

Thr Gly Asp Leu Gly Pro Thr Asp Ile Gln Lys Lys Lys Leu Val Asp

Ala Ile Ile Ser Gly Asp Thr Ser Arg Leu Met Lys Ile Leu Gln Pro

Gln Asp Val Asp Leu Val Leu Asp Ser

FIG. 36A
SEQ ID NO: 30

Ser Ala Ser Leu Leu His Leu Ala Val

Glu Ala Gly Gln Glu Glu Cys Val Lys Trp Leu Leu Leu Asn Asn Ala

Asn Pro Asn Leu Thr Asn Arg Lys Gly Ser Thr Pro Leu His Met Ala

Val Glu Arg Lys Gly Arg Gly Ile Val Glu Leu Leu Leu Ala Arg Lys

Thr Ser Val Asn Ala Lys Asp Glu Asp Gln Trp Thr Ala Leu His Phe

Ala Ala Gln Asn Gly Asp Glu Ala Ser Thr Arg Leu Leu Leu Glu Lys

Asn Ala Ser Val Asn Glu Val Asp Phe Glu Gly Arg Thr Pro Met His

Val Ala Cys Gln His Gly Gln Glu Asn Ile Val Arg Thr Leu Leu Arg

Arg Gly Val Asp Val Gly Leu Gln Gly Lys Asp Ala Trp Leu Pro Leu

His Tyr Ala Ala Trp Gln Gly His Leu Pro Ile Val Lys Leu Leu Ala

Lys Gln Pro Gly Val Ser Val Asn Ala Gln Thr Leu Asp Gly Arg Thr

Pro Leu His Leu Ala Ala Gln Arg Gly His Tyr Arg Val Ala Arg Ile

Leu Ile Asp Leu Cys Ser Asp Val Asn Ile Cys Ser Leu Gln Ala Gln

Thr Pro Leu His Val Ala Ala Glu Thr Gly His Thr Ser Thr Ala Arg

Leu Leu Leu His Arg Gly Ala Gly Lys Glu Ala Leu Thr Ser Glu Gly

Tyr Thr Ala Leu His Leu Ala Ala Gln Asn Gly His Leu Ala Thr Val

Lys Leu Leu Ile Glu Glu Lys Ala Asp Val Met Ala Arg Gly Pro Leu

FIG. 36B

Asn Gln Thr Ala Leu His Leu Ala Ala Ala Arg Gly His Ser Glu Val

Val Glu Glu Leu Val Ser Ala Asp Leu Ile Asp Leu Ser Asp Glu Gln

Gly Leu Ser Ala Leu His Leu Ala Ala Gln Gly Arg His Ser Gln Thr

Val Glu Thr Leu Leu Lys His Gly Ala His Ile Asn Leu Gln Ser Leu

Lys Phe Gln Gly Gly Gln Ser Ser Ala Ala Thr Leu Leu Arg Arg Ser

Lys Thr

FIG. 37A
SEQ ID NO: 31

Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
            20                  25                  30

Phe Gly Gln Val Tyr Lys Val Arg His Val His Trp Lys Thr Trp Leu
        35                  40                  45

Ala Ile Lys Cys Ser Pro Ser Leu His Val Asp Asp Arg Glu Arg Met
        50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
        115                 120                 125

Met Asn Phe Leu His Cys Met Ser Pro Pro Leu Leu His Leu Ala Leu
        130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
            165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

FIG. 37B

Phe Ala Ile Val Ile Trp Gly Val Leu Thr Gln Lys Lys Pro Phe Ala
210              215              220

Asp Glu Lys Asn Ile Leu His Ile Met Met Lys Val Val Lys Gly His
225              230              235              240

Arg Pro Glu Leu Pro Pro Ile Cys Arg Pro Arg Pro Arg Ala Cys Ala
                 245              250              255

Ser Leu Ile Gly Leu Met Gln Arg Cys Trp His Ala Asp Pro Gln Val
             260              265              270

Arg Pro Thr Phe Gln Glu Ile Thr Ser Glu Thr Glu Asp Leu Cys Glu
        275              280              285

Lys Pro Asp Glu Glu Val Lys Asp Leu Ala His Glu Pro Gly Glu Lys
        290              295              300

Ser Ser Leu Glu Ser Lys Ser Glu Ala Arg Pro Glu Ser Ser Arg Leu
305              310              315              320

Lys Arg Ala Ser Ala Pro Pro Phe Asp Asn Asp Cys Ser Leu Ser Glu
                 325              330              335

Leu Leu Ser Gln Leu Asp Ser Gly Ile Ser Gln Thr Leu Glu Gly Pro
             340              345              350

Glu Glu Leu Ser Arg Ser Ser Ser Glu Cys Lys Leu Pro Ser Ser Ser
         355              360              365

Ser Gly Lys Arg Leu Ser Gly Val Ser Ser Val Asp Ser Ala Phe Ser
370              375              380

Ser Arg Gly Ser Leu Ser Leu Ser Phe Glu Arg Glu Ala Ser Thr Gly
385              390              395              400

Asp Leu Gly Pro Thr Asp Ile Gln Lys Lys Lys Leu Val Asp Ala Ile
             405              410              415

Ile Ser Gly Asp Thr Ser Arg Leu Met Lys Ile Leu Gln Pro Gln Asp
             420              425              430

FIG. 37C

Val Asp Leu Val Leu Asp Ser Ser Ala Ser Leu Leu His Leu Ala Val
    435             440             445

Glu Ala Gly Gln Glu Cys Val Lys Trp Leu Leu Leu Asn Asn Ala
    450             455             460

Asn Pro Asn Leu Thr Asn Arg Lys Gly Ser Thr Pro Leu His Met Ala
465             470             475                 480

Val Glu Arg Lys Gly Arg Gly Ile Val Glu Leu Leu Leu Ala Arg Lys
                485             490             495

Thr Ser Val Asn Ala Lys Asp Glu Asp Gln Trp Thr Ala Leu His Phe
            500             505             510

Ala Ala Gln Asn Gly Asp Glu Ala Ser Thr Arg Leu Leu Leu Glu Lys
        515             520             525

Asn Ala Ser Val Asn Glu Val Asp Phe Glu Gly Arg Thr Pro Met His
    530             535             540

Val Ala Cys Gln His Gly Gln Glu Asn Ile Val Arg Thr Leu Leu Arg
545             550             555             560

Arg Gly Val Asp Val Gly Leu Gln Gly Lys Asp Ala Trp Leu Pro Leu
            565             570             575

His Tyr Ala Ala Trp Gln Gly His Leu Pro Ile Val Lys Leu Leu Ala
            580             585             590

Lys Gln Pro Gly Val Ser Val Asn Ala Gln Thr Leu Asp Gly Arg Thr
        595             600             605

Pro Leu His Leu Ala Ala Gln Arg Gly His Tyr Arg Val Ala Arg Ile
    610             615             620

Leu Ile Asp Leu Cys Ser Asp Val Asn Ile Cys Ser Leu Gln Ala Gln
625             630             635             640

Thr Pro Leu His Val Ala Ala Glu Thr Gly His Thr Ser Thr Ala Arg
            645             650             655

Leu Leu Leu His Arg Gly Ala Gly Lys Glu Ala Leu Thr Ser Glu Gly

FIG. 37D

```
          660                    665                      670
Tyr Thr Ala Leu His Leu Ala Ala Gln Asn Gly His Leu Ala Thr Val
        675                 680                685

Lys Leu Leu Ile Glu Glu Lys Ala Asp Val Met Ala Arg Gly Pro Leu
    690                 695                700                --

Asn Gln Thr Ala Leu His Leu Ala Ala Ala Arg Gly His Ser Glu Val
705                 710                715                720

Val Glu Glu Leu Val Ser Ala Asp Leu Ile Asp Leu Ser Asp Glu Gln
                725                 730                735

Gly Leu Ser Ala Leu His Leu Ala Ala Gln Gly Arg His Ser Gln Thr
            740                 745                750

Val Glu Thr Leu Leu Lys His Gly Ala His Ile Asn Leu Gln Ser Leu
        755                 760                765

Lys Phe Gln Gly Gly Gln Ser Ser Ala Ala Thr Leu Leu Arg Arg Ser
    770                 775                780

Lys Thr
785
```

FIG. 38A
SEQ ID NO: 32

Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
            20                  25                  30

Phe Gly Gln Val Tyr Lys Val Arg His Val His Trp Lys Thr Trp Leu
            35                  40                  45

Ala Ile Lys Cys Ser Pro Ser Leu His Val Asp Asp Arg Glu Arg Met
50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
                100                 105                 110

Leu Pro Trp Asp Leu Arg Phe Arg Ile Val His Glu Thr Ala Val Gly
            115                 120                 125

Met Asn Phe Leu His Cys Met Ser Pro Pro Leu Leu His Leu Asp Leu
            130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ala His Ala His Asp Leu
                165                 170                 175

Ala Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
            195                 200                 205

FIG. 38B

Phe Ala Ile Val Ile Trp Gly Val Leu Thr Gln Lys Lys Pro Phe Ala
210                215                220

Asp Glu Lys Asn Ile Leu His Ile Met Met Lys Val Val Lys Gly His
225                230                235                240

Arg Pro Glu Leu Pro Pro Ile Cys Arg Pro Arg Pro Arg Ala Cys Ala
                245                250                255

Ser Leu Ile Gly Leu Met Gln Arg Cys Trp His Ala Asp Pro Gln Val
                260                265                270

Arg Pro Thr Phe Gln Glu Ile Thr Ser Glu Thr Glu Asp Leu Cys Glu
                275                280                285

Lys Pro Asp Glu Glu Val Lys Asp Leu Ala His Glu Pro Gly Glu Lys
                290                295                300

Ser Ser Leu Glu Ser Lys Ser Glu Ala Arg Pro Glu Ser Ser Arg Leu
305                310                315                320

Lys Arg Ala Ser Ala Pro Pro Phe Asp Asn Asp Cys Ser Leu Ser Glu
                325                330                335

Leu Leu Ser Gln Leu Asp Ser Gly Ile Ser Gln Thr Leu Glu Gly Pro
                340                345                350

Glu Glu Leu Ser Arg Ser Ser Ser Glu Cys Lys Leu Pro Ser Ser Ser
                355                360                365

Ser Gly Lys Arg Leu Ser Gly Val Ser Ser Val Asp Ser Ala Phe Ser
                370                375                380

Ser Arg Gly Ser Leu Ser Leu Ser Phe Glu Arg Glu Ala Ser Thr Gly
385                390                395                400

Asp Leu Gly Pro Thr Asp Ile Gln Lys Lys Lys Leu Val Asp Ala Ile
                405                410                415

Ile Ser Gly Asp Thr Ser Arg Leu Met Lys Ile Leu Gln Pro Gln Asp
                420                425                430

FIG. 38C

```
Val Asp Leu Val Leu Asp Ser Ser Ala Ser Leu Leu His Leu Ala Val
    435             440             445
Glu Ala Gly Gln Glu Glu Cys Val Lys Trp Leu Leu Leu Asn Asn Ala
    450             455             460
Asn Pro Asn Leu Thr Asn Arg Lys Gly Ser Thr Pro Leu His Met Ala
465             470             475             480
Val Glu Arg Lys Gly Arg Gly Ile Val Glu Leu Leu Leu Ala Arg Lys
            485             490             495
Thr Ser Val Asn Ala Lys Asp Glu Asp Gln Trp Thr Ala Leu His Phe
            500             505             510
Ala Ala Gln Asn Gly Asp Glu Ala Ser Thr Arg Leu Leu Leu Glu Lys
            515             520             525
Asn Ala Ser Val Asn Glu Val Asp Phe Glu Gly Arg Thr Pro Met His
    530             535             540
Val Ala Cys Gln His Gly Gln Glu Asn Ile Val Arg Thr Leu Leu Arg
545             550             555             560
Arg Gly Val Asp Val Gly Leu Gln Gly Lys Asp Ala Trp Leu Pro Leu
            565             570             575
His Tyr Ala Ala Trp Gln Gly His Leu Pro Ile Val Lys Leu Leu Ala
            580             585             590
Lys Gln Pro Gly Val Ser Val Asn Ala Gln Thr Leu Asp Gly Arg Thr
    595             600             605
Pro Leu His Leu Ala Ala Gln Arg Gly His Tyr Arg Val Ala Arg Ile
    610             615             620
Leu Ile Asp Leu Cys Ser Asp Val Asn Ile Cys Ser Leu Gln Ala Gln
625             630             635             640
Thr Pro Leu His Val Ala Ala Glu Thr Gly His Thr Ser Thr Ala Arg
            645             650             655
Leu Leu Leu His Arg Gly Ala Gly Lys Glu Ala Leu Thr Ser Glu Gly
```

Tyr Thr Ala Leu His Leu Ala Ala Gln Asn Gly His Leu Ala Thr Val
            675                 680                 685

Lys Leu Leu Ile Glu Glu Lys Ala Asp Val Met Ala Arg Gly Pro Leu
            690                 695             700                 —

Asn Gln Thr Ala Leu His Leu Ala Ala Ala Arg Gly His Ser Glu Val
    705                 710                 715                 720

Val Glu Glu Leu Val Ser Ala Asp Leu Ile Asp Leu Ser Asp Glu Gln
                    725                 730                 735

Gly Leu Ser Ala Leu His Leu Ala Ala Gln Gly Arg His Ser Gln Thr
                    740                 745             750

Val Glu Thr Leu Leu Lys His Gly Ala His Ile Asn Leu Gln Ser Leu
            755                 760                 765

Lys Phe Gln Gly Gly Gln Ser Ser Ala Ala Thr Leu Leu Arg Arg Ser
            770                 775             780

Lys Thr
    785
```

FIG. 39A
SEQ ID NO: 33

Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
            20                  25                  30

Phe Gly Gln Val Tyr Lys Val Arg His Val His Trp Lys Thr Trp Leu
            35                  40                  45

Ala Ile Lys Cys Ser Pro Ser Leu His Val Asp Asp Arg Glu Arg Met
        50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
        115                 120                 125

Met Asn Phe Leu His Cys Met Ser Pro Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Glu His Glu His Asp Leu
                165                 170                 175

Glu Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

FIG. 39B

| | | | | | | | | | | | | | |
|---|---|---|---|---|---|---|---|---|---|---|---|---|---|
|Phe|Ala|Ile|Val|Ile|Trp|Gly|Val|Leu|Thr|Gln|Lys|Lys|Pro|Phe|Ala|
|210| | | | |215| | | |220| | | | |

```
Phe Ala Ile Val Ile Trp Gly Val Leu Thr Gln Lys Lys Pro Phe Ala
210                 215                 220

Asp Glu Lys Asn Ile Leu His Ile Met Met Lys Val Val Lys Gly His
225                 230                 235                 240

Arg Pro Glu Leu Pro Pro Ile Cys Arg Pro Arg Pro Arg Ala Cys Ala
                245                 250                 255

Ser Leu Ile Gly Leu Met Gln Arg Cys Trp His Ala Asp Pro Gln Val
                260                 265                 270

Arg Pro Thr Phe Gln Glu Ile Thr Ser Glu Thr Glu Asp Leu Cys Glu
        275                 280                 285

Lys Pro Asp Glu Glu Val Lys Asp Leu Ala His Glu Pro Gly Glu Lys
290                 295                 300

Ser Ser Leu Glu Ser Lys Ser Glu Ala Arg Pro Glu Ser Ser Arg Leu
305                 310                 315                 320

Lys Arg Ala Ser Ala Pro Pro Phe Asp Asn Asp Cys Ser Leu Ser Glu
                325                 330                 335

Leu Leu Ser Gln Leu Asp Ser Gly Ile Ser Gln Thr Leu Glu Gly Pro
                340                 345                 350

Glu Glu Leu Ser Arg Ser Ser Ser Glu Cys Lys Leu Pro Ser Ser Ser
        355                 360                 365

Ser Gly Lys Arg Leu Ser Gly Val Ser Ser Val Asp Ser Ala Phe Ser
370                 375                 380

Ser Arg Gly Ser Leu Ser Leu Ser Phe Glu Arg Glu Ala Ser Thr Gly
385                 390                 395                 400

Asp Leu Gly Pro Thr Asp Ile Gln Lys Lys Lys Leu Val Asp Ala Ile
                405                 410                 415

Ile Ser Gly Asp Thr Ser Arg Leu Met Lys Ile Leu Gln Pro Gln Asp
                420                 425                 430
```

FIG. 39C

```
Val Asp Leu Val Leu Asp Ser Ser Ala Ser Leu Leu His Leu Ala Val
    435             440                 445
Glu Ala Gly Gln Glu Glu Cys Val Lys Trp Leu Leu Leu Asn Asn Ala
    450                 455                 460
Asn Pro Asn Leu Thr Asn Arg Lys Gly Ser Thr Pro Leu His Met Ala
465             470                 475                 480
Val Glu Arg Lys Gly Arg Gly Ile Val Glu Leu Leu Leu Ala Arg Lys
                485                 490                 495
Thr Ser Val Asn Ala Lys Asp Glu Asp Gln Trp Thr Ala Leu His Phe
                500                 505                 510
Ala Ala Gln Asn Gly Asp Glu Ala Ser Thr Arg Leu Leu Leu Glu Lys
        515                 520                 525
Asn Ala Ser Val Asn Glu Val Asp Phe Glu Gly Arg Thr Pro Met His
    530                 535                 540
Val Ala Cys Gln His Gly Gln Glu Asn Ile Val Arg Thr Leu Leu Arg
545                 550                 555                 560
Arg Gly Val Asp Val Gly Leu Gln Gly Lys Asp Ala Trp Leu Pro Leu
                565                 570                 575
His Tyr Ala Ala Trp Gln Gly His Leu Pro Ile Val Lys Leu Leu Ala
            580                 585                 590
Lys Gln Pro Gly Val Ser Val Asn Ala Gln Thr Leu Asp Gly Arg Thr
            595                 600                 605
Pro Leu His Leu Ala Ala Gln Arg Gly His Tyr Arg Val Ala Arg Ile
    610                 615                 620
Leu Ile Asp Leu Cys Ser Asp Val Asn Ile Cys Ser Leu Gln Ala Gln
625                 630                 635                 640
Thr Pro Leu His Val Ala Ala Glu Thr Gly His Thr Ser Thr Ala Arg
            645                 650                 655
Leu Leu Leu His Arg Gly Ala Gly Lys Glu Ala Leu Thr Ser Glu Gly
```

Tyr Thr Ala Leu His Leu Ala Ala Gln Asn Gly His Leu Ala Thr Val
        675                 680                 685

Lys Leu Leu Ile Glu Glu Lys Ala Asp Val Met Ala Arg Gly Pro Leu
        690                 695                 700

Asn Gln Thr Ala Leu His Leu Ala Ala Ala Arg Gly His Ser Glu Val
705                 710                 715                     720

Val Glu Glu Leu Val Ser Ala Asp Leu Ile Asp Leu Ser Asp Glu Gln
                725                 730                 735

Gly Leu Ser Ala Leu His Leu Ala Ala Gln Gly Arg His Ser Gln Thr
            740                 745                 750

Val Glu Thr Leu Leu Lys His Gly Ala His Ile Asn Leu Gln Ser Leu
        755                 760                 765

Lys Phe Gln Gly Gly Gln Ser Ser Ala Ala Thr Leu Leu Arg Arg Ser
        770                 775                 780

Lys Thr
785
```

RICK3 NUCLEIC ACIDS AND PROTEINS

This application is a divisional of application Ser. No. 10/128,174, filed Apr. 23, 2002 now abandoned, which is herein incorporated by reference in its entirety.

This patent application was supported in part by grants CA-84064 and GM60421 from the National Institutes of Health. The government has certain rights in the invention.

FIELD OF THE INVENTION

The present invention related to methods and compositions for modulating cellular signaling. In particular, the present invention relates to PKK and RICK3 proteins. The present invention further relates to the use of PKK and RICK3 proteins in modulating NF-κB signaling.

BACKGROUND OF THE INVENTION

All forms of diabetes are characterized by chronic hyperglycemia and the development of diabetes-specific microvascular pathology in the retina, renal glomerulus and peripheral nerve. As a consequence of its microvascular pathology, diabetes is a leading cause of blindness, end-stage renal disease and a variety of debilitating neuropathies. Diabetes is also associated with accelerated atherosclerotic macrovascular disease affecting arteries that supply the heart, brain and lower extremities. As a result, patients with diabetes have a much higher risk of myocardial infarction, stroke and limb amputation. Large prospective clinical studies show a strong relationship between glycaemia and diabetic microvascular complications in both type 1 and type 2 diabetes (The Diabetes Control and Complications Trial Research Group. *N. Engl. J. Med.* 329, 977–986 (1993); UK Prospective Diabetes Study (UKPDS) Group Lancet 352: 837–853 [1998]).

Hyperglycaemia and insulin resistance both seem to have important roles in the pathogenesis of macrovascular complications (UK Prospective Diabetes Study (UKPDS) Group Lancet 352:837–853 [1998]). Diabetes-specific microvascular disease in the retina, glomerulus and vasa nervorum has similar pathophysiological features. Early in the course of diabetes, intracellular hyperglycaemia causes abnormalities in blood flow and increased vascular permeability. This reflects decreased activity of vasodilators such as nitric oxide, increased activity of vasoconstrictors such as angiotensin II and endothelin-1, and elaboration of permeability factors such as vascular endothelial growth factor (VEGF). Quantitative and qualitative abnormalities of extracellular matrix contribute to an irreversible increase in vascular permeability.

With time, microvascular cell loss occurs, in part as a result of programmed cell death. This results in progressive capillary occlusion due both to extracellular matrix overproduction induced by growth factors such as transforming growth factor-β (TGF-β), and to deposition of extravasated periodic acid Schiff-positive plasma proteins. Hyperglycaemia may- also decrease production of trophic factors for endothelial and neuronal cells. Together, these changes lead to oedema, ischaemia and hypoxia-induced neovascularization in the retina, proteinuria, mesangial matrix expansion and glomerulosclerosis in the kidney, and multifocal axonal degeneration in peripheral nerves.

The pathogenesis of arteriosclerosis in non-diabetics has been extensively described in recent reviews, and begins with endothelial dysfunction (Lusis, Nature 407:233–241 [2000]). In diabetic arteries, endothelial dysfunction seems to involve both insulin resistance specific to the phosphatidylinositol-3-OH kinase pathway and hyperglycaemia. Pathway-selective insulin resistance results in decreased endothelial production of the anti-atherogenic molecule nitric oxide, and increased potentiation of proliferation of vascular smooth muscle cells and production of plasminogen activator inhibitor-1 (PAI-1) via the Ras-Raf-MEK kinase mitogen-activated protein (MAP) kinase pathway (Hsueh and Law, Am. J. Med. 105:4S–14S [1998]). Hyperglycaemia itself also inhibits production of nitric oxide in arterial endothelial cells stimulates production of PAI-1 (Williams et al., Circulation 97:1695–1701 [1998]; Du et al., Proc. Natl Acad. Sci. USA 97:12222–12226 [2000]).

Both insulin resistance and hyperglycaemia have also been implicated in the pathogenesis of diabetic dyslipidaemia. The role of insulin resistance has been reviewed recently (Ginsberg, J. Clin. Invest 106: 453–458 [2000]). Hyperglycaemia seems to cause raised levels of atherogenic cholesterol-enriched apolipoprotein B-containing remnant particles by reducing expression of the heparan sulphate proteoglycan perlecan on hepatocytes. Associations of arteriosclerosis and arteriosclerosis risk factors with glycemia have been shown over a broad range of glucose tolerance, from normal to diabetic. Postprandial hyperglycemia may be more predictive of atherosclerosis than is fasting plasma glucose level or haemoglobin A1c (Temelkova-Kurktschiev et al., Diabetes Care 12:1830–1834 [2000]).

Thus, the art is in need of therapies that specifically target the underlying biochemical causes of diabetes complications.

SUMMARY OF THE INVENTION

The present invention related to methods and compositions for modulating cellular signaling. In particular, the present invention relates to PKK and RICK3 proteins. The present invention further relates the to use of PKK and RICK3 proteins in modulating NF-κB signaling.

For example, in some embodiments, the present invention provides an isolated and purified nucleic acid comprising a sequence encoding a protein selected from the group consisting of SEQ ID NOs: 3 and sequences that are at least 90% identical to SEQ ID NO:3. In certain embodiments, the sequence is operably linked to a heterologous promoter. In some embodiments, the sequence is contained within a vector. In further embodiments, the vector is within a host cell.

The present invention also provides an isolated and purified nucleic acid sequence that hybridizes under conditions of low stringency to a nucleic acid selected from the group including, but not limited to, SEQ ID NOs: 2, 4, 5, 6, 7, 8, 9, and 10. The present invention additionally provides an isolated and purified nucleic acid sequence that is at least 90%, and preferably at least 95% identical to a nucleic acid sequence selected from the group consisting of SEQ ID NOs: 2 4, 5, 6, 7, 8, 9, and 10. In some embodiments, the nucleic acid sequence is selected from the group including, but not limited to, SEQ ID NOs: 2 4, 5, 6, 7, 8, 9, and 10. In some embodiments, the nucleic acid is SEQ ID NO:2. In certain embodiments, the sequence encodes a protein that binds to PKK. In some embodiments, the present invention provides a vector comprising the nucleic acid sequence of claim 5. In some embodiments, the vector is in a host cell. In some embodiments, the host cell is located in an organism selected from the group consisting of a plant and an animal.

The present invention further provides a protein encoded by a nucleic acid selected from the group including, but not limited to, SEQ ID NOs: 2 4, 5, 6, 7, 8, 9, and 10 and variants thereof that are at least 80% identical to SEQ ID NOs: 2 4, 5, 6, 7, 8, 9, and 10, wherein the protein has at least one activity of RICK3. In some embodiments, the activity is binding to PKK. In other embodiments, the activity is inhibition of PKK induced NF-κB activation. In some embodiments, the protein is at least 90%, and preferably, at least 95% identical to SEQ ID NO: 3. In some embodiments, the protein is SEQ ID NO:3.

In still further embodiments, the present invention provides a nucleic acid encoding RICK3, wherein the RICK3 competes for binding to PKK with a protein encoded by a nucleic acid sequence selected from the group including, but not limited to, SEQ ID NOs: 2, 4, 5, 6, 7, 8, 9, and 10.

In yet other embodiments, the present invention provides a method for producing variants of RICK3 comprising providing a nucleic acid sequence selected from the group including, but not limited to, SEQ ID NOs: 2 4, 5, 6, 7, 8, 9, and 10; mutating the nucleic acid sequence to generate a variant of RICK3; and screening the variant for RICK3 activity.

In still additional embodiments, the present invention provides a composition comprising a nucleic acid that inhibits the binding of at least a portion of a nucleic acid selected from the group including, but not limited to, SEQ ID NOs: 2 4, 5, 6, 7, 8, 9, and 10 to their complementary sequences.

The present invention further provides a method for screening compounds, comprising providing a first polypeptide sequence comprising at least a portion of PKK; a second polypeptide sequence comprising at least a portion of a protein known to interact with PKK; and one or more test compounds; combining in any order, the first polypeptide sequence comprising at least a portion of PKK, the second polypeptide sequence comprising at least a portion of a protein known to interact with PKK, and the one or more test compounds under conditions such that the first polypeptide sequence, the second polypeptide sequence, and the test compound interact; and detecting the presence or absence of an interaction between the polypeptide sequence comprising at least a portion of PKK and the polypeptide sequence comprising at least a portion of a protein known to interact with PKK. In some embodiments, the first polypeptide comprises SEQ ID NO: 12. In other embodiments, the first polypeptide comprises a fragment of SEQ ID NO: 12. In still further embodiments, the first polypeptide comprises SEQ ID NO: 13 or a fragment thereof. In yet other embodiments, the second polypeptide comprises PKC. In still further embodiments, the second polypeptide comprises RICK3. In some embodiments, the test compound is a drug. In some embodiments, the present invention provides a drug identified by the method.

The present invention also provides a compound capable of inhibiting the binding of a RICK3 to a PKK polypeptide.

The present invention additionally provides a method for screening compounds, comprising providing a polypeptide sequence comprising at least a portion of a polypeptide selected from the group consisting of PKK and RICK3, wherein the polypeptide comprises protein kinase activity; and one or more test compounds; and contacting the test compound and the polypeptide; and detecting the level of kinase activity. In some embodiments, the level of kinase activity is altered (e.g., increased or decreased) relative to the level of kinase activity in the absence of the test compound. In some embodiments, the polypeptide comprises SEQ ID NO: 12. In other embodiments, the polypeptide comprises a fragment of SEQ ID NO: 12. In still further embodiments, the polypeptide comprises SEQ ID NO: 3. In yet other embodiments, the polypeptide comprises a fragment of SEQ ID NO: 3. In still other embodiments, the polypetide comprises SEQ ID NO: 13 or a fragment therof. In some embodiments, the test compound is a drug. In some embodiments, the method further comprises the step of providing a kinase substrate.

DESCRIPTION OF THE FIGURES

FIG. 1 shows homology between PKK and RICK-related Proteins. FIG. 1(A) shows a schematic representation of PKK and related kinases. Kinase domain, KD; intermediate region, IM; ankyrin repeats-containing domain, ARD; caspase-recruitment domain, CARD; death domain, DD. FIG. 1(B) shows homology among PKK and related kinases. The homology between PKK (GenBank accession numbers human, AJ278016; mouse, AF302127; zebrafish, AF487541), RICK (human, AC004003; mouse, AF487539; zebrafish, AF487540), RIP (human, NM003804; mouse, NM009068) and RIP3 (human, AF156884; mouse, AF178953) was calculated by BLASTP and is given as an E value.

FIG. 2(A) shows that PKK activates NF-κB in a dose-dependent manner. HEK293T cells were transfected with control plasmid (−) or indicated amount of pcDNA3-Myc-PKK. Induction of NF-κB activation was determined from triplicate culture of HEK293T cells co-transfected with the indicated amount of wt or mutant PKK expression plasmids in the presence of pBVIx-Luc and pEF-BOS-β-gal. Values represent mean of normalized values ±SD of triplicate cultures. Expression of Myc-tagged PKK protein was determined in cell extracts by immunoblotting (inset). Arrowhead indicates PKK protein. FIG. 2(B) shows the specific activation of NF-κB and AP-1 by PKK. HEK293T cells were co-transfected with control plasmid (−), 3.3 ng of pcDNA3-Myc-PKK, 33 ng of pcDNA3-p53, 0.33 ng of pcDNA3-Flag-DC-CIITA, 17 ng of pCEP4-HA-rMEKK1 and 17 ng of pcDNA3-Flag-IRF-1 plasmid DNA. Specific transactivation by NF-κB, AP-1, NF-AT, NF-IL6, p53, CIITA, and IRF-1 activation was determined using 3.3 ng of the corresponding luciferase reporter constructs and pEF-BOS-β-gal as described. Values represent mean of normalized values ±SD of triplicate cultures.

FIG. 3(A) shows wild type (WT) and mutant PKK proteins. KD, IM and ARD are indicated by black, open, and hatched boxes, respectively. Numbers represent the position of amino acid residues in PKK protein. FIG. 3(B) shows an amino acid alignment of the putative loop region of PKKs. Amino acid sequences (163 to 183) from human (Hs), mouse (Ms) and zebrafish (Dr) PKK proteins are shown. Serine residues in the putative activation loop region are indicated by asterisks. FIG. 3(C) shows functional and expression analysis of wt and mutant PKK proteins. HEK293T cells were transfected with control plasmid (−) or indicated amount of Myc-tagged PKK plasmid DNA. Induction of NF-κB activation was determined from triplicate culture of HEK293T cells co-transfected with the indicated amount of wt or mutant PKK expression plasmids in the presence of pBVIx-Luc and pEF-BOS-β-gal as described. Values represent mean of normalized values ±SD of triplicate cultures. Immunoblotting analysis of the expressed Myc-tagged PKK proteins is shown on top panel. Molecular weight markers are indicated on the left.

FIG. 4(A) shows inhibition of PMA/Ca$^{2+}$-ionophore-induced NF-κB activation by dominant negative PKK. Induction of NF-κB activation was determined in triplicate cultures of HEK293T cells cotransfected with 3 ng of pcDNA3-Bimp1-Flag, 30 ng of pcDNA3-Bcl10-Flag, 67 ng of pcDNA3-MALT1(324-813)-Fpk3-Myc, or stimulated with 50 ng/ml PMA and 0.7 µg/ml Ca$^{2+}$-ionophore A23187 for 6 hr or 10 ng/ml TNFα for 2 hrs in the presence of 167 ng of pcDNA3-HA-PKK D143A, pRK7-Flag-IKKβ-K44A or control plasmid in the presence of pBVIx-Luc and pEF-BOS-β-gal. Results are presented as a percent of values obtained with Bimp1 and control plasmid. MALT1(324-813)-Fpk3 was oligomerized by incubation with 100 nM AP1510 for 6 hrs. In the experiment shown, Bimp1, Bcl10, oligomerized MALT1, PMA and Ca$^{2+}$ ionophore, and TNFα induced 141±12, 96±6, 13±1, 9±1 and 138±26 fold activation of NF-κB, respectively. Values represent mean of normalized values ±SD of triplicate cultures. FIG. 4(B) shows that inhibition of PMA/Ca$^{2+}$-ionophore-induced NF-κB activation is reverted by PKCβI but not PKCε. Induction of NF-κB activation was determined from triplicate culture of HEK293T cells co-transfected with 167 ng of pTB701-HA-PKCβI, pTB701-HA-PKCε, or control plasmid and 67 ng of pcDNA3-HA-PKK D143A in the presence of pBVIx-Luc and pEF-BOS-β-gal and stimulated with 50 ng/ml PMA and 0.7 µg/ml A23187 for 6 hrs. Results from cells transfected with PKCβI, PKCε, or control plasmid alone are shown on the left panel. FIG. 4(C) shows inhibition of PMA/ionophore-mediated AP-1 activation by dominant negative PKK. Induction of NF-κB activation was determined in triplicate cultures of HEK293T cells transfected with 167 ng of pcDNA3-HA-PKK D143A and stimulated with 50 ng/ml PMA and 0.7 µg/ml of the dimerizer A23187 for 6 hrs or left alone in the presence of AP-1 luc and pEF-BOS-β-gal. Results are presented as a percent of values obtained with control plasmid.

FIG. 5(A) shows that PKK-induced NF-κB activation is inhibited by dominant negative forms of IKKα and IKKβ but not by those of IKKγ, Bimp1, nor MyD88. Induction of NF-κB activation was determined in triplicate cultures of HEK293T cells transfected with 1.6 ng of pcDNA3-Myc-PKK, or stimulated with 50 ng/ml PMA and 0.7 µg/ml of A23187, 10 ng/ml IL-1β or 10 ng/ml TNFα for 4 hrs in the presence of pBVIx-Luc and pEF-BOS-β-gal. Results are presented as a percent of values obtained with PKK and control plasmid. In the experiment shown, PKK, PMA/Ca$^{2+}$-ionophore, IL-1β and TNFα induced 55±3, 196±15, 423±22 and 183±55 fold activation of NF-κB, respectively. Values represent mean of normalized values ±SD of triplicate cultures. FIG. 5(B) shows that PKK-mediated NF-κB activation requires IKKα and IKKβ. Induction of NF-κB activation was determined in wt, IKKα$^{-/-}$, IKKβ$^{-/-}$ and IKKα$^{-/-}$/IKKβ$^{-/-}$ mouse embryonic fibroblasts transfected with 100 ng of pcDNA3-Flag-PKK, pcDNA3-Nod1-Flag and pcDNA-IKKβ-Myc in the presence of pBVIx-Luc and pEF-BOS-β-gal. FIG. 5(C) shows induction of NF-κB in parental Rat-1 and IKKγ-deficient 5R cells. Induction of NF-κB activation was determined in wt, IKKα$^{-/-}$, IKKβ$^{-/-}$ and IKKα$^{-/-}$/IKKβ$^{-/-}$ mouse embryonic fibroblasts transfected with 100 ng of pcDNA3-Flag-PKK, pcDNA3-Nod1-Flag and pcDNA-IKKβ-Myc in the presence of pBVIx-Luc and pEF-BOS-β-gal. FIG. 5(D) shows PKK-mediated activation of NF-κB in the absence of Bcl10. Bcl10$^{+/-}$ and Bcl10$^{-/-}$ mouse embryonic fibroblasts were transfected with 900 ng of the indicated expression plasmid: pcDNA3-Flag-PKK, pcDNA3-Nod1-HA or pcDNA3-Bimp1-Flag.

FIG. 6 shows the nucleic acid sequence of human PKK (SEQ ID NO: 1).

FIG. 7 shows the nucleic acid sequence of human RICK3 (SEQ ID NO: 2).

FIG. 8 shows the amino acid sequence of human RICK3 (SEQ ID NO: 3).

FIG. 9 shows the nucleic acid sequence of SEQ ID NO: 4.

FIG. 10 shows the nucleic acid sequence of SEQ ID NO: 5.

FIG. 11 shows the nucleic acid sequence of SEQ ID NO: 6.

FIG. 12 shows the nucleic acid sequence of SEQ ID NO: 7.

FIG. 13 shows the nucleic acid sequence of SEQ ID NO: 8.

FIG. 14 shows the nucleic acid sequence of SEQ ID NO: 9.

FIG. 15 shows the nucleic acid sequence of SEQ ID NO: 10.

FIG. 16 shows the nucleic acid sequence of mouse PKK (SEQ ID NO: 11).

FIG. 17 shows the amino acid sequence of human PKK (SEQ ID NO: 12).

FIG. 18 shows the amino acid sequence of mouse PKK (SEQ ID NO: 13).

FIG. 23 shows the nucleic acid sequence of SEQ ID NO: 14.

FIG. 24 shows the nucleic acid sequence of SEQ ID NO: 15.

FIG. 25 shows the nucleic acid sequence of SEQ ID NO: 16.

FIG. 26 shows the nucleic acid sequence of SEQ ID NO: 17.

FIG. 27 shows the nucleic acid sequence of SEQ ID NO: 18.

FIG. 28 shows the nucleic acid sequence of SEQ ID NO: 19.

FIG. 29 shows the nucleic acid sequence of SEQ ID NO: 20.

FIG. 30 shows the nucleic acid sequence of SEQ ID NO: 21.

FIG. 31 shows the nucleic acid sequence of SEQ ID NO: 22.

FIG. 32 shows the nucleic acid sequence of SEQ ID NO: 23.

FIG. 33 shows the amino acid sequence of SEQ ID NO: 27.

Figure 34C:
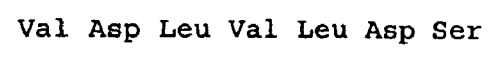

FIG. 34 shows the amino acid sequence of SEQ ID NO: 28.

FIG. 35 shows the amino acid sequence of SEQ ID NO: 29.

FIG. 36 shows the amino acid sequence of SEQ ID NO: 30.

FIG. 37 shows the amino acid sequence of SEQ ID NO: 31.

FIG. 38 shows the amino acid sequence of SEQ ID NO: 32.

FIG. 39 shows the amino acid sequence of SEQ ID NO: 33.

GENERAL DESCRIPTION OF THE INVENTION

Figure 2:
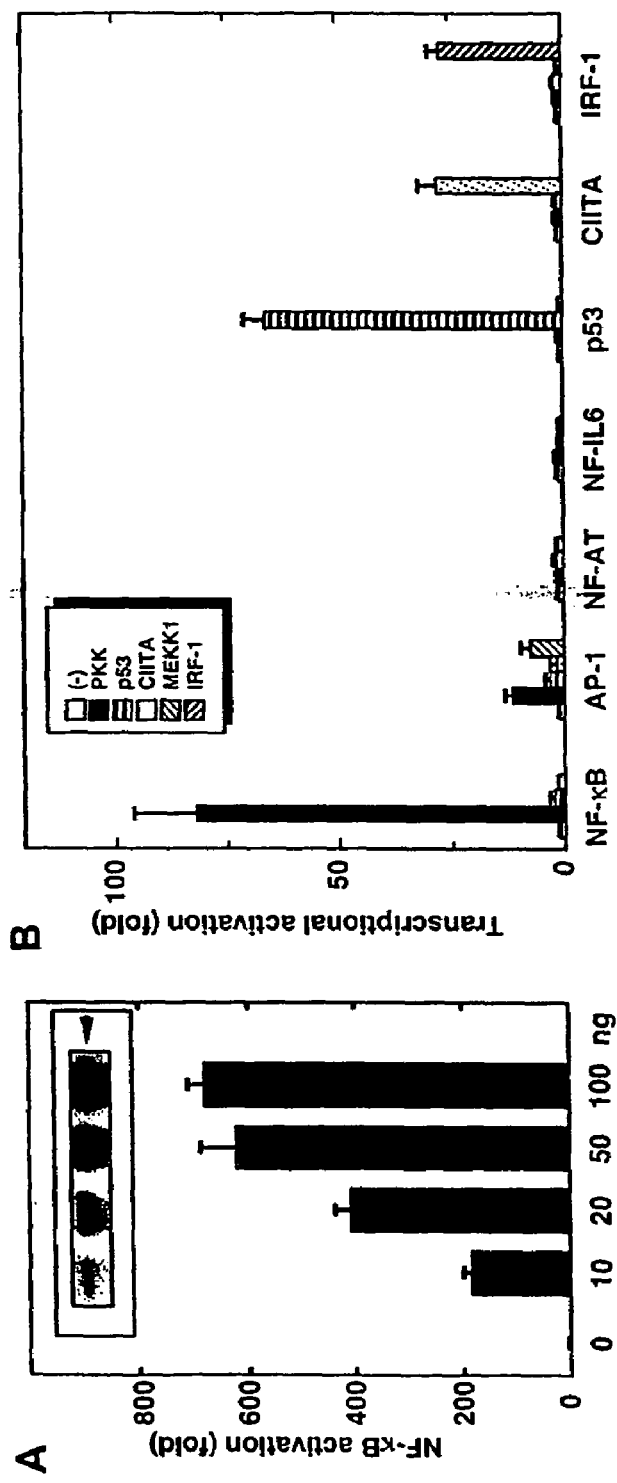
FIG. 2 shows that expression of PKK activates NF-κB and AP-1.

NF-κB is a transcription factor that mediates the activation of a large array of target genes that are involved in the regulation of diverse functions including inflammation, cell proliferation and survival (Ghosh et al., Ann. Rev. Immunol., 16:225 [1998]). During inflammatory responses, NF-κB is activated in response to multiple stimuli including tumor necrosis factor (TNF), lipopolysaccharides (LPS) and interleukin-1 (IL-1) (Ghosh et al., supra). These trigger molecules interact with surface receptors or specific intracellular sensors which lead to the activation of NF-κB through signal-specific mediators and common downstream effectors such as IκBα and IκB kinase (IKK) (Ghosh et al., Annu. Rev. Immunol. 16:225 [1998]; Karin and Ben-Neriah Annu. Rev. Immunol. 18:621 [2000]). RICK and RIP are highly related kinases which mediate NF-κB activation in the Nod1 (or Nod2) and TNFR1 (or TRAIL) receptor signaling pathways, respectively (Inohara et al., J. Biol. Chem. 274, 14560–14568 [1999]; Ogura et al., J. Biol. Chem. 276:4812–4818 [2001]; Kelliher et al., Immunity 8:297–303 [1998]; Lin et al., Mol. Cell. Biol: 20:6638–6645 [2000]; Bertin et al., J. Biol. Chem:.274: 12955–12958 [1999]; Inohara et al., J. Biol. Chem. 275:27823–27831 [2000]). RICK and RIP each contain an N-terminal kinase domain linked to intermediate (IM) regions but different C-terminal domains: a caspase-recruitment domain (CARD) and a death domain (DD), respectively (Inohara et al., J. Biol. Chem. 273:12296–12300 [1998]; McCarthy et al., J. Biol. Chem. 273:16968–16975 [1998]; Thome et al., Curr. Biol. 8:885–888 [1998]; Stanger et al., Cell 81:513–523 [1995]; Hsu et al., Immunity 4:387–396 [1996]). These C-terminal domains mediate the recruitment of RIP and RICK to upstream signaling components, whereas the IM regions link these kinases to the common regulator IKK. The IM region of both RIP and RICK is essential for NF-κB activation (Inohara et al., J. Biol. Chem. 273:12296 [1998], Hsu et al., [1996] supra). Thus, RICK and RIP serve as bridging molecules connecting signal-specific components to common mediators of NF-κB activation. These observations suggest that proteins carrying kinase domains homologous to those of RIP and RICK but different C-terminal domains might be involved in the activation of novel NF-κB signaling pathways.

The activation of protein kinase C (PKC) isoforms has been shown to be involved in the development of diabetes-related complications. The PKC family comprises at least eleven isoforms, nine of which are activated by the lipid second messenger DAG. Intracellular hyperglycemia increases the amount of DAG in cultured microvascular cells and in the retina and renal glomeruli of diabetic animals (Brownlee, Nature 414:813 [2001]). In addition, disruption of IKKβ signaling via salicylates has been shown to reduce hyperglycemia and insulin resistance in rodents (Yuan et al., Science, 293:1673 [2001]).

PKK, a mouse kinase composed of an N-terminal kinase domain, an IM region, and C-terminal domain containing 11 ankyrin repeats was recently identified for its ability to interact with protein kinase C (PKC) isoform PKCβI while its human counterpart, named DIK, was shown to associate with PKCδ (Chen et al., J Biol Chem. 276:21737 [2001]; Bähr et al., J. Biol. Chem. 275:36350 [2000]). It has been hypothesized that PKK and its human orthologue are involved in a PKC-associated signaling pathway (Chen et al., [2001], supra; Bähr et al., supra). PKCs mediate intracellular signals triggered by stimulation of a variety of extracellular ligands including those associated with G-coupled and antigen receptors (Krappmann et al., Mol. Cell. Biol. 21, 6640 [2001]). Classical and novel PKCs are known to be activated by phorbol ester and intracellular $Ca^{2+}$ and by phorbol ester only, respectively, and to induce the activation of multiple transcription factors' such as NF-κB and AP-1 (Krappmann et al, [2001], supra). However, the particular signaling pathway in which PKK functions has not been previously addressed.

Experiments conducted during the development of the present invention revealed that PKK is highly homologous to RIP and RICK. Expression of PKK induces the activation of NF-κB, and this activity involves a kinase domain. PKK was also shown to mediate the NF-κB activation induced by phorbol ester and $Ca^{2+}$-ionophore and specifically by PKCβI. The present invention is not limited to a particular mechanism. Indeed, an understanding of the mechanism is not necessary to practice the present invention. Nonetheless, it is contemplated that these studies indicate that PKK is a RICK/RIP-like molecule that is involved in a NF-κB signaling pathway mediated by particular PKC isoforms.

The activity of PKK is consistent with its homology to RICK and RIP, two serine-threonine kinases that activate NF-κB. Another member of the family, RIP3 has been shown to activate or inhibit NF-κB activation, probably depending on the cellular context (Yu et al., Curr. Biol. 9:539–542 [1999]; Sun et al., J. Biol. Chem. 274:16871–16875 [1999]; Pazdernik et al., Mol. Cell. Biol. 19:6500–6508 [1999]). The present invention is not limited to a particular mechanism. Indeed, an understanding of the mechanism is not necessary to practice the present invention. Nonetheless, it is contemplated that PKK represents the fourth member of the RIP/RICK family of NF-κB activating kinases. Unlike RIP and RICK (Inohara et al., [2000], supra), the catalytic activity of PKK was required for NF-κB activation. These results indicate that PKK is unique among the RICK-related kinases and suggest that at least a part of the mechanism by which PKK activates NF-κB is distinct from that utilized by RIP and RICK. The present invention is not limited to a particular mechanism. Indeed, an understanding of the mechanism is not necessary to practice the present invention. Nonetheless, it is contemplated that PKK activates NF-κB through the phosphorylation of protein target(s).

PKK was originally identified for its interaction with PKCβI and suggested to function in a PKC signaling pathway (Chen et al., J. Biol. Chem., 276:21737 [2001]). Experiments conducted during the course of development of the present invention demonstrated that a dominant negative mutant of PKK inhibits PMA/ionophore-mediated NF-κB activation, an effect that was reverted by expression of PKCβI. Several studies have implicated PKCβI in the activation of NF-κB in cells derived from several tissues including the heart and kidney (Ishii et al., Science 272:728 [1996]; Kumar et al., Am. J. Physiol. Renal. Physiol. 281: F613–619 [2001]; Malhotra et al., Diabetes 50:1918–1926 [2001]) which have been reported to exhibit high expression of PKK (Chen et al., supra, Bahr et al., supra). The present invention is not limited to a particular mechanism. Indeed, an understanding of the mechanism is not necessary to practice the present invention. Nonetheless, it is contemplated that PKK functions in these tissues to regulate a PKCβI-dependent signaling pathway of NF-κB activation.

The present invention further provides the nucleic acid and amino acid sequence of a novel RICK protein, RICK3. Experiments conducted during the course of development of the present invention indicated that RICK3 inhibits NF-κB activation of PKK and that PKK and RICK3 physically interact. The present invention thus provides novel drug targets for drug screening and the identification of therapeutics for conditions involving abnormal NF-κB signaling.

DEFINITIONS

To facilitate understanding of the invention, a number of terms are defined below.

As used herein, the term PKK/DIK refers to either the mouse or human PKK protein or the human homologue, DIK, or variants thereof Human PKK and DIK refer to the same gene.

As used herein, the term "activates NF-κB," when used in reference to any molecule that activates NF-κB, refers to a molecule (e.g., a protein) that induces the activity of the NF-κB transcription factor through a cell signaling pathway. Assays for determining if a molecule activates NF-κB utilize, for example, NF-κB responsive reporter gene constructs. Suitable assays include, but are not limited to, those described in Examples 1 and 3.

As used herein, the term "activity of PKK" refers to any activity of wild type RICK3. The term is intended to encompass all activities of (e.g., including, but not limited to, binding to PKK/DIK and inhibiting NF-κB and AP-1 activation by PKK/DIK).

As used herein, the term "known to interact" as in "known to interact with PKK" refers to a polypeptide that has a demonstrated physical (e.g., binding) association with PKK.

As used herein, the term "wherein said polypeptide comprises kinase activity" refers to a polypeptide with protein kinase activity. The kinase activity may be active on any protein substrate, including the polypeptide itself.

As used herein, the term "detecting the level of kinase activity of said polypeptide" refers to a qualitative or quantitative measure of the kinase activity of a polypeptide. Kinase activity may be detected using any suitable assay, including, but not limited to, those described in Bahr et al., (J. Biol. Chem. 275:36350 [2000] and Chen et al., J. Biol. Chem., 276:21737 [2001]). As used herein, the term "Wherein said kinase activity is increased relative to the kinase activity in the absence of the test compound" refers to an increase in protein kinase activity of a polypeptide in the presence of a test compound. The increase may be detected qualitatively or quantitatively. As used herein, the term "Wherein said kinase activity is decreased relative to the kinase activity in the absence of the test compound" refers to an decrease in protein kinase activity of a polypeptide in the presence of a test compound. The decrease may be detected qualitatively or quantitatively.

As used herein, the term "apoptosis" refers to non-necrotic cell death that takes place in metazoan animal cells following activation of an intrinsic cell suicide program. Apoptosis is a normal process in the development and homeostasis of metazoan animals. Apoptosis involves characteristic morphological and biochemical changes, including cell shrinkage, zeiosis, or blebbing, of the plasma membrane, and nuclear collapse and fragmentation of the nuclear chromatin, at intranucleosomal sites, due to activation of an endogenous nuclease.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., precursors of PKK/DIK or RICK3). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "gene" refers to the full-length nucleotide sequence. However, it is also intended that the term encompass fragments of the sequence, as well as other domains within the full-length nucleotide sequence. Furthermore, the terms "nucleotide sequence" or "polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic-acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less. "High stringency conditions" when used in reference to nucleic acid hybridization comprise conditions equivalent to binding or hybridization at 42° C. in a solution consisting of 5× SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisions between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci. (U.S.A.)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., PKK/DIK or RICK3).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

As used herein, the term "detection assay" refers to an assay for detecting the presence of absence of variant nucleic acid sequences (e.g., polymorphism or mutations) in a given allele of a particular gene (e.g., the PKK/DIK or RICK3 genes). Examples of suitable detection assays include, but are not limited to, those described below in Section I.D.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of a nucleic acid of interest. In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding PKK/DIK or RICK3 includes, by way of example, such nucleic acid in cells ordinarily expressing PKK/DIK or RICK3 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and antisense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.). For example, "at least a portion of RICK3" or "at least a portion of PKK/DIK" refer to fragments of the RICK3 or "PKK/DIK" nucleic acid sequence (e.g., SEQ ID NO:2). In some embodiments, the fragments of encode polypeptides having at least one activity of RICK3 or PKK/DIK.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, antibodies are purified by removal of contaminating non-immunoglobulin proteins; they are also purified by the removal of immunoglobulin that does not bind to the protein of interest (e.g., PKK/DIK or RICK3). The removal of non-immunoglobulin proteins and/or the removal of immunoglobulins that do not bind to PKK/DIK or RICK3 results in an increase in the percent of PKK/DIK or RICK3-reactive immunoglobulins in the sample. In another example, recombinant PKK/DIK or RICK3 polypeptides are expressed in bacterial host cells and the polypeptides are purified by the removal of host cell proteins; the percent of recombinant PKK/DIK or RICK3 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid. For example, "at least a portion of RICK3" refers to fragments of RICK3. In some embodiments, fragments of RICK3 have at least one activity of RICK3.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual,* Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced sequence of interest (e.g., PKK/DIK or RICK3) transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding (e.g., SEQ ID NOs: 1 and 2) or fragments thereof may be employed as hybridization probes. In this case, the polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "membrane receptor protein" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases is the tyrosine kinases (TKs), which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity. Tyrosine kinases can also be cytoplasmic, non-receptor-type enzymes and act as a downstream component of a signal transduction pathway.

As used herein, the term "signal transduction protein" refers to proteins that are activated or otherwise affected by ligand binding to a membrane or cytostolic receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249–257 [1995]). Typically, GPCRs contain seven transmembrane domains. Putative GPCRs can be identified on the basis of sequence homology to known GPCRs.

GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an $\alpha$ subunit, which binds and hydrolyses GTP, and a dimeric $\beta\gamma$ subunit. In the basal, inactive state, the G-protein exists as a heterotrimer of the $\alpha$ and $\beta\gamma$ subunits. When the G-protein is inactive, guanosine diphosphate (GDP) is associated with the a subunit of the G-protein. When a GPCR is bound and activated by a ligand, the GPCR binds to the G-protein heterotrimer and decreases the affinity of the G$\alpha$ subunit for GDP. In its active state, the G subunit exchanges GDP for guanine triphosphate (GTP) and active G$\alpha$ subunit disassociates from both the receptor and the dimeric $\beta\gamma$ subunit. The disassociated, active G$\alpha$ subunit transduces signals to effectors that are "downstream" in the G-protein signaling pathway within the cell. Eventually, the G-protein's endogenous GTPase activity returns active G subunit to its inactive state, in which it is associated with GDP and the dimeric $\beta\gamma$ subunit.

Numerous members of the heterotrimeric G-protein family have been cloned, including more than 20 genes encoding various G$\alpha$ subunits. The various G subunits have been categorized into four families, on the basis of amino acid sequences and functional homology. These four families are termed G$\alpha_s$, G$\alpha_i$, G$\alpha_q$, and G$\alpha_{12}$. Functionally, these four families differ with respect to the intracellular signaling pathways that they activate and the GPCR to which they couple.

For example, certain GPCRs normally couple with G$\alpha_s$ and, through G$\alpha_s$, these GPCRs stimulate adenylyl cyclase activity. Other GPCRs normally couple with GG$\alpha_q$, and through GG$\alpha_q$, these GPCRs can activate phospholipase C (PLC), such as the $\beta$ isoform of phospholipase C (i.e., PLC$\beta$, Stermweis and Smrcka, Trends in Biochem. Sci. 17:502–506 [1992]).

As used herein, the term "nucleic acid binding protein" refers to proteins that bind to nucleic acid, and in particular to proteins that cause increased (i.e., activators or transcription factors) or decreased (i.e., inhibitors) transcription from a gene.

As used herein, the term "ion channel protein" refers to proteins that control the ingress or egress of ions across cell membranes. Examples of ion channel proteins include, but are not limited to, the Na$^+$-K$^+$ ATPase pump, the Ca$^{2+}$ pump, and the K$^+$ leak channel.

As used herein, the term "protein kinase" refers to proteins that catalyze the addition of a phosphate group from a nucleoside triphosphate to an amino acid side chain in a protein. Kinases comprise the largest known enzyme superfamily and vary widely in their target proteins. Kinases may be categorized as protein tyrosine kinases (PTKs), which phosphorylate tyrosine residues, and protein serine/threonine kinases (STKs), which phosphorylate serine and/or threonine residues. Some kinases have dual specificity for both serine/threonine and tyrosine residues. Almost all kinases contain a conserved 250–300 amino acid catalytic domain. This domain can be further divided into 11 subdomains. N-terminal subdomains I–IV fold into a two-lobed structure that binds and orients the ATP donor molecule, and subdomain V spans the two lobes. C-terminal subdomains VI–XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. STKs and PTKs also contain distinct sequence motifs in subdomains VI and VIII, which may confer hydroxyamino acid specificity. Some STKs and PTKs possess structural characteristics of both families. In addition, kinases may also be classified by additional amino acid sequences, generally between 5 and 100 residues, which either flank or occur within the kinase domain.

Non-transmembrane PTKs form signaling complexes with the cytosolic domains of plasma membrane receptors. Receptors that signal through non-transmembrane PTKs include cytokine, hormone, and antigen-specific lymphocytic receptors. Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (See, e.g., Carbonneau, H. and Tonks, Annu. Rev. Cell Biol. 8:463–93 [1992]). Regulation of PTK activity may therefore be an important strategy in controlling some types of cancer.

As used herein, the term "protein phosphatase" refers to proteins that remove a phosphate group from a protein. Protein phosphatases are generally divided into two groups, receptor and non-receptor type proteins. Most receptor-type protein tyrosine phosphatases contain two conserved catalytic domains, each of which encompasses a segment of 240 amino acid residues. (See, e.g., Saito et al., Cell Growth and Diff. 2:59–65 [1991]). Receptor protein tyrosine phosphatases can be subclassified further based upon the amino acid sequence diversity of their extracellular domains (See, e.g., Krueger et al., Proc. Natl. Acad. Sci. USA 89:7417–7421 [1992]).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

The present invention provides PKK/DIK and RICK3 nucleic acids and polypeptides. The present invention further provides methods of using PKK/DIK and RICK3 to screen for compounds that modulate NF-κB signaling. In further embodiments, the present invention provides methods of screening for compounds that alter PKC activation and modulate its signaling activity.

I. PKK/DIK and RICK3 Polynucleotides

In some embodiments, the present invention provides PKK/DIK and RICK3 polynucleotides and variants thereof. The present invention further provides methods of generating, expressing and detecting wildtype and variant PKK/DIK and RICK3 polynucleotides.

A. PKK/DIK

Protein kinase C-associated kinase (PKK/DIK) is a recently described kinase of unknown function that was identified on the basis of its specific interaction with PKCβ. PKK/DIK contains N-terminal kinase and C-terminal ankyrin repeats domains linked to an intermediate region. Experiments conducted during the course of development of the present invention revealed that the kinase domain of PKK/DIK is highly homologous to that of two mediators of nuclear factor-κB (NF-κB) activation, RICK and RIP, but these related kinases have different C-terminal domains for binding to upstream factors. Expression of PKK, like RICK and RIP, was found to induce NF-κB activation. Mutational analysis revealed that the kinase domain of PKK is essential for NF-κB activation whereas replacement of serine residues in the putative activation loop did not affect the ability of PKK to activate NF-κB. A catalytic inactive PKK mutant inhibited NF-κB activation induced by phorphol ester and $Ca^{2+}$-ionophore but it did not block that mediated by tumor necrosis factor α, interleukin-1β or Nod1. Inhibition of NF-κB activation by dominant negative PKK was reverted by co-expression of PKCβI, suggesting a functional association between PKK and PKCβI. PKK-mediated NF-κB activation required IKKα and IKKβ but not IKKγ, the regulatory subunit of the IKK complex. Moreover, NF-κB activation induced by PKK was not inhibited by dominant negative Bimp1 and proceeded in the absence of Bcl10, two components of a recently described PKC signaling pathway. The present invention is not limited to a particular mechanism. Indeed, an understanding of the mechanism is not necessary to practice the present invention. Nonetheless, it is contemplated that these results suggest that PKK is a member of the RICK/RIP family of kinases which is involved in a PKC-activated NF-κB signaling pathway that is independent of Bcl10 and IKKγ.

B. RICK3

The present invention also provides RICK3 nucleic acids and polypeptides (e.g., SEQ ID NOs: 2, 3, 4, 5, 6, 7, 8). RICK3 contains a kinase domain and an ankyrin repeat containing domain. Experiments conducted during the course of development of the present invention demonstrated that RICK3 inhibits the NF-κB and AP-1 activation activity of PKK.

C. Variants of PKK/DIK and RICK3

Accordingly, the present invention provides nucleic acids encoding PKK/DIK and RICK3 genes, homologs, variants (e.g., polymorphisms and mutants), including but not limited to, those described in SEQ ID NOs: 4–10 and 14–23). In some embodiments, the present invention provide polynucleotide sequences that are capable of hybridizing to SEQ ID NOs: b 1, 2, 4–10 and 14–23 under conditions of low to high stringency (e.g., polynucleotide sequences capable of hybridizing that encode a protein that retains a biological activity of the naturally occurring PKK/DIK or RICK3). In some embodiments, the protein that retains a biological activity of naturally occurring PKK/DIK or RICK3 is 70% homologous to wild-type PKK/DIK or RICK3, preferably 80% homologous to wild-type PKK/DIK or RICK3, more preferably 90% homologous to wild-type PKK/DIK or RICK3, and most preferably 95% homologous to wild-type PKK/DIK or RICK3. In preferred embodiments, hybridization conditions are based on the melting temperature ($T_m$) of the nucleic acid binding complex and confer a defined "stringency" as explained above (See e.g., Wahl, et al., Meth. Enzymol., 152:399–407 [1987], incorporated herein by reference).

In other embodiments of the present invention, additional alleles of PKK/DIK or RICK3 are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Examples of the alleles of the present invention include those encoded by SEQ ID NOs: 1 and 2 (wild type) and 4–10 and 14–23 (variant) alleles.

In yet other embodiments, one or more mutations are introduced to reduce or eliminate activity. Such molecules find use as negative control or for generating functional knockout cell lines or animals (e.g., through homologous recombination).

In still other embodiments of the present invention, the nucleotide sequences of the present invention may be engineered in order to alter a PKK/DIK or RICK3 coding sequence for a variety of reasons, including but not limited to, alterations that modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of PKK/DIK or RICK3 may be extended utilizing the nucleotide sequences (e.g., SEQ ID NOs: 1, 2, 4–10 and 14–23) in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318–22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055–60 [1991]). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed PKK or RICK3 sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., PKK/DIK or RICK3 function) for such purposes as altering (e.g., increasing or decreasing) the binding affinity of the PKK/DIK for RICK3 or another regulator or altering the effect of PKK/DIK or RICK3 on NF-κB or AP-1 signaling. Such modified peptides are considered functional equivalents of peptides having an activity of PKK/DIK or RICK3 as defined herein. A modified peptide can be produced in which the nucleotide sequence encoding the polypeptide has been altered, such as by substitution, deletion, or addition. In particularly preferred embodiments, these modifications do not significantly reduce the synthetic activity of the modified PKK/DIK or RICK3. In other words, construct "X" can be evaluated in order to determine whether it is a member of the genus of modified or variant PKK/DIK or RICK3's of the present invention as defined functionally, rather than structurally. In preferred embodiments, the activity of variant PKK/DIK or RICK3 polypeptides is evaluated by the methods described in Example 1. Accordingly, in some embodiments, the present invention provides nucleic acids encoding a PKK/DIK that activates NF-κB (e.g., activates an inflammatory response). In preferred embodiments, the activity of a PKK/DIK or RICK3 variant in enhancing or inhibiting NF-κB signaling is evaluated by transfecting HEK293T cells with and expression construct encoded the variant or mutant PKK/DIK or RICK3. In particularly preferred embodiments, the cells contain a reporter luciferase construct containing enhancer regions that are responsive to NF-κB. In other embodiments, the PKK/DIK or RICK3 variant may be capable of binding a protein (e.g., in the case of PKK/DIK, RICK3 or PKC, and in the case of RICK3, PKK/DIK) but not activating NF-κB. These variants can be screened for by the immunoprecipitation methods described in Example 10.

Moreover, as described above, variant forms of PKK/DIK or RICK3 are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of PKK/DIK or RICK3 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17–21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a PKK/DIK or RICK3 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference; etc.)

In some embodiments, the wild-type RICK3 sequence (SEQ ID NO:3) is altered at one or more positions to generate RICK3 variants. In some embodiments, the changes are conservative substitutions. In other embodiments, the changes are non-conservative (e.g., the replacement of aspartate 145 with alanine). This aspartate is equivalent to the conserved aspartate in the kinase catalytic site of PKK. For example, in some embodiments, the variants described in Table 1 are generated.

TABLE 1

| Variant | SEQ ID NO |
|---------|-----------|
| D145A   | 34        |
| E126D   | 35        |
| K168R   | 36        |
| A240G   | 37        |
| G186A   | 38        |
| A240V   | 39        |
| G186S   | 40        |
| G186I   | 41        |
| Y178W   | 42        |
| N66Q    | 43        |
| Q177N   | 44        |

D. Detection of PKK/DIK or RICK3 Alleles

Accordingly, the present invention provides methods for determining whether an individual has a variant PKK/DIK or RICK3 allele. In some preferred embodiments, the variation results in altered biological activity of the PKK/DIK or RICK3 (e.g., altered activation of NF-κB)

A number of methods are available for analysis of variant (e.g., mutant or polymorphic) nucleic acid sequences. Assays for detection variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of PKK/DIK or RICK3 (e.g., to the region of polymorphism or mutation). Both sets of primers are used to amplify a sample of DNA. If only the mutant primers result in a PCR product, then the patient has the mutant PKK/DIK or RICK3 allele. If only the wild-type primers result in a PCR product, then the patient has the wild type allele of PKK/DIK or RICK3.

3. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

4. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

5. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3–5 second including repetitive data collection. The SpectroTYPER software then calculates, records, compares and reports the genotypes at the rate of three seconds per sample.

II. PKK/DIK and RICK3 Polypeptides

In other embodiments, the present invention provides RICK3 and PKK/DIK polynucleotide sequences that encode RICK3 and PKK/DIK polypeptide sequences. PKK/DIK and RICK3 polypeptides (e.g., SEQ ID NOs: 3 and 12) are described in FIGS. 8 and 17. Other embodiments of the present invention provide fragments, fusion proteins or functional equivalents of these PKK/DIK and RICK3 proteins. In still other embodiment of the present invention, nucleic acid sequences corresponding to PKK/DIK and RICK3 variants, homologs, and mutants may be used to generate recombinant DNA molecules that direct the expression of the PKK/DIK and RICK3 variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO: 1 and 2 that encode substantially the same or a functionally equivalent amino acid sequence, may be used to clone and express PKK/DIK or RICK3. In general, such polynucleotide sequences hybridize to SEQ ID NO: 1 and 2 under conditions of high to medium stringency as described above. As will be understood by those of skill in the art, it may be advantageous to produce PKK/DIK or RICK3-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of PKK/DIK or RICK3 expression or to produce recombinant RNA transcripts having desirable properties, such as a longer half-life, than transcripts produced from naturally occurring sequence.

A. Vectors for Production of PKK/DIK and RICK3

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOS: 1,2,4–10, and 14–23). In some embodiments of the present invention, the constructs comprise a vector, such as a plasmid or viral vector, into which a sequence of the invention has been inserted, in a forward or reverse orientation. In still other embodiments, the heterologous structural sequences (e.g., SEQ ID NOs: 1 and 2) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of PKK/DIK and RICK3

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis,* and various species within the genera *Pseudomonas, Streptomyces,* and *Staphylococcus,* as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be empolyed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

C. Purification of PKK/DIK and RICK3

The present invention also provides methods for recovering and purifying PKK/DIK and RICK3 from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NOs: 1 and 2) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

D. Fusion Proteins Containing PKK/DIK and RICK3

The present invention also provides fusion proteins incorporating all or part of PKK/DIK or RICK3. Accordingly, in some embodiments of the present invention, the coding sequences for the polypeptides can be incorporated as a part of a fusion gene including a nucleotide sequence encoding a different polypeptide. It is contemplated that this type of expression system will find use under conditions where it is desirable to produce an immunogenic fragment of a PKK/DIK or RICK3 protein. In some embodiments of the present invention, the VP6 capsid protein of rotavirus is used as an immunologic carrier protein for portions of the PKK/DIK and RICK3 polypeptides, either in the monomeric form or in the form of a viral particle. In other embodiments of the present invention, the nucleic acid sequences corresponding to the portion of PKK/DIK and RICK3 against which antibodies are to be raised can be incorporated into a fusion gene construct which includes coding sequences for a late vaccinia virus structural protein to produce a set of recombinant viruses expressing fusion proteins comprising a portion of PKK/DIK and RICK3 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of PKK/DIK or RICK3 and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of PKK/DIK or RICK3 is obtained directly from organochemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the PKK/DIK or RICK3 proteins can also be expressed and presented by bacterial cells.

In addition to utilizing fusion proteins to enhance immunogenicity, it is widely appreciated that fusion proteins can also facilitate the expression of proteins, such as the PKK/DIK and RICK3 proteins of the present invention. Accordingly, in some embodiments of the present invention, fusion proteins can be generated as a glutathione-S-transferase (i.e., GST fusion protein). It is contemplated that such GST fusion proteins will enable easy purification of the proteins of the present invention, such as by the use of glutathione-derivatized matrices (See e.g, Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of PKK/DIK or RICK3, can allow purification of the expressed fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

E. Variants of PKK/DIK or RICK3

Still other embodiments of the present invention provide mutant or variant forms of PKK/DIK or RICK3. It is possible to modify the structure of a peptide having an activity of PKK/DIK or RICK3 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject proteins as defined herein. A modified peptide can be produced in which the amino acid sequence has been altered, such as by amino acid substitution, deletion, or addition.

Moreover, as described above, variant forms (e.g., mutants or polymorphic sequences) of the subject PKK/DIK and RICK3 proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present PKK/DIK and RICK3 proteins, as well as truncation mutants, and is especially useful for identifying potential variant sequences (i.e., mutants or polymorphic sequences) that are functional in binding to each other or other regulators in the NF-κB signaling pathway and signaling an inflammatory response. The purpose of screening such combinatorial libraries is to generate, for example, novel PKK/DIK or RICK3 variants that can act as either agonists or antagonists, or alternatively, possess novel activities all together.

Therefore, in some embodiments of the present invention, PKK/DIK or RICK3 variants are engineered by the present method to provide altered (e.g., increased or decreased) activation of NF-κB. In other embodiments of the present invention, combinatorially-derived variants are generated which have a selective potency relative to a naturally occurring PKK/DIK or RICK3. Such proteins, when expressed from recombinant DNA constructs, can be used in gene therapy protocols.

Still other embodiments of the present invention provide PKK/DIK and RICK3 variants that have intracellular half-lives dramatically different than the corresponding wild-type protein. For example, the altered protein can be rendered either more stable or less stable to proteolytic degradation or other cellular process that result in destruction of, or otherwise inactivate PKK/DIK and RICK3. Such variants, and the genes which encode them, can be utilized to alter the location of PKK/DIK and RICK3 expression by modulating the half-life of the protein. For instance, a short half-life can give rise to more transient PKK/DIK and RICK3 biological effects and, when part of an inducible expression system, can allow tighter control of PKK/DIK and RICK3 levels within the cell. As above, such proteins, and particularly their recombinant nucleic acid constructs, can be used in gene therapy protocols.

In still other embodiments of the present invention, PKK/DIK and RICK3 variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of PKK/DIK and RICK3 homologs, variants or other related proteins are aligned, preferably to promote the highest homology possible. Such a population of variants can include, for example, PKK/DIK and RICK3 homologs from one or more species, or PKK/DIK and RICK3 variants from the same species but which differ due to mutation or polymorphisms. Amino acids that appear at each position of the aligned sequences are selected to create a degenerate set of combinatorial sequences.

In a preferred embodiment of the present invention, the combinatorial PKK/DIK or RICK3 library is produced by way of a degenerate library of genes encoding a library of polypeptides which each include at least a portion of potential PKK/DIK or RICK3 protein sequences. For example, a mixture of synthetic oligonucleotides can be enzymatically ligated into gene sequences such that the degenerate set of potential PKK/DIK or RICK3 sequences are expressible as individual polypeptides, or alternatively, as a set of larger fusion proteins (e.g., for phage display) containing the set of PKK/DIK or RICK3 sequences therein.

There are many ways by which the library of potential PKK/DIK or RICK3 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential PKK/DIK or RICK3 sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules,* Elsevier, Amsterdam, pp 273–289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; as well as U.S. Pat. Nos. 5,223,409, 5,198,346, and 5,096,815; each of which is incorporated herein by reference).

It is contemplated that the PKK/DIK and/or RICK3 nucleic acids (e.g., SEQ ID NO:, and fragments and variants thereof) can be utilized as starting nucleic acids for directed evolution. These techniques can be utilized to develop PKK/DIK and/or RICK3 variants having desirable properties such as increased or decreased binding affinity for their respective binding partners (e.g., each other).

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17–24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for PKK/DIK and RICK3 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for PKK/DIK and/or RICK3 activity by the methods described in Examples 1–10 below.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of PKK/DIK and/or RICK3 homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

F. Chemical Synthesis of PKK/DIK and/or RICK3

In an alternate embodiment of the invention, the coding sequence of PKK/DIK and/or RICK3 is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire PKK/DIK and/or RICK3 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles,* W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example; using ABI 431A Peptide Synthesizer (Perkin Elmer) in accordance with the instructions provided by the manufacturer. Additionally, the amino acid sequence of PKK/DIK or RICK3, or any part thereof, may be altered during direct synthesis and/or combined using chemical methods with other sequences to produce a variant polypeptide.

III. Generation of PKK/DIK and/or RICK3 Antibodies

Antibodies can be generated to allow for the detection of PKK/DIK and/or RICK3 protein. The antibodies may be prepared using various immunogens. In one embodiment, the immunogen is a human or mouse PKK/DIK and/or RICK3 peptide to generate antibodies that recognize human or mouse PKK/DIK and/or RICK3. Such antibodies include, but are not limited to polyclonal, monoclonal, chimeric, single chain, Fab fragments, and Fab expression libraries.

Various procedures known in the art may be used for the production of polyclonal antibodies directed against PKK/DIK and/or RICK3. For the production of antibody, various host animals can be immunized by injection with the peptide corresponding to the PKK/DIK and/or RICK3 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g. aluminum hydroxide), surface active substances (e.g., lysolecithin, pluronic polyols, polyarions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward PKK/DIK and/or RICK3, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press,* Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy,* Alan R. Liss, Inc., pp. 77–96 [1985]).

In an additional embodiment of the invention, monoclonal antibodies are produced in germ-free animals utilizing technology such as that described in PCT/US90/02545. Furthermore, it is contemplated that human antibodies will be generated by human hybridomas (Cote et al., Proc. Natl. Acad. Sci. USA 80:2026–2030 [1983]) or by transforming human B cells with EBV virus in vitro (Cole et al., in *Monoclonal Antibodies and Cancer Therapy,* Alan R. Liss, pp. 77–96 [1985]).

In addition, it is contemplated that techniques described for the production of single chain antibodies (U.S. Pat. No. 4,946,778; herein incorporated by reference) will find use in producing PKK/DIK and/or RICK3 specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for PKK/DIK or RICK3.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of PKK/ DIK and/or RICK3 (e.g., for Western blotting), measuring levels thereof in appropriate biological samples, etc. The antibodies can be used to detect PKK/DIK and/or RICK3 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human PKK/DIK and/or RICK3 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of PKK/DIK and/or RICK3 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of PKK/DIK, RICK3 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of NF-κB. Such antibodies can also be used diagnostically to measure abnormal expression of PKK/DIK and/or RICK3, or the aberrant formation of protein complexes, which may be indicative of a disease state.

IV. Gene Therapy Using PKK/DIK and/or RICK3

The present invention also provides methods and compositions suitable for gene therapy to alter PKK/DIK or RICK3 expression, production, or function. As described above, the present invention provides human PKK/DIK or RICK3 genes and provides methods of obtaining PKK/DIK or RICK3 genes from other species. Thus, the methods described below are generally applicable across many species. In some embodiments, it is contemplated that the gene therapy is performed by providing a subject with a wild-type allele of PKK/DIK or RICK3 (i.e., nucleic acid change (e.g., polymorphisms or mutations). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980–990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320–330 [1991]), defective herpes virus vector lacking a glycoprotein L gene (See e.g., Patent Publication RD 371005 A), or other defective herpes virus vectors (See e.g., WO 94/21807, and WO 92/05263); an attenuated adenovirus vector, such as the vector discribed by Stratford-Perricaudet et al. (J. Clin. Invest., 90:626–630 [1992]; See also, La Salle et al., Science 259:988–990 [1993]); and a defective adeno-associated virus vector (Samulski et al., J. Virol., 61:3096–3101 [1987]; Samulski et al., J. Virol., 63:3822–3828 [1989]; and Lebkowski et al., Mol. Cell. Biol., 8:3988–3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mavl, Beard et al., Virol., 75–81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. Nos. 4,797,368; 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/

US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus") MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413–7417 [1987]; See also, Mackey, et al., Proc. Natl. Acad. Sci. USA 85:8027–8031 [1988]; Ulmer et al., Science 259:1745–1748 [1993]). The use of cationic lipids may promote encapsulation of negatively charged nucleic acids, and also promote fusion with negatively charged cell membranes (Felgner and Ringold, Science 337:387–388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/2193 1), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

V. Transgenic Animals Expressing Exogenous PKK/DIK and/or RICK3 Genes and Homologs, Mutants, and Variants Thereof The present invention contemplates the generation of transgenic animals comprising an exogenous PKK/DIK and/or RICK3 gene or homologs, mutants, or variants thereof. In preferred embodiments, the transgenic animal displays an altered phenotype as compared to wild-type animals. In some embodiments, the altered phenotype is the overexpression of mRNA for a PKK/DIK and/or RICK3 gene as compared to wild-type levels of PKK/DIK and/or RICK3 expression. In other embodiments, the altered phenotype is the decreased expression of mRNA for an endogenous PKK/DIK and/or RICK3 gene as compared to wild-type levels of endogenous PKK/DIK and/or RICK3 expression. Methods for analyzing the presence or absence of such phenotypes include Northern blotting, mRNA protection assays, and RT-PCR. In other embodiments, the transgenic mice have a knock out mutation of the PKK/DIK and/or RICK3 gene. In still further embodiments, expression of a PKK/DIK and/or RICK3 variant gene (e.g., single nucleotide substitution variants or mutants).

The transgenic animals of the present invention find use in dietary, drug and disease screens. In some embodiments, the transgenic animals (e.g., animals displaying a diabetes) are fed test or control diets and the response of the animals to the diets is evaluated. In other embodiments, test compounds (e.g., a drug that is suspected of being useful to treat diabetes complications) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo,* Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which PKK/DIK or RICK3 coding sequences are partially or completely deleted). Methods for homologous recombination are described in U.S. Pat. No. 5,614,396, incorporated herein by reference.

VI. Drug Screening Using PKK/DIK and/or RICK3

The present invention provides methods and compositions for using PKK/DIK and/or RICK3 as a target for screening drugs that can alter, for example, PKK/DIK or RICK3 signaling, and thus the physiological effects of NF-κB. For example, drugs that induce or inhibit NF-κB mediated inflammatory responses can be identified by screening for compounds that target PKK/DIK and/or RICK3 binding to other signaling molecules or that regulate PKK/DIK and/or RICK3 kinase activity. In particular, it is contemplated that such screens are capable of identifying compounds that are useful for inhibiting NF-κB activity and thus for treating diabetes complications.

In some preferred screening methods, assays are designed to screen for compounds that inhibit or enhance the kinase activity of PKK/DIK or RICK3. In such assays, PKK/DIK or RICK3 is incubated with a substrate protein (e.g., histone). In other embodiments, given the fact that PKK/DIK has autophosphorylation activity (See e.g., Bahr et al., supra), no additional substrate is included. Libraries of compounds are then screened for their ability to inhibit or enhance the kinase activity of PKK/DIK or RICK3.

In other embodiments, drug-screening assays utilize NF-κB activation assays to test the ability of compounds to inhibit or enhance PKK/DIK or RICK3 activity. For example, in some embodiments, libraries of small molecule compounds are screened for their ability to inhibit or enhance the ability of PKK/DIK or RICK3 to regulate NF-κB or AP-1 activation (e.g., using the activation assays described below or in animals (e.g., animal models of disease)). In other embodiments, libraries of compounds are screened for their ability to inhibit or enhance any other functional activity of PKK or RICK3.

In some embodiments, libraries of compounds are first screened for their ability to inhibit or enhance a biochemical activity of PKK or RICK3 (e.g., phosphorylation of a protein or peptide substrate). Positive molecules identified in such a screen are then screened in the functional assays described herein (e.g., NF-κB activation, AP-1 activation, or any other a functional activity of PKK or RICK3).

In still further embodiments, drug screening assays are used to screen for compounds that block PKK/DIK binding to PKC, RICK3, or other effectors. The binding need not employ full-length PKK/DIK, PKC or RICK3. Indeed, portions of PKC and PKK/DIK and/or RICK3 may be utilized in the binding assays.

In one screening method, the two-hybrid system is used to screen for compounds (e.g., drugs) capable of altering (e.g., inhibiting or enhancing) PKK/DIK or RICK3 function(s) (e.g., NF-κB-mediated signal transduction) in vitro or in vivo. In one embodiment, a GAL4 binding site, linked to a reporter gene such as lacZ, is contacted in the presence and absence of a candidate compound with a GAL4 binding domain linked to a PKC or PKK/DIK fragment and a GAL4 transactivation domain II linked to a NF-κB fragment. Expression of the reporter gene is monitored and a decrease in the expression is an indication that the candidate compound inhibits the interaction of PKK/DIK with NF-κB. Alternately, the effect of candidate compounds on the interaction of PKK/DIK or RICK3 with other proteins (e.g., proteins known to interact directly or indirectly with NF-κB) can be tested in a similar manner.

In another screening method, candidate compounds are evaluated for their ability to alter PKK/DIK or RICK3 signaling by contacting PKK/DIK, RICK3 or associated proteins, or fragments thereof, with the candidate compound and determining binding of the candidate compound to the peptide. The protein or protein fragments is/are immobilized using methods known in the art such as binding a GST-PKK/DIK or GST-RICK3 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., E. coli XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate PKK/DIK or RICK3 physiological effects (e.g., PKC signaling).

In another screening method, one of the components of the PKK/DIK/RICK3/NF-κB signaling system, such as PKK/DIK, RICK3 or a fragment thereof, is immobilized. Polypeptides can be immobilized using methods known in the art, such as adsorption onto a plastic microtiter plate or specific binding of a GST-fusion protein to a polymeric bead containing glutathione. For example, GST-peptide is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of PKK/DIK or RICK3 with the other peptide. A variation of this method allows for the screening of compounds that are capable of disrupting a previously-formed protein/protein complex. For example, in some embodiments a complex comprising PKK/DIK, RICK3, or a fragment thereof bound to another peptide is immobilized as described above and contacted with a candidate compound. The dissolution of the complex by the candidate compound correlates with the ability of the compound to disrupt or inhibit the interaction between PKK/DIK or RICK3 and the other peptide.

Another technique for drug screening provides high throughput screening for compounds having suitable binding affinity to PKK/DIK or RICK3 peptides and is described in detail in WO 84/03564, incorporated herein by reference. Briefly, large numbers of different small peptide test compounds are synthesized on a solid substrate, such as plastic pins or some other surface. The peptide test compounds are then reacted with PKK/DIK or RICK3 peptides and washed. Bound peptides are then detected by methods well known in the art.

Another technique uses PKK/DIK or RICK3 antibodies, generated as discussed above. Such antibodies capable of specifically binding to PKK/DIK or RICK3 peptides compete with a test compound for binding to PKK/DIK or RICK3. In this manner, the antibodies can be used to detect the presence of any peptide that shares one or more antigenic determinants of the PKK/DIK or RICK3 peptides.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with PKK/DIK, RICK3 and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding PKK/DIK, RICK3 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431–39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g. FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescence intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. As described above, it is contemplated that PKK/DIK binds to PKC, and this binding results in the activation on NF-κB. Therefore, in some embodiments, the reporter gene construct comprises the 5' regulatory region (e.g., promoters and/or enhancers) of a protein whose expression is controlled by NF-κB in operable association with a reporter gene (See Inohara et al., J. Biol. Chem. 275:27823 [2000] for a description of the luciferase reporter construct pBVIx-Luc). Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, calorimetric, or bioluminecent products of specific substrates (e.g., X-gal and luciferin). Comparisons between compounds of known and unknown activities may be conducted as described above.

VII. Pharmaceutical Compositions Containing PKK/DIK and/or RICK3 Nucleic Acid, Peptides, and Analogs The present invention further provides pharmaceutical compositions which may comprise all or portions of PKK/DIK or RICK3 polynucleotide sequences, polypeptides, inhibitors or antagonists of PKK/DIK or RICK3 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by PKC activation and/or other NF-κB mediated effects. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, PKK/DIK or RICK3 nucleotide and amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, PKK/DIK or RICK3 polynucleotide sequences or amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts PKK/DIK, RICK3, or modulators thereof levels.

A therapeutically effective dose refers to that amount of the pharmaceutical agent that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be-expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); U (units); mU (milliunits); min. (minutes); sec. (seconds); % (percent); kb (kilobase); bp (base pair); PCR (polymerase chain reaction); BSA (bovine serum albumin); Sigma (Sigma Chemical Co., St. Louis, Mo.); Collaborative Biomedical Products (Collaborative Biomedical Products, Bedford, Mass.); Stratagene (Stratagene Inc., La Jolla, Calif.); National Biosciences (National Biosciences Inc, Plymouth Minn.); CARD (caspase-recruitment domain); EST (expressed sequence tag), HA (hemagglutinin); IκB (inhibitor of NF-κB); IKK (IκB kinase); LRRs (leucine-rich repeats); NBD (nucleotide-binding domain); NF-κB (nuclear factor κB); TNFα (tumor necrosis factor α); wt (wild-type); Ab (antibody); IL-1 (interleukin 1); IL-1R (IL-1 receptor); LPS (lipopolysaccharide); LTA (lipoteichoic acid); PGN (peptidoglycan); SBLP (synthetic bacterial lipoprotein); and TLR (Toll-like receptor).

EXAMPLE 1

Methods

Cell Lines and Materials

Mouse embryonic fibroblasts lacking IKKα, IKKβ, both IKKα and IKKβ, Bcl10 and Rat-1 5R were described previously (Li et al., Genes Dev. 14:1729 [2000]; Ruland et al., Cell. 104:33 [2001]; Yamaoka et al., Cell 93, 1231 [1998]) and maintained in Dulbecco MEM containing 10% fetal calf serum and antibiotics. IL-1β and TNFα were purchased from Collaborative Biomedical Products. PMA, A23187 and other reagents were purchased from Sigma Chemicals. The partial nucleotide sequences of zebrafish cDNAs encoding peptides with homology to RICK3 were found in EST databases of GenBank using the TBLASTN program. The entire nucleotide sequence of EST clones GenBank BF158596 (zebrafish PKK) and BG737635 (zebrafish RICK) were determined by dideoxy sequencing.

Construction of Expression Plasmids

The open reading frame of mouse PKK was amplified by polymerase chain reaction (PCR) from random-primed mouse embryo E15 cDNA and cloned into pcDNA3-Flag, pcDNA3-Myc, and pcDNA3-HA (Inohara et al., EMBO J. 17:2526 [1998]). Deletion and site-directed mutants of PKK (residues 1–286 for KD, 1–439 for AARD, 440–786 for ARD, 287–439 for IM, D143A, S171A/S173A/S177A for SSSAAA and S171E/S173E/S177E for SSSEEE) were constructed by a PCR method and cloned into pcDNA3-Myc. The authenticity of all constructs was confirmed by sequencing. pcDNA3-Nod1-Flag, pcDNA3-Nod1-HA, pcDNA3-

Bimp1-Flag, pcDNA3-Bimp1 (117–1021)-Flag, pcDNA3-Bcl10(CIPER)-Flag, pcDNA3-MALT1-(324–813)-Fpk3-Myc, pcDNA3-IKKβ-Myc, pRK7-Flag-IKKα-K44A, RSVMad-3MSS(Iκ-Bα-S32A/S36A), pRK7-Flag-IKKβ-K44A, pcDNA3-HA-IKKγ(134–419), pcDNA3-MyD88 (1–109), pCEP4-HA-MEKK1, pcDNA3-Flag-IRF-1, pcDNA3-p53, pTB701-HA-PKCβI, pTB701-HA-PKCε, pcDNA3-Flag-DC-CIITA, pEF-BOS-β-gal, pBVIx-Luc, pGL3-AP-1-luc (Stratagene), pGL3-(NF-AT)6-luc, MHC-II (Eα)-luc, pGL3-mdm2-luc, have been described previously (Inohara et al., EMBO J. 17:2526 [1998]; Koseki et al., J. Biol. Chem. 274:9955 [1999]; McAllister-Lucas et al., J. Biol. Chem. 276:30589 [2001]; Lucas et al., J. Biol. Chem. 276:19012 [2001]; Nickerson et al., J. Biol. Chem. 276:19089 [2001]; Kuroda et al., J. Biol. Chem. 271:31029 [1996]; Xu et al., Proc. Natl. Acad. Sci. USA. 93:5291 [1996]; Liang et al., J. Biol. Chem. 273:19817 [1998]; Wu et al., Proc. Natl. Acad. Sci. USA. 91: 3602 [1994]; Liu et al., J. Biol. Chem. 272: 168 [1997]; Zheng et al., EMBO J. 13:1123 [1994]; Delhase et al., Science 284:309 [1999]; Wesche et al., Immunity 7:837 [1997]; Mercurio et al., Mol. Cell Biol. 19:1526 [1999]; Rothwarf et al., Nature 395:297 [1998]; Inohara et al., J. Biol. Chem. 275:27823 [2000]).

Immunodetection of Tagged Proteins

HEK293T cells were co-transfected with pcDNA3-Myc-PKK and various expression plasmids as described (Inohara et al., [2000], supra). Detection of expressed proteins was performed by immunoblotting as described (Inohara et al., [2000], supra).

NF-κB Activation Assay

NF-κB activation assay was performed as described (Inohara et al., [2000], supra). Briefly, Rat1 fibroblasts, its derivative 5R cell line, mouse embryonic fibroblasts as well as HEK293T cells were co-transfected with 33 ng of the reporter construct pBVIx-Luc, plus indicated amounts of each expression plasmid and 330 ng of pEF-BOS-β-gal in triplicate as described (Inohara et al., [2000], supra). The total amount of transfected plasmid DNA was adjusted with pcDNA3 vector such that it was constant within each individual experiment. 24 hr post-transfection, cell extracts were prepared and luciferase activity was measured as described (Inohara et al., [2000], supra). Results were normalized for transfection efficiency with values obtained with pEF-BOS-β-gal.

Example 2

PKK is Highly Related to RICK

Figure 1:
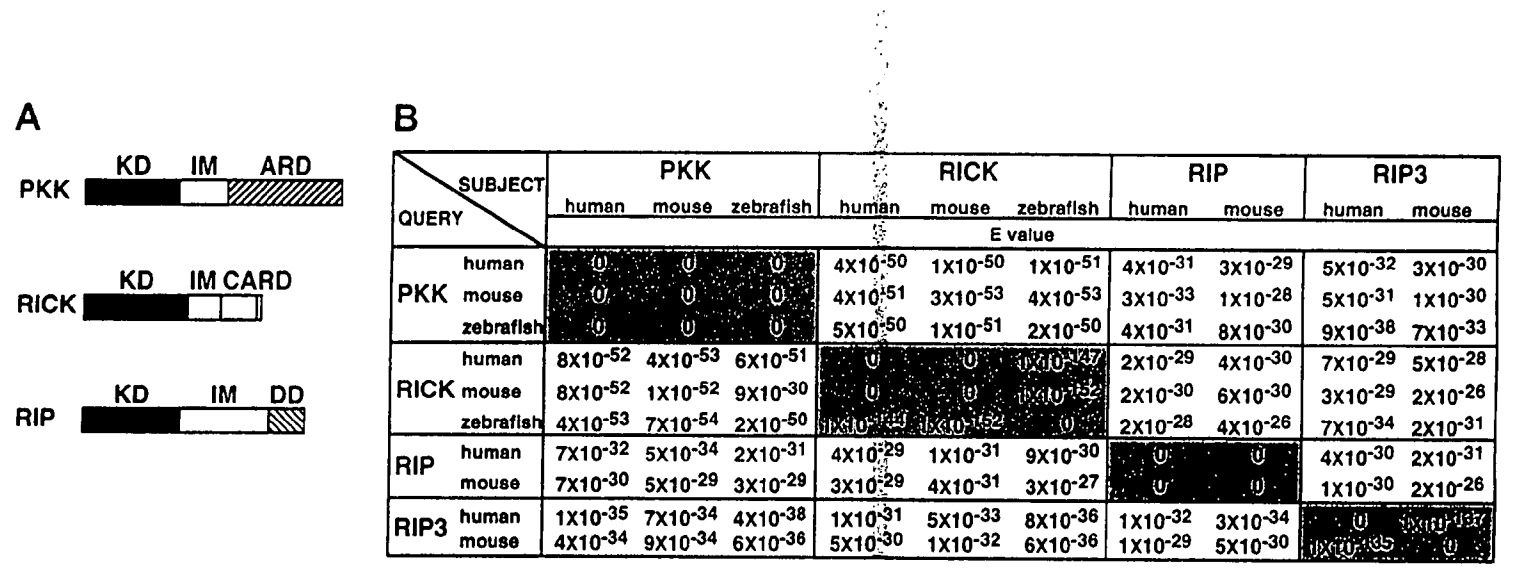

To identify novel RICK-like molecules, public protein and nucleotide databases were searched for homologous proteins using the entire RICK sequence (Inohara et al., J. Biol. Chem. 273:12296 [1998]). The search identified RIP (E values; $4 \times 10^{-29}$ and $3 \times 10^{-29}$ for human and mouse RIP, respectively) and its homologue RIP3 (E values; $1 \times 10^{-31}$ and $5 \times 10^{-30}$ for human and mouse RIP3, respectively) as molecules with significant homology to RICK (FIG. 1). In addition, the search identified PKK, a kinase of unknown function, as the most homologous protein to RICK in available databases (E=$4 \times 10^{-51}$ for mouse PKK and $4 \times 10^{-50}$ for human PKK). The search also identified zebrafish orthologues of PKK and RICK. The domain structure of the fish PKK and RICK was identical to that of their mammalian orthologues (FIG. 1A). Zebrafish PKK was more homologous to human RICK (E=$5 \times 10^{-50}$) than human RICK to human RIP or RIP3 (FIG. 1B). PKK also exhibited significant similarity to RIP (E=$4 \times 10^{-31}$) and RIP3 (E=$5 \times 10^{-32}$ and E=$3 \times 10^{-30}$ for human and mouse, respectively) (FIG. 1B). These results indicate that PKK is a novel member of the RICK/RIP family of kinases. Further analysis of protein sequences revealed that the homology between PKK and RICK-related kinases was restricted to their kinase domains in that no significant similarity was identified in the IM and C-terminal domains. Consistent with these findings, RICK and RIP have C-terminal CARD and DD, respectively, whereas PKK contains 11 ankyrin repeats in its C-terminus (FIG. 1A). The IM region of RICK and RIP is serine/threonine-rich and essential for the interaction with IKKγ and NF-κB inducing activity (Inohara et al., [2000], supra, Li et al., Proc. Natl. Acad. Sci. USA. 96:1042 [1999]). The IM region of PKK was also serine-theonine-rich, but it did not exhibit any significant amino acid homology to that of RICK and RIP.

Example 3

PKK Activates NF-κB and AP-1

This example describes that the expression of PKK activates NF-κB. Transfection of the wild-type PKK cDNA into HEK293T cells induced activation of NF-κB in a dose-dependent manner, as measured with a reporter luciferase construct (FIG. 2A). The induction of NF-κB by PKK was specific in that transfection of the PKK cDNA did not induce transactivation of NF-AT, NF-IL6, p53, IRF-1 and class II MHC-dependent promoters (FIG. 2B). In control experiments, the transcriptional activity of the reporter constructs was stimulated by expression of proteins known to induce their activation (FIG. 2B). Expression of PKK induced significant activation of AP-1 (FIG. 2B) as did expression of MEKK1, a known activator of AP-1 (Xu et al., Proc. Natl. Acad. Sci. USA. 93:5291 [1996]).

Example 4

The Kinase Domain of PKK is Essential for NF-κB Activation

To identify the domains of PKK that are required for NF-κB activation, a series of deletion mutants carrying each domain alone or in combination were constructed (FIG. 3A). Expression of PKK mutants containing the kinase domain alone (SEQ ID NO:27) or a combination with other domains such as the IM domain (SEQ ID NO:28) resulted in NF-κB activation, while mutants containing the IM region (SEQ ID NO:29) and/or ankyrin repeats-containing domain (ARD) alone (SEQ ID NO:30) were inactive (FIG. 3C). Immunoblotting analysis showed that the lack of activity of the mutants could not be explained by different expression levels of the mutant proteins (FIG. 3C, inset). Thus, the kinase domain of PKK is necessary and sufficient for NF-κB activation. The present invention is not limited to a particular mechanism. Indeed an understanding of the mechanism is not necessary to practice the present invention. Nonetheless, it is contemplated that this result suggests that the catalytic region acts as an effector domain in PKK signaling. Consistent with this hypothesis, replacement of the conserved aspartate residue (D143) in the catalytic site for alanine rendered PKK inactive (FIG. 3C; SEQ ID NO:31).

Human and mouse PKK contain a Ser-X-X-X-Ser motif (SHDLS) at positions 173–177 in their putative activation loops (FIG. 3B). The corresponding serine residues of MAP kinase kinases and IKKs are often phosphorylated by other serine protein kinases resulting in kinase transactivation (Zheng et al., supra; Delhase et al., supra). Substitution of the conserved serine residues, S173 and S177 as well as S171 for alanine (SEQ ID NO:32), did not alter the ability of PKK to induce NF-κB when compared to the wild-type kinase (FIG. 3C). Similarly, replacement of S171, S173 and S177 for glutamic acid residues (SEQ ID NO:33), which is associated with constitutive activation of serine/threonine kinases did not enhance the ability of PKK to induce NF-κB (FIG. 3C). Close inspection of zebrafish PKK revealed that the fish kinase lacks serine at position 171 and 173 and tyrosine residues in its putative activation loop (FIG. 3B). This finding indicates that the canonical motif in the activation loop of kinases is not evolutionarily conserved in PKK. Together, these observations suggest that the ability of PKK to activate NF-κB is not regulated by phosphorylation of its activation loop.

Example 5

PKK is Involved in PMA/$Ca^{2+}$-ionophore-induced NF-κB Activation

Figure 4:
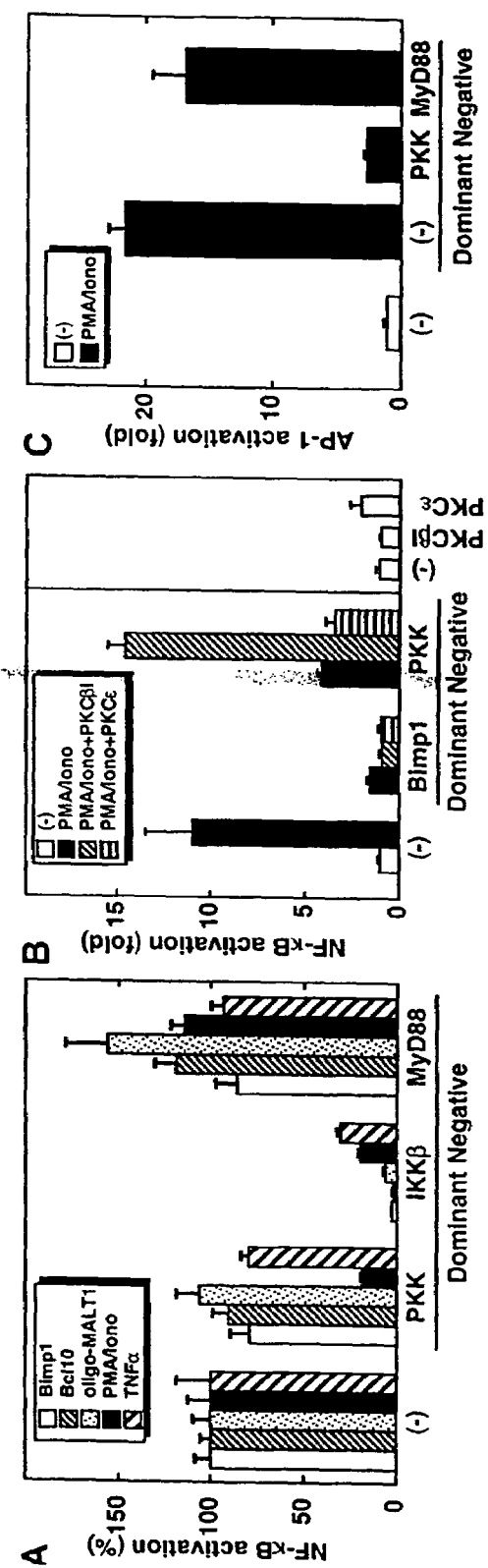
FIG. 4 shows that PKK mediates Phorbol Ester-induced NF-κB activation.

PKK is known to interact with PKCβI, suggesting that PKK may function in a common signaling pathway (Chen et al., J. Biol. Chem., 276:21737 [2001]). Recent studies have revealed that Bimp1, Bcl10 and Malt1 are components of a receptor-mediated signaling pathway which links PKC activation to NF-κB induction (Ruland et al., Cell. 104:33 [2001]; McAllister-Lucas et al., supra). It was next tested whether PKK regulated a NF-κB signaling pathway mediated by Bimp1, Bcl10 and Malt1 in HEK293T cells which are known to express endogenous PKK (Bähr et al., J. Biol. Chem., 275:36350 [2000]). Treatment of HEK293T cells with PMA/ionophore induced NF-κB activation, which was inhibited by the PKK mutant carrying an alanine substitution at the catalytic asparatate residue (D143A) (FIG. 4A). The inhibitory effect was specific in that expression of PKK D143A did not block NF-κB activation induced by Bimp1, Bcl10, oligomerized MALT1, TNFα (FIG. 4A), IL-1β or Nod1. Additional control experiments shown in FIG. 4A revealed that activation of NF-κB induced by PKK, Bimp1, Bcl10, oligomerized MALT1, PMA/$Ca^{2+}$-ionophore or TNFα could be inhibited by a dominant interfering form of IKKβ but not by that of MyD88, an essential mediator of IL-1/Toll receptor signaling (Wesche et al., Immunity 7:837 [1997]). Because PKK associates with PKCβI (Chen et al., supra), the effect of a PKK D 143A mutant on the inhibition of PMA-induced NF-κB activation through a functional interaction with PKCβI was investigated. Expression of PKCβI reverted the effect of the PKK D143A mutant, whereas PKCε did not (FIG. 4B). These results suggest that PKK acts in a PMA-induced NF-κB signaling pathway activated by PKCβI. The selective effect of PKCβI is consistent with the observation that PKK interacts with PKCβI but not with PKCε. In addition, activation of AP-1 induced by PMA/$Ca^{2+}$-ionophore was specifically inhibited by PKK dominant negative (FIG. 4C), suggesting that PKK also acts in a PMA-induced AP-1 signaling pathway activated by PKCβI.

Example 6

NF-κB Activation Induced by PKK Requires IKKα and IKKβ but not IKKγ

Figure 5:
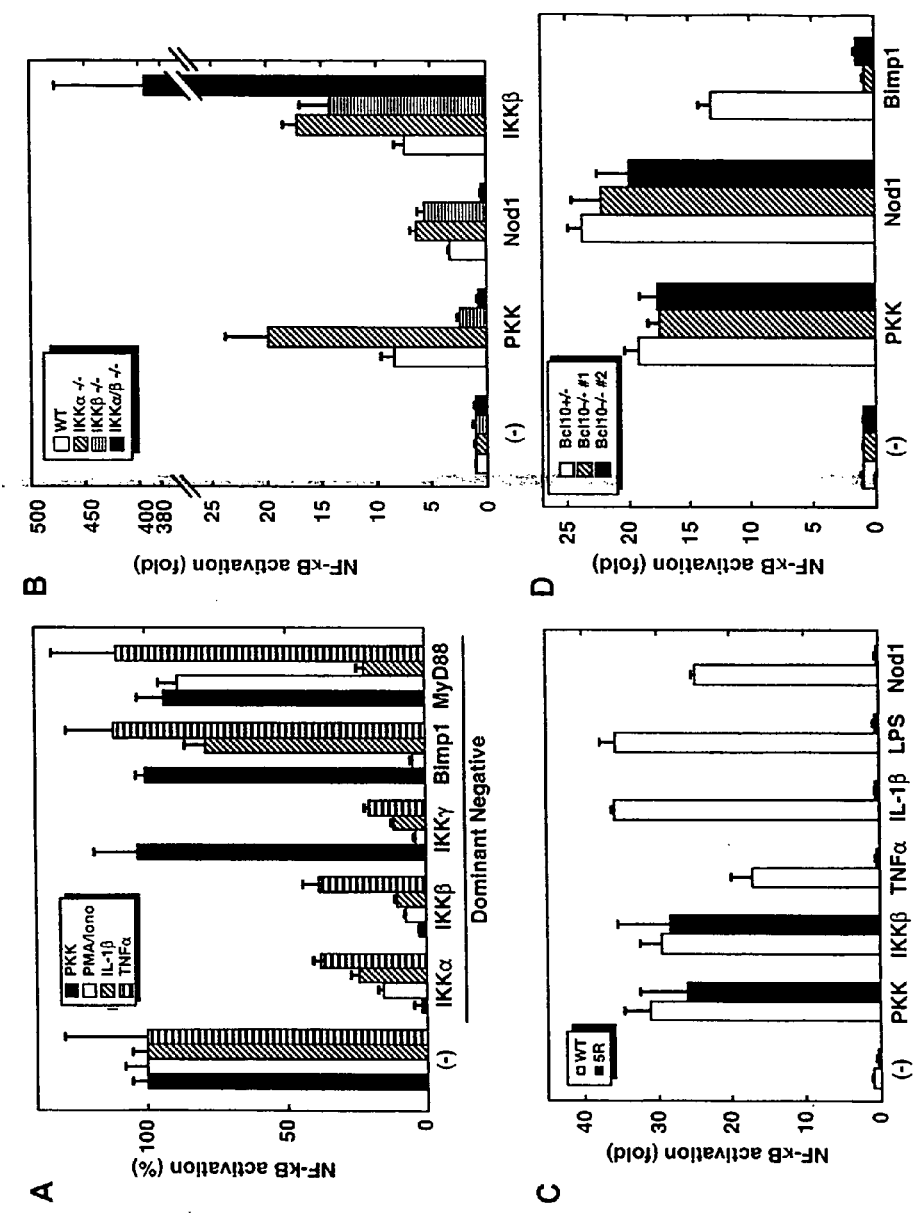
FIG. 5 demonstrates that PKK Acts through the IKK complex and independently of Bcl10 to activate NF-κB.
Figure 19:
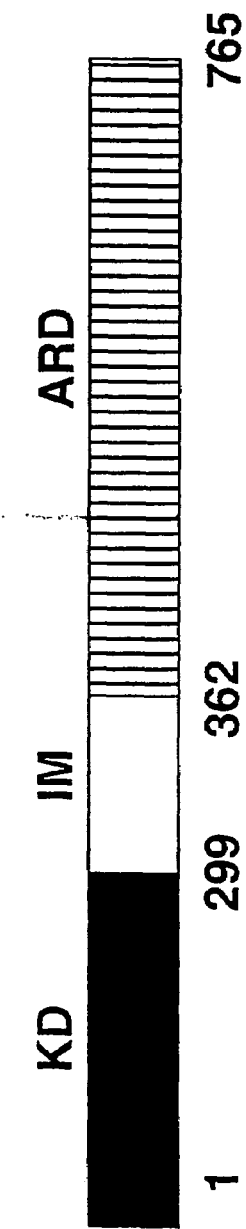
FIG. 19 shows the domain organization of human RICK3. KD refers to kinase domain; IM refers to intermediate region; ARD refers to ankyrin repeat containing domain. Numbers represent amino acid position.

NF-κB activation by RICK and RIP is mediated by the IKK complex, a universal regulator, which phosphorylates IκBα resulting in degradation of IκBα and nuclear translocation of NF-κB (Karin and Ben-Neriah, Annu. Rev. Immunol. 18:621 [2000]; Inohara et al., [2000], supra). To determine whether NF-κB activation by PKK is also dependent on IKKs, PKK was co-expressed with the catalytic inactive forms of IKKα and IKKβ. As it was found with its related RICK and RIP kinases (Inohara et al., [2000], supra), NF-κB activation induced by PKK as well as that induced by PMA/$Ca^{2+}$-ionophore, IL-1β and TNFα, was inhibited by catalytic inactive IKKα and IKKβ (FIG. 5A). In control experiments, PKK-mediated NF-κB activation was not affected by dominant negative forms of Bimp1 or MyD88 (FIG. 5A). The ability of PKK to activate NF-κB was also determined in mouse embryonic fibroblasts lacking IKKα and IKKβ. Whereas NF-κB was activated in wt fibroblasts, PKK failed to induce NF-κB activation in cells lacking both IKKα and IKKβ, and was greatly impaired in fibroblasts lacking IKKβ (FIG. 5B). These results suggest that NF-κB activation induced by PKK requires catalytic proteins of IKKs.

Figure 3:
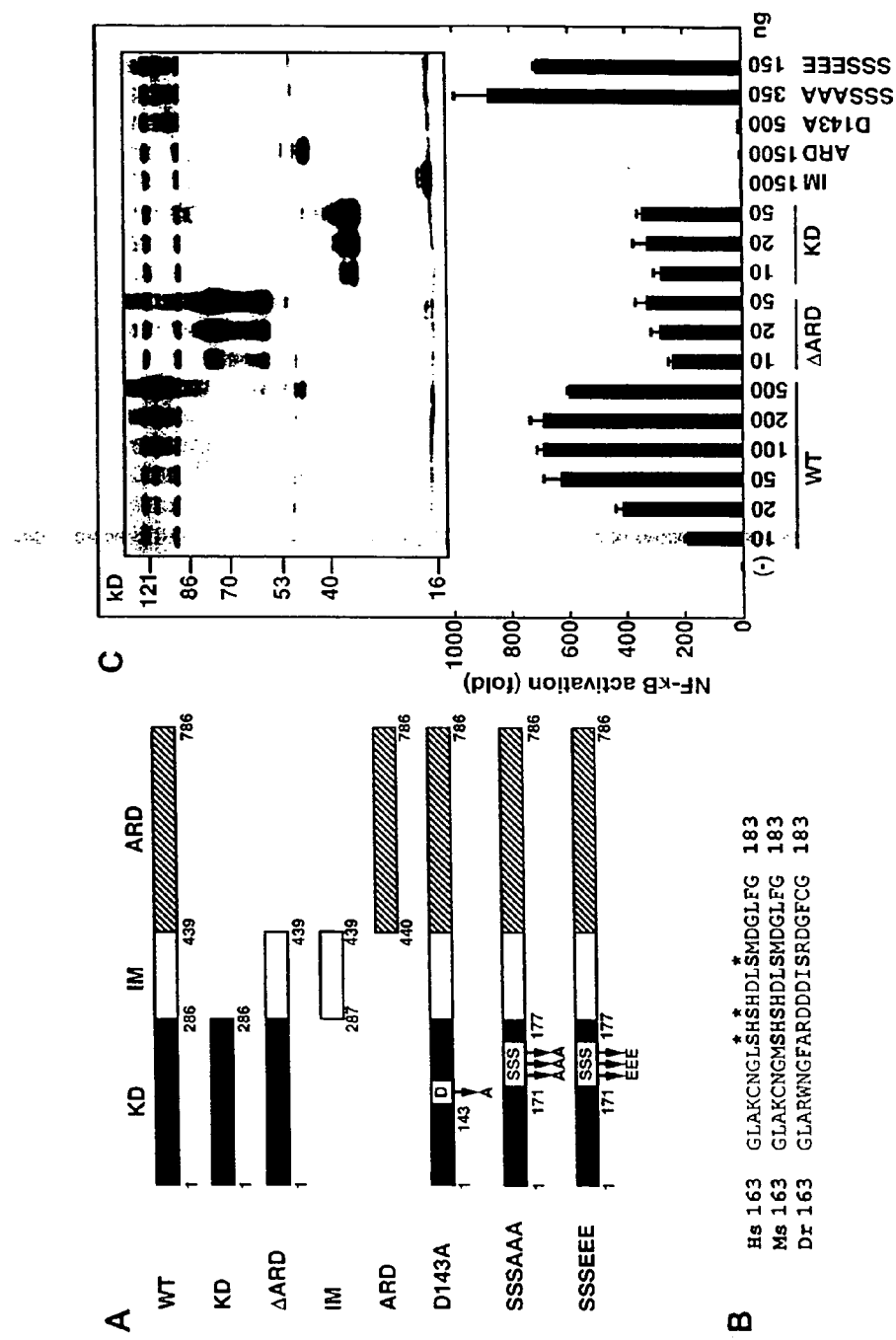
FIG. 3 shows mutational analysis of PKK.

It was next tested if NF-κB activation by PKK requires IKKγ, a regulatory component of IKK complex (Mercurio et al., Mol. Cell Biol. 19:1526 [1999]; Rothwarf et al., Nature 395:297 [1998]; Li et al., Proc. Natl. Acad. Sci. USA. 96:1042 [1999]). PKK was co-expressed with a truncated mutant of IKKγ (residues 134–419), which inhibits NF-κB activation induced by RIP and RICK (Inohara et al., [2000], supra). Co-expression of the IKKγ mutant did not inhibit PKK-mediated NF-κB activation (FIG. 5A). To verify the latter result, the ability of PKK to activate NF-κB in parental Rat1 fibroblasts and IKKγ-deficient 5R cells, a Rat1 derivative cell line that is defective in IKKγ (Yamaoka et al., Cell 93:1231 [1998]) was tested. Expression of PKK induced NF-κB activity not only in parental Rat1 cells but also in 5R cells (FIG. 5C). As a control, stimulation with TNFα, IL-1β, LPS, or expression of Nod1, which require IKKγ, induced NF-κB activation in parental Rat1 but not in 5R cells (FIG. 5C). FIG. 3 shows that the IM region of PKK is not essential for NF-κB activation, in contrast, the same region of RIP and RICK is essential for NF-κB activation and mediates the interaction with IKKγ (Inohara et al., [2000], surpra, Li et al., supra).

Example 7

Bcl10 is not Required for PKK-mediated NF-κB Activation

Bimp1 and its interacting partner Bcl10 have been shown to act downstream of PKC in a signaling pathway leading to NF-κB activation (Ruland et al., Cell 104:33 [2001], McAllister-Lucas et al., supra). FIG. 4A shows that NF-κB activation induced by Bimp1, Bcl10 and oligomerized Malt1 is unaffected by dominant negative PKK. To determine whether PKK could act upstream of Bcl10, the ability of PKK to induce NF-κB in MEFs deficient in Bcl10 was tested. Both PKK and Nod1-induced NF-κB activation in both Bcl10± and Bcl10–/– MEFs (FIG. 5D). In control experiments shown in FIG. 5D, Bcl10 was required for NF-κB activation induced by Bimp1, a protein that acts upstream of Bcl10 to activate NF-κB (McAllister-Lucas et al., supra). Together with the results shown in FIG. 4A, these results suggest that PKK functions in a PKC signaling pathway of NF-κB activation that is independent from Bcl10.

Example 8

Regulation of PKK-mediated NF-κB Activation by RICK3

Figure 20:
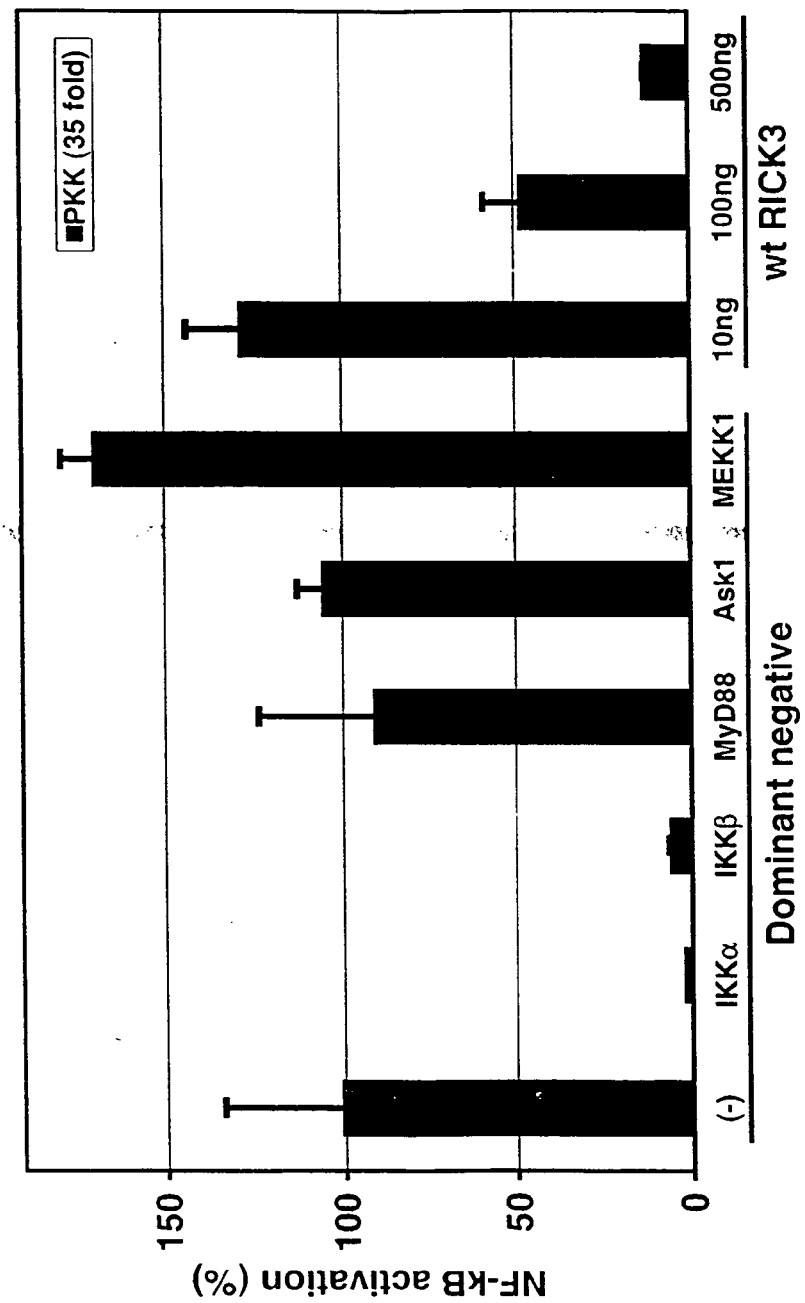
FIG. 20 shows the inhibition of PKK induced activation of NF-κB by wt RICK3.

This example describes the regulation of PKK-mediated NF-κB activation by RICK3 and dominant negative forms of IKKα, IKKβ, MyD88, Ask1 and MEKK1. Induction of NF-κB activation was determined in triplicate cultures of HEK293T cells cotransfected with DNA expression plasmids or control plasmid and PKK plasmid in the presence of pBVIx-Luc and pEF-BOS-b-gal (See Example 1 for methods). Results are shown in FIG. 20. Results are presented as a percent of values obtained with PKK plasmid (35-fold induction). Values represent mean of normalized values ±SD of triplicate cultures. The results demonstrate that RICK3 inhibits the PKK induced activation of NF-κB.

Example 9

Regulation of AP-1 Activation by RICK3

This example describes the regulation of PMA/ionomycin-mediated AP-1 activation by RICK3 and dominant negative forms of PKK, MyD88, and MEKK1. Induction of AP-1 activation was determined in triplicate cultures of HEK293T cells transfected with various amounts of RICK3 plasmid or PKK, MyD88, and MEKK1 plasmid and stimulated with 50 ng/ml PMA (phorbol ester) and A23187 (ionophore) for 6 hrs or left alone in the presence of AP-1 luc and pEF-BOS-b-gal.

Figure 21:
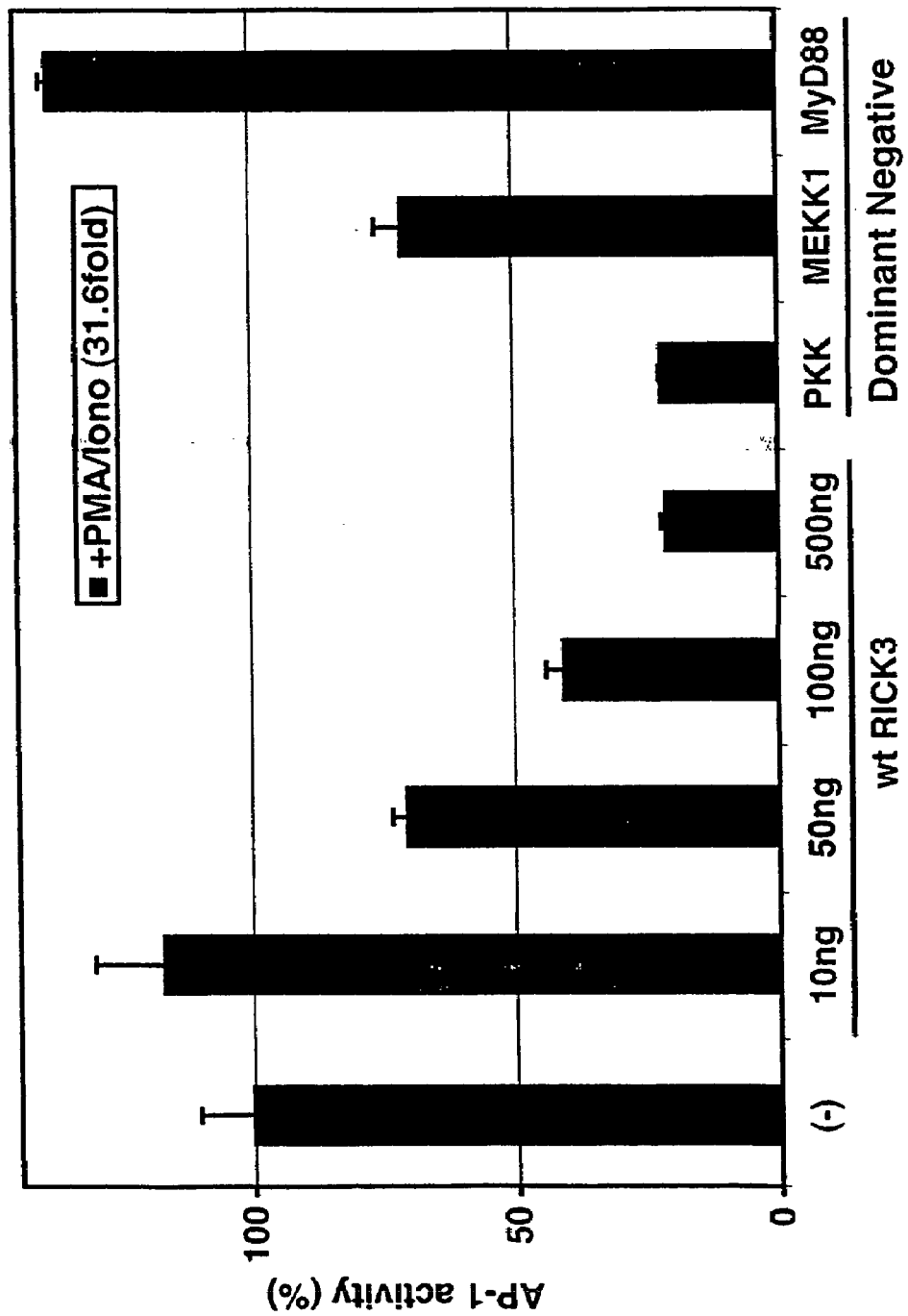
FIG. 21 shows the inhibition of AP-1 activation by RICK3.

Results are shown in FIG. 21. Fold-induction generated with PMA/ionophoro and control plasmid was 31.6 as indicated. The results are presented as a percent of values obtained with control plasmid. The results indicate that RICK3 inhibits AP-1 activation.

Example 10

RICK3 Interacts with PKK

Figure 22:
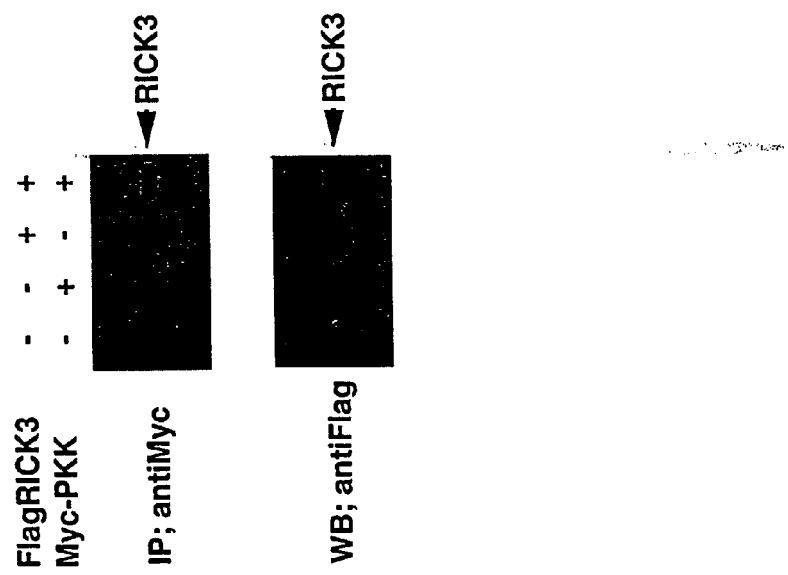
FIG. 22 shows a physical interaction of PKK and RICK3 by immunoprecipitation.

This Example describes a physical interaction between PKK and RICK3. HEK293T cells were transfected with plasmids and protein extracts were immunoprecipitated with anti-Myc antibody (top panel of FIG. 22). Interaction of PKK with RICK3 was revealed by immunoblotting with anti-Flag (top panel). Immunoblotting analysis of total lysates using anti-Flag antibody is shown in the lower panel of FIG. 22.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. An isolated and purified nucleic acid comprising a sequence encoding a protein selected from the group consisting of SEQ ID NOs: 3 and sequences that are at least 90% identical to SEQ ID NO:3.

2. The nucleic acid sequence of claim 1, wherein said sequence is operably linked to a heterologous promoter.

3. The nucleic acid sequence of claim 1, wherein said sequence is contained within a vector.

4. The nucleic acid sequence of claim 3, wherein said vector is within a host cell.

* * * * *

SEQUENCE LISTING

<160> NUMBER OF SEQ ID NOS: 44

<210> SEQ ID NO 1
<211> LENGTH: 2355
<212> TYPE: DNA
<213> ORGANISM: Homo sapiens

<400> SEQUENCE: 1

| | | | | | |
|---|---|---|---|---|---|
| atggagggcg | acggcgggac | cccatgggcc | ctggcgctgc | tgcgcacctt | cgacgcgggc | 60 |
| gagttcacgg | gctgggagaa | ggtgggctcg | ggcggcttcg | ggcaggtgta | caaggtgcgc | 120 |
| catgtccact | ggaagacctg | gctggccatc | aagtgctcgc | ccagcctgca | cgtcgacgac | 180 |
| agggagcgca | tggagctttt | ggaagaagcc | aagaagatgg | agatggccaa | gtttcgctac | 240 |
| atcctgcctg | tgtatggcat | ctgccgcgaa | cctgtcggcc | tggtcatgga | gtacatggag | 300 |
| acgggctccc | tggaaaagct | gctggcttcg | gagccattgc | catgggatct | ccggttccga | 360 |
| atcatccacg | agacggcggt | gggcatgaac | ttcctgcact | gcatggcccc | gccactcctg | 420 |
| cacctggacc | tcaagcccgc | gaacatcctg | ctggatgccc | actaccacgt | caagatttct | 480 |
| gattttggtc | tggccaagtg | caacgggctg | tcccactcgc | atgacctcag | catggatggc | 540 |
| ctgtttggca | caatcgccta | cctccctcca | gagcgcatca | gggagaagag | ccggctcttc | 600 |
| gacaccaagc | acgatgtata | cagctttgcg | atcgtcatct | ggggcgtgct | cacacagaag | 660 |
| aagccgtttg | cagatgagaa | gaacatcctg | cacatcatgg | tgaaggtggt | gaagggccac | 720 |
| cgccccgagc | tgccgcccgt | gtgcagagcc | cggccgcgcg | cctgcagcca | cctgatacgc | 780 |
| ctcatgcagc | ggtgctggca | ggggatccg | cgagttaggc | ccaccttcca | agaaattact | 840 |

-continued

| | |
|---|---|
| tctgaaaccg aggacctgtg tgaaaagcct gatgacgaag tgaaagaaac tgctcatgat | 900 |
| ctggacgtga aagcccccc ggagcccagg agcgaggtgg tgcctgcgag gctcaagcgg | 960 |
| gcctctgccc ccaccttcga taacgactac agcctctccg agctgctctc acagctggac | 1020 |
| tctggagttt cccaggctgt cgagggcccc gaggagctca gccgcagctc ctctgagtcc | 1080 |
| aagctgccat cgtccggcag tgggaagagg ctctcggggg tgtcctcggt ggactccgcc | 1140 |
| ttctcttcca gaggatcact gtcgctgtcc tttgagcggg aaccttcaac cagcgatctg | 1200 |
| ggcaccacag acgtccagaa gaagaagctt gtggatgcca tcgtgtccgg gacaccagc | 1260 |
| aaactgatga agatcctgca gccgcaggac gtggacctgg cactggacag cggtgccagc | 1320 |
| ctgctgcacc tggcggtgga ggccgggcaa gaggagtgcg ccaagtggct gctgctcaac | 1380 |
| aatgccaacc ccaacctgag caaccgtagg ggctccaccc cgttgcacat ggccgtggag | 1440 |
| aggagggtgc ggggtgtcgt ggagctcctg ctggcgcgga agatcagtgt caacgccaag | 1500 |
| gatgaggacc agtggacagc cctccacttt gcagcccaga acggggacga gtctagcaca | 1560 |
| cggctgctgt tggagaagaa cgcctcggtc aacgaggtgg actttgaggg ccggacgccc | 1620 |
| atgcacgtgg cctgccagca cgggcaggag aatatcgtgc gcatcctgct gcgccgaggc | 1680 |
| gtggacgtga gcctgcaggg caaggatgcc tggctgccac tgcactacgc tgcctggcag | 1740 |
| ggccacctgc ccatcgtcaa gctgctggcc aagcagccgg gggtgagtgt gaacgcccag | 1800 |
| acgctggatg ggaggacgcc attgcacctg ccgcacagc gcgggcacta ccgcgtggcc | 1860 |
| cgcatcctca tcgacctgtg ctccgacgtc aacgtctgca gcctgctggc acagacaccc | 1920 |
| ctgcacgtgg ccgcggagac ggggcacacg agcactgcca ggctgctcct gcatcggggc | 1980 |
| gctggcaagg aggccgtgac ctcagacggc tacaccgctc tgcacctggc tgcccgcaac | 2040 |
| ggacacctgg ccactgtcaa gctgcttgtc gaggagaagg ccgatgtgct ggcccgggga | 2100 |
| cccctgaacc agacggcgct gcacctggct gccgcccacg gcactcgga ggtggtggag | 2160 |
| gagttggtca gcgccgatgt cattgacctg ttcgacgagc aggggctcag cgcgctgcac | 2220 |
| ctggccgccc agggccggca cgcacagacg gtggagactc tgctcaggca tggggcccac | 2280 |
| atcaacctgc agagcctcaa gttccagggc ggccatggcc ccgccgccac actcctgcgg | 2340 |
| cgaagcaaga cctag | 2355 |

<210> SEQ ID NO 2
<211> LENGTH: 2696
<212> TYPE: DNA
<213> ORGANISM: Homo sapiens

<400> SEQUENCE: 2

| | |
|---|---|
| taaataaact ggatccaact tctcaggctg gacttcttcc agcttcggga caccttctcc | 60 |
| cagcatccct ccctaggggg aactggggaa aatcaaaggc tgagacaggg gaaatgcgag | 120 |
| ggcttcggag ggacataccc tcttccccag gcccaggtcg ctccatccct gctggggcct | 180 |
| cagggctcat gtctgggatt tccccacctt tgcggggcag gagcggctcc tcttgggcgg | 240 |
| ggaaggaggc agggccggct cgtctccca ttccctctc ccggacccga ggagcaggaa | 300 |
| gcggcggctc cttcggccac ccaggcagca gccacagcgg ggagtgcgcg gcgcggggac | 360 |
| aggaagagag gggcaatggc tgccgacccc accgagctgc ggctgggcag cctccccgtc | 420 |
| ttcacccgcg acgacttcga gggcgactgg cgcctagtgg ccagcggcgg cttcagccag | 480 |
| gtgttccagg cgcggcacag gcgctggcgg acggagtacg ccatcaagtg cgcccccctgc | 540 |

-continued

| | |
|---|---|
| cttccacccg acgccgccag ctctgatgtg aattacctca ttgaagaagc tgccaaaatg | 600 |
| aagaagatca agtttcagca catcgtgtcc atctacgggg tgtgcaagca gcccctgggt | 660 |
| attgtgatgg agtttatggc caacggctcc ctggagaagg tgctgtccac ccacagcctc | 720 |
| tgctggaagc tcaggttccg catcatccat gagaccagct tggccatgaa cttcctgcac | 780 |
| agcattaagc cgcctctgct ccacctggac ctcaagccgg gcaacatcct cctggacagc | 840 |
| aacatgcatg tcaaaatttc agacttcggc ctgtccaagt ggatggaaca gtccacccgg | 900 |
| atgcagtaca tcgagaggtc ggctctgcgg ggcatgctca gctacatccc ccctgagatg | 960 |
| ttcctggaga gtaacaaggc cccaggacct aaatatgatg tgtacagctt tgcaattgtc | 1020 |
| atctgggagc tactcactca gaagaaacca tactcagggt tcaacatgat gatgattatt | 1080 |
| atccgagtgg cggcaggcat gcggccctcc ctacagcctg tctctgacca atggccaagc | 1140 |
| gaggcccagc agatggtgga cctgatgaaa cgctgctggg accaggaccc caagaagagg | 1200 |
| ccatgctttc tagacattac catcgagaca gacatactgc tgtcactgct gcagagtcgt | 1260 |
| gtggcagtcc agagagcaa ggccctggcc aggaaggtgt cctgcaagct gtcgctgcgc | 1320 |
| cagcccaggg aggttaatga ggacatcagc caggaactga tggacagtga ctcaggaaac | 1380 |
| tacctgaagc gggcccttca gctctccgac cgtaagaatt tggtcccgag agatgaggaa | 1440 |
| ctgtgtatct atgagaacaa ggtcaccccc ctccaattcc tggtggccca gggcagtgtg | 1500 |
| gagcaggtga ggttgctgct ggcccacgag gtagacgtgg actgccagac ggcctctgga | 1560 |
| tacacgcccc tcctgatcgc cgcccaggac cagcaacccg acctctgtgc cctgcttttg | 1620 |
| gcacatggtg ctgatgccaa ccgagtggat gaggatggct gggccccact gcactttgca | 1680 |
| gcccagaatg gggatgaccg cactgcgcgc ctgctcctgg accacggggc ctgtgtggat | 1740 |
| gcccaggaac gtgaagggtg gaccctctt cacctggctg cacagaataa ctttgagaat | 1800 |
| gtggcacggc ttctggtctc ccgtcaggct gaccccaacc tgcgtgaggc tgagggcaag | 1860 |
| accccctcc atgtggccgc ctactttggc catgttagcc tggtcaagct gctgaccagc | 1920 |
| caggggctg agttggatgc tcagcagaga aacctgagaa caccactgca cctggcagta | 1980 |
| gagcggggca agtgagggc catccaacac ctgctgaaga gtggagcggt ccctgatgcc | 2040 |
| cttgaccaga gcggctatgg cccactgcac actgcagctg ccaggggcaa atacctgatc | 2100 |
| tgcaagatgc tgctcaggta cggagccagc cttgagctgc ccacccacca gggctggaca | 2160 |
| cccctgcatc tagcagccta caagggccac ctggagatca tccatctgct ggcagagagc | 2220 |
| cacgcaaaca tgggtgctct tggagctgtg aactggactc ccctgcacct agctgcacgc | 2280 |
| cacggggagg aggcggtggt gtcagcactg ctgcagtgtg gggctgaccc caatgctgca | 2340 |
| gagcagtcag gctggacacc cctccacctg gcggtccaga ggagcacctt cctgagtgtc | 2400 |
| atcaacctcc tagaacatca cgcaaatgtc cacgcccgca acaaggtggg ctggacaccc | 2460 |
| gcccacctgg ccgccctcaa gggcaacaca gccatcctca agtgctggt cgaggcaggc | 2520 |
| gcccagctgg acgtccagga tggagtgagc tgcacacccc tgcaactggc cctccgcagc | 2580 |
| cgaaagcagg gcatcatgtc cttcctagag ggcaaggagc cgtcagtggc cactctgggt | 2640 |
| ggttctaagc caggagccga gatggaaatt tagacaactt ggccagccgt ggtggc | 2696 |

<210> SEQ ID NO 3
<211> LENGTH: 765
<212> TYPE: PRT
<213> ORGANISM: Homo sapiens

<400> SEQUENCE: 3

```
Met Ala Ala Asp Pro Thr Glu Leu Arg Leu Gly Ser Leu Pro Val Phe
1               5                   10                  15

Thr Arg Asp Asp Phe Glu Gly Asp Trp Arg Leu Val Ala Ser Gly Gly
            20                  25                  30

Phe Ser Gln Val Phe Gln Ala Arg His Arg Arg Trp Arg Thr Glu Tyr
        35                  40                  45

Ala Ile Lys Cys Ala Pro Cys Leu Pro Pro Asp Ala Ala Ser Ser Asp
    50                  55                  60

Val Asn Tyr Leu Ile Glu Ala Ala Lys Met Lys Lys Ile Lys Phe
65              70                  75                  80

Gln His Ile Val Ser Ile Tyr Gly Val Cys Lys Gln Pro Leu Gly Ile
                85                  90                  95

Val Met Glu Phe Met Ala Asn Gly Ser Leu Glu Lys Val Leu Ser Thr
                100                 105                 110

His Ser Leu Cys Trp Lys Leu Arg Phe Arg Ile Ile His Glu Thr Ser
        115                 120                 125

Leu Ala Met Asn Phe Leu His Ser Ile Lys Pro Pro Leu Leu His Leu
130                 135                 140

Asp Leu Lys Pro Gly Asn Ile Leu Leu Asp Ser Asn Met His Val Lys
145                 150                 155                 160

Ile Ser Asp Phe Gly Leu Ser Lys Trp Met Glu Gln Ser Thr Arg Met
                165                 170                 175

Gln Tyr Ile Glu Arg Ser Ala Leu Arg Gly Met Leu Ser Tyr Ile Pro
            180                 185                 190

Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
    210                 215                 220

Pro Tyr Ser Gly Phe Asn Met Met Met Ile Ile Ile Arg Val Ala Ala
225                 230                 235                 240

Gly Met Arg Pro Ser Leu Gln Pro Val Ser Asp Gln Trp Pro Ser Glu
                245                 250                 255

Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
        275                 280                 285

Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
        355                 360                 365

Leu Val Ala Gln Gly Ser Val Glu Gln Val Arg Leu Leu Leu Ala His
    370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                405                 410                 415
```

His Gly Ala Asp Ala Asn Arg Val Asp Glu Asp Gly Trp Ala Pro Leu
            420                 425                 430
His Phe Ala Ala Gln Asn Gly Asp Asp Arg Thr Ala Arg Leu Leu Leu
            435                 440                 445
Asp His Gly Ala Cys Val Asp Ala Gln Glu Arg Glu Gly Trp Thr Pro
            450                 455                 460
Leu His Leu Ala Ala Gln Asn Asn Phe Glu Asn Val Ala Arg Leu Leu
465                 470                 475                 480
Val Ser Arg Gln Ala Asp Pro Asn Leu Arg Glu Ala Glu Gly Lys Thr
            485                 490                 495
Pro Leu His Val Ala Ala Tyr Phe Gly His Val Ser Leu Val Lys Leu
            500                 505                 510
Leu Thr Ser Gln Gly Ala Glu Leu Asp Ala Gln Gln Arg Asn Leu Arg
            515                 520                 525
Thr Pro Leu His Leu Ala Val Glu Arg Gly Lys Val Arg Ala Ile Gln
            530                 535                 540
His Leu Leu Lys Ser Gly Ala Val Pro Asp Ala Leu Asp Gln Ser Gly
545                 550                 555                 560
Tyr Gly Pro Leu His Thr Ala Ala Arg Gly Lys Tyr Leu Ile Cys
            565                 570                 575
Lys Met Leu Leu Arg Tyr Gly Ala Ser Leu Glu Leu Pro Thr His Gln
            580                 585                 590
Gly Trp Thr Pro Leu His Leu Ala Ala Tyr Lys Gly His Leu Glu Ile
            595                 600                 605
Ile His Leu Leu Ala Glu Ser His Ala Asn Met Gly Ala Leu Gly Ala
            610                 615                 620
Val Asn Trp Thr Pro Leu His Leu Ala Ala Arg His Gly Glu Glu Ala
625                 630                 635                 640
Val Val Ser Ala Leu Leu Gln Cys Gly Ala Asp Pro Asn Ala Ala Glu
            645                 650                 655
Gln Ser Gly Trp Thr Pro Leu His Leu Ala Val Gln Arg Ser Thr Phe
            660                 665                 670
Leu Ser Val Ile Asn Leu Leu Glu His His Ala Asn Val His Ala Arg
            675                 680                 685
Asn Lys Val Gly Trp Thr Pro Ala His Leu Ala Ala Leu Lys Gly Asn
            690                 695                 700
Thr Ala Ile Leu Lys Val Leu Val Glu Ala Gly Ala Gln Leu Asp Val
705                 710                 715                 720
Gln Asp Gly Val Ser Cys Thr Pro Leu Gln Leu Ala Leu Arg Ser Arg
            725                 730                 735
Lys Gln Gly Ile Met Ser Phe Leu Glu Gly Lys Glu Pro Ser Val Ala
            740                 745                 750
Thr Leu Gly Gly Ser Lys Pro Gly Ala Glu Met Glu Ile
            755                 760                 765

<210> SEQ ID NO 4
<211> LENGTH: 2696
<212> TYPE: DNA
<213> ORGANISM: Homo sapiens

<400> SEQUENCE: 4
taaataaact ggatccaact tctcaggctg gacttcttcc agcttcggga caccttctcc    60
cagcatccct ccctaggggg aactggggaa aatcaaaggc tgagacaggg gaaatgcgag   120
ggcttcggag ggacataccc tcttccccag gcccaggtcg ctccatccct gctggggcct   180

-continued

```
cagggctcat gtctgggatt tccccacctt tgcggggcag gagcggctcc tcttgggcgg      240
ggaaggaggc agggccggct cgtctcccca ttcccctctc ccggacccga ggagcaggaa      300
gcggcggctc cttcggccac ccaggcagca gccacagcgg ggagtgcgcg gcgcggggac      360
aggaagagag gggcaatggc tgccgacccc accgagctgc ggctgggcag cctccccgtc      420
ttcacccgcg acgacttcga gggcgactgg cgcctagtgg ccagcggcgg cttcagccag      480
gtgttccagg cgcggcacag gcgctggcgg acggagtacg ccatcaagtg cgcccctgc       540 cttccacccg acgccgccag ctctgatgtg aattacctca ttgaagaagc tgccaaaatg      600
aagaagatca agtttcagca catcgtgtct atctacgggg tgtgcaagca gcccctgggt      660
attgtgatgg agtttatggc caacggctcc ctggagaagg tgctgtccac ccacagcctc      720
tgctggaagc tcaggttccg catcatccat gagaccagct ggccatgaa  cttcctgcac      780 agcattaagc cgcctctgct ccacctggac ctcaagccgg gcaacatcct cctggacagc      840
aacatgcatg tcaaaatttc agacttcggc ctgtccaagt ggatggaaca gtccacccgg      900
atgcagtaca tcgagaggtc ggctctgcgg ggcatgctca gctacatccc ccctgagatg      960
ttcctggaga gtaacaaggc cccaggacct aaatatgatg tgtacagctt tgcaattgtc     1020
atctgggagc tactcactca gaagaaacca tactcagggt tcaacatgat gatgattatt     1080
atccgagtgg cggcaggcat gcggccctcc ctacagcctg tctctgacca atggccaagc     1140
gaggcccagc agatggtgga cctgatgaaa cgctgctggg accaggaccc caagaagagg     1200
ccatgctttc tagacattac catcgagaca gacatactgc tgtcactgct gcagagtcgt     1260
gtggcagtcc cagagagcaa ggccctggcc aggaaggtgt cctgcaagct gtcgctgcgc     1320
cagcccaggg aggttaatga ggacatcagc caggaactga tggacagtga ctcaggaaac     1380
tacctgaagc gggcccttca gctctccgac cgtaagaatt tggtcccgag agatgaggaa     1440
ctgtgtatct atgagaacaa ggtcaccccc ctccaattcc tggtgcccca gggcagtgtg     1500
gagcaggtga ggttgctgct ggcccacgag gtagacgtgg actgccagac ggcctctgga     1560
tacacgcccc tcctgatcgc cgcccaggac cagcaacccg acctctgtgc cctgcttttg     1620
gcacatggtg ctgatgccaa ccgagtggat gaggatggct gggccccact gcactttgca     1680
gcccagaatg gggatgaccg cactgcgcgc ctgctcctgg accacggggc ctgtgtggat     1740
gcccaggaac gtgaagggtg gacccctctt cacctggctg cacagaataa ctttgagaat     1800
gtggcacggc ttctggtctc ccgtcaggct gaccccaacc tgcgtgaggc tgagggcaag     1860 accccccctcc atgtggccgc ctactttggc catgttagcc tggtcaagct gctgaccagc     1920 caggggctg agttggatgc tcagcagaga aacctgagaa caccactgca cctggcagta     1980
gagcggggca agtgagggc catccaacac ctgctgaaga gtggagcggt ccctgatgcc     2040
cttgaccaga gcggctatgg cccactgcac actgcagctg ccaggggcaa atacctgatc     2100
tgcaagatgc tgctcaggta cggagccagc cttgagctgc ccacccacca gggctggaca     2160
cccctgcatc tagcagccta caaggccac ctggagatca tccatctgct ggcagagagc     2220
cacgcaaaca tgggtgctct tggagctgtg aactggactc ccctgcacct agctgcacgc     2280
cacggggagg aggcggtggt gtcagcactg ctgcagtgtg gggctgaccc caatgctgca     2340
gagcagtcag gctggacacc cctccacctg gcggtccaga ggagcacctt cctgagtgtc     2400
atcaacctcc tagaacatca cgcaaatgtc cacgcccgca acaaggtggg ctggacaccc     2460
gcccacctgg ccgccctcaa gggcaacaca gccatcctca agtgctggt cgaggcaggc     2520
```

| | |
|---|---|
| gcccagctgg acgtccagga tggagtgagc tgcacacccc tgcaactggc cctccgcagc | 2580 |
| cgaaagcagg gcatcatgtc cttcctagag ggcaaggagc cgtcagtggc cactctgggt | 2640 |
| ggttctaagc caggagccga gatggaaatt tagacaactt ggccagccgt ggtggc | 2696 |

<210> SEQ ID NO 5
<211> LENGTH: 2696
<212> TYPE: DNA
<213> ORGANISM: Homo sapiens

<400> SEQUENCE: 5

| | |
|---|---|
| taaataaact ggatccaact tctcaggctg gacttcttcc agcttcggga caccttctcc | 60 |
| cagcatccct ccctaggggg aactggggaa atcaaaggc tgagacaggg gaaatgcgag | 120 |
| ggcttcggag ggacataccc tcttccccag gcccaggtcg ctccatccct gctgggcct | 180 |
| cagggctcat gtctgggatt tccccacctt tgcggggcag gagcggctcc tcttgggcgg | 240 |
| ggaaggaggc agggccggct cgtctcccca ttcccctctc ccggacccga ggagcaggaa | 300 |
| gcggcggctc cttcggccac ccaggcagca gccacagcgg ggagtgcgcg gcgcggggac | 360 |
| aggaagagag gggcaatggc tgccgacccc accgagctgc ggctgggcag cctccccgtc | 420 |
| ttcacccgcg acgacttcga gggcgactgg cgcctagtgg ccagcggcgg cttcagccag | 480 |
| gtgttccagg cgcggcacag gcgctggcgg acggagtacg ccatcaagtg cgcccccgtc | 540 |
| cttccacccg acgccgccag ctctgatgtg aattacctca ttgaagaagc tgccaaaatg | 600 |
| aagaagatca gtttcagca catcgtgtct atctacgggg tgtgcaagca gcccctgggt | 660 |
| attgtgatgg agtttatggc caacggctcc ctggagaagg tgctgtccac ccacagcctc | 720 |
| tgctggaagc tcaggttccg catcatccat gagaccagct tggccatgaa cttcctgcac | 780 |
| agcattaagc cgcctctgct ccacctggac ctcaagccgg caacatact cctggacagc | 840 |
| aacatgcatg tcaaaatttc agacttcggc ctgtccaagt ggatggaaca gtccaccccgg | 900 |
| atgcagtaca tcgagaggtc ggctctgcgg ggcatgctca gctacatccc ccctgagatg | 960 |
| ttcctggaga gtaacaaggc cccaggacct aaatatgatg tgtacagctt tgcaattgtc | 1020 |
| atctgggagc tactcactca gaagaaacca tactcagggt tcaacatgat gatgattatt | 1080 |
| atccgagtgg cggcaggcat gcggccctcc ctacagcctg tctctgacca atggccaagc | 1140 |
| gaggcccagc agatggtgga cctgatgaaa cgctgctggg accaggaccc caagaagagg | 1200 |
| ccatgctttc tagacattac catcgagaca gacatactgc tgtcactgct gcagagtcgt | 1260 |
| gtggcagtcc cagagagcaa ggccctggcc aggaaggtgt cctgcaagct gtcgctgcgc | 1320 |
| cagcccaggg aggttaatga ggacatcagc caggaactga tggacagtga ctcaggaaac | 1380 |
| tacctgaagc gggcccttca gctctccgac cgtaagaatt tggtcccgag agatgaggaa | 1440 |
| ctgtgtatct atgagaacaa ggtcaccccc ctccaattcc tggtggccca gggcagtgtg | 1500 |
| gagcaggtga ggttgctgct ggcccacgag gtagacgtgg actgccagac ggcctctgga | 1560 |
| tacacgcccc tcctgatcgc cgcccaggac cagcaacccg acctctgtgc cctgcttttg | 1620 |
| gcacatggtg ctgatgccaa ccgagtggat gaggatggct gggcccccact gcactttgca | 1680 |
| gcccagaatg gggatgaccg cactgcgcgc ctgctcctgg accacggggc ctgtgtggat | 1740 |
| gcccaggaac gtgaagggtg gacccctctt cacctggctg cacagaataa ctttgagaat | 1800 |
| gtggcacgga ttctggtctc ccgtcaggct gaccccaacc tgcgtgaggc tgaggcaag | 1860 |
| accccctcc atgtggccgc ctactttggc catgttagcc tggtcaagct gctgaccagc | 1920 |
| caggggctg agttggatgc tcagcagaga aacctgagaa caccactgca cctggcagta | 1980 |

```
gagcggggca aagtgagggc catccaacac ctgctgaaga gtggagcggt ccctgatgcc    2040
cttgaccaga gcggctatgg cccactgcac actgcagctg ccaggggcaa atacctgatc    2100
tgcaagatgc tgctcaggta cggagccagc cttgagctgc ccaccacca gggctggaca    2160 cccctgcatc tagcagccta aagggccac ctggagatca tccatctgct ggcagagagc    2220
cacgcaaaca tgggtgctct tggagctgtg aactggactc ccctgcacct agctgcacgc    2280
cacggggagg aggcggtggt gtcagcactg ctgcagtgtg gggctgaccc caatgctgca    2340
gagcagtcag gctggacacc cctccacctg gcggtccaga ggagcacctt cctgagtgtc    2400
atcaacctcc tagaacatca cgcaaatgtc cacgcccgca acaaggtggg ctggacaccc    2460
gcccacctgg ccgccctcaa gggcaacaca gccatcctca aagtgctggt cgaggcaggc    2520
gcccagctgg acgtccagga tggagtgagc tgcacacccc tgcaactggc cctccgcagc    2580
cgaaagcagg gcatcatgtc cttcctagag ggcaaggagc cgtcagtggc cactctgggt    2640
ggttctaagc caggagccga gatggaaatt tagacaactt ggccagccgt ggtggc        2696

<210> SEQ ID NO 6
<211> LENGTH: 2696
<212> TYPE: DNA
<213> ORGANISM: Homo sapiens

<400> SEQUENCE: 6
taaataaact ggatccaact tctcaggctg gacttcttcc agcttcggga caccttctcc      60
cagcatccct ccctaggggg aactgggaa atcaaaggc tgagacaggg gaaatgcgag       120
ggcttcggag ggacataccc tcttccccag gcccaggtcg ctccatccct gctgggcct      180 cagggctcat gtctgggatt tccccacctt tgcggggcag gagcggctcc tcttgggcgg     240
ggaaggaggc agggccggct cgtctcccca ttcccctctc ccggacccga ggagcaggaa     300
gcggcggctc cttcggccac ccaggcagca gccacagcgg ggagtgcgcg cgcggggac      360 aggaagagag gggcaatggc tgccgacccc accgagctgc ggctgggcag cctccccgtc     420
ttcacccgcg acgacttcga gggcgactgg cgcctagtgg ccagcggcgg cttcagccag    480
gtgttccagg cgcggcacag gcgctggcgg acggagtacg ccatcaagtg cgccccctgc    540
cttccacccg acgccgccag ctctgatgtg aattacctca ttgaagaagc tgccaaaatg    600
aagaagatca gtttcagca catcgtgtct atctacgggg tgtgcaagca gcccctgggt    660
attgtgatga gtttatggc caacggctcc tggagaagg tgctgtccac ccacagcctc      720
tgctggaagc tcaggttccg catcatccat gagaccagct tggccatgaa cttcctgcac    780
agcattaagc gcctctgct ccacctggac ctcaagccgg caacatact cctgacagc       840 aacatgcatg tcaaaatttc agacttcggc ctgtccaagt ggatggaaca gtccacccgg    900
atgcagtaca tcgagaggtc ggctctgcgg gcatgctca gctacatccc ccctgagatg    960
ttcctggaga gtaacaaggc cccaggacct aaatatgatg tgtacagctt tgcaattgtc    1020
atctgggagc tactcactca gaagaaacca tactcagggt tcaacatgat gatgattatt   1080
atccgagtgg cggcaggcat gcggccctcc ctacagcctg tctctgacca atggccaagc   1140
gaggcccagc agatggtgga cctgatgaaa cgctgctggg accaggaccc caagaagagg   1200
ccatgctttc tagacattac catcgagaca gacatactgc tgtcactgct gcagagtcgt   1260
gtggcagtcc cagagagcaa ggccctggcc aggaaggtgt cctgcaagct gtcgctgcgc   1320
cagcccgggg aggttaatga ggacatcagc caggaactga tggacagtga ctcaggaaac   1380
```

```
tacctgaagc gggcccttca gctctccgac cgtaagaatt tggtcccgag agatgaggaa    1440
ctgtgtatct atgagaacaa ggtcaccccc ctccaattcc tggtgcccca gggcagtgtg    1500
gagcaggtga ggttgctgct ggcccacgag gtagacgtgg actgccagac ggcctctgga    1560
tacacgcccc tcctgatcgc cgcccaggac cagcaacccg acctctgtgc cctgcttttg    1620
gcacatggtg ctgatgccaa ccgagtggat gaggatggct gggcccccact gcactttgca    1680 gcccagaatg gggatgaccg cactgcgcgc tgctcctgg accacgggc ctgtgtggat       1740 gcccaggaac gtgaagggtg gaccctctt cacctggctg cacagaataa ctttgagaat     1800
gtggcacggc ttctggtctc ccgtcaggct gaccccaacc tgcgtgaggc tgagggcaag    1860 accccctcc atgtggccgc ctactttggc catgttagcc tggtcaagct gctgaccagc     1920
cagggggctg agttggatgc tcagcagaga aacctgagaa caccactgca cctggcagta    1980
gagcggggca aagtgagggc catccaacac ctgctgaaga gtggagcggt ccctgatgcc    2040
cttgaccaga gcggctatgg cccactgcac actgcagctg ccaggggcaa atacctgatc    2100
tgcaagatgc tgctcaggta cggagccagc cttgagctgc ccacccacca gggctggaca    2160
cccctgcatc tagcagccta aagggccac ctggagatca tccatctgct ggcagagagc     2220
cacgcaaaca tgggtgctct tggagctgtg aactggactc ccctgcacct agctgcacgc    2280
cacggggagg aggcggtggt gtcagcactg ctgcagtgtg gggctgaccc caatgctgca    2340
gagcagtcag gctggacacc cctccacctg gcggtccaga ggagcacctt cctgagtgtc    2400
atcaacctcc tagaacatca cgcaaatgtc cacgcccgca acaaggtggg ctggacaccc    2460
gcccacctgg ccgccctcaa gggcaacaca gccatcctca aagtgctggt cgaggcaggc    2520
gcccagctgg acgtccagga tggagtgagc tgcacacccc tgcaactggc cctccgcagc    2580
cgaaagcagg gcatcatgtc cttcctagag ggcaaggagc cgtcagtggc cactctgggt    2640
ggttctaagc caggagccga gatggaaatt tagacaactt ggccagccgt ggtggc         2696
```

<210> SEQ ID NO 7
<211> LENGTH: 2696
<212> TYPE: DNA
<213> ORGANISM: Homo sapiens

<400> SEQUENCE: 7

```
taaataaact ggatccaact tctcaggctg gacttcttcc agcttcggga caccttctcc      60
cagcatccct ccctagggg aactgggaa atcaaaggc tgagacaggg gaaatgcgag        120
ggcttcggag ggacataccc tcttccccag gcccaggtcg ctccatccct gctggggcct     180
cagggctcat gtctgggatt tccccacctt tgcggggcag gagcggctcc tcttgggcgg     240
ggaaggaggc agggccggct cgtctcccca ttccctctc ccggacccga ggagcaggaa      300
gcggcggctc cttcggccac ccaggcagca gccacagcgg ggagtgcgcg gcgcggggac    360
aggaagagag gggcaatggc tgccgacccc accgagctgc ggctgggcag cctcccccgtc  420 ttcacccgcg acgacttcga gggcgactgg cgcctagtgg ccagcggcgg cttcagccag   480
gtgttccagg cgcggcacag gcgctggcgg acggagtacg ccatcaagtg cgcccccctgc  540 cttccacccg acgccgccag ctctgatgtg aattacctca ttgaagaagc tgccaaaatg    600
aagaagatca gtttcagca catcgtgtct atctacgggg tgtgcaagca gcccctgggt    660
attgtgatgg agtttatggc caacggctcc ctggagaagg tgctgtccac ccacagcctc    720
tgctggaagc tcaggttccg catcatccat gagaccagct tggccatgaa cttcctgcac    780
agcattaagc cgcctctgct ccacctggac ctcaagccgg gcaacatact cctggacagc    840
```

```
aacatgcatg tcaaaatttc agacttcggc ctgtccaagt ggatggaaca gtccacccgg      900
atgcagtaca tcgagaggtc ggctctgcgg ggcatgctca gctacatccc ccctgagatg      960
ttcctggaga gtaacaaggc cccaggacct aaatatgatg tgtacagctt tgcaattgtc     1020
atctgggagc tactcactca aagaaaacca tactcagggt tcaacatgat gatgattatt     1080
atccgagtgg cggcaggcat gcggccctcc ctacagcctg tctctgacca atggccaagc     1140
gaggcccagc agatggtgga cctgatgaaa cgctgctggg accaggaccc caagaagagg     1200
ccatgctttc tagacattac catcgagaca gacatactgc tgtcactgct gcagagtcgt     1260
gtggcagtcc cagagagcaa ggccctggcc aggaaggtgt cctgcaagct gtcgctgcgc     1320
cagcccgggg aggttaatga ggacatcagc caggaactga tggacagtga ctcaggaaac     1380
tacctgaagc gggcccttca gctctccgac cgtaagaatt tggtcccgag agatgaggaa     1440
ctgtgtatct atgagaacaa ggtcaccccc ctccacttcc tggtggccca gggcagtgtg     1500
gagcaggtga ggttgctgct ggcccacgag gtagacgtgg actgccagac ggcctctgga     1560
tacacgcccc tcctgatcgc cgcccaggac cagcaacccg acctctgtgc cctgcttttg     1620
gcacatggtg ctgatgccaa ccgagtggat gaggatgggct gggcccccact gcactttgca     1680 gcccagaatg gggatgaccg cactgcgcgc ctgctcctgg accacggggc ctgtgtggat     1740
gcccaggaac gtgaagggtg acccctctt cacctggctg cacagaataa ctttgagaat      1800
gtggcacggc ttctggtctc ccgtcaggct gaccccaacc tgcgtgaggc tgagggcaag     1860
acccccctcc atgtggccgc ctactttggc catgttagcc tggtcaagct gctgaccagc     1920 caggggctg agttggatgc tcagcagaga aacctgagaa caccactgca cctggcagta      1980
gagcggggca aagtgagggc catccaacac ctgctgaaga gtggagcggt ccctgatgcc     2040
cttgaccaga gcggctatgg cccactgcac actgcagctg ccaggggcaa atacctgatc     2100
tgcaagatgc tgctcaggta cggagccagc cttgagctgc ccacccacca gggctggaca     2160 ccctgcatc tagcagccta caagggccac ctggagatca tccatctgct ggcagagagc      2220
cacgcaaaca tgggtgctct tggagctgtg aactggactc ccctgcacct agctgcacgc     2280
cacggggagg aggcggtggt gtcagcactg ctgcagtgtg gggctgaccc caatgctgca     2340
gagcagtcag gctggacacc cctccacctg gcggtccaga ggagcacctt cctgagtgtc     2400
atcaacctcc tagaacatca cgcaaatgtc cacgcccgca acaaggtggg ctggacaccc     2460
gcccacctgg ccgccctcaa gggcaacaca gccatcctca aagtgctggt cgaggcaggc     2520
gcccagctgg acgtccagga tggagtgagc tgcacacccc tgcaactggc cctccgcagc     2580
cgaaagcagg gcatcatgtc cttcctagag ggcaaggagc cgtcagtggc cactctgggt     2640
ggttctaagc caggagccga gatggaaatt tagacaactt ggccagccgt ggtggc         2696
```

<210> SEQ ID NO 8
<211> LENGTH: 2696
<212> TYPE: DNA
<213> ORGANISM: Homo sapiens

<400> SEQUENCE: 8

```
taaataaact ggatccaact tctcaggctg gacttcttcc agcttcggga caccttctcc       60
cagcatccct ccctaggggg aactggggaa aatcaaaggc tgagacaggg gaaatgcgag      120
ggcttcggag ggacataccc tcttccccag gcccaggtcg ctccatccct gctggggcct     180
cagggctcat gtctgggatt tccccacctt tgcggggcag gagcggctcc tcttgggcgg     240
```

-continued

| | |
|---|---|
| ggaaggaggc agggccggct cgtctcccca ttccctctc ccggacccga ggagcaggaa | 300 |
| gcggcggctc cttcggccac ccaggcagca gccacacgg ggagtgcgcg gcgcggggac | 360 |
| aggaagagag gggcaatggc tgccgacccc accgagctgc ggctgggcag cctccccgtc | 420 |
| ttcacccgcg acgacttcga gggcgactgg cgcctagtgg ccagcggcgg cttcagccag | 480 |
| gtgttccagg cgcggcacag gcgctggcgg acggagtacg ccatcaagtg cgcccctgc | 540 |
| cttccacccg acgccgccag ctctgatgtg aattacctca ttgaagaagc tgccaaaatg | 600 |
| aagaagatca agtttcagca catcgtgtct atctacgggg tgtgcaagca gcccctgggt | 660 |
| attgtgatgg agtttatggc caacggctcc ctggagaagg tgctgtccac ccacagcctc | 720 |
| tgctggaagc tcaggttccg catcatccat gagaccagct tggccatgaa cttcctgcac | 780 |
| agcattaagc cgcctctgct ccacctggac ctcaagccgg caacatact cctggacagc | 840 |
| aacatgcatg tcaaaatttc agacttcggc ctgtccaagt ggatggaaca gtccacccgg | 900 |
| atgcagtaca tcgagaggtc ggctctgcgg ggcatgctca gctacatccc cctgagatg | 960 |
| ttcctggaga gtaacaaggc cccaggacct aaatatgatg tgtacagctt gcaattgtc | 1020 |
| atctgggagc tactcactca gaagaaacca tactcagggt tcaacatgat gatgattatt | 1080 |
| atccgagtgg cggcaggcat gcggccctcc ctacagcctg tctctgacca atggccaagc | 1140 |
| gaggcccagc agatggtgga cctgatgaaa cgctgctggg accaggaccc caagaagagg | 1200 |
| ccatgctttc tagacattac catcgagaca gacatactgc tgtcactgct gcagagtcgt | 1260 |
| gtggcagtcc cagagagcaa ggccctggcc aggaaggtgt cctgcaagct gtcgctgcgc | 1320 |
| cagcccgggg aggttaatga ggacatcagc caggaactga tggacagtga ctcaggaaac | 1380 |
| tacctgaagc gggcccttca gctctccgac cgtaagaatt tggtcccgag agatgaggaa | 1440 |
| ctgtgtatct atgagaacaa ggtcaccccc ctccacttcc tggtggccca gggcagtgtg | 1500 |
| gagcaggtga ggttgctgct ggcccacgag gtagacgtgg actgcagac ggcctctgga | 1560 |
| tacacgcccc tcctgatcgc cgcccaggac cagcaacccg acctctgtgc cctgcttttg | 1620 |
| gcacatggtg ctgatgccaa ccgagtggat gaggatggct gggcccccact gcactttgca | 1680 |
| gcccagaatg gggatgacgg cactgcgcgc ctgctcctgg accacggggc ctgtgtggat | 1740 |
| gcccaggaac gtgaagggtg gaccctctt cacctggctg cacagaataa ctttgagaat | 1800 |
| gtggcacggc ttctggtctc ccgtcaggct gaccccaacc tgcgtgaggc tgagggcaag | 1860 |
| accccctcc atgtgccgc ctactttggc catgttagcc tggtcaagct gctgaccagc | 1920 |
| caggggctg agttggatgc tcagcagaga aacctgagaa caccactgca cctggcagta | 1980 |
| gagcggggca agtgagggc catccaacac ctgctgaaga gtggagcggt ccctgatgcc | 2040 |
| cttgaccaga gcggctatgg cccactgcac actgcagctg ccaggggcaa atacctgatc | 2100 |
| tgcaagatgc tgctcaggta cggagccagc cttgagctgc ccacccacca gggctggaca | 2160 |
| cccctgcatc tagcagccta caaggccac ctggagatca tccatctgct ggcagagagc | 2220 |
| cacgcaaaca tgggtgctct tggagctgtg aactggactc ccctgcacct agctgcacgc | 2280 |
| cacggggagg aggcggtggt gtcagcactg ctgcagtgtg ggctgaccc caatgctgca | 2340 |
| gagcagtcag gctggacacc cctccacctg gcggtccaga ggagcacctt cctgagtgtc | 2400 |
| atcaacctcc tagaacatca cgcaaatgtc cacgcccgca acaaggtggg ctggacaccc | 2460 |
| gcccacctgg ccgccctcaa gggcaacaca gccatcctca agtgctggt cgaggcaggc | 2520 |
| gcccagctga cgtccagga tggagtgagc tgcacacccc tgcaactggc cctccgcagc | 2580 |
| cgaaagcagg gcatcatgtc cttcctagag ggcaaggagc cgtcagtggc cactctgggt | 2640 |

-continued

```
ggttctaagc caggagccga gatggaaatt tagacaactt ggccagccgt ggtggc          2696
```

<210> SEQ ID NO 9
<211> LENGTH: 2696
<212> TYPE: DNA
<213> ORGANISM: Homo sapiens

<400> SEQUENCE: 9

```
taaataaact ggatccaact tctcaggctg gacttcttcc agcttcggga caccttctcc        60
cagcatccct ccctaggggg aactgggaaa atcaaaggc tgagacaggg gaaatgcgag       120
ggcttcggag ggacataccc tcttcccag gcccaggtcg ctccatccct gctgggcct        180
cagggctcat gtctgggatt tccccacctt tgcggggcag gagcggctcc tcttgggcgg      240
ggaaggaggc agggccggct cgtctcccca ttcccctctc ccggacccga ggagcaggaa      300
gcggcggctc cttcggccac ccaggcagca gccacagcgg ggagtgcgcg gcgcggggac      360
aggaagagag gggcaatggc tgccgacccc accgagctgc ggctgggcag cctccccgtc      420
ttcacccgcg acgacttcga gggcgactgg cgcctagtgg ccagcggcgg cttcagccag      480
gtgttccagg cgcggcacag gcgctggcgg acggagtacg ccatcaagtg cgcccctgc       540
cttccacccg acgccgccag ctctgatgtg aattacctca ttgaagaagc tgccaaaatg      600
aagaagatca gtttcagca catcgtgtct atctacgggg tgtgcaagca gcccctgggt      660
attgtgatgg agtttatggc caacggctcc ctggagaagg tgctgtccac ccacagcctc      720
tgctggaagc tcaggttccg catcatccat gagaccagct tggccatgaa cttcctgcac      780
agcattaagc gcctctgct ccacctggac ctcaagccgg caacatact cctggacagc       840
aacatgcatg tcaaaatttc agacttcggc ctgtccaagt ggatggaaca gtccacccgg      900
atgcagtaca tcgagaggtc ggctctgcgg ggcatgctca gctacatccc ccctgagatg      960
ttcctggaga gtaacaaggc cccaggacct aaatatgatg tgtacagctt tgcaattgtc     1020
atctgggagc tactcactca gaagaaacca tactcagggt tcaacatgat gatgattatt     1080
atccgagtgg cggcaggcat gcggccctcc ctacagcctg tctctgacca atggccaagc     1140
gaggcccagc agatggtgga cctgatgaaa cgctgctggg accaggaccc caagaagagg     1200
ccatgctttc tagacattac catcgagaca gacatactgc tgtcactgct gcagagtcgt     1260
gtggcagtcc cagagagcaa ggccctggcc aggaaggtgt cctgcaagct gtcgctgcgc     1320
cagcccgggg aggttaatga ggacatcagc caggaactga tggacagtga ctcaggaaac     1380
tacctgaagc gggcccttca gctctccgac cgtaagaatt tggtcccgag agatgaggaa     1440
ctgtgtatct atgagaacaa ggtcaccccc ctccacttcc tggtgccca gggcagtgtg      1500
gagcaggtga ggttgctgct ggcccacgag gtagacgtgg actgccagac ggcctctgga     1560
tacacgcccc tcctgatcgc cgcccaggac cagcaacccg acctctgtgc cctgcttttg     1620
gcacatggtg ctgatgccaa ccgagtggat gaggatggct gggccccact gcactttgca     1680
gcccagaatg gggatgacgg cactcgcgcg ctgctcctgg accacggggc ctgtgtggat     1740
gcccaggaac gtgaagggtg gacccctctt cacctggctg cacagaataa ctttgagaat     1800
gtggcacggt ttctggtctc ccgtcaggct gaccccaacc tgcatgaggc tgagggcaag     1860
acccccctcc atgtggccgc ctactttggc catgttagcc tggtcaagct gctgaccagc     1920
caggggctg agttggatgc tcagcagaga aacctgagaa caccactgca cctggcagta     1980
gagcggggca aagtgaggc catccaacac ctgctgaaga gtggagcggt ccctgatgcc     2040
```

-continued

| | |
|---|---|
| cttgaccaga gcggctatgg cccactgcac actgcagctg ccaggggcaa atacctgatc | 2100 |
| tgcaagatgc tgctcaggta cggagccagc cttgagctgc ccacccacca gggctggaca | 2160 |
| cccctgcatc tagcagccta caagggccac ctggagatca tccatctgct ggcagagagc | 2220 |
| cacgcaaaca tgggtgctct tggagctgtg aactggactc ccctgcacct agctgcacgc | 2280 |
| cacggggagg aggcggtggt gtcagcactg ctgcagtgtg gggctgaccc caatgctgca | 2340 |
| gagcagtcag gctggacacc cctccacctg gcggtccaga ggagcacctt cctgagtgtc | 2400 |
| atcaacctcc tagaacatca cgcaaatgtc cacgcccgca acaaggtggg ctggacaccc | 2460 |
| gcccacctgg ccgccctcaa gggcaacaca gccatcctca agtgctggt cgaggcaggc | 2520 |
| gcccagctgg acgtccagga tggagtgagc tgcacacccc tgcaactggc cctccgcagc | 2580 |
| cgaaagcagg gcatcatgtc cttcctagag ggcaaggagc cgtcagtggc cactctgggt | 2640 |
| ggttctaagc caggagccga gatggaaatt tagacaactt ggccagccgt ggtggc | 2696 |

<210> SEQ ID NO 10
<211> LENGTH: 2696
<212> TYPE: DNA
<213> ORGANISM: Homo sapiens

<400> SEQUENCE: 10

| | |
|---|---|
| taaataaact ggatccaact tctcaggctg gacttcttcc agcttcggga caccttctcc | 60 |
| cagcatccct ccctaggggg aactggggaa aatcaaaggc tgagacaggg gaaatgcgag | 120 |
| ggcttcggag ggacataccc tcttccccag gcccaggtcg ctccatccct gctggggcct | 180 |
| cagggctcat gtctgggatt tccccacctt tgcggggcag gagcggctcc tcttgggcgg | 240 |
| ggaaggaggc agggccggct cgtctcccca ttcccctctc ccggacccga ggagcaggaa | 300 |
| gcggcggctc cttcggccac ccaggcagca gccacagcgg ggagtgcgcg cgcggggac | 360 |
| aggaagagag gggcaatggc tgccgacccc accgagctgc ggctgggcag cctccccgtc | 420 |
| ttcacccgcg acgacttcga gggcgactgg cgcctagtgg ccagcggcgg cttcagccag | 480 |
| gtgttccagg cgcggcacag gcgctggcgg acggagtacg ccatcaagtg cgcccctgc | 540 |
| cttccacccg acgccgccag ctctgatgtg aattacctca ttgaagaagc tgccaaaatg | 600 |
| aagaagatca gtttcagca catcgtgtct atctacgggg tgtgcaagca gcccctgggt | 660 |
| attgtgatgg agtttatggc caacggctcc ctggagaagg tgctgtccac ccacagcctc | 720 |
| tgctggaagc tcaggttccg catcatccat gagaccagct tggccatgaa cttcctgcac | 780 |
| agcattaagc cgcctctgct ccacctggac ctcaagccgg gcaacatact cctggacagc | 840 |
| aacatgcatg tcaaaatttc agacttcggc ctgtccaagt ggatggaaca gtccacccgg | 900 |
| atgcagtaca tcgagaggtc ggctctgcgg ggcatgctca gctacatccc ccctgagatg | 960 |
| ttcctggaga gtaacaaggc cccaggacct aaatatgatg tgtacagctt tgcaattgtc | 1020 |
| atctgggagc tactcactca gaagaaacca tactcagggt tcaacatgat gatgattatt | 1080 |
| atccgagtgg cggcaggcat gcggccctcc ctacagcctg tctctgacca atggccaagc | 1140 |
| gaggcccagc agatggtgga cctgatgaaa cgctgctggg accaggaccc caagaagagg | 1200 |
| ccatgctttc tagacattac catcgagaca gacatactgc tgtcactgct gcagagtcgt | 1260 |
| gtggcagtcc cagagagcaa ggccctggcc aggaaggtgt cctgcaagct gtcgctgcgc | 1320 |
| cagcccgggg aggttaatga ggacatcagc caggaactga tggacagtga ctcaggaaac | 1380 |
| tacctgaagc gggcccttca gctctccgac cgtaagaatt tggtcccgag agatgaggaa | 1440 |

-continued

```
ctgtgtatct atgagaacaa ggtcaccccc ctccacttcc tggtggccca gggcagtgtg       1500
gagcaggtga ggttgctgct ggcccacgag gtagacgtgg actgccagac ggcctctgga       1560
tacacgcccc tcctgatcgc cgcccaggac cagcaacccg acctctgtgc cctgcttttg       1620
gcacatggtg ctgatgccaa ccgagtggat gaggatggct gggccccact gcactttgca       1680
gcccagaatg gggatgacgg cactgcgcgc tgctcctgg accacggggc ctgtgtggat        1740
gcccaggaac gtgaagggtg gacccctctt cacctggctg cacagaataa ctttgagaat       1800
gtggcacggc ttctggtctc ccgtcaggct gaccccaacc tgcatgaggc tgagggcaag       1860 accccctcc atgtggccgc ctactttggc catgttagcc tggtcaagct gctgaccagc        1920 caggggctg agttggatgc tcagcagaga aacctgagaa caccactgca cctggcagta       1980
gagcggggca aagtgagggc catccaacac ctgctgaaga gtggagcggt ccctgatgcc       2040
cttgaccaga cggctacgg cccactgcac actgcagctg ccaggggcaa atacctgatc        2100
tgcaagatgc tgctcaggta cggagccagc cttgagctgc ccaccacca gggctggaca       2160 cccctgcatc tagcagccta caagggccac ctggagatca tccatctgct ggcagagagc       2220
cacgcaaaca tgggtgctct tggagctgtg aactggactc ccctgcacct agctgcacgc       2280
cacggggagg aggcggtggt gtcagcactg ctgcagtgtg gggctgaccc caatgctgca       2340
gagcagtcag gctggacacc cctccacctg gcggtccaga ggagcacctt cctgagtgtc       2400
atcaacctcc tagaacatca cgcaaatgtc cacgcccgca acaaggtggg ctggacaccc       2460
gcccacctgg ccgccctcaa gggcaacaca gccatcctca agtgctggt cgaggcaggc        2520 gcccagctgg acgtccagga tggagtgagc tgcacacccc tgcaactggc cctccgcagc       2580
cgaaagcagg gcatcatgtc cttcctagag gcaaggagc cgtcagtggc cactctgggt        2640
ggttctaagc caggagccga gatggaaatt tagacaactt ggccagccgt ggtggc          2696
```

<210> SEQ ID NO 11
<211> LENGTH: 2361
<212> TYPE: DNA
<213> ORGANISM: Mus musculus

<400> SEQUENCE: 11

```
atggagggcg agggccgggg ccggtgggct ctggggctgc tgcgcacctt cgacgccggc        60
gaattcgcag gctgggagaa ggtgggctcg ggcggcttcg ggcaggtgta caaggtgcgc       120
catgtgcact ggaagacgtg gctcgcgatc aagtgctcgc cagtctgca cgtcgacgac        180 agggaacgaa tggagctcct ggaggaagct aagaagatgg agatggccaa gttccgatac       240
attctacctg tgtacggcat atgccaggaa cctgtcggct tggtcatgga gtacatggag       300
acaggctccc tggagaagct gctggcctca gagccattgc cttgggacct gcgctttcgc       360
atcgtgcacg agacagccgt gggcatgaac ttcctgcatt gcatgtctcc gccactgctg       420
cacctagacc tgaagccagc gaacatcctg ctggatgccc actaccatgt caagatttct       480
gactttgggc tggccaagtg caatggcatg tcccactctc atgacctcag catggatggc       540
ctgtttggta caatcgctta cctccctcca gagcgaattc gtgagaagag ccgcttgttt       600
gacaccaaac atgatgtata cagcttcgcc attgtgatct gggtgtgct acacagaaga        660 aagccatttg cagatgaaaa gaacatccta cacatcatga tgaaagtggt aaagggccac       720
cgcccagagc tgccacccat ctgcagaccc ggccgcgtg cctgtgccag cctgataggg        780
ctcatgcaac ggtgctggca tgcagaccca caggtgcggc ccaccttcca agaaattacc       840
```

-continued

```
tctgaaacag aagacctttg tgagaagcct gatgaggagg tgaaagacct ggctcatgag      900
ccaggcgaga aagctctct agagtccaag agtgaggcca ggcccgagtc ctcacgcctc       960
aagcgcgcct ctgctccccc cttcgataac gactgcagtc tctccgagtt gctgtcacag     1020
ttggactctg ggatctccca gactcttgaa ggccccgaag agctcagccg aagttcctct     1080
gaatgcaagc tcccatcgtc cagcagtggc aagaggctct cgggggtgtc ctcagtggac     1140
tcagcctttt cctccagagg atcgctgtca ctgtcttttg agcgggaagc ttcaacaggc     1200
gacctgggcc ccacagacat ccagaagaag aagctagtgg atgccatcat atcaggggac     1260
accagcaggc tgatgaagat cctacagccc aagatgtgg acttggttct agacagcagt     1320
gccagcctgc tgcacctggc tgtggaggcc ggacaggagg agtgtgtcaa gtggctgctg     1380
cttaacaatg ccaaccccaa cctgaccaac aggaagggct ctacaccact gcatatggct     1440
gtggagcgga agggacgtgg aattgtggag ctactgctag cccggaagac cagtgtcaat     1500
gccaaggatg aagaccagtg gactgccctg cactttgcag cccagaatgg ggatgaggcc     1560
agcacaaggc tgctgctaga gaagaatgct tctgtcaatg aggtggactt tgagggccga     1620
acacccatgc atgtagcctg ccagcatgga caggagaaca ttgtgcgcac cctgctccgc     1680
cgtggtgtgg atgtgggcct gcagggaaag gatgcctggt tgcctctgca ctatgctgcc     1740
tggcagggcc accttcccat tgttaagctg ctagccaagc agcctgggt gagtgtgaat      1800
gcccagacac tagacgggag gacaccctg cacctggctg tcagagggg gcattaccgt       1860
gtggctcgca ttctcattga cctgtgctct gatgttaaca tctgcagcct acaggcacag     1920
acacctctgc atgttgctgc agagactgga cacactagta ctgccaggct actcttgcat     1980
cgtggtgctg gcaaggaggc tttgacctca gagggctata ctgccttgca cctggcagcc     2040
cagaatggac acctggctac tgtcaagctg ctcatagagg agaaggctga tgtgatggct     2100
cggggtcccc tgaatcagac agcactgcac ctggctgctg cccgtggaca ctcagaggtg     2160
gtagaagagc tggtcagtgc tgacctcatt gacctgtctg atgagcaggg cctcagcgca     2220
ctgcacctag ctgctcaggg caggcattca cagactgtgg agacactgct caaacatgga     2280
gcacacatca acttgcagag tctcaagttc caaggaggcc agagctctgc tgccacgttg     2340
ctccgacgca gcaagaccta g                                               2361
```

SEQ ID NO 12
LENGTH: 784
TYPE: PRT
<213> ORGANISM: Homo sapiens

<400> SEQUENCE: 12

```
Met Glu Gly Asp Gly Gly Thr Pro Trp Ala Leu Ala Leu Leu Arg Thr
1               5                   10                  15

Phe Asp Ala Gly Glu Phe Thr Gly Trp Glu Lys Val Gly Ser Gly Gly
            20                  25                  30

Phe Gly Gln Val Tyr Lys Val Arg His Val His Trp Lys Thr Trp Leu
        35                  40                  45

Ala Ile Lys Cys Ser Pro Ser Leu His Val Asp Asp Arg Glu Arg Met
    50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Arg Glu Pro Val Gly Leu Val Met
                85                  90                  95
```

```
Glu Tyr Met Glu Thr Gly Ser Leu Glu Lys Leu Leu Ala Ser Glu Pro
            100                 105                 110

Leu Pro Trp Asp Leu Arg Phe Arg Ile Ile His Glu Thr Ala Val Gly
            115                 120                 125

Met Asn Phe Leu His Cys Met Ala Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Leu Ser His Ser His Asp Leu
                165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
            195                 200                 205

Phe Ala Ile Val Ile Trp Gly Val Leu Thr Gln Lys Lys Pro Phe Ala
            210                 215                 220

Asp Glu Lys Asn Ile Leu His Ile Met Val Lys Val Lys Gly His
225                 230                 235                 240

Arg Pro Glu Leu Pro Pro Val Cys Arg Ala Arg Pro Arg Ala Cys Ser
                245                 250                 255

His Leu Ile Arg Leu Met Gln Arg Cys Trp Gln Gly Asp Pro Arg Val
            260                 265                 270

Arg Pro Thr Phe Gln Glu Ile Thr Ser Glu Thr Glu Asp Leu Cys Glu
            275                 280                 285

Lys Pro Asp Asp Glu Val Lys Glu Thr Ala His Asp Leu Asp Val Lys
    290                 295                 300

Ser Pro Pro Glu Pro Arg Ser Glu Val Val Pro Ala Arg Leu Lys Arg
305                 310                 315                 320

Ala Ser Ala Pro Thr Phe Asp Asn Asp Tyr Ser Leu Ser Glu Leu Leu
                325                 330                 335

Ser Gln Leu Asp Ser Gly Val Ser Gln Ala Val Glu Gly Pro Glu Glu
            340                 345                 350

Leu Ser Arg Ser Ser Glu Ser Lys Leu Pro Ser Ser Gly Ser Gly
            355                 360                 365

Lys Arg Leu Ser Gly Val Ser Ser Val Asp Ser Ala Phe Ser Ser Arg
370                 375                 380

Gly Ser Leu Ser Leu Ser Phe Glu Arg Glu Pro Ser Thr Ser Asp Leu
385                 390                 395                 400

Gly Thr Thr Asp Val Gln Lys Lys Lys Leu Val Asp Ala Ile Val Ser
                405                 410                 415

Gly Asp Thr Ser Lys Leu Met Lys Ile Leu Gln Pro Gln Asp Val Asp
                420                 425                 430

Leu Ala Leu Asp Ser Gly Ala Ser Leu Leu His Leu Ala Val Glu Ala
            435                 440                 445

Gly Gln Glu Glu Cys Ala Lys Trp Leu Leu Leu Asn Asn Ala Asn Pro
    450                 455                 460

Asn Leu Ser Asn Arg Arg Gly Ser Thr Pro Leu His Met Ala Val Glu
465                 470                 475                 480

Arg Arg Val Arg Gly Val Val Glu Leu Leu Ala Arg Lys Ile Ser
                485                 490                 495

Val Asn Ala Lys Asp Glu Asp Gln Trp Thr Ala Leu His Phe Ala Ala
            500                 505                 510

Gln Asn Gly Asp Glu Ser Ser Thr Arg Leu Leu Leu Glu Lys Asn Ala
```

```
              515                 520                 525
Ser Val Asn Glu Val Asp Phe Glu Gly Arg Thr Pro Met His Val Ala
    530                 535                 540

Cys Gln His Gly Gln Glu Asn Ile Val Arg Ile Leu Leu Arg Arg Gly
545                 550                 555                 560

Val Asp Val Ser Leu Gln Gly Lys Asp Ala Trp Leu Pro Leu His Tyr
                565                 570                 575

Ala Ala Trp Gln Gly His Leu Pro Ile Val Lys Leu Leu Ala Lys Gln
            580                 585                 590

Pro Gly Val Ser Val Asn Ala Gln Thr Leu Asp Gly Arg Thr Pro Leu
        595                 600                 605

His Leu Ala Ala Gln Arg Gly His Tyr Arg Val Ala Arg Ile Leu Ile
    610                 615                 620

Asp Leu Cys Ser Asp Val Asn Val Cys Ser Leu Leu Ala Gln Thr Pro
625                 630                 635                 640

Leu His Val Ala Ala Glu Thr Gly His Thr Ser Thr Ala Arg Leu Leu
                645                 650                 655

Leu His Arg Gly Ala Gly Lys Glu Ala Val Thr Ser Asp Gly Tyr Thr
            660                 665                 670

Ala Leu His Leu Ala Ala Arg Asn Gly His Leu Ala Thr Val Lys Leu
        675                 680                 685

Leu Val Glu Lys Ala Asp Val Leu Ala Arg Gly Pro Leu Asn Gln
    690                 695                 700

Thr Ala Leu His Leu Ala Ala His Gly His Ser Glu Val Val Glu
705                 710                 715                 720

Glu Leu Val Ser Ala Asp Val Ile Asp Leu Phe Asp Glu Gln Gly Leu
                725                 730                 735

Ser Ala Leu His Leu Ala Ala Gln Gly Arg His Ala Gln Thr Val Glu
            740                 745                 750

Thr Leu Leu Arg His Gly Ala His Ile Asn Leu Gln Ser Leu Lys Phe
        755                 760                 765

Gln Gly Gly His Gly Pro Ala Ala Thr Leu Leu Arg Arg Ser Lys Thr
    770                 775                 780

<210> SEQ ID NO 13
<211> LENGTH: 786
<212> TYPE: PRT
<213> ORGANISM: Mus musculus

<400> SEQUENCE: 13

Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
                20                  25                  30

Phe Gly Gln Val Tyr Lys Val Arg His Val His Trp Lys Thr Trp Leu
            35                  40                  45

Ala Ile Lys Cys Ser Pro Ser Leu His Val Asp Asp Arg Glu Arg Met
        50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110
```

```
Leu Pro Trp Asp Leu Arg Phe Arg Ile Val His Glu Thr Ala Val Gly
        115                 120                 125

Met Asn Phe Leu His Cys Met Ser Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
                165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

Phe Ala Ile Val Ile Trp Gly Val Leu Thr Gln Lys Lys Pro Phe Ala
    210                 215                 220

Asp Glu Lys Asn Ile Leu His Ile Met Met Lys Val Val Lys Gly His
225                 230                 235                 240

Arg Pro Glu Leu Pro Pro Ile Cys Arg Pro Arg Pro Arg Ala Cys Ala
                245                 250                 255

Ser Leu Ile Gly Leu Met Gln Arg Cys Trp His Ala Asp Pro Gln Val
            260                 265                 270

Arg Pro Thr Phe Gln Glu Ile Thr Ser Glu Thr Glu Asp Leu Cys Glu
        275                 280                 285

Lys Pro Asp Glu Glu Val Lys Asp Leu Ala His Glu Pro Gly Glu Lys
    290                 295                 300

Ser Ser Leu Glu Ser Lys Ser Glu Ala Arg Pro Glu Ser Ser Arg Leu
305                 310                 315                 320

Lys Arg Ala Ser Ala Pro Pro Phe Asp Asn Asp Cys Ser Leu Ser Glu
                325                 330                 335

Leu Leu Ser Gln Leu Asp Ser Gly Ile Ser Gln Thr Leu Glu Gly Pro
            340                 345                 350

Glu Glu Leu Ser Arg Ser Ser Glu Cys Lys Leu Pro Ser Ser Ser
        355                 360                 365

Ser Gly Lys Arg Leu Ser Gly Val Ser Ser Val Asp Ser Ala Phe Ser
    370                 375                 380

Ser Arg Gly Ser Leu Ser Leu Ser Phe Glu Arg Glu Ala Ser Thr Gly
385                 390                 395                 400

Asp Leu Gly Pro Thr Asp Ile Gln Lys Lys Leu Val Asp Ala Ile
                405                 410                 415

Ile Ser Gly Asp Thr Ser Arg Leu Met Lys Ile Leu Gln Pro Gln Asp
            420                 425                 430

Val Asp Leu Val Leu Asp Ser Ala Ser Leu Leu His Leu Ala Val
        435                 440                 445

Glu Ala Gly Gln Glu Glu Cys Val Lys Trp Leu Leu Leu Asn Asn Ala
    450                 455                 460

Asn Pro Asn Leu Thr Asn Arg Lys Gly Ser Thr Pro Leu His Met Ala
465                 470                 475                 480

Val Glu Arg Lys Gly Arg Gly Ile Val Glu Leu Leu Leu Ala Arg Lys
                485                 490                 495

Thr Ser Val Asn Ala Lys Asp Glu Asp Gln Trp Thr Ala Leu His Phe
            500                 505                 510

Ala Ala Gln Asn Gly Asp Glu Ala Ser Thr Arg Leu Leu Leu Glu Lys
        515                 520                 525

Asn Ala Ser Val Asn Glu Val Asp Phe Glu Gly Arg Thr Pro Met His
```

```
        530             535             540
Val Ala Cys Gln His Gly Gln Glu Asn Ile Val Arg Thr Leu Leu Arg
545                 550                 555                 560

Arg Gly Val Asp Val Gly Leu Gln Gly Lys Asp Ala Trp Leu Pro Leu
                565                 570                 575

His Tyr Ala Ala Trp Gln Gly His Leu Pro Ile Val Lys Leu Leu Ala
                580                 585                 590

Lys Gln Pro Gly Val Ser Val Asn Ala Gln Thr Leu Asp Gly Arg Thr
                595                 600                 605

Pro Leu His Leu Ala Ala Gln Arg Gly His Tyr Arg Val Ala Arg Ile
                610                 615                 620

Leu Ile Asp Leu Cys Ser Asp Val Asn Ile Cys Ser Leu Gln Ala Gln
625                 630                 635                 640

Thr Pro Leu His Val Ala Ala Glu Thr Gly His Thr Ser Thr Ala Arg
                645                 650                 655

Leu Leu His Arg Gly Ala Gly Lys Glu Ala Leu Thr Ser Glu Gly
                660                 665                 670

Tyr Thr Ala Leu His Leu Ala Ala Gln Asn Gly His Leu Ala Thr Val
                675                 680                 685

Lys Leu Leu Ile Glu Glu Lys Ala Asp Val Met Ala Arg Gly Pro Leu
                690                 695                 700

Asn Gln Thr Ala Leu His Leu Ala Ala Arg Gly His Ser Glu Val
705                 710                 715                 720

Val Glu Glu Leu Val Ser Ala Asp Leu Ile Asp Leu Ser Asp Glu Gln
                725                 730                 735

Gly Leu Ser Ala Leu His Leu Ala Ala Gln Gly Arg His Ser Gln Thr
                740                 745                 750

Val Glu Thr Leu Leu Lys His Gly Ala His Ile Asn Leu Gln Ser Leu
                755                 760                 765

Lys Phe Gln Gly Gly Gln Ser Ser Ala Ala Thr Leu Leu Arg Arg Ser
                770                 775                 780

Lys Thr
785

<210> SEQ ID NO 14
<211> LENGTH: 2355
<212> TYPE: DNA
<213> ORGANISM: Homo sapiens

<400> SEQUENCE: 14
atggagggcg acggcgggac cccatgggcc ctggcgctgc tgcgcacctt cgacgcgggc      60
gagttcacgg gctgggagaa ggtgggctcg ggcggcttcg gcaggtgta caaggtgcgc     120 catgtccact ggaagacctg gctggccatc aagtgctcgc cagcctgca cgtcgacgac     180 agggagcgca tggagctttt ggaagaagcc aagaagatgg agatggccaa gtttcgctac     240
atcctgcctg tgtatggcat ctgccgcgaa cctgtcggcc tggtcatgga gtacatggag     300
acgggctccc tggaaaagct gctggcttcg agccattgc catgggatct ccggttccga     360
atcatccacg agacggcggt gggcatgaac ttcctgcact gcatggcccc gccactcctg     420
cacctggacc tcaagcccgc gaacatcctg ctggatgccc actaccacgt caagatttct     480
gattttggtc tggccaagtg caacgggctg tcccactcgc atgacctcag catggatggc     540
ctgtttggca caatcgccta cctccctcca gagcgcatca gggagaagag ccggctctcc     600
gacaccaagc acgatgtata cagctttgcg atcgtcatct ggggcgtgct cacacagaag     660
```

-continued

```
aagccgtttg cagatgagaa gaacatcctg cacatcatgg tgaaggtggt gaagggccac      720
cgccccgagc tgccgcccgt gtgcagagcc cggccgcgcg cctgcagcca cctgatacgc      780
ctcatgcagc ggtgctggca gggggatccg cgagttaggc ccaccttcca agaaattact      840
tctgaaaccg aggacctgtg tgaaaagcct gatgacgaag tgaaagaaac tgctcatgat      900
ctggacgtga aaagcccccc ggagcccagg agcgaggtgg tgcctgcgag gctcaagcgg      960
gcctctgccc ccaccttcga taacgactac agcctctccg agctgctctc acagctggac     1020
tctggagttt cccaggctgt cgagggcccc gaggagctca gccgcagctc ctctgagtcc     1080
aagctgccat cgtccggcag tgggaagagg ctctcggggg tgtcctcggt ggactccgcc     1140
ttctcttcca gaggatcact gtcgctgtcc tttgagcggg aaccttcaac cagcgatctg     1200
ggcaccacag acgtccagaa gaagaagctt gtggatgcca tcgtgtccgg ggacaccagc     1260
aaactgatga agatcctgca gccgcaggac gtggacctgg cactggacag cggtgccagc     1320
ctgctgcacc tggcggtgga ggccgggcaa gaggagtgcg ccaagtggct gctgctcaac     1380
aatgccaacc ccaacctgag caaccgtagg ggctccaccc cgttgcacat ggccgtggag     1440
aggagggtgc ggggtgtcgt ggagctcctg ctggcgcgga agatcagtgt caacgccaag     1500
gatgaggacc agtggacagc cctccacttt gcagcccaga acgggacga gtctagcaca     1560 cggctgctgt tggagaagaa cgcctcggtc aacgaggtgg actttgaggg ccggacgccc     1620
atgcacgtgg cctgccagca cgggcaggag aatatcgtgc gcatcctgct gcgccgaggc     1680
gtggacgtga gcctgcaggg caaggatgcc tggctgccac tgcactacgc tgcctggcag     1740
ggccacctgc ccatcgtcaa gctgctggcc aagcagccgg gggtgagtgt gaacgcccag     1800
acgctggatg gaggacgcc attgcacctg ccgcacagc gcgggcacta ccgcgtggcc      1860
cgcatcctca tcgacctgtg ctccgacgtc aacgtctgca gcctgctggc acagacaccc     1920
ctgcacgtgg ccgcggagac ggggcacacg agcactgcca ggctgctcct gcatcggggc     1980
gctggcaagg aggccgtgac ctcagacggc tacaccgctc tgcacctggc tgcccgcaac     2040
ggacacctgc ccactgtcaa gctgcttgtc gaggagaagg ccgatgtgct ggcccgggga     2100
cccctgaacc agacggcgct gcacctggct gccgcccacg ggcactcgga ggtggtggag     2160
gagttggtca gcgccgatgt cattgacctg ttcgacgagc aggggctcag cgcgctgcac     2220
ctggccgccc agggccggca cgcacagacg gtggagactc tgctcaggca tggggcccac     2280
atcaacctgc agagcctcaa gttccagggc ggccatggcc ccgccgccac actcctgcgg     2340
cgaagcaaga cctag                                                     2355
```

<210> SEQ ID NO 15
<211> LENGTH: 2355
<212> TYPE: DNA
<213> ORGANISM: Homo sapiens

<400> SEQUENCE: 15

```
atggagggcg acggcgggac cccatgggcc ctggcgctgc tgcgcacctt cgacgcgggc       60
gagttcacgg gctgggagaa ggtgggctcg ggcggcttcg ggcaggtgta caaggtgcgc      120
catgtccact ggaagacctg gctggccatc aagtgctcgc ccagcctgca cgtcgacgac      180
agggagcgca tggagctttt ggaagaagcc aagaagatgg agatggccaa gtttcgctac      240
atcctgcctg tgtatggcat ctgccgcgaa cctgtcggcc tggtcatgga gtacatggag      300
acgggctccc tggaaaagct gctggcttcg gagccattgc catgggatct ccggttccga      360
```

```
atcatccacg agacggcggt gggcatgaac ttcctgcact gcatggcccc gccactcctg      420
cacctggacc tcaagcccgc gaacatcctg ctggatgccc actaccacgt caagatttct      480
gattttggtc tggccaagtg caacgggctg tcccactcgc atgacctcag catggatggc      540
ctgtttggca caatcgccta cctccctcca gagcgcatca gggagaagag ccggctcttc      600
gacaccaagc acgatgtata cagctttgcg atcgtcatct ggggcgtgct cacacagaag      660
aagccgtttg cagatgagaa gaacatcctg cacatcatgt gaaggtggt gaagggccac       720 cgccccgagc tgccgcccgt gtgcagagcc cggccgcgcg cctgcagcca cctgatacgc      780
ctcatgcagc ggtgctggca gggggatccg cgagttaggc ccaccttcca agaaattact      840
tctgaaaccg aggacctgtg tgaaaagcct gatgacgaag tgaaagaaac tgctcatgat      900
ctggacgtga aaagcccccc ggagcccagg agcgaggtgg tgcctgcgag gctcaagcgg      960
gcctctgccc ccaccttcga taacgactac agcctctccg agcttctctc acagctggac     1020
tctggagttt cccaggctgt cgaggcccc gaggagctca gccgcagctc ctctgagtcc      1080
aagctgccat cgtccggcag tgggaagagg ctctcggggg tgtcctcggt ggactccgcc     1140
ttctcttcca gaggatcact gtcgctgtcc tttgagcggg aaccttcaac cagcgatctg     1200
ggcaccacag acgtccagaa gaagaagctt gtggatgcca tcgtgtccgg ggacaccagc     1260
aaactgatga gatcctgca gccgcaggac gtggacctgg cactggacag cggtgccagc      1320
ctgctgcacc tggcggtgga ggccgggcaa gaggagtgcg ccaagtggct gctgctcaac     1380
aatgccaacc caacctgag caaccgtagg ggctccaccc cgttgcacat ggccgtggag      1440
aggagggtgc ggggtgtcgt ggagctcctg ctggcgcgga agatcagtgt caacgccaag     1500
gatgaggacc agtggacagc cctccacttt gcagcccaga cgggacga gtctagcaca       1560 cggctgctgt tggagaagaa cgcctcggtc aacgaggtgg actttgaggg ccggacgccc     1620
atgcacgtgg cctgccagca cgggcaggag aatatcgtgc gcatcctgct cgccgaggc     1680 gtggacgtga gcctgcaggg caaggatgcc tggctgccac tgcactacgc tgcctggcag     1740
ggccacctgc ccatcgtcaa gctgctggcc aagcagccgg gggtgagtgt gaacgcccag     1800
acgctggatg ggaggacgcc attgcacctg gccgcacagc gcgggcacta ccgcgtggcc     1860
cgcatcctca tcgacctgtg ctccgacgtc aacgtctgca gcctgctggc acagacaccc     1920
ctgcacgtgg ccgcggagac ggggcacacg agcactgcca ggctgctcct gcatcggggc     1980
gctggcaagg aggccgtgac ctcagacggc tacaccgctc tgcacctggc tgcccgcaac     2040
ggacacctgg ccactgtcaa gctgcttgtc gaggagaagg ccgatgtgct ggcccgggga     2100
cccctgaacc agacggcgct gcacctggct gccgcccacg gcactcgga ggtggtggag       2160 gagttggtca gcgccgatgt cattgacctg ttcgacgagc aggggctcag cgcgctgcac     2220
ctggccgccc agggccggca cgcacagacg gtggagactc tgctcaggca tggggcccac     2280
atcaacctgc agagcctcaa gttccagggc ggccatggcc ccgccgccac actcctgcgg     2340
cgaagcaaga cctag                                                      2355
```

<210> SEQ ID NO 16
<211> LENGTH: 2355
<212> TYPE: DNA
<213> ORGANISM: Homo sapiens

<400> SEQUENCE: 16

```
atggagggcg acggcgggac cccatggggcc ctggcgctgc tgcgcacctt cgacgcgggc       60
gagttcacgg gctgggagaa ggtgggctcg ggcggcttcg ggcaggtgta caaggtgcgc     120
```

-continued

| | |
|---|---|
| catgtccact ggaagacctg gctggccatc aagtgctcgc ccagcctgca cgtcgacgac | 180 |
| agggagcgca tggagctttt ggaagaagcc aagaagatgg agatggccaa gtttcgctac | 240 |
| atcctgcctg tgtatggcat ctgccgcgaa cctgtcggcc tggtcatgga gtacatggag | 300 |
| acgggctccc tggaaaagct gctggcttcg gagccattgc catgggatct ccggttccga | 360 |
| atcatccacg agacggcggt gggcatgaac ttcctgcact gcatggcccc gccactcctg | 420 |
| cacctggacc tcaagcccgc gaacatcctg ctggatgccc actaccacgt caagatttct | 480 |
| gattttggtc tggccaagtg caacgggctg tcccactcgc atgacctcag catggatggc | 540 |
| ctgtttggca caatcgccta cctccctcca gagcgcatca gggagaagag ccggctcttc | 600 |
| gacaccaagc acgatgtata cagctttgcg atcgtcatct ggggcgtgct cacacagaag | 660 |
| aagccgtttg cagatgagaa gaacatcctg cacatcatgt gaaggtggt gaagggccac | 720 |
| cgccccgagc tgccgcccgt gtgcagagcc cggccgcgcg cctgcagcca cctgatacgc | 780 |
| ctcatgcagc ggtgctggca gggggatccg cgagttaggc ccaccttcca agaaaattact | 840 |
| tctgaaaccg aggacctgtg tgaaaagcct gatgacgaag tgaaagaaac tgctcatgat | 900 |
| ctggacgtga aaagccccc ggagcccagg agcgaggtgg tgcctgcgag gctcaagcgg | 960 |
| gcctctgccc ccaccttcga taacgactac agcctctccg agctgctctc acagctggac | 1020 |
| tctggagttt cccaggctgt cgagggcccc gaggagctca ccgcagctc ctctgagtcc | 1080 |
| aagctgccat cgtccggcag tgggaagagg ctctcggggg tgtcctcggt ggactccgcc | 1140 |
| ttctcttcca gaggatcact gtcgctgtcc tttgagcggg aaccttcaac cagcgatctg | 1200 |
| ggtaccacag acgtccagaa gaagaagctt gtggatgcca tcgtgtccgg ggacaccagc | 1260 |
| aaactgatga agatcctgca gccgcaggac gtggacctgg cactggacag cggtgccagc | 1320 |
| ctgctgcacc tggcggtgga ggccgggcaa gaggagtgcg ccaagtggct gctgctcaac | 1380 |
| aatgccaacc caacctgag caaccgtagg ggctccaccc cgttgcacat ggccgtggag | 1440 |
| aggagggtgc ggggtgtcgt ggagctcctg ctggcgcgga agatcagtgt caacgccaag | 1500 |
| gatgaggacc agtggacagc cctccacttt gcagcccaga acgggacga gtctagcaca | 1560 |
| cggctgctgt tggagaagaa cgcctcggtc aacgaggtgg actttgaggg ccggacgccc | 1620 |
| atgcacgtgg cctgccagca cgggcaggag aatatcgtgc gcatcctgct gcgccgaggc | 1680 |
| gtggacgtga gcctgcaggg caaggatgcc tggctgccac tgcactacgc tgcctggcag | 1740 |
| ggccacctgc ccatcgtcaa gctgctggcc aagcagccgg gggtgagtgt gaacgcccag | 1800 |
| acgctggatg ggaggacgcc attgcacctg gccgcacagc gcgggcacta ccgcgtggcc | 1860 |
| cgcatcctca tcgacctgtg ctccgacgtc aacgtctgca gcctgctggc acagacaccc | 1920 |
| ctgcacgtgg ccgcggagac ggggcacacg agcactgcca ggctgctcct gcatcggggc | 1980 |
| gctggcaagg aggccgtgac ctcagacggc tacaccgctc tgcacctggc tgcccgcaac | 2040 |
| ggacacctgg ccactgtcaa gctgcttgtc gaggagaagg ccgatgtgct ggcccgggga | 2100 |
| cccctgaacc agacgcgct gcacctggct gccgcccacg ggcactcgga ggtggtggag | 2160 |
| gagttggtca gcgccgatgt cattgacctg ttcgacgagc aggggctcag cgcgctgcac | 2220 |
| ctggccgccc aggccggca cgcacagacg gtggagactc tgctcaggca tgggccccac | 2280 |
| atcaacctgc agagcctcaa gttccagggc ggccatggcc ccgccgccac actcctgcgg | 2340 |
| cgaagcaaga cctag | 2355 |

<210> SEQ ID NO 17

<211> LENGTH: 2355
<212> TYPE: DNA
<213> ORGANISM: Homo sapiens

<400> SEQUENCE: 17

```
atggagggcg acggcgggac cccatgggcc ctggcgctgc tgcgcacctt cgacgcgggc      60
gagttcacgg gctgggagaa ggtgggctcg ggcggcttcg ggcaggtgta caaggtgcgc     120
catgtccact ggaagacctg gctggccatc aagtgctcgc ccagcctgca cgtcgacgac     180
agggagcgca tggagctttt ggaagaagcc aagaagatgg agatggccaa gtttcgctac     240
atcctgcctg tgtatggcat ctgccgcgaa cctgtcggcc tggtcatgga gtacatggag     300
acgggctccc tggaaaagct gctggcttcg gagccattgc catgggatct ccggttccga     360
atcatccacg agacgcggt gggcatgaac ttcctgcact gcatggcccc gccactcctg     420
cacctggacc tcaagcccgc gaacatcctg ctggatgccc actaccacgt caagatttct     480
gattttggtc tggccaagtg caacgggctg tcccactcgc atgacctcag catggatggc     540
ctgtttggca caatcgccta cctccctcca gagcgcatca gggagaagag ccggctcttc     600
gacaccaagc acgatgtata cagctttgcg atcgtcatct ggggcgtgct cacacagaag     660
aagccgtttg cagatgagaa gaacatcctg cacatcatgg tgaaggtggt gaagggccac     720
cgccccgagc tgccgcccgt gtgcagagcc cggccgcgcg cctgcagcca cctgatacgc     780
ctcatgcagc ggtgctggca gggggatccg cgagttaggc ccaccttcca agaaattact     840
tctgaaaccg aggacctgtg tgaaaagcct gatgacgaag tgaaagaaac tgctcatgat     900
ctggacgtga aaagccccc ggagcccagg agcgaggtgg tgcctgcgag gctcaagcgg     960
gcctctgccc ccaccttcga taacgactac agcctctccg agctgctctc acagctggac    1020
tctggagttt cccaggctgt cgagggcccc gaggagctca gccgcagctc ctctgagtcc    1080
aagctgccat cgtccggcag tgggaagagg ctctcggggg tgtcctcggt ggactccgcc    1140
ttctcttcca gaggatcact gtcgctgtcc tttgagcggg aaccttcaac cagcgatctg    1200
ggcaccacag acgtccagaa gaagaagctt gtggatgcca tcgtgtccgg gacaccagc    1260
aaactgatga agatcctgca gccgcaggac gtggacctgg cactggacag cggtgccagc    1320
ctgctgcacc tggcggtgga ggccgggcaa gaggagtgcg ccaagtggct gctgctcaac    1380
aatgccaacc caacctgag caaccgtagg ggctccaccc cgttgcacat ggccgtggag    1440
aggagggtgc ggggtgtcgt ggagcgcctg ctggcgcgga agatcagtgt caacgccaag    1500
gatgaggacc agtggacagc cctccacttt gcagcccaga acgggacga gtctagcaca    1560
cggctgctgt tgggaagaa cgcctcggtc aacgaggtgg actttgaggg ccggacgccc    1620
atgcacgtgg cctgccagca cgggcaggag aatatcgtgc gcatcctgct cgccgaggc    1680
gtggacgtga gcctgcaggg caaggatgcc tggctgccac tgcactacgc tgcctggcag    1740
ggccacctgc ccatcgtcaa gctgctggcc aagcagccgg gggtgagtgt gaacgcccag    1800
acgctggatg ggaggacgcc attgcacctg gccgcacagc gcgggcacta ccgcgtggcc    1860
cgcatcctca tcgacctgtg ctccgacgtc aacgtctgca gcctgctggc acagacaccc    1920
ctgcacgtgg ccgcggagac ggggcacacg agcactgcca ggctgctcct gcatcggggc    1980
gctggcaagg aggccgtgac ctcagacggc tacaccgctc tgcacctggc tgcccgcaac    2040
ggacacctgg ccactgtcaa gctgcttgtc gaggagaagg ccgatgtgct ggcccgggga    2100
cccctgaacc agacggcgct gcacctggct gccgccacg ggcactcgga ggtggtggag    2160
gagttggtca gcgccgatgt cattgacctg ttcgacgagc aggggctcag cgcgctgcac    2220
```

```
ctggccgccc agggccggca cgcacagacg gtggagactc tgctcaggca tggggcccac    2280
atcaacctgc agagcctcaa gttccagggc ggccatggcc ccgccgccac actcctgcgg    2340
cgaagcaaga cctag                                                    2355

<210> SEQ ID NO 18
<211> LENGTH: 2355
<212> TYPE: DNA
<213> ORGANISM: Homo sapiens

<400> SEQUENCE: 18
atggagggcg acggcgggac cccatgggcc ctggcgctgc tgcgcacctt cgacgcgggc      60
gagttcacgg gctgggagaa ggtgggctcg gcggcttcg gcaggtgta caaggtgcgc      120 catgtccact ggaagacctg ctggccatc aagtgctcgc ccagcctgca cgtcgacgac      180
agggagcgca tggagctttt ggaagaagcc aagaagatgg agatggccaa gtttcgctac      240
atcctgcctg tgtatggcat ctgccgcgaa cctgtcggcc tggtcatgga gtacatggag      300
acgggctccc tggaaaagct gctggcttcg gagccattgc catgggatct ccggttccga      360
atcatccacg agacggcggt gggcatgaac ttcctgcact gcatggcccc gccactcctg      420
cacctggacc tcaagcccgc gaacatcctg ctggatgccc actaccacgt caagatttct      480
gattttggtc tggccaagtg caacgggctg tcccactcgc atgacctcag catggatggc      540
ctgtttggca caatcgccta cctccctcca gagcgcatca gggagaagag ccggctcttc      600
gacaccaagc acgatgtata cagctttgcg atcgtcatct ggggcgtgct cacacagaag      660
aagccgtttg cagatgagaa gaacatcctg cacatcatgg tgaaggtggt gaagggccac      720 cgcccccgagc tgccgcccgt gtgcagagcc cggccgcgcg cctgcagcca cctgatacgc      780
ctcatgcagc ggtgctggca gggggatccg cgagttaggc ccaccttcca agaaattact      840
tctgaaaccg aggacctgtg tgaaaagcct gatgacgaag tgaaagaaac tgctcatgat      900
ctggacgtga aaagcccccc ggagcccagg agcgaggtgg tgcctgcgag gctcaagcgg      960
gcctctgccc ccaccttcga taacgactac agcctctccg agctgctctc acagctggac     1020
tctggagttt cccaggctgt cgagggcccc gaggagctca gccgcagctc ctctgagtcc     1080
aagctgccat cgtccggcag tgggaagagg ctctcggggg tgtcctcggt ggactccgcc     1140
ttctcttcca gaggatcact gtcgctgtcc tttgagcggg aaccttcaac cagcgatctg     1200
ggcaccacag acgtccagaa gaagaagctt gtggatgcca tcgtgtccgg gacaccagc     1260 aaactgatga agatcctgca ccgcaggac gtggacctgg cactggacag cggtgccagc     1320
ctgctgcacc tggcggtgga ggccgggcaa gaggagtgcg ccaagtggct gctgctcaac     1380
aatgccaacc caacctgag caaccgtagg ggctccaccc cgttgcacat ggccgtggag     1440
aggagggtgc ggggtgtcgt ggagctcctg ctggcacgga gatcagtgt caacgccaag     1500 gatgaggacc agtggacagc cctccacttt gcagcccaga cggggacga gtctagcaca     1560 cggctgctgt tggagaagaa cgcctcggtc aacgaggtgg actttgaggg ccggacgccc     1620
atgcacgtgg cctgccagca cgggcaggag aatatcgtgc gcatcctgct gcgccgaggc     1680
gtggacgtga gctgcagggg caaggatgcc tggctgccac tgcactacgc tgcctggcag     1740
ggccacctgc ccatcgtcaa gctgctggcc aagcagccgg gggtgagtgt gaacgcccag     1800
acgctggatg ggaggacgcc attgcacctg gccgcacagc gcgggcacta ccgcgtggcc     1860
cgcatcctca tcgacctgtg ctccgacgtc aacgtctgca gcctgctggc acagacaccc     1920
```

-continued

| | |
|---|---|
| ctgcacgtgg ccgcggagac ggggcacacg agcactgcca ggctgctcct gcatcggggc | 1980 |
| gctggcaagg aggccgtgac ctcagacggc tacaccgctc tgcacctggc tgcccgcaac | 2040 |
| ggacacctgg ccactgtcaa gctgcttgtc gaggagaagg ccgatgtgct ggcccgggga | 2100 |
| cccctgaacc agacggcgct gcacctggct gccgcccacg gcactcgga ggtggtggag | 2160 |
| gagttggtca cgccgatgt cattgacctg ttcgacgagc aggggctcag cgcgctgcac | 2220 |
| ctggccgccc agggccggca cgcacagacg gtggagactc tgctcaggca tggggcccac | 2280 |
| atcaacctgc agagcctcaa gttccagggc ggccatggcc ccgccgccac actcctgcgg | 2340 |
| cgaagcaaga cctag | 2355 |

<210> SEQ ID NO 19
<211> LENGTH: 2355
<212> TYPE: DNA
<213> ORGANISM: Homo sapiens

<400> SEQUENCE: 19

| | |
|---|---|
| atggagggcg acggcgggac cccatgggcc ctggcgctgc tgcgcacctt cgacgcgggc | 60 |
| gagttcacgg gctgggagaa ggtgggctcg ggcggcttcg ggcaggtgta caaggtgcgc | 120 |
| catgtccact ggaagacctg gctggccatc aagtgctcgc ccagcctgca cgtcgacgac | 180 |
| agggagcgca tggagctttt ggaagaagcc aagaagatgg agatggccaa gtttcgctac | 240 |
| atcctgcctg tgtatggcat ctgccgcgaa cctgtcggcc tggtcatgga gtacatggag | 300 |
| acgggctccc tggaaaagct gctggcttcg gagccattgc catgggatct ccggttccga | 360 |
| atcatccacg agacggcggt gggcatgaac ttcctgcact gcatggcccc gccactcctg | 420 |
| cacctggacc tcaagcccgc gaacatcctg ctggatgccc actaccacgt caagatttct | 480 |
| gattttggtc tggccaagtg caacgggctg tcccactcgc atgacctcag catggatggc | 540 |
| ctgtttggca caatcgccta cctccctcca gagcgcatca gggagaagag ccggctcttc | 600 |
| gacaccaagc acgatgtata cagctttgcg atcgtcatct ggggcgtgct cacacagaag | 660 |
| aagccgtttg cagatgagaa gaacatcctg cacatcatgg tgaaggtggt gaagggccac | 720 |
| cgccccgagc tgccgcccgt gtgcagagcc cggccgcgcg cctgcagcca cctgatacgc | 780 |
| ctcatgcagc ggtgctggca gggggatccg cgagttaggc ccaccttcca agaaattact | 840 |
| tctgaaaccg aggacctgtg tgaaaagcct gatgacgaag tgaaagaaac tgctcatgat | 900 |
| ctggacgtga aaagccccc ggagcccagg agcgaggtgg tgcctgcgag gctcaagcgg | 960 |
| gcctctgccc ccaccttcga taacgactac agcctctccg agctgctctc acagctggac | 1020 |
| tctggagttt ccaggctgt cgagggcccc gaggagctca gccgcagctc ctctgagtcc | 1080 |
| aagctgccat cgtccggcag tgggaagagg ctctcggggg tgtcctcggt ggactccgcc | 1140 |
| ttctcttcca gaggatcact gtcgctgtcc tttgagcggg aaccttcaac cagcgatctg | 1200 |
| ggcaccacag acgtccagaa gaagaagctt gtggatgcca tcgtgtccgg ggacaccagc | 1260 |
| aaactgatga agatcctgca gccgcaggac gtggacctgg cactggacag cggtgccagc | 1320 |
| ctgctgcacc tggcggtgga ggccgggcaa gaggagtgcg ccaagtggct gctgctcaac | 1380 |
| aatgccaacc caacctgag caaccgtagg ggctccaccc cgttgcacat ggccgtggag | 1440 |
| aggagggtgc ggggtgtcgt ggagctcctg ctggcgcgga agatcagtgt caacgccaag | 1500 |
| gatgaggacc agtggacagc cctccacttt gcagcccaga acgggatga gtctagcaca | 1560 |
| cggctgctgt tggagaagaa cgcctcggtc aacgaggtgg actttgaggg ccggacgccc | 1620 |
| atgcacgtgg cctgccagca cgggcaggag aatatcgtgc gcatcctgct gcgccgaggc | 1680 |

-continued

```
gtggacgtga gcctgcaggg caaggatgcc tggctgccac tgcactacgc tgcctggcag   1740
ggccacctgc ccatcgtcaa gctgctggcc aagcagccgg gggtgagtgt gaacgcccag   1800
acgctggatg ggaggacgcc attgcacctg gccgcacagc gcgggcacta ccgcgtggcc   1860
cgcatcctca tcgacctgtg ctccgacgtc aacgtctgca gcctgctggc acagacaccc   1920
ctgcacgtgg ccgcggagac ggggcacacg agcactgcca ggctgctcct gcatcggggc   1980
gctggcaagg aggccgtgac ctcagacggc tacaccgctc tgcacctggc tgcccgcaac   2040
ggacacctgg ccactgtcaa gctgcttgtc gaggagaagg ccgatgtgct ggcccgggga   2100
cccctgaacc agacggcgct gcacctggct gccgcccacg ggcactcgga ggtggtggag   2160
gagttggtca gcgccgatgt cattgacctg ttcgacgagc aggggctcag cgcgctgcac   2220
ctggccgccc agggccggca cgcacagacg gtggagactc tgctcaggca tggggcccac   2280
atcaacctgc agagcctcaa gttccagggc ggccatggcc ccgccgccac actcctgcgg   2340
cgaagcaaga cctag                                                    2355
```

<210> SEQ ID NO 20
<211> LENGTH: 2355
<212> TYPE: DNA
<213> ORGANISM: Homo sapiens

<400> SEQUENCE: 20

```
atggagggcg acggcgggac cccatgggcc ctggcgctgc tgcgcacctt cgacgcgggc     60
gagttcacgg gctgggagaa ggtgggctcg ggcggcttcg ggcaggtgta caaggtgcgc    120
catgtccact ggaagacctg gctggccatc aagtgctcgc ccagcctgca cgtcgacgac    180
agggagcgca tggagctttt ggaagaagcc aagaagatgg agatggccaa gtttcgctac    240
atcctgcctg tgtatggcat ctgccgcgaa cctgtcggcc tggtcatgga gtacatggag    300
acgggctccc tggaaaagct gctggcttcg gagccattgc catgggatct ccggttccga    360
atcatccacg agacggcggt gggcatgaac ttcctgcact gcatggcccc gccactcctg    420
cacctggacc tcaagcccgc gaacatcctg ctggatgccc actaccacgt caagatttct    480
gattttggtc tggccaagtg caacgggctg tcccactcgc atgacctcag catggatggc    540
ctgtttggca caatcgccta cctccctcca gagcgcatca gggagaagag ccggctcttc    600
gacaccaagc acgatgtata cagctttgcg atcgtcatct ggggcgtgct cacacagaag    660
aagccgtttg cagatgagaa gaacatcctg cacatcatgg tgaaggtggt gaagggccac    720
cgccccgagc tgccgcccgt gtgcagagcc cggccgcgcg cctgcagcca cctgatacgc    780
ctcatgcagc ggtgctggca gggggatccg cgagttaggc ccaccttcca agaaattact    840
tctgaaaccg aggacctgtg tgaaaagcct gatgacgaag tgaaagaaac tgctcatgat    900
ctggacgtga aaagcccccc ggagcccagg agcgaggtgg tgcctgcgag gctcaagcgg    960
gcctctgccc ccaccttcga taacgactac agcctctccg agctgctctc acagctggac   1020
tctggagttt cccaggctgt cgagggcccc gaggagctca gccgcagctc ctctgagtcc   1080
aagctgccat cgtccggcag tgggaagagg ctctcggggg tgtcctcggt ggactccgcc   1140
ttctcttcca gaggatcact gtcgctgtcc tttgagcggg aaccttcaac cagcgatctg   1200
ggcaccacag acgtccagaa gaagaagctt gtggatgcca tcgtgtccgg ggacaccagc   1260
aaactgatga agatcctgca gccgcaggac gtggacctgg cactggacag cggtgccagc   1320
ctgctgcacc tggcggtgga ggccgggcaa gaggagtgcg ccaagtggct gctgctcaac   1380
```

| | |
|---|---|
| aatgccaacc ccaacctgag caaccgtagg ggctccaccc cgttgcacat ggccgtggag | 1440 |
| aggagggtgc ggggtgtcgt ggagctcctg ctggcgcgga agatcagtgt caacgccaag | 1500 |
| gatgaggacc agtggacagc cctccacttt gcagcccaga acggggacga gtctagcaca | 1560 |
| cggctgctgt tggagaagaa cgcctcggtc aacgaggtgg actttgaggg cctgacgccc | 1620 |
| atgcacgtgg cctgccagca cgggcaggag aatatcgtgc gcatcctgct gcgccgaggc | 1680 |
| gtggacgtga gcctgcaggg caaggatgcc tggctgccac tgcactacgc tgcctggcag | 1740 |
| ggccacctgc ccatcgtcaa gctgctggcc aagcagccgg gggtgagtgt gaacgcccag | 1800 |
| acgctggatg ggaggacgcc attgcacctg ccgcacagc gcgggcacta ccgcgtggcc | 1860 |
| cgcatcctca tcgacctgtg ctccgacgtc aacgtctgca gcctgctggc acagacaccc | 1920 |
| ctgcacgtgc cgcggagac ggggcacacg agcactgcca ggctgctcct gcatcggggc | 1980 |
| gctggcaagg aggccgtgac ctcagacggc tacaccgctc tgcacctggc tgcccgcaac | 2040 |
| ggacacctgg ccactgtcaa gctgcttgtc gaggagaagg ccgatgtgct ggcccggga | 2100 |
| cccctgaacc agacggcgct gcacctggct gccgcccacg ggcactcgga ggtggtggag | 2160 |
| gagttggtca gcgccgatgt cattgacctg ttcgacgagc aggggctcag cgcgctgcac | 2220 |
| ctggccgccc agggccggca cgcacagacg gtggagactc tgctcaggca tggggcccac | 2280 |
| atcaacctgc agagcctcaa gttccagggc ggccatggcc ccgccgccac actcctgcgg | 2340 |
| cgaagcaaga cctag | 2355 |

<210> SEQ ID NO 21
<211> LENGTH: 2355
<212> TYPE: DNA
<213> ORGANISM: Homo sapiens

<400> SEQUENCE: 21

| | |
|---|---|
| atggagggcg acggcgggac cccatggggcc ctggcgctgc tgcgcacctt cgacgcgggc | 60 |
| gagttcacgg gctgggagaa ggtgggctcg ggcggcttcg ggcaggtgta caaggtgcgc | 120 |
| catgtccact ggaagacctg gctggccatc aagtgctcgc ccagcctgca cgtcgacgac | 180 |
| agggagcgca tggagctttt ggaagaagcc aagaagatgg agatggccaa gtttcgctac | 240 |
| atcctgcctg tgtatggcat ctgccgcgaa cctgtcggcc tggtcatgga gtacatggag | 300 |
| acgggctccc tggaaaagct gctggcttcg gagccattgc catgggatct ccggttccga | 360 |
| atcatccacg agacggcggt gggcatgaac ttcctgcact gcatggcccc gccactcctg | 420 |
| cacctggacc tcaagcccgc gaacatcctg ctggatgccc actaccacgt caagatttct | 480 |
| gattttggtc tggccaagtg caacgggctg tcccactcgc atgacctcag catggatggc | 540 |
| ctgtttggca caatcgccta cctccctcca gagcgcatca gggagaagag ccggctcttc | 600 |
| gacaccaagc acgatgtata cagctttgcg atcgtcatct ggggcgtgct cacacagaag | 660 |
| aagccgtttg cagatgagaa gaacatcctg cacatcatgt gaaggtggt gaagggccac | 720 |
| cgccccgagc tgccgcccgt gtgcagagcc cggccgcgcg cctgcagcca cctgatacgc | 780 |
| ctcatgcagc ggtgctggca gggggatccg cgagttaggc ccaccttcca agaaattact | 840 |
| tctgaaaccg aggacctgtg tgaaaagcct gatgacgaag tgaaagaaac tgctcatgat | 900 |
| ctggacgtga aaagccccc ggagcccagg agcgaggtgg tgcctgcgag gctcaagcgg | 960 |
| gcctctgccc ccaccttcga taacgactac agcctctccg agctgctctc acagctggac | 1020 |
| tctggagttt ccaggctgt cgagggcccc gaggagctca gccgcagctc ctctgagtcc | 1080 |
| aagctgccat cgtccggcag tgggaagagg ctctcggggg tgtcctcggt ggactccgcc | 1140 |

-continued

| | |
|---|---|
| ttctcttcca gaggatcact gtcgctgtcc tttgagcggg aaccttcaac cagcgatctg | 1200 |
| ggcaccacag acgtccagaa gaagaagctt gtggatgcca tcgtgtccgg ggacaccagc | 1260 |
| aaactgatga agatcctgca gccgcaggac gtggacctgg cactggacag cggtgccagc | 1320 |
| ctgctgcacc tggcggtgga ggccgggcaa gaggagtgcg ccaagtggct gctgctcaac | 1380 |
| aatgccaacc ccaacctgag caaccgtagg ggctccaccc cgttgcacat ggccgtggag | 1440 |
| aggagggtgc ggggtgtcgt ggagctcctg ctggcgcgga agatcagtgt caacgccaag | 1500 |
| gatgaggacc agtggacagc cctccacttt gcagcccaga acgggacga gtctagcaca | 1560 |
| cggctgctgt tggagaagaa cgcctcggtc aacgaggtgg actttgaggg ccggacgccc | 1620 |
| atgcacgtgg cctgccagca cgggcaggag aatatcgtgc gcatcctgct cgccgaggc | 1680 |
| gtggacgtga gcctgcaggg caaggatgcc tggctgccac tgcactacgc tgcctggcag | 1740 |
| ggccacctgc ccatcgtcaa gctgctggcc aagcagccgg gggtgagtgt gaacgcccag | 1800 |
| acgctggatg ggaggacgcc attgcacctg gccgcacagc gcgggcacta ccgcgtggcc | 1860 |
| cgcatcctca tcgacctgtg ctccgacgtc aacgtctgca gcctgctggc acagacaccc | 1920 |
| ctgcacgtgg ccgcggagac ggggcacacg agcactgcca ggctgctcct gcatcggggc | 1980 |
| gctggcaaga aggccgtgac ctcagacggc tacaccgctc tgcacctggc tgcccgcaac | 2040 |
| ggacacctgg ccactgtcaa gctgcttgtc gaggagaagg ccgatgtgct ggcccgggga | 2100 |
| cccctgaacc agacggcgct gcacctggct gccgcccacg ggcactcgga ggtggtggag | 2160 |
| gagttggtca gcgccgatgt cattgacctg ttcgacgagc aggggctcag cgcgctgcac | 2220 |
| ctggccgccc agggccggca cgcacagacg gtggagactc tgctcaggca tggggcccac | 2280 |
| atcaacctgc agagcctcaa gttccagggc ggccatggcc ccgccgccac actcctgcgg | 2340 |
| cgaagcaaga cctag | 2355 |

<210> SEQ ID NO 22
<211> LENGTH: 2355
<212> TYPE: DNA
<213> ORGANISM: Homo sapiens

<400> SEQUENCE: 22

| | |
|---|---|
| atggagggcg acggcgggac cccatgggcc ctggcgctgc tgcgcacctt cgacgcgggc | 60 |
| gagttcacgg gctgggagaa ggtgggctcg ggcggcttcg ggcaggtgta caaggtgcgc | 120 |
| catgtccact ggaagacctg gctggccatc aagtgctcgc ccagcctgca cgtcgacgac | 180 |
| agggagcgca tggagctttt ggaagaagcc aagaagatgg agatggccaa gtttcgctac | 240 |
| atcctgcctg tgtatggcat ctgccgcgaa cctgtcggcc tggtcatgga gtacatggag | 300 |
| acgggctccc tggaaaagct gctggcttcg gagccattgc catgggatct ccggttccga | 360 |
| atcatccacg agacgcggt gggcatgaac ttcctgcact gcatggcccc gccactcctg | 420 |
| cacctggacc tcaagcccgc gaacatcctg ctggatgccc actaccacgt caagatttct | 480 |
| gattttggtc tggccaagtg caacgggctg tcccactcgc atgacctcag catggatggc | 540 |
| ctgtttggca caatcgccta cctccctcca gagcgcatca gggagaagag ccggctcttc | 600 |
| gacaccaagc acgatgtata cagctttgcg atcgtcatct gggcgtgct cacacagaag | 660 |
| aagccgtttg cagatgagaa gaacatcctg cacatcatgt gaaggtggt gaagggccac | 720 |
| cgccccgagc tgccgcccgt gtgcagagcc cggccgcgcg cctgcagcca cctgatacgc | 780 |
| ctcatgcagc ggtgctggca gggggatccg cgagttaggc ccaccttcca agaaattact | 840 |

-continued

| | |
|---|---|
| tctgaaaccg aggacctgtg tgaaaagcct gatgacgaag tgaaagaaac tgctcatgat | 900 |
| ctggacgtga aaagcccccc ggagcccagg agcgaggtgg tgcctgcgag gctcaagcgg | 960 |
| gcctctgccc ccaccttcga taacgactac agcctctccg agctgctctc acagctggac | 1020 |
| tctggagttt cccaggctgt cgagggcccc gaggagctca gccgcagctc ctctgagtcc | 1080 |
| aagctgccat cgtccggcag tgggaagagg ctctcggggg tgtcctcggt ggactccgcc | 1140 |
| ttctcttcca gaggatcact gtcgctgtcc tttgagcggg aaccttcaac cagcgatctg | 1200 |
| ggcaccacag acgtccagaa gaagaagctt gtggatgcca tcgtgtccgg ggacaccagc | 1260 |
| aaactgatga agatcctgca gccgcaggac gtggacctgg cactggacag cggtgccagc | 1320 |
| ctgctgcacc tggcggtgga ggccgggcaa gaggagtgcg ccaagtggct gctgctcaac | 1380 |
| aatgccaacc caacctgag caaccgtagg ggctccaccc cgttgcacat ggccgtggag | 1440 |
| aggagggtgc ggggtgtcgt ggagctcctg ctggcgcgga agatcagtgt caacgccaag | 1500 |
| gatgaggacc agtggacagc cctccacttt gcagcccaga acgggacga gtctagcaca | 1560 |
| cggctgctgt tggagaagaa cgcctcggtc aacgaggtgg actttgaggg ccggacgccc | 1620 |
| atgcacgtgg cctgccagca cgggcaggag aatatcgtgc gcatcctgct cgccgaggc | 1680 |
| gtggacgtga gcctgcaggg caaggatgcc tggctgccac tgcactacgc tgcctggcag | 1740 |
| ggccacctgc ccatcgtcaa gctgctggcc aagcagccgg gggtgagtgt gaacgcccag | 1800 |
| acgctggatg ggaggacgcc attgcacctg ccgcacagc gcgggcacta ccgcgtggcc | 1860 |
| cgcatcctca tcgacctgtg ctccgacgtc aacgtctgca gcctgctggc acagacaccc | 1920 |
| ctgcacgtgg ccgcggagac ggggcacacg agcactgcca ggctgctcct gcatcgggc | 1980 |
| gctggcaagg aggccatgac ctcagacggc tacaccgctc tgcacctggc tgcccgcaac | 2040 |
| ggacacctgg ccactgtcaa gctgcttgtc gaggagaagg ccgatgtgct ggcccgggga | 2100 |
| ccctgaacc agacggcgct gcacctggct gccgcccacg ggcactcgga ggtggtggag | 2160 |
| gagttggtca gcgccgatgt cattgacctg ttcgacgagc aggggctcag cgcgctgcac | 2220 |
| ctggccgccc agggccggca cgcacagacg gtggagactc tgctcaggca tggggcccac | 2280 |
| atcaacctgc agagcctcaa gttccagggc ggccatggcc ccgccgccac actcctgcgg | 2340 |
| cgaagcaaga cctag | 2355 |

<210> SEQ ID NO 23
<211> LENGTH: 2355
<212> TYPE: DNA
<213> ORGANISM: Homo sapiens

<400> SEQUENCE: 23

| | |
|---|---|
| atggagggcg acggcgggac cccatgggcc ctggcgctgc tgcgcacctt cgacgcgggc | 60 |
| gagttcacgg gctgggagaa ggtgggctcg ggcggcttcg ggcaggtgta caaggtgcgc | 120 |
| catgtccact ggaagacctg gctggccatc aagtgctcgc ccagcctgca cgtcgacgac | 180 |
| agggagcgca tggagctttt ggaagaagcc aagaagatgg agatggccaa gtttcgctac | 240 |
| atcctgcctg tgtatggcat ctgccgcgaa cctgtcggcc tggtcatgga gtacatggag | 300 |
| acgggctccc tggaaaagct gctggcttcg agccattgc catgggatct ccggttccga | 360 |
| atcatccacg agacgcggt gggcatgaac ttcctgcact gcatggcccc gccactcctg | 420 |
| cacctggacc tcaagcccgc gaacatcctg ctggatgccc actaccacgt caagatttct | 480 |
| gattttggtc tggccaagtg caacgggctg tcccactcgc atgacctcag catggatggc | 540 |
| ctgtttggca caatcgccta cctccctcca gagcgcatca gggagaagag ccggctcttc | 600 |

-continued

```
gacaccaagc acgatgtata cagctttgcg atcgtcatct ggggcgtgct cacacagaag    660
aagccgtttg cagatgagaa gaacatcctg cacatcatgg tgaaggtggt gaagggccac    720
cgccccgagc tgccgcccgt gtgcagagcc cggccgcgcg cctgcagcca cctgatacgc    780
ctcatgcagc ggtgctggca gggggatccg cgagttaggc ccaccttcca agaaattact    840
tctgaaaccg aggacctgtg tgaaaagcct gatgacgaag tgaaagaaac tgctcatgat    900
ctggacgtga aaagcccccc ggagcccagg agcgaggtgg tgcctgcgag gctcaagcgg    960
gcctctgccc ccaccttcga taacgactac agcctctccg agctgctctc acagctggac   1020
tctggagttt cccaggctgt cgagggcccc gaggagctca gccgcagctc ctctgagtcc   1080
aagctgccat cgtccggcag tgggaagagg ctctcggggg tgtcctcggt ggactccgcc   1140
ttctcttcca gaggatcact gtcgctgtcc tttgagcggg aaccttcaac cagcgatctg   1200
ggcaccacag acgtccagaa gaagaagctt gtggatgcca tcgtgtccgg ggacaccagc   1260
aaactgatga agatcctgca gccgcaggac gtggacctgg cactggacag cggtgccagc   1320
ctgctgcacc tggcggtgga ggccgggcaa gaggagtgcg ccaagtggct gctgctcaac   1380
aatgccaacc ccaacctgag caaccgtagg ggctccaccc cgttgcacat ggccgtggag   1440
aggagggtgc ggggtgtcgt ggagctcctg ctggcgcgga agatcagtgt caacgccaag   1500
gatgaggacc agtggacagc cctccacttt gcagcccaga acggggacga gtctagcaca   1560
cggctgctgt tggagaagaa cgcctcggtc aacgaggtgg actttgaggg ccggacgccc   1620
atgcacgtgg cctgccagca cggcaggag aatatcgtgc gcatcctgct cgccgaggc   1680 gtggacgtga gcctgcaggg caaggatgcc tggctgccac tgcactacgc tgcctggcag   1740
ggccacctgc ccatcgtcaa gctgctggcc aagcagccgg gggtgagtgt gaacgcccag   1800
acgctggatg ggaggacgcc attgcacctg ccgcacagc gcgggcacta ccgcgtggcc   1860
cgcatcctca tcgacctgtg ctccgacgtc aacgtctgca gcctgctggc acagacaccc   1920
ctgcacgtgg ccgcggagac ggggcacacg agcactgcca ggctgctcct gcatcggggc   1980
gctggcaagg aggccgtgac ctcagacggc tacaccgctc tgcacctggc tgcccgcaac   2040
ggacacctgg ccactgtcaa gctgcttgtc gaggagaagg ccgatgtgct ggcccgggga   2100
cccctgaacc agacggcgct gcacctggct gccgcccacg ggcactcgga ggtggtggag   2160
gagttggtca gcgccgatgt cattgacctg ttcgacgagc aggggctcag cgcgctgcac   2220
ctggccgccc agggccggca cgcacagacg gtggagactc tgctcaggca tgggcccac   2280 atcaacctgc agagcctcaa gttccagggc ggccatggcc ccgccgccac gctcctgcgg   2340
cgaagcaaga cctag                                                    2355
```

<210> SEQ ID NO 24
<211> LENGTH: 21
<212> TYPE: PRT
<213> ORGANISM: Homo sapiens

<400> SEQUENCE: 24

Gly Leu Ala Lys Cys Asn Gly Leu Ser His Ser His Asp Leu Ser Met
1               5                   10                  15

Asp Gly Leu Phe Gly
            20

<210> SEQ ID NO 25
<211> LENGTH: 21
<212> TYPE: PRT

<213> ORGANISM: Homo sapiens

<400> SEQUENCE: 25

```
Gly Leu Ala Lys Cys Asn Gly Met Ser His Ser His Asp Leu Ser Met
1               5                   10                  15
Asp Gly Leu Phe Gly
            20
```

<210> SEQ ID NO 26
<211> LENGTH: 21
<212> TYPE: PRT
<213> ORGANISM: Homo sapiens

<400> SEQUENCE: 26

```
Gly Leu Ala Arg Trp Asn Gly Phe Ala Arg Asp Asp Ile Ser Arg
1               5                   10                  15
Asp Gly Phe Cys Gly
            20
```

<210> SEQ ID NO 27
<211> LENGTH: 286
<212> TYPE: PRT
<213> ORGANISM: Mus musculus

<400> SEQUENCE: 27

```
Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
            20                  25                  30

Phe Gly Gln Val Tyr Lys Val Arg His Val His Trp Lys Thr Trp Leu
        35                  40                  45

Ala Ile Lys Cys Ser Pro Ser Leu His Val Asp Asp Arg Glu Arg Met
    50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
        115                 120                 125

Met Asn Phe Leu His Cys Met Ser Pro Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
                165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

Phe Ala Ile Val Ile Trp Gly Val Leu Thr Gln Lys Lys Pro Phe Ala
    210                 215                 220

Asp Glu Lys Asn Ile Leu His Ile Met Met Lys Val Val Lys Gly His
225                 230                 235                 240

Arg Pro Glu Leu Pro Pro Ile Cys Arg Pro Arg Pro Arg Ala Cys Ala
                245                 250                 255
```

```
Ser Leu Ile Gly Leu Met Gln Arg Cys Trp His Ala Asp Pro Gln Val
            260                 265                 270

Arg Pro Thr Phe Gln Glu Ile Thr Ser Glu Thr Glu Asp Leu
            275                 280                 285

<210> SEQ ID NO 28
<211> LENGTH: 439
<212> TYPE: PRT
<213> ORGANISM: Mus musculus

<400> SEQUENCE: 28

Met Glu Gly Glu Gly Arg Gly Arg Trp Ala Leu Gly Leu Leu Arg Thr
1               5                   10                  15

Phe Asp Ala Gly Glu Phe Ala Gly Trp Glu Lys Val Gly Ser Gly Gly
            20                  25                  30

Phe Gly Gln Val Tyr Lys Val Arg His Val His Trp Lys Thr Trp Leu
            35                  40                  45

Ala Ile Lys Cys Ser Pro Ser Leu His Val Asp Asp Arg Glu Arg Met
    50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Gln Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
            115                 120                 125

Met Asn Phe Leu His Cys Met Ser Pro Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
                165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
            195                 200                 205

Phe Ala Ile Val Ile Trp Gly Val Leu Thr Gln Lys Lys Pro Phe Ala
    210                 215                 220

Asp Glu Lys Asn Ile Leu His Ile Met Met Lys Val Val Lys Gly His
225                 230                 235                 240

Arg Pro Glu Leu Pro Pro Ile Cys Arg Pro Arg Pro Arg Ala Cys Ala
                245                 250                 255

Ser Leu Ile Gly Leu Met Gln Arg Cys Trp His Ala Asp Pro Gln Val
            260                 265                 270

Arg Pro Thr Phe Gln Glu Ile Thr Ser Glu Thr Glu Asp Leu Cys Glu
            275                 280                 285

Lys Pro Asp Glu Glu Val Lys Asp Leu Ala His Glu Pro Gly Glu Lys
    290                 295                 300

Ser Ser Leu Glu Ser Lys Ser Glu Ala Arg Pro Glu Ser Ser Arg Leu
305                 310                 315                 320

Lys Arg Ala Ser Ala Pro Pro Phe Asp Asn Asp Cys Ser Leu Ser Glu
                325                 330                 335

Leu Leu Ser Gln Leu Asp Ser Gly Ile Ser Gln Thr Leu Glu Gly Pro
```

```
                   340                 345                 350
Glu Glu Leu Ser Arg Ser Ser Glu Cys Lys Leu Pro Ser Ser Ser
            355                 360                 365

Ser Gly Lys Arg Leu Ser Gly Val Ser Ser Val Asp Ser Ala Phe Ser
        370                 375                 380

Ser Arg Gly Ser Leu Ser Leu Ser Phe Glu Arg Glu Ala Ser Thr Gly
385                 390                 395                 400

Asp Leu Gly Pro Thr Asp Ile Gln Lys Lys Leu Val Asp Ala Ile
                405                 410                 415

Ile Ser Gly Asp Thr Ser Arg Leu Met Lys Ile Leu Gln Pro Gln Asp
            420                 425                 430

Val Asp Leu Val Leu Asp Ser
        435

<210> SEQ ID NO 29
<211> LENGTH: 153
<212> TYPE: PRT
<213> ORGANISM: Mus musculus

<400> SEQUENCE: 29

Cys Glu Lys Pro Asp Glu Val Lys Asp Leu Ala His Glu Pro Gly
1               5                   10                  15

Glu Lys Ser Ser Leu Glu Ser Lys Ser Glu Ala Arg Pro Glu Ser Ser
            20                  25                  30

Arg Leu Lys Arg Ala Ser Ala Pro Pro Phe Asp Asn Asp Cys Ser Leu
        35                  40                  45

Ser Glu Leu Leu Ser Gln Leu Asp Ser Gly Ile Ser Gln Thr Leu Glu
    50                  55                  60

Gly Pro Glu Glu Leu Ser Arg Ser Ser Ser Glu Cys Lys Leu Pro Ser
65                  70                  75                  80

Ser Ser Ser Gly Lys Arg Leu Ser Gly Val Ser Ser Val Asp Ser Ala
                85                  90                  95

Phe Ser Ser Arg Gly Ser Leu Ser Leu Ser Phe Glu Arg Glu Ala Ser
            100                 105                 110

Thr Gly Asp Leu Gly Pro Thr Asp Ile Gln Lys Lys Leu Val Asp
        115                 120                 125

Ala Ile Ile Ser Gly Asp Thr Ser Arg Leu Met Lys Ile Leu Gln Pro
    130                 135                 140

Gln Asp Val Asp Leu Val Leu Asp Ser
145                 150

<210> SEQ ID NO 30
<211> LENGTH: 347
<212> TYPE: PRT
<213> ORGANISM: Mus musculus

<400> SEQUENCE: 30

Ser Ala Ser Leu Leu His Leu Ala Val Glu Ala Gly Gln Glu Glu Cys
1               5                   10                  15

Val Lys Trp Leu Leu Asn Asn Ala Asn Pro Asn Leu Thr Asn Arg
            20                  25                  30

Lys Gly Ser Thr Pro Leu His Met Ala Val Glu Arg Lys Gly Arg Gly
        35                  40                  45

Ile Val Glu Leu Leu Leu Ala Arg Lys Thr Ser Val Asn Ala Lys Asp
    50                  55                  60

Glu Asp Gln Trp Thr Ala Leu His Phe Ala Ala Gln Asn Gly Asp Glu
```

```
                65                  70                  75                  80
    Ala Ser Thr Arg Leu Leu Glu Lys Asn Ala Ser Val Asn Glu Val
                        85                  90                  95
    Asp Phe Glu Gly Arg Thr Pro Met His Val Ala Cys Gln His Gly Gln
                        100                 105                 110
    Glu Asn Ile Val Arg Thr Leu Arg Arg Gly Val Asp Val Gly Leu
                115                 120                 125
    Gln Gly Lys Asp Ala Trp Leu Pro Leu His Tyr Ala Ala Trp Gln Gly
            130                 135                 140
    His Leu Pro Ile Val Lys Leu Leu Ala Lys Gln Pro Gly Val Ser Val
    145                 150                 155                 160
    Asn Ala Gln Thr Leu Asp Gly Arg Thr Pro Leu His Leu Ala Ala Gln
                    165                 170                 175
    Arg Gly His Tyr Arg Val Ala Arg Ile Leu Ile Asp Leu Cys Ser Asp
                    180                 185                 190
    Val Asn Ile Cys Ser Leu Gln Ala Gln Thr Pro Leu His Val Ala Ala
                195                 200                 205
    Glu Thr Gly His Thr Ser Thr Ala Arg Leu Leu His Arg Gly Ala
        210                 215                 220
    Gly Lys Glu Ala Leu Thr Ser Glu Gly Tyr Thr Ala Leu His Leu Ala
    225                 230                 235                 240
    Ala Gln Asn Gly His Leu Ala Thr Val Lys Leu Leu Ile Glu Glu Lys
                    245                 250                 255
    Ala Asp Val Met Ala Arg Gly Pro Leu Asn Gln Thr Ala Leu His Leu
                260                 265                 270
    Ala Ala Ala Arg Gly His Ser Glu Val Val Glu Glu Leu Val Ser Ala
            275                 280                 285
    Asp Leu Ile Asp Leu Ser Asp Glu Gln Gly Leu Ser Ala Leu His Leu
        290                 295                 300
    Ala Ala Gln Gly Arg His Ser Gln Thr Val Glu Thr Leu Leu Lys His
    305                 310                 315                 320
    Gly Ala His Ile Asn Leu Gln Ser Leu Lys Phe Gln Gly Gly Gln Ser
                    325                 330                 335
    Ser Ala Ala Thr Leu Leu Arg Arg Ser Lys Thr
                340                 345

<210> SEQ ID NO 31
<211> LENGTH: 786
<212> TYPE: PRT
<213> ORGANISM: Mus musculus

<400> SEQUENCE: 31

Met Glu Gly Glu Gly Arg Gly Arg Trp Ala Leu Gly Leu Leu Arg Thr
1               5                   10                  15
Phe Asp Ala Gly Glu Phe Ala Gly Trp Glu Lys Val Gly Ser Gly Gly
                20                  25                  30
Phe Gly Gln Val Tyr Lys Val Arg His Val His Trp Lys Thr Trp Leu
            35                  40                  45
Ala Ile Lys Cys Ser Pro Ser Leu His Val Asp Asp Arg Glu Arg Met
        50                  55                  60
Glu Leu Leu Glu Glu Ala Lys Lys Met Glu Met Ala Lys Phe Arg Tyr
65                  70                  75                  80
Ile Leu Pro Val Tyr Gly Ile Cys Gln Glu Pro Val Gly Leu Val Met
                85                  90                  95
```

```
Glu Tyr Met Glu Thr Gly Ser Leu Glu Lys Leu Leu Ala Ser Glu Pro
            100                 105                 110

Leu Pro Trp Asp Leu Arg Phe Arg Ile Val His Glu Thr Ala Val Gly
            115                 120                 125

Met Asn Phe Leu His Cys Met Ser Pro Leu Leu His Leu Ala Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Ser His Ser His Asp Leu
                165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
            195                 200                 205

Phe Ala Ile Val Ile Trp Gly Val Leu Thr Gln Lys Lys Pro Phe Ala
        210                 215                 220

Asp Glu Lys Asn Ile Leu His Ile Met Met Lys Val Val Lys Gly His
225                 230                 235                 240

Arg Pro Glu Leu Pro Pro Ile Cys Arg Pro Arg Pro Arg Ala Cys Ala
                245                 250                 255

Ser Leu Ile Gly Leu Met Gln Arg Cys Trp His Ala Asp Pro Gln Val
            260                 265                 270

Arg Pro Thr Phe Gln Glu Ile Thr Ser Glu Thr Glu Asp Leu Cys Glu
        275                 280                 285

Lys Pro Asp Glu Glu Val Lys Asp Leu Ala His Glu Pro Gly Glu Lys
        290                 295                 300

Ser Ser Leu Glu Ser Lys Ser Glu Ala Arg Pro Glu Ser Ser Arg Leu
305                 310                 315                 320

Lys Arg Ala Ser Ala Pro Pro Phe Asp Asn Asp Cys Ser Leu Ser Glu
                325                 330                 335

Leu Leu Ser Gln Leu Asp Ser Gly Ile Ser Gln Thr Leu Glu Gly Pro
            340                 345                 350

Glu Glu Leu Ser Arg Ser Ser Glu Cys Lys Leu Pro Ser Ser Ser
            355                 360                 365

Ser Gly Lys Arg Leu Ser Gly Val Ser Ser Val Asp Ser Ala Phe Ser
    370                 375                 380

Ser Arg Gly Ser Leu Ser Leu Ser Phe Glu Arg Glu Ala Ser Thr Gly
385                 390                 395                 400

Asp Leu Gly Pro Thr Asp Ile Gln Lys Lys Leu Val Asp Ala Ile
                405                 410                 415

Ile Ser Gly Asp Thr Ser Arg Leu Met Lys Ile Leu Gln Pro Gln Asp
            420                 425                 430

Val Asp Leu Val Leu Asp Ser Ala Ser Leu Leu His Leu Ala Val
        435                 440                 445

Glu Ala Gly Gln Glu Glu Cys Val Lys Trp Leu Leu Leu Asn Asn Ala
        450                 455                 460

Asn Pro Asn Leu Thr Asn Arg Lys Gly Ser Thr Pro Leu His Met Ala
465                 470                 475                 480

Val Glu Arg Lys Gly Arg Gly Ile Val Glu Leu Leu Leu Ala Arg Lys
                485                 490                 495

Thr Ser Val Asn Ala Lys Asp Glu Asp Gln Trp Thr Ala Leu His Phe
            500                 505                 510

Ala Ala Gln Asn Gly Asp Glu Ala Ser Thr Arg Leu Leu Leu Glu Lys
```

```
                515                 520                 525
Asn Ala Ser Val Asn Glu Val Asp Phe Glu Gly Arg Thr Pro Met His
            530                 535                 540
Val Ala Cys Gln His Gly Gln Glu Asn Ile Val Arg Thr Leu Leu Arg
545                 550                 555                 560
Arg Gly Val Asp Val Gly Leu Gln Gly Lys Asp Ala Trp Leu Pro Leu
                565                 570                 575
His Tyr Ala Ala Trp Gln Gly His Leu Pro Ile Val Lys Leu Leu Ala
            580                 585                 590
Lys Gln Pro Gly Val Ser Val Asn Ala Gln Thr Leu Asp Gly Arg Thr
        595                 600                 605
Pro Leu His Leu Ala Ala Gln Arg Gly His Tyr Arg Val Ala Arg Ile
    610                 615                 620
Leu Ile Asp Leu Cys Ser Asp Val Asn Ile Cys Ser Leu Gln Ala Gln
625                 630                 635                 640
Thr Pro Leu His Val Ala Ala Glu Thr Gly His Thr Ser Thr Ala Arg
                645                 650                 655
Leu Leu Leu His Arg Gly Ala Gly Lys Glu Ala Leu Thr Ser Glu Gly
            660                 665                 670
Tyr Thr Ala Leu His Leu Ala Ala Gln Asn Gly His Leu Ala Thr Val
        675                 680                 685
Lys Leu Leu Ile Glu Glu Lys Ala Asp Val Met Ala Arg Gly Pro Leu
    690                 695                 700
Asn Gln Thr Ala Leu His Leu Ala Ala Ala Arg Gly His Ser Glu Val
705                 710                 715                 720
Val Glu Glu Leu Val Ser Ala Asp Leu Ile Asp Leu Ser Asp Glu Gln
                725                 730                 735
Gly Leu Ser Ala Leu His Leu Ala Ala Gln Gly Arg His Ser Gln Thr
            740                 745                 750
Val Glu Thr Leu Leu Lys His Gly Ala His Ile Asn Leu Gln Ser Leu
        755                 760                 765
Lys Phe Gln Gly Gln Ser Ser Ala Ala Thr Leu Leu Arg Arg Ser
    770                 775                 780
Lys Thr
785

<210> SEQ ID NO 32
<211> LENGTH: 786
<212> TYPE: PRT
<213> ORGANISM: Mus musculus

<400> SEQUENCE: 32

Met Glu Gly Glu Gly Arg Gly Arg Trp Ala Leu Gly Leu Leu Arg Thr
1               5                   10                  15
Phe Asp Ala Gly Glu Phe Ala Gly Trp Glu Lys Val Gly Ser Gly Gly
            20                  25                  30
Phe Gly Gln Val Tyr Lys Val Arg His Val His Trp Lys Thr Trp Leu
        35                  40                  45
Ala Ile Lys Cys Ser Pro Ser Leu His Val Asp Asp Arg Glu Arg Met
    50                  55                  60
Glu Leu Leu Glu Glu Ala Lys Lys Met Glu Met Ala Lys Phe Arg Tyr
65                  70                  75                  80
Ile Leu Pro Val Tyr Gly Ile Cys Gln Glu Pro Val Gly Leu Val Met
                85                  90                  95
```

-continued

```
Glu Tyr Met Glu Thr Gly Ser Leu Glu Lys Leu Leu Ala Ser Glu Pro
            100                 105                 110
Leu Pro Trp Asp Leu Arg Phe Arg Ile Val His Glu Thr Ala Val Gly
            115                 120                 125
Met Asn Phe Leu His Cys Met Ser Pro Leu Leu His Leu Asp Leu
    130                 135                 140
Lys Pro Ala Asn Ile Leu Leu Asp Ala His Tyr His Val Lys Ile Ser
145                 150                 155                 160
Asp Phe Gly Leu Ala Lys Cys Asn Gly Met Ala His Ala His Asp Leu
                165                 170                 175
Ala Met Asp Gly Leu Phe Gly Thr Ile Ala Tyr Leu Pro Pro Glu Arg
            180                 185                 190
Ile Arg Glu Lys Ser Arg Leu Phe Asp Thr Lys His Asp Val Tyr Ser
            195                 200                 205
Phe Ala Ile Val Ile Trp Gly Val Leu Thr Gln Lys Lys Pro Phe Ala
    210                 215                 220
Asp Glu Lys Asn Ile Leu His Ile Met Met Lys Val Val Lys Gly His
225                 230                 235                 240
Arg Pro Glu Leu Pro Pro Ile Cys Arg Pro Arg Pro Arg Ala Cys Ala
                245                 250                 255
Ser Leu Ile Gly Leu Met Gln Arg Cys Trp His Ala Asp Pro Gln Val
            260                 265                 270
Arg Pro Thr Phe Gln Glu Ile Thr Ser Glu Thr Glu Asp Leu Cys Glu
            275                 280                 285
Lys Pro Asp Glu Glu Val Lys Asp Leu Ala His Glu Pro Gly Glu Lys
        290                 295                 300
Ser Ser Leu Glu Ser Lys Ser Glu Ala Arg Pro Glu Ser Ser Arg Leu
305                 310                 315                 320
Lys Arg Ala Ser Ala Pro Pro Phe Asp Asn Asp Cys Ser Leu Ser Glu
                325                 330                 335
Leu Leu Ser Gln Leu Asp Ser Gly Ile Ser Gln Thr Leu Glu Gly Pro
            340                 345                 350
Glu Glu Leu Ser Arg Ser Ser Glu Cys Lys Leu Pro Ser Ser Ser
            355                 360                 365
Ser Gly Lys Arg Leu Ser Gly Val Ser Ser Val Asp Ser Ala Phe Ser
    370                 375                 380
Ser Arg Gly Ser Leu Ser Leu Ser Phe Glu Arg Glu Ala Ser Thr Gly
385                 390                 395                 400
Asp Leu Gly Pro Thr Asp Ile Gln Lys Lys Lys Leu Val Asp Ala Ile
                405                 410                 415
Ile Ser Gly Asp Thr Ser Arg Leu Met Lys Ile Leu Gln Pro Gln Asp
            420                 425                 430
Val Asp Leu Val Leu Asp Ser Ala Ser Leu Leu His Leu Ala Val
            435                 440                 445
Glu Ala Gly Gln Glu Glu Cys Val Lys Trp Leu Leu Leu Asn Asn Ala
    450                 455                 460
Asn Pro Asn Leu Thr Asn Arg Lys Gly Ser Thr Pro Leu His Met Ala
465                 470                 475                 480
Val Glu Arg Lys Gly Arg Gly Ile Val Glu Leu Leu Leu Ala Arg Lys
                485                 490                 495
Thr Ser Val Asn Ala Lys Asp Glu Asp Gln Trp Thr Ala Leu His Phe
            500                 505                 510
Ala Ala Gln Asn Gly Asp Glu Ala Ser Thr Arg Leu Leu Leu Glu Lys
```

```
                515                 520                 525
Asn Ala Ser Val Asn Glu Val Asp Phe Glu Gly Arg Thr Pro Met His
            530                 535                 540
Val Ala Cys Gln His Gly Gln Glu Asn Ile Val Arg Thr Leu Leu Arg
545                 550                 555                 560
Arg Gly Val Asp Val Gly Leu Gln Gly Lys Asp Ala Trp Leu Pro Leu
                565                 570                 575
His Tyr Ala Ala Trp Gln Gly His Leu Pro Ile Val Lys Leu Leu Ala
            580                 585                 590
Lys Gln Pro Gly Val Ser Val Asn Ala Gln Thr Leu Asp Gly Arg Thr
            595                 600                 605
Pro Leu His Leu Ala Ala Gln Arg Gly His Tyr Arg Val Ala Arg Ile
            610                 615                 620
Leu Ile Asp Leu Cys Ser Asp Val Asn Ile Cys Ser Leu Gln Ala Gln
625                 630                 635                 640
Thr Pro Leu His Val Ala Ala Glu Thr Gly His Thr Ser Thr Ala Arg
                645                 650                 655
Leu Leu Leu His Arg Gly Ala Gly Lys Glu Ala Leu Thr Ser Glu Gly
            660                 665                 670
Tyr Thr Ala Leu His Leu Ala Ala Gln Asn Gly His Leu Ala Thr Val
            675                 680                 685
Lys Leu Leu Ile Glu Glu Lys Ala Asp Val Met Ala Arg Gly Pro Leu
            690                 695                 700
Asn Gln Thr Ala Leu His Leu Ala Ala Arg Gly His Ser Glu Val
705                 710                 715                 720
Val Glu Glu Leu Val Ser Ala Asp Leu Ile Asp Leu Ser Asp Glu Gln
                725                 730                 735
Gly Leu Ser Ala Leu His Leu Ala Ala Gln Gly Arg His Ser Gln Thr
            740                 745                 750
Val Glu Thr Leu Leu Lys His Gly Ala His Ile Asn Leu Gln Ser Leu
            755                 760                 765
Lys Phe Gln Gly Gly Gln Ser Ser Ala Ala Thr Leu Leu Arg Arg Ser
            770                 775                 780
Lys Thr
785

<210> SEQ ID NO 33
<211> LENGTH: 786
<212> TYPE: PRT
<213> ORGANISM: Mus musculus

<400> SEQUENCE: 33

Met Glu Gly Glu Gly Arg Gly Arg Trp Ala Leu Gly Leu Leu Arg Thr
1               5                   10                  15
Phe Asp Ala Gly Glu Phe Ala Gly Trp Glu Lys Val Gly Ser Gly Gly
            20                  25                  30
Phe Gly Gln Val Tyr Lys Val Arg His Val His Trp Lys Thr Trp Leu
        35                  40                  45
Ala Ile Lys Cys Ser Pro Ser Leu His Val Asp Asp Arg Glu Arg Met
    50                  55                  60
Glu Leu Leu Glu Glu Ala Lys Lys Met Glu Met Ala Lys Phe Arg Tyr
65                  70                  75                  80
Ile Leu Pro Val Tyr Gly Ile Cys Gln Glu Pro Val Gly Leu Val Met
                85                  90                  95
```

```
Glu Tyr Met Glu Thr Gly Ser Leu Glu Lys Leu Leu Ala Ser Glu Pro
                100                 105                 110

Leu Pro Trp Asp Leu Arg Phe Arg Ile Val His Glu Thr Ala Val Gly
            115                 120                 125

Met Asn Phe Leu His Cys Met Ser Pro Leu Leu His Leu Asp Leu
130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Met Glu His Glu His Asp Leu
                165                 170                 175

Glu Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

Phe Ala Ile Val Ile Trp Gly Val Leu Thr Gln Lys Lys Pro Phe Ala
    210                 215                 220

Asp Glu Lys Asn Ile Leu His Ile Met Met Lys Val Val Lys Gly His
225                 230                 235                 240

Arg Pro Glu Leu Pro Pro Ile Cys Arg Pro Arg Pro Arg Ala Cys Ala
                245                 250                 255

Ser Leu Ile Gly Leu Met Gln Arg Cys Trp His Ala Asp Pro Gln Val
            260                 265                 270

Arg Pro Thr Phe Gln Glu Ile Thr Ser Glu Thr Glu Asp Leu Cys Glu
        275                 280                 285

Lys Pro Asp Glu Glu Val Lys Asp Leu Ala His Glu Pro Gly Glu Lys
    290                 295                 300

Ser Ser Leu Glu Ser Lys Ser Glu Ala Arg Pro Glu Ser Ser Arg Leu
305                 310                 315                 320

Lys Arg Ala Ser Ala Pro Pro Phe Asp Asn Asp Cys Ser Leu Ser Glu
                325                 330                 335

Leu Leu Ser Gln Leu Asp Ser Gly Ile Ser Gln Thr Leu Glu Gly Pro
            340                 345                 350

Glu Glu Leu Ser Arg Ser Ser Glu Cys Lys Leu Pro Ser Ser Ser
        355                 360                 365

Ser Gly Lys Arg Leu Ser Gly Val Ser Ser Val Asp Ser Ala Phe Ser
    370                 375                 380

Ser Arg Gly Ser Leu Ser Leu Ser Phe Glu Arg Glu Ala Ser Thr Gly
385                 390                 395                 400

Asp Leu Gly Pro Thr Asp Ile Gln Lys Lys Lys Leu Val Asp Ala Ile
                405                 410                 415

Ile Ser Gly Asp Thr Ser Arg Leu Met Lys Ile Leu Gln Pro Gln Asp
            420                 425                 430

Val Asp Leu Val Leu Asp Ser Ala Ser Leu Leu His Leu Ala Val
        435                 440                 445

Glu Ala Gly Gln Glu Glu Cys Val Lys Trp Leu Leu Asn Asn Ala
    450                 455                 460

Asn Pro Asn Leu Thr Asn Arg Lys Gly Ser Thr Pro Leu His Met Ala
465                 470                 475                 480

Val Glu Arg Lys Gly Arg Gly Ile Val Glu Leu Leu Ala Arg Lys
                485                 490                 495

Thr Ser Val Asn Ala Lys Asp Glu Asp Gln Trp Thr Ala Leu His Phe
            500                 505                 510

Ala Ala Gln Asn Gly Asp Glu Ala Ser Thr Arg Leu Leu Leu Glu Lys
```

```
                515                 520                 525
Asn Ala Ser Val Asn Glu Val Asp Phe Glu Gly Arg Thr Pro Met His
            530                 535                 540
Val Ala Cys Gln His Gly Gln Glu Asn Ile Val Arg Thr Leu Leu Arg
545                 550                 555                 560
Arg Gly Val Asp Val Gly Leu Gln Gly Lys Asp Ala Trp Leu Pro Leu
                565                 570                 575
His Tyr Ala Ala Trp Gln Gly His Leu Pro Ile Val Lys Leu Leu Ala
            580                 585                 590
Lys Gln Pro Gly Val Ser Val Asn Ala Gln Thr Leu Asp Gly Arg Thr
            595                 600                 605
Pro Leu His Leu Ala Ala Gln Arg Gly His Tyr Arg Val Ala Arg Ile
            610                 615                 620
Leu Ile Asp Leu Cys Ser Asp Val Asn Ile Cys Ser Leu Gln Ala Gln
625                 630                 635                 640
Thr Pro Leu His Val Ala Ala Glu Thr Gly His Thr Ser Thr Ala Arg
                645                 650                 655
Leu Leu Leu His Arg Gly Ala Gly Lys Glu Ala Leu Thr Ser Glu Gly
            660                 665                 670
Tyr Thr Ala Leu His Leu Ala Ala Gln Asn Gly His Leu Ala Thr Val
            675                 680                 685
Lys Leu Leu Ile Glu Glu Lys Ala Asp Val Met Ala Arg Gly Pro Leu
            690                 695                 700
Asn Gln Thr Ala Leu His Leu Ala Ala Arg Gly His Ser Glu Val
705                 710                 715                 720
Val Glu Glu Leu Val Ser Ala Asp Leu Ile Asp Leu Ser Asp Glu Gln
                725                 730                 735
Gly Leu Ser Ala Leu His Leu Ala Ala Gln Gly Arg His Ser Gln Thr
            740                 745                 750
Val Glu Thr Leu Leu Lys His Gly Ala His Ile Asn Leu Gln Ser Leu
            755                 760                 765
Lys Phe Gln Gly Gly Gln Ser Ser Ala Ala Thr Leu Leu Arg Arg Ser
            770                 775                 780
Lys Thr
785

<210> SEQ ID NO 34
<211> LENGTH: 765
<212> TYPE: PRT
<213> ORGANISM: Homo sapiens

<400> SEQUENCE: 34

Met Ala Ala Asp Pro Thr Glu Leu Arg Leu Gly Ser Leu Pro Val Phe
1               5                   10                  15
Thr Arg Asp Asp Phe Glu Gly Asp Trp Arg Leu Val Ala Ser Gly Gly
            20                  25                  30
Phe Ser Gln Val Phe Gln Ala Arg His Arg Arg Trp Arg Thr Glu Tyr
        35                  40                  45
Ala Ile Lys Cys Ala Pro Cys Leu Pro Pro Asp Ala Ala Ser Ser Asp
    50                  55                  60
Val Asn Tyr Leu Ile Glu Glu Ala Ala Lys Met Lys Lys Ile Lys Phe
65                  70                  75                  80
Gln His Ile Val Ser Ile Tyr Gly Val Cys Lys Gln Pro Leu Gly Ile
                85                  90                  95
```

-continued

```
Val Met Glu Phe Met Ala Asn Gly Ser Leu Glu Lys Val Leu Ser Thr
            100                 105                 110
His Ser Leu Cys Trp Lys Leu Arg Phe Arg Ile Ile His Glu Thr Ser
        115                 120                 125
Leu Ala Met Asn Phe Leu His Ser Ile Lys Pro Leu Leu His Leu
    130                 135                 140
Ala Leu Lys Pro Gly Asn Ile Leu Leu Asp Ser Asn Met His Val Lys
145                 150                 155                 160
Ile Ser Asp Phe Gly Leu Ser Lys Trp Met Glu Gln Ser Thr Arg Met
                165                 170                 175
Gln Tyr Ile Glu Arg Ser Ala Leu Arg Gly Met Leu Ser Tyr Ile Pro
            180                 185                 190
Pro Glu Met Phe Leu Glu Ser Asn Lys Ala Pro Gly Pro Lys Tyr Asp
        195                 200                 205
Val Tyr Ser Phe Ala Ile Val Ile Trp Glu Leu Leu Thr Gln Lys Lys
    210                 215                 220
Pro Tyr Ser Gly Phe Asn Met Met Met Ile Ile Ile Arg Val Ala Ala
225                 230                 235                 240
Gly Met Arg Pro Ser Leu Gln Pro Val Ser Asp Gln Trp Pro Ser Glu
                245                 250                 255
Ala Gln Gln Met Val Asp Leu Met Lys Arg Cys Trp Asp Gln Asp Pro
            260                 265                 270
Lys Lys Arg Pro Cys Phe Leu Asp Ile Thr Ile Glu Thr Asp Ile Leu
        275                 280                 285
Leu Ser Leu Leu Gln Ser Arg Val Ala Val Pro Glu Ser Lys Ala Leu
    290                 295                 300
Ala Arg Lys Val Ser Cys Lys Leu Ser Leu Arg Gln Pro Arg Glu Val
305                 310                 315                 320
Asn Glu Asp Ile Ser Gln Glu Leu Met Asp Ser Asp Ser Gly Asn Tyr
                325                 330                 335
Leu Lys Arg Ala Leu Gln Leu Ser Asp Arg Lys Asn Leu Val Pro Arg
            340                 345                 350
Asp Glu Glu Leu Cys Ile Tyr Glu Asn Lys Val Thr Pro Leu Gln Phe
        355                 360                 365
Leu Val Ala Gln Gly Ser Val Glu Gln Val Arg Leu Leu Ala His
    370                 375                 380
Glu Val Asp Val Asp Cys Gln Thr Ala Ser Gly Tyr Thr Pro Leu Leu
385                 390                 395                 400
Ile Ala Ala Gln Asp Gln Gln Pro Asp Leu Cys Ala Leu Leu Leu Ala
                405                 410                 415
His Gly Ala Asp Ala Asn Arg Val Asp Glu Asp Gly Trp Ala Pro Leu
            420                 425                 430
His Phe Ala Ala Gln Asn Gly Asp Asp Arg Thr Ala Arg Leu Leu Leu
        435                 440                 445
Asp His Gly Ala Cys Val Asp Ala Gln Glu Arg Glu Gly Trp Thr Pro
    450                 455                 460
Leu His Leu Ala Ala Gln Asn Asn Phe Glu Asn Val Ala Arg Leu Leu
465                 470                 475                 480
Val Ser Arg Gln Ala Asp Pro Asn Leu Arg Glu Ala Glu Gly Lys Thr
                485                 490                 495
Pro Leu His Val Ala Ala Tyr Phe Gly His Val Ser Leu Val Lys Leu
            500                 505                 510
Leu Thr Ser Gln Gly Ala Glu Leu Asp Ala Gln Gln Arg Asn Leu Arg
```

-continued

```
                515                 520                 525
Thr Pro Leu His Leu Ala Val Glu Arg Gly Lys Val Arg Ala Ile Gln
            530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
            580                 585                 590

Gly Trp Thr Pro Leu His Leu Ala Ala Tyr Lys Gly His Leu Glu Ile
            595                 600                 605

Ile His Leu Leu Ala Glu Ser His Ala Asn Met Gly Ala Leu Gly Ala
        610                 615                 620

Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
                645                 650                 655

Gln Ser Gly Trp Thr Pro Leu His Leu Ala Val Gln Arg Ser Thr Phe
            660                 665                 670

Leu Ser Val Ile Asn Leu Leu Glu His His Ala Asn Val His Ala Arg
            675                 680                 685

Asn Lys Val Gly Trp Thr Pro Ala His Leu Ala Ala Leu Lys Gly Asn
        690                 695                 700

Thr Ala Ile Leu Lys Val Leu Val Glu Ala Gly Ala Gln Leu Asp Val
705                 710                 715                 720

Gln Asp Gly Val Ser Cys Thr Pro Leu Gln Leu Ala Leu Arg Ser Arg
                725                 730                 735

Lys Gln Gly Ile Met Ser Phe Leu Glu Gly Lys Glu Pro Ser Val Ala
            740                 745                 750

Thr Leu Gly Gly Ser Lys Pro Gly Ala Glu Met Glu Ile
        755                 760                 765

<210> SEQ ID NO 35
<211> LENGTH: 765
<212> TYPE: PRT
<213> ORGANISM: Homo sapiens

<400> SEQUENCE: 35

Met Ala Ala Asp Pro Thr Glu Leu Arg Leu Gly Ser Leu Pro Val Phe
1               5                   10                  15

Thr Arg Asp Asp Phe Glu Gly Asp Trp Arg Leu Val Ala Ser Gly Gly
            20                  25                  30

Phe Ser Gln Val Phe Gln Ala Arg His Arg Arg Trp Arg Thr Glu Tyr
        35                  40                  45

Ala Ile Lys Cys Ala Pro Cys Leu Pro Pro Asp Ala Ala Ser Ser Asp
    50                  55                  60

Val Asn Tyr Leu Ile Glu Glu Ala Ala Lys Met Lys Lys Ile Lys Phe
65                  70                  75                  80

Gln His Ile Val Ser Ile Tyr Gly Val Cys Lys Gln Pro Leu Gly Ile
                85                  90                  95

Val Met Glu Phe Met Ala Asn Gly Ser Leu Glu Lys Val Leu Ser Thr
            100                 105                 110

His Ser Leu Cys Trp Lys Leu Arg Phe Arg Ile Ile His Asp Thr Ser
        115                 120                 125
```

-continued

```
Leu Ala Met Asn Phe Leu His Ser Ile Lys Pro Pro Leu His Leu
    130                 135                 140

Asp Leu Lys Pro Gly Asn Ile Leu Leu Asp Ser Asn Met His Val Lys
145                 150                 155                 160

Ile Ser Asp Phe Gly Leu Ser Lys Trp Met Glu Gln Ser Thr Arg Met
                165                 170                 175

Gln Tyr Ile Glu Arg Ser Ala Leu Arg Gly Met Leu Ser Tyr Ile Pro
            180                 185                 190

Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
    210                 215                 220

Pro Tyr Ser Gly Phe Asn Met Met Met Ile Ile Ile Arg Val Ala Ala
225                 230                 235                 240

Gly Met Arg Pro Ser Leu Gln Pro Val Ser Asp Gln Trp Pro Ser Glu
                245                 250                 255

Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
        275                 280                 285

Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
        355                 360                 365

Leu Val Ala Gln Gly Ser Val Glu Gln Val Arg Leu Leu Leu Ala His
    370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
        435                 440                 445

Asp His Gly Ala Cys Val Asp Ala Gln Glu Arg Glu Gly Trp Thr Pro
    450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Arg Asn Leu Arg
        515                 520                 525

Thr Pro Leu His Leu Ala Val Glu Arg Gly Lys Val Arg Ala Ile Gln
    530                 535                 540

His Leu Leu Lys Ser Gly Ala Val Pro Asp Ala Leu Asp Gln Ser Gly
```

```
                545                 550                 555                 560
Tyr Gly Pro Leu His Thr Ala Ala Arg Gly Lys Tyr Leu Ile Cys
                565                 570                 575
Lys Met Leu Leu Arg Tyr Gly Ala Ser Leu Glu Leu Pro Thr His Gln
                580                 585                 590
Gly Trp Thr Pro Leu His Leu Ala Ala Tyr Lys Gly His Leu Glu Ile
                595                 600                 605
Ile His Leu Leu Ala Glu Ser His Ala Asn Met Gly Ala Leu Gly Ala
                610                 615                 620
Val Asn Trp Thr Pro Leu His Leu Ala Ala Arg His Gly Glu Glu Ala
625                 630                 635                 640
Val Val Ser Ala Leu Leu Gln Cys Gly Ala Asp Pro Asn Ala Ala Glu
                645                 650                 655
Gln Ser Gly Trp Thr Pro Leu His Leu Ala Val Gln Arg Ser Thr Phe
                660                 665                 670
Leu Ser Val Ile Asn Leu Leu Glu His His Ala Asn Val His Ala Arg
                675                 680                 685
Asn Lys Val Gly Trp Thr Pro Ala His Leu Ala Ala Leu Lys Gly Asn
                690                 695                 700
Thr Ala Ile Leu Lys Val Leu Val Glu Ala Gly Ala Gln Leu Asp Val
705                 710                 715                 720
Gln Asp Gly Val Ser Cys Thr Pro Leu Gln Leu Ala Leu Arg Ser Arg
                725                 730                 735
Lys Gln Gly Ile Met Ser Phe Leu Glu Gly Lys Glu Pro Ser Val Ala
                740                 745                 750
Thr Leu Gly Gly Ser Lys Pro Gly Ala Glu Met Glu Ile
                755                 760                 765

<210> SEQ ID NO 36
<211> LENGTH: 765
<212> TYPE: PRT
<213> ORGANISM: Homo sapiens

<400> SEQUENCE: 36

Met Ala Ala Asp Pro Thr Glu Leu Arg Leu Gly Ser Leu Pro Val Phe
1                   5                   10                  15
Thr Arg Asp Asp Phe Glu Gly Asp Trp Arg Leu Val Ala Ser Gly Gly
                20                  25                  30
Phe Ser Gln Val Phe Gln Ala Arg His Arg Arg Trp Arg Thr Glu Tyr
            35                  40                  45
Ala Ile Lys Cys Ala Pro Cys Leu Pro Pro Asp Ala Ala Ser Ser Asp
        50                  55                  60
Val Asn Tyr Leu Ile Glu Glu Ala Ala Lys Met Lys Lys Ile Lys Phe
65                  70                  75                  80
Gln His Ile Val Ser Ile Tyr Gly Val Cys Lys Gln Pro Leu Gly Ile
                85                  90                  95
Val Met Glu Phe Met Ala Asn Gly Ser Leu Glu Lys Val Leu Ser Thr
                100                 105                 110
His Ser Leu Cys Trp Lys Leu Arg Phe Arg Ile Ile His Glu Thr Ser
            115                 120                 125
Leu Ala Met Asn Phe Leu His Ser Ile Lys Pro Pro Leu Leu His Leu
        130                 135                 140
Asp Leu Lys Pro Gly Asn Ile Leu Leu Asp Ser Asn Met His Val Lys
145                 150                 155                 160
```

-continued

```
Ile Ser Asp Phe Gly Leu Ser Arg Trp Met Gln Ser Thr Arg Met
                165                 170                 175

Gln Tyr Ile Glu Arg Ser Ala Leu Arg Gly Met Leu Ser Tyr Ile Pro
            180                 185                 190

Pro Glu Met Phe Leu Glu Ser Asn Lys Ala Pro Gly Pro Lys Tyr Asp
                195                 200                 205

Val Tyr Ser Phe Ala Ile Val Ile Trp Glu Leu Thr Gln Lys Lys
        210                 215                 220

Pro Tyr Ser Gly Phe Asn Met Met Ile Ile Ile Arg Val Ala Ala
225                 230                 235                 240

Gly Met Arg Pro Ser Leu Gln Pro Val Ser Asp Gln Trp Pro Ser Glu
                    245                 250                 255

Ala Gln Gln Met Val Asp Leu Met Lys Arg Cys Trp Asp Gln Asp Pro
                260                 265                 270

Lys Lys Arg Pro Cys Phe Leu Asp Ile Thr Ile Glu Thr Asp Ile Leu
                275                 280                 285

Leu Ser Leu Leu Gln Ser Arg Val Ala Val Pro Glu Ser Lys Ala Leu
            290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                        325                 330                 335

Leu Lys Arg Ala Leu Gln Leu Ser Asp Arg Lys Asn Leu Val Pro Arg
                340                 345                 350

Asp Glu Glu Leu Cys Ile Tyr Glu Asn Lys Val Thr Pro Leu Gln Phe
                355                 360                 365

Leu Val Ala Gln Gly Ser Val Glu Gln Val Arg Leu Leu Leu Ala His
            370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                    405                 410                 415

His Gly Ala Asp Ala Asn Arg Val Asp Glu Asp Gly Trp Ala Pro Leu
                420                 425                 430

His Phe Ala Ala Gln Asn Gly Asp Asp Arg Thr Ala Arg Leu Leu Leu
            435                 440                 445

Asp His Gly Ala Cys Val Asp Ala Gln Glu Arg Glu Gly Trp Thr Pro
    450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
                500                 505                 510

Leu Thr Ser Gln Gly Ala Glu Leu Asp Ala Gln Gln Arg Asn Leu Arg
            515                 520                 525

Thr Pro Leu His Leu Ala Val Glu Arg Gly Lys Val Arg Ala Ile Gln
        530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
```

```
                    580                 585                 590
Gly Trp Thr Pro Leu His Leu Ala Ala Tyr Lys Gly His Leu Glu Ile
            595                 600                 605
Ile His Leu Leu Ala Glu Ser His Ala Asn Met Gly Ala Leu Gly Ala
        610                 615                 620
Val Asn Trp Thr Pro Leu His Leu Ala Ala Arg His Gly Glu Glu Ala
625                 630                 635                 640
Val Val Ser Ala Leu Leu Gln Cys Gly Ala Asp Pro Asn Ala Ala Glu
                645                 650                 655
Gln Ser Gly Trp Thr Pro Leu His Leu Ala Val Gln Arg Ser Thr Phe
            660                 665                 670
Leu Ser Val Ile Asn Leu Leu Glu His His Ala Asn Val His Ala Arg
        675                 680                 685
Asn Lys Val Gly Trp Thr Pro Ala His Leu Ala Ala Leu Lys Gly Asn
690                 695                 700
Thr Ala Ile Leu Lys Val Leu Val Glu Ala Gly Ala Gln Leu Asp Val
705                 710                 715                 720
Gln Asp Gly Val Ser Cys Thr Pro Leu Gln Leu Ala Leu Arg Ser Arg
                725                 730                 735
Lys Gln Gly Ile Met Ser Phe Leu Glu Gly Lys Glu Pro Ser Val Ala
            740                 745                 750
Thr Leu Gly Gly Ser Lys Pro Gly Ala Glu Met Glu Ile
        755                 760                 765

<210> SEQ ID NO 37
<211> LENGTH: 765
<212> TYPE: PRT
<213> ORGANISM: Homo sapiens

<400> SEQUENCE: 37

Met Ala Ala Asp Pro Thr Glu Leu Arg Leu Gly Ser Leu Pro Val Phe
1               5                   10                  15
Thr Arg Asp Asp Phe Glu Gly Asp Trp Arg Leu Val Ala Ser Gly Gly
            20                  25                  30
Phe Ser Gln Val Phe Gln Ala Arg His Arg Arg Trp Arg Thr Glu Tyr
        35                  40                  45
Ala Ile Lys Cys Ala Pro Cys Leu Pro Pro Asp Ala Ala Ser Ser Asp
    50                  55                  60
Val Asn Tyr Leu Ile Glu Glu Ala Lys Met Lys Lys Ile Lys Phe
65                  70                  75                  80
Gln His Ile Val Ser Ile Tyr Gly Val Cys Lys Gln Pro Leu Gly Ile
                85                  90                  95
Val Met Glu Phe Met Ala Asn Gly Ser Leu Glu Lys Val Leu Ser Thr
            100                 105                 110
His Ser Leu Cys Trp Lys Leu Arg Phe Arg Ile Ile His Glu Thr Ser
        115                 120                 125
Leu Ala Met Asn Phe Leu His Ser Ile Lys Pro Pro Leu Leu His Leu
    130                 135                 140
Asp Leu Lys Pro Gly Asn Ile Leu Leu Asp Ser Asn Met His Val Lys
145                 150                 155                 160
Ile Ser Asp Phe Gly Leu Ser Lys Trp Met Glu Gln Ser Thr Arg Met
                165                 170                 175
Gln Tyr Ile Glu Arg Ser Ala Leu Arg Gly Met Leu Ser Tyr Ile Pro
            180                 185                 190
```

-continued

```
Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
        210                 215                 220

Pro Tyr Ser Gly Phe Asn Met Met Ile Ile Arg Val Ala Gly
225                 230                 235                 240

Gly Met Arg Pro Ser Leu Gln Pro Val Ser Asp Gln Trp Pro Ser Glu
                245                 250                 255

Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
        275                 280                 285

Leu Ser Leu Leu Gln Ser Arg Val Ala Val Pro Glu Ser Lys Ala Leu
        290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
        355                 360                 365

Leu Val Ala Gln Gly Ser Val Glu Gln Val Arg Leu Leu Ala His
        370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
        435                 440                 445

Asp His Gly Ala Cys Val Asp Ala Gln Glu Arg Glu Gly Trp Thr Pro
        450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Arg Asn Leu Arg
        515                 520                 525

Thr Pro Leu His Leu Ala Val Glu Arg Gly Lys Val Arg Ala Ile Gln
        530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
            580                 585                 590

Gly Trp Thr Pro Leu His Leu Ala Ala Tyr Lys Gly His Leu Glu Ile
        595                 600                 605

Ile His Leu Leu Ala Glu Ser His Ala Asn Met Gly Ala Leu Gly Ala
```

```
                    610                 615                 620
Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
            645                 650                 655

Gln Ser Gly Trp Thr Pro Leu His Leu Ala Val Gln Arg Ser Thr Phe
        660                 665                 670

Leu Ser Val Ile Asn Leu Leu Glu His His Ala Asn Val His Ala Arg
    675                 680                 685

Asn Lys Val Gly Trp Thr Pro Ala His Leu Ala Ala Leu Lys Gly Asn
690                 695                 700

Thr Ala Ile Leu Lys Val Leu Val Glu Ala Gly Ala Gln Leu Asp Val
705                 710                 715                 720

Gln Asp Gly Val Ser Cys Thr Pro Leu Gln Leu Ala Leu Arg Ser Arg
            725                 730                 735

Lys Gln Gly Ile Met Ser Phe Leu Glu Gly Lys Glu Pro Ser Val Ala
        740                 745                 750

Thr Leu Gly Gly Ser Lys Pro Gly Ala Glu Met Glu Ile
    755                 760                 765

<210> SEQ ID NO 38
<211> LENGTH: 765
<212> TYPE: PRT
<213> ORGANISM: Homo sapiens

<400> SEQUENCE: 38

Met Ala Ala Asp Pro Thr Glu Leu Arg Leu Gly Ser Leu Pro Val Phe
1               5                   10                  15

Thr Arg Asp Asp Phe Glu Gly Asp Trp Arg Leu Val Ala Ser Gly Gly
            20                  25                  30

Phe Ser Gln Val Phe Gln Ala Arg His Arg Arg Trp Arg Thr Glu Tyr
        35                  40                  45

Ala Ile Lys Cys Ala Pro Cys Leu Pro Pro Asp Ala Ala Ser Ser Asp
    50                  55                  60

Val Asn Tyr Leu Ile Glu Glu Ala Ala Lys Met Lys Lys Ile Lys Phe
65                  70                  75                  80

Gln His Ile Val Ser Ile Tyr Gly Val Cys Lys Gln Pro Leu Gly Ile
                85                  90                  95

Val Met Glu Phe Met Ala Asn Gly Ser Leu Glu Lys Val Leu Ser Thr
            100                 105                 110

His Ser Leu Cys Trp Lys Leu Arg Phe Arg Ile Ile His Glu Thr Ser
        115                 120                 125

Leu Ala Met Asn Phe Leu His Ser Ile Lys Pro Pro Leu Leu His Leu
    130                 135                 140

Asp Leu Lys Pro Gly Asn Ile Leu Leu Asp Ser Asn Met His Val Lys
145                 150                 155                 160

Ile Ser Asp Phe Gly Leu Ser Lys Trp Met Glu Gln Ser Thr Arg Met
                165                 170                 175

Gln Tyr Ile Glu Arg Ser Ala Leu Arg Ala Met Leu Ser Tyr Ile Pro
            180                 185                 190

Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
    210                 215                 220
```

```
Pro Tyr Ser Gly Phe Asn Met Met Ile Ile Ile Arg Val Ala Ala
225                 230                 235                 240

Gly Met Arg Pro Ser Leu Gln Pro Val Ser Asp Gln Trp Pro Ser Glu
            245                 250                 255

Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
            275                 280                 285

Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
            355                 360                 365

Leu Val Ala Gln Gly Ser Val Glu Gln Val Arg Leu Leu Leu Ala His
    370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
            405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
    435                 440                 445

Asp His Gly Ala Cys Val Asp Ala Gln Glu Arg Glu Gly Trp Thr Pro
450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
            485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Gln Arg Asn Leu Arg
    515                 520                 525

Thr Pro Leu His Leu Ala Val Glu Arg Gly Lys Val Arg Ala Ile Gln
530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
            565                 570                 575

Lys Met Leu Leu Arg Tyr Gly Ala Ser Leu Glu Leu Pro Thr His Gln
            580                 585                 590

Gly Trp Thr Pro Leu His Leu Ala Ala Tyr Lys Gly His Leu Glu Ile
        595                 600                 605

Ile His Leu Leu Ala Glu Ser His Ala Asn Met Gly Ala Leu Gly Ala
            610                 615                 620

Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
```

```
                    645                 650                 655
Gln Ser Gly Trp Thr Pro Leu His Leu Ala Val Gln Arg Ser Thr Phe
            660                 665                 670

Leu Ser Val Ile Asn Leu Leu Glu His His Ala Asn Val His Ala Arg
            675                 680                 685

Asn Lys Val Gly Trp Thr Pro Ala His Leu Ala Ala Leu Lys Gly Asn
            690                 695                 700

Thr Ala Ile Leu Lys Val Leu Val Glu Ala Gly Ala Gln Leu Asp Val
705                 710                 715                 720

Gln Asp Gly Val Ser Cys Thr Pro Leu Gln Leu Ala Leu Arg Ser Arg
            725                 730                 735

Lys Gln Gly Ile Met Ser Phe Leu Glu Gly Lys Glu Pro Ser Val Ala
            740                 745                 750

Thr Leu Gly Gly Ser Lys Pro Gly Ala Glu Met Glu Ile
            755                 760                 765

<210> SEQ ID NO 39
<211> LENGTH: 765
<212> TYPE: PRT
<213> ORGANISM: Homo sapiens

<400> SEQUENCE: 39

Met Ala Ala Asp Pro Thr Glu Leu Arg Leu Gly Ser Leu Pro Val Phe
1               5                   10                  15

Thr Arg Asp Asp Phe Glu Gly Asp Trp Arg Leu Val Ala Ser Gly Gly
            20                  25                  30

Phe Ser Gln Val Phe Gln Ala Arg His Arg Arg Trp Arg Thr Glu Tyr
        35                  40                  45

Ala Ile Lys Cys Ala Pro Cys Leu Pro Pro Asp Ala Ala Ser Ser Asp
    50                  55                  60

Val Asn Tyr Leu Ile Glu Glu Ala Ala Lys Met Lys Lys Ile Lys Phe
65                  70                  75                  80

Gln His Ile Val Ser Ile Tyr Gly Val Cys Lys Gln Pro Leu Gly Ile
                85                  90                  95

Val Met Glu Phe Met Ala Asn Gly Ser Leu Glu Lys Val Leu Ser Thr
            100                 105                 110

His Ser Leu Cys Trp Lys Leu Arg Phe Arg Ile Ile His Glu Thr Ser
        115                 120                 125

Leu Ala Met Asn Phe Leu His Ser Ile Lys Pro Pro Leu Leu His Leu
    130                 135                 140

Asp Leu Lys Pro Gly Asn Ile Leu Leu Asp Ser Asn Met His Val Lys
145                 150                 155                 160

Ile Ser Asp Phe Gly Leu Ser Lys Trp Met Glu Gln Ser Thr Arg Met
                165                 170                 175

Gln Tyr Ile Glu Arg Ser Ala Leu Arg Gly Met Leu Ser Tyr Ile Pro
            180                 185                 190

Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
    210                 215                 220

Pro Tyr Ser Gly Phe Asn Met Met Met Ile Ile Arg Val Ala Val
225                 230                 235                 240

Gly Met Arg Pro Ser Leu Gln Pro Val Ser Asp Gln Trp Pro Ser Glu
                245                 250                 255
```

-continued

```
Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
        275                 280                 285

Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Arg Lys Asn Leu Val Pro Arg
            340                 345                 350

Asp Glu Glu Leu Cys Ile Tyr Glu Asn Lys Val Thr Pro Leu Gln Phe
        355                 360                 365

Leu Val Ala Gln Gly Ser Val Glu Gln Val Arg Leu Leu Ala His
    370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
        435                 440                 445

Asp His Gly Ala Cys Val Asp Ala Gln Glu Arg Glu Gly Trp Thr Pro
450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Gln Arg Asn Leu Arg
        515                 520                 525

Thr Pro Leu His Leu Ala Val Glu Arg Gly Lys Val Arg Ala Ile Gln
    530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
            580                 585                 590

Gly Trp Thr Pro Leu His Leu Ala Ala Tyr Lys Gly His Leu Glu Ile
        595                 600                 605

Ile His Leu Leu Ala Glu Ser His Ala Asn Met Gly Ala Leu Gly Ala
    610                 615                 620

Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
                645                 650                 655

Gln Ser Gly Trp Thr Pro Leu His Leu Ala Val Gln Arg Ser Thr Phe
            660                 665                 670

Leu Ser Val Ile Asn Leu Leu Glu His His Ala Asn Val His Ala Arg
```

```
                675                 680                 685
Asn Lys Val Gly Trp Thr Pro Ala His Leu Ala Ala Leu Lys Gly Asn
            690                 695                 700
Thr Ala Ile Leu Lys Val Leu Val Glu Ala Gly Ala Gln Leu Asp Val
705                 710                 715                 720
Gln Asp Gly Val Ser Cys Thr Pro Leu Gln Leu Ala Leu Arg Ser Arg
                725                 730                 735
Lys Gln Gly Ile Met Ser Phe Leu Glu Gly Lys Glu Pro Ser Val Ala
                740                 745                 750
Thr Leu Gly Gly Ser Lys Pro Gly Ala Glu Met Glu Ile
                755                 760                 765

<210> SEQ ID NO 40
<211> LENGTH: 765
<212> TYPE: PRT
<213> ORGANISM: Homo sapiens

<400> SEQUENCE: 40

Met Ala Ala Asp Pro Thr Glu Leu Arg Leu Gly Ser Leu Pro Val Phe
1               5                   10                  15
Thr Arg Asp Asp Phe Glu Gly Asp Trp Arg Leu Val Ala Ser Gly Gly
            20                  25                  30
Phe Ser Gln Val Phe Gln Ala Arg His Arg Arg Trp Arg Thr Glu Tyr
        35                  40                  45
Ala Ile Lys Cys Ala Pro Cys Leu Pro Pro Asp Ala Ala Ser Ser Asp
    50                  55                  60
Val Asn Tyr Leu Ile Glu Glu Ala Lys Met Lys Lys Ile Lys Phe
65                  70                  75                  80
Gln His Ile Val Ser Ile Tyr Gly Val Cys Lys Gln Pro Leu Gly Ile
                85                  90                  95
Val Met Glu Phe Met Ala Asn Gly Ser Leu Glu Lys Val Leu Ser Thr
            100                 105                 110
His Ser Leu Cys Trp Lys Leu Arg Phe Arg Ile Ile His Glu Thr Ser
        115                 120                 125
Leu Ala Met Asn Phe Leu His Ser Ile Lys Pro Pro Leu Leu His Leu
    130                 135                 140
Asp Leu Lys Pro Gly Asn Ile Leu Leu Asp Ser Asn Met His Val Lys
145                 150                 155                 160
Ile Ser Asp Phe Gly Leu Ser Lys Trp Met Glu Gln Ser Thr Arg Met
                165                 170                 175
Gln Tyr Ile Glu Arg Ser Ala Leu Arg Ser Met Leu Ser Tyr Ile Pro
            180                 185                 190
Pro Glu Met Phe Leu Glu Ser Asn Lys Ala Pro Gly Pro Lys Tyr Asp
        195                 200                 205
Val Tyr Ser Phe Ala Ile Val Ile Trp Glu Leu Thr Gln Lys Lys
    210                 215                 220
Pro Tyr Ser Gly Phe Asn Met Met Met Ile Ile Ile Arg Val Ala Ala
225                 230                 235                 240
Gly Met Arg Pro Ser Leu Gln Pro Val Ser Asp Gln Trp Pro Ser Glu
                245                 250                 255
Ala Gln Gln Met Val Asp Leu Met Lys Arg Cys Trp Asp Gln Asp Pro
            260                 265                 270
Lys Lys Arg Pro Cys Phe Leu Asp Ile Thr Ile Glu Thr Asp Ile Leu
        275                 280                 285
```

```
Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
            355                 360                 365

Leu Val Ala Gln Gly Ser Val Glu Gln Val Arg Leu Leu Leu Ala His
    370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
    435                 440                 445

Asp His Gly Ala Cys Val Asp Ala Gln Glu Arg Glu Gly Trp Thr Pro
450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Gln Arg Asn Leu Arg
    515                 520                 525

Thr Pro Leu His Leu Ala Val Glu Arg Gly Lys Val Arg Ala Ile Gln
530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
            580                 585                 590

Gly Trp Thr Pro Leu His Leu Ala Ala Tyr Lys Gly His Leu Glu Ile
    595                 600                 605

Ile His Leu Leu Ala Glu Ser His Ala Asn Met Gly Ala Leu Gly Ala
    610                 615                 620

Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
                645                 650                 655

Gln Ser Gly Trp Thr Pro Leu His Leu Ala Val Gln Arg Ser Thr Phe
            660                 665                 670

Leu Ser Val Ile Asn Leu Leu Glu His Ala Asn Val His Ala Arg
    675                 680                 685

Asn Lys Val Gly Trp Thr Pro Ala His Leu Ala Ala Leu Lys Gly Asn
690                 695                 700

Thr Ala Ile Leu Lys Val Leu Val Glu Ala Gly Ala Gln Leu Asp Val
```

```
                    705                 710                 715                 720
Gln Asp Gly Val Ser Cys Thr Pro Leu Gln Leu Ala Leu Arg Ser Arg
                725                 730                 735
Lys Gln Gly Ile Met Ser Phe Leu Glu Gly Lys Glu Pro Ser Val Ala
            740                 745                 750
Thr Leu Gly Gly Ser Lys Pro Gly Ala Glu Met Glu Ile
        755                 760                 765

<210> SEQ ID NO 41
<211> LENGTH: 765
<212> TYPE: PRT
<213> ORGANISM: Homo sapiens

<400> SEQUENCE: 41

Met Ala Ala Asp Pro Thr Glu Leu Arg Leu Gly Ser Leu Pro Val Phe
1               5                  10                  15
Thr Arg Asp Asp Phe Glu Gly Asp Trp Arg Leu Val Ala Ser Gly Gly
            20                  25                  30
Phe Ser Gln Val Phe Gln Ala Arg His Arg Arg Trp Arg Thr Glu Tyr
        35                  40                  45
Ala Ile Lys Cys Ala Pro Cys Leu Pro Pro Asp Ala Ala Ser Ser Asp
    50                  55                  60
Val Asn Tyr Leu Ile Glu Glu Ala Ala Lys Met Lys Lys Ile Lys Phe
65                  70                  75                  80
Gln His Ile Val Ser Ile Tyr Gly Val Cys Lys Gln Pro Leu Gly Ile
                85                  90                  95
Val Met Glu Phe Met Ala Asn Gly Ser Leu Glu Lys Val Leu Ser Thr
            100                 105                 110
His Ser Leu Cys Trp Lys Leu Arg Phe Arg Ile Ile His Glu Thr Ser
        115                 120                 125
Leu Ala Met Asn Phe Leu His Ser Ile Lys Pro Pro Leu Leu His Leu
    130                 135                 140
Asp Leu Lys Pro Gly Asn Ile Leu Leu Asp Ser Asn Met His Val Lys
145                 150                 155                 160
Ile Ser Asp Phe Gly Leu Ser Lys Trp Met Glu Gln Ser Thr Arg Met
                165                 170                 175
Gln Tyr Ile Glu Arg Ser Ala Leu Arg Ile Met Leu Ser Tyr Ile Pro
            180                 185                 190
Pro Glu Met Phe Leu Glu Ser Asn Lys Ala Pro Gly Pro Lys Tyr Asp
        195                 200                 205
Val Tyr Ser Phe Ala Ile Val Ile Trp Glu Leu Leu Thr Gln Lys Lys
    210                 215                 220
Pro Tyr Ser Gly Phe Asn Met Met Met Ile Ile Arg Val Ala Ala
225                 230                 235                 240
Gly Met Arg Pro Ser Leu Gln Pro Val Ser Asp Gln Trp Pro Ser Glu
                245                 250                 255
Ala Gln Gln Met Val Asp Leu Met Lys Arg Cys Trp Asp Gln Asp Pro
            260                 265                 270
Lys Lys Arg Pro Cys Phe Leu Asp Ile Thr Ile Glu Thr Asp Ile Leu
        275                 280                 285
Leu Ser Leu Leu Gln Ser Arg Val Ala Val Pro Glu Ser Lys Ala Leu
    290                 295                 300
Ala Arg Lys Val Ser Cys Lys Leu Ser Leu Arg Gln Pro Arg Glu Val
305                 310                 315                 320
```

-continued

```
Asn Glu Asp Ile Ser Gln Glu Leu Met Asp Ser Asp Ser Gly Asn Tyr
            325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
            355                 360                 365

Leu Val Ala Gln Gly Ser Val Glu Gln Val Arg Leu Leu Ala His
            370                 375                 380

Glu Val Asp Val Asp Cys Gln Thr Ala Ser Gly Tyr Thr Pro Leu Leu
385                 390                 395                 400

Ile Ala Ala Gln Asp Gln Pro Asp Leu Cys Ala Leu Leu Leu Ala
                405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
            435                 440                 445

Asp His Gly Ala Cys Val Asp Ala Gln Glu Arg Glu Gly Trp Thr Pro
        450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Gln Arg Asn Leu Arg
            515                 520                 525

Thr Pro Leu His Leu Ala Val Glu Arg Gly Lys Val Arg Ala Ile Gln
            530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
            580                 585                 590

Gly Trp Thr Pro Leu His Leu Ala Ala Tyr Lys Gly His Leu Glu Ile
            595                 600                 605

Ile His Leu Leu Ala Glu Ser His Ala Asn Met Gly Ala Leu Gly Ala
            610                 615                 620

Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
                645                 650                 655

Gln Ser Gly Trp Thr Pro Leu His Leu Ala Val Gln Arg Ser Thr Phe
            660                 665                 670

Leu Ser Val Ile Asn Leu Leu Glu His His Ala Asn Val His Ala Arg
            675                 680                 685

Asn Lys Val Gly Trp Thr Pro Ala His Leu Ala Ala Leu Lys Gly Asn
            690                 695                 700

Thr Ala Ile Leu Lys Val Leu Glu Ala Gly Ala Gln Leu Asp Val
705                 710                 715                 720

Gln Asp Gly Val Ser Cys Thr Pro Leu Gln Leu Ala Leu Arg Ser Arg
                725                 730                 735

Lys Gln Gly Ile Met Ser Phe Leu Glu Gly Lys Glu Pro Ser Val Ala
```

```
                        740                 745                 750
Thr Leu Gly Gly Ser Lys Pro Gly Ala Glu Met Glu Ile
            755                 760                 765

<210> SEQ ID NO 42
<211> LENGTH: 765
<212> TYPE: PRT
<213> ORGANISM: Homo sapiens

<400> SEQUENCE: 42

Met Ala Ala Asp Pro Thr Glu Leu Arg Leu Gly Ser Leu Pro Val Phe
1               5                   10                  15

Thr Arg Asp Asp Phe Glu Gly Asp Trp Arg Leu Val Ala Ser Gly Gly
            20                  25                  30

Phe Ser Gln Val Phe Gln Ala Arg His Arg Arg Trp Arg Thr Glu Tyr
        35                  40                  45

Ala Ile Lys Cys Ala Pro Cys Leu Pro Pro Asp Ala Ala Ser Ser Asp
    50                  55                  60

Val Asn Tyr Leu Ile Glu Glu Ala Ala Lys Met Lys Lys Ile Lys Phe
65                  70                  75                  80

Gln His Ile Val Ser Ile Tyr Gly Val Cys Lys Gln Pro Leu Gly Ile
                85                  90                  95

Val Met Glu Phe Met Ala Asn Gly Ser Leu Glu Lys Val Leu Ser Thr
            100                 105                 110

His Ser Leu Cys Trp Lys Leu Arg Phe Arg Ile Ile His Glu Thr Ser
        115                 120                 125

Leu Ala Met Asn Phe Leu His Ser Ile Lys Pro Pro Leu Leu His Leu
    130                 135                 140

Asp Leu Lys Pro Gly Asn Ile Leu Leu Asp Ser Asn Met His Val Lys
145                 150                 155                 160

Ile Ser Asp Phe Gly Leu Ser Lys Trp Met Glu Gln Ser Thr Arg Met
                165                 170                 175

Gln Trp Ile Glu Arg Ser Ala Leu Arg Gly Met Leu Ser Tyr Ile Pro
            180                 185                 190

Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
    210                 215                 220

Pro Tyr Ser Gly Phe Asn Met Met Met Ile Ile Ile Arg Val Ala Ala
225                 230                 235                 240

Gly Met Arg Pro Ser Leu Gln Pro Val Ser Asp Gln Trp Pro Ser Glu
                245                 250                 255

Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
        275                 280                 285

Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350
```

```
Asp Glu Glu Leu Cys Ile Tyr Glu Asn Lys Val Thr Pro Leu Gln Phe
            355                 360                 365

Leu Val Ala Gln Gly Ser Val Glu Gln Val Arg Leu Leu Ala His
    370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
        435                 440                 445

Asp His Gly Ala Cys Val Asp Ala Gln Glu Arg Glu Gly Trp Thr Pro
    450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Gln Arg Asn Leu Arg
        515                 520                 525

Thr Pro Leu His Leu Ala Val Glu Arg Gly Lys Val Arg Ala Ile Gln
    530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
            580                 585                 590

Gly Trp Thr Pro Leu His Leu Ala Ala Tyr Lys Gly His Leu Glu Ile
        595                 600                 605

Ile His Leu Leu Ala Glu Ser His Ala Asn Met Gly Ala Leu Gly Ala
    610                 615                 620

Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
                645                 650                 655

Gln Ser Gly Trp Thr Pro Leu His Leu Ala Val Gln Arg Ser Thr Phe
            660                 665                 670

Leu Ser Val Ile Asn Leu Leu Glu His His Ala Asn Val His Ala Arg
        675                 680                 685

Asn Lys Val Gly Trp Thr Pro Ala His Leu Ala Ala Leu Lys Gly Asn
    690                 695                 700

Thr Ala Ile Leu Lys Val Leu Val Glu Ala Gly Ala Gln Leu Asp Val
705                 710                 715                 720

Gln Asp Gly Val Ser Cys Thr Pro Leu Gln Leu Ala Leu Arg Ser Arg
                725                 730                 735

Lys Gln Gly Ile Met Ser Phe Leu Glu Gly Lys Glu Pro Ser Val Ala
            740                 745                 750

Thr Leu Gly Gly Ser Lys Pro Gly Ala Glu Met Glu Ile
        755                 760                 765
```

-continued

<210> SEQ ID NO 43
<211> LENGTH: 765
<212> TYPE: PRT
<213> ORGANISM: Homo sapiens

<400> SEQUENCE: 43

Met Ala Ala Asp Pro Thr Glu Leu Arg Leu Gly Ser Leu Pro Val Phe
1               5                   10                  15

Thr Arg Asp Asp Phe Glu Gly Asp Trp Arg Leu Val Ala Ser Gly Gly
            20                  25                  30

Phe Ser Gln Val Phe Gln Ala Arg His Arg Arg Trp Arg Thr Glu Tyr
        35                  40                  45

Ala Ile Lys Cys Ala Pro Cys Leu Pro Pro Asp Ala Ala Ser Ser Asp
    50                  55                  60

Val Gln Tyr Leu Ile Glu Ala Ala Lys Met Lys Lys Ile Lys Phe
65                  70                  75                  80

Gln His Ile Val Ser Ile Tyr Gly Val Cys Lys Gln Pro Leu Gly Ile
                85                  90                  95

Val Met Glu Phe Met Ala Asn Gly Ser Leu Glu Lys Val Leu Ser Thr
            100                 105                 110

His Ser Leu Cys Trp Lys Leu Arg Phe Arg Ile Ile His Glu Thr Ser
        115                 120                 125

Leu Ala Met Asn Phe Leu His Ser Ile Lys Pro Pro Leu Leu His Leu
    130                 135                 140

Asp Leu Lys Pro Gly Asn Ile Leu Leu Asp Ser Asn Met His Val Lys
145                 150                 155                 160

Ile Ser Asp Phe Gly Leu Ser Lys Trp Met Glu Gln Ser Thr Arg Met
                165                 170                 175

Asn Tyr Ile Glu Arg Ser Ala Leu Arg Gly Met Leu Ser Tyr Ile Pro
            180                 185                 190

Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
    210                 215                 220

Pro Tyr Ser Gly Phe Asn Met Met Met Ile Ile Ile Arg Val Ala Ala
225                 230                 235                 240

Gly Met Arg Pro Ser Leu Gln Pro Val Ser Asp Gln Trp Pro Ser Glu
                245                 250                 255

Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
        275                 280                 285

Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
        355                 360                 365

Leu Val Ala Gln Gly Ser Val Glu Gln Val Arg Leu Leu Leu Ala His
    370                 375                 380

```
Glu Val Asp Val Asp Cys Gln Thr Ala Ser Gly Tyr Thr Pro Leu Leu
385                 390                 395                 400

Ile Ala Ala Gln Asp Gln Pro Asp Leu Cys Ala Leu Leu Leu Ala
        405                 410                 415

His Gly Ala Asp Ala Asn Arg Val Asp Glu Asp Gly Trp Ala Pro Leu
            420                 425                 430

His Phe Ala Ala Gln Asn Gly Asp Asp Arg Thr Ala Arg Leu Leu Leu
        435                 440                 445

Asp His Gly Ala Cys Val Asp Ala Gln Glu Arg Glu Gly Trp Thr Pro
450                 455                 460

Leu His Leu Ala Ala Gln Asn Asn Phe Glu Asn Val Ala Arg Leu Leu
465                 470                 475                 480

Val Ser Arg Gln Ala Asp Pro Asn Leu Arg Glu Ala Glu Gly Lys Thr
                485                 490                 495

Pro Leu His Val Ala Ala Tyr Phe Gly His Val Ser Leu Val Lys Leu
            500                 505                 510

Leu Thr Ser Gln Gly Ala Glu Leu Asp Ala Gln Gln Arg Asn Leu Arg
        515                 520                 525

Thr Pro Leu His Leu Ala Val Glu Arg Gly Lys Val Arg Ala Ile Gln
530                 535                 540

His Leu Leu Lys Ser Gly Ala Val Pro Asp Ala Leu Asp Gln Ser Gly
545                 550                 555                 560

Tyr Gly Pro Leu His Thr Ala Ala Arg Gly Lys Tyr Leu Ile Cys
                565                 570                 575

Lys Met Leu Leu Arg Tyr Gly Ala Ser Leu Glu Leu Pro Thr His Gln
                580                 585                 590

Gly Trp Thr Pro Leu His Leu Ala Ala Tyr Lys Gly His Leu Glu Ile
            595                 600                 605

Ile His Leu Leu Ala Glu Ser His Ala Asn Met Gly Ala Leu Gly Ala
610                 615                 620

Val Asn Trp Thr Pro Leu His Leu Ala Ala Arg His Gly Glu Glu Ala
625                 630                 635                 640

Val Val Ser Ala Leu Leu Gln Cys Gly Ala Asp Pro Asn Ala Ala Glu
                645                 650                 655

Gln Ser Gly Trp Thr Pro Leu His Leu Ala Val Gln Arg Ser Thr Phe
            660                 665                 670

Leu Ser Val Ile Asn Leu Leu Glu His His Ala Asn Val His Ala Arg
        675                 680                 685

Asn Lys Val Gly Trp Thr Pro Ala His Leu Ala Ala Leu Lys Gly Asn
690                 695                 700

Thr Ala Ile Leu Lys Val Leu Val Glu Ala Gly Ala Gln Leu Asp Val
705                 710                 715                 720

Gln Asp Gly Val Ser Cys Thr Pro Leu Gln Leu Ala Leu Arg Ser Arg
            725                 730                 735

Lys Gln Gly Ile Met Ser Phe Leu Glu Gly Lys Glu Pro Ser Val Ala
                740                 745                 750

Thr Leu Gly Gly Ser Lys Pro Gly Ala Glu Met Glu Ile
        755                 760                 765
```

<210> SEQ ID NO 44
<211> LENGTH: 765
<212> TYPE: PRT
<213> ORGANISM: Homo sapiens

<400> SEQUENCE: 44

```
Met Ala Ala Asp Pro Thr Glu Leu Arg Leu Gly Ser Leu Pro Val Phe
1               5                   10                  15

Thr Arg Asp Asp Phe Glu Gly Asp Trp Arg Leu Val Ala Ser Gly Gly
            20                  25                  30

Phe Ser Gln Val Phe Gln Ala Arg His Arg Arg Trp Arg Thr Glu Tyr
        35                  40                  45

Ala Ile Lys Cys Ala Pro Cys Leu Pro Pro Asp Ala Ala Ser Ser Asp
    50                  55                  60

Val Asn Tyr Leu Ile Glu Glu Ala Ala Lys Met Lys Lys Ile Lys Phe
65                  70                  75                  80

Gln His Ile Val Ser Ile Tyr Gly Val Cys Lys Gln Pro Leu Gly Ile
                85                  90                  95

Val Met Glu Phe Met Ala Asn Gly Ser Leu Glu Lys Val Leu Ser Thr
            100                 105                 110

His Ser Leu Cys Trp Lys Leu Arg Phe Arg Ile Ile His Glu Thr Ser
        115                 120                 125

Leu Ala Met Asn Phe Leu His Ser Ile Lys Pro Pro Leu Leu His Leu
    130                 135                 140

Asp Leu Lys Pro Gly Asn Ile Leu Leu Asp Ser Asn Met His Val Lys
145                 150                 155                 160

Ile Ser Asp Phe Gly Leu Ser Lys Trp Met Glu Gln Ser Thr Arg Met
                165                 170                 175

Gln Tyr Ile Glu Arg Ser Ala Leu Arg Gly Met Leu Ser Tyr Ile Pro
            180                 185                 190

Pro Glu Met Phe Leu Glu Ser Asn Lys Ala Pro Gly Pro Lys Tyr Asp
        195                 200                 205

Val Tyr Ser Phe Ala Ile Val Ile Trp Glu Leu Leu Thr Gln Lys Lys
    210                 215                 220

Pro Tyr Ser Gly Phe Asn Met Met Met Ile Ile Ile Arg Val Ala Ala
225                 230                 235                 240

Gly Met Arg Pro Ser Leu Gln Pro Val Ser Asp Gln Trp Pro Ser Glu
                245                 250                 255

Ala Gln Gln Met Val Asp Leu Met Lys Arg Cys Trp Asp Gln Asp Pro
            260                 265                 270

Lys Lys Arg Pro Cys Phe Leu Asp Ile Thr Ile Glu Thr Asp Ile Leu
        275                 280                 285

Leu Ser Leu Leu Gln Ser Arg Val Ala Val Pro Glu Ser Lys Ala Leu
    290                 295                 300

Ala Arg Lys Val Ser Cys Lys Leu Ser Leu Arg Gln Pro Arg Glu Val
305                 310                 315                 320

Asn Glu Asp Ile Ser Gln Glu Leu Met Asp Ser Asp Ser Gly Asn Tyr
                325                 330                 335

Leu Lys Arg Ala Leu Gln Leu Ser Asp Arg Lys Asn Leu Val Pro Arg
            340                 345                 350

Asp Glu Glu Leu Cys Ile Tyr Glu Asn Lys Val Thr Pro Leu Gln Phe
        355                 360                 365

Leu Val Ala Gln Gly Ser Val Glu Gln Val Arg Leu Leu Leu Ala His
    370                 375                 380

Glu Val Asp Val Asp Cys Gln Thr Ala Ser Gly Tyr Thr Pro Leu Leu
385                 390                 395                 400

Ile Ala Ala Gln Asp Gln Gln Pro Asp Leu Cys Ala Leu Leu Leu Ala
                405                 410                 415
```

```
-continued

His Gly Ala Asp Ala Asn Arg Val Asp Glu Asp Gly Trp Ala Pro Leu
            420             425             430

His Phe Ala Ala Gln Asn Gly Asp Asp Arg Thr Ala Arg Leu Leu Leu
            435             440             445

Asp His Gly Ala Cys Val Asp Ala Gln Glu Arg Glu Gly Trp Thr Pro
    450             455             460

Leu His Leu Ala Ala Gln Asn Asn Phe Glu Asn Val Ala Arg Leu Leu
465             470             475             480

Val Ser Arg Gln Ala Asp Pro Asn Leu Arg Glu Ala Glu Gly Lys Thr
                485             490             495

Pro Leu His Val Ala Ala Tyr Phe Gly His Val Ser Leu Val Lys Leu
            500             505             510

Leu Thr Ser Gln Gly Ala Glu Leu Asp Ala Gln Arg Asn Leu Arg
            515             520             525

Thr Pro Leu His Leu Ala Val Glu Arg Gly Lys Val Arg Ala Ile Gln
    530             535             540

His Leu Leu Lys Ser Gly Ala Val Pro Asp Ala Leu Asp Gln Ser Gly
545             550             555             560

Tyr Gly Pro Leu His Thr Ala Ala Arg Gly Lys Tyr Leu Ile Cys
                565             570             575

Lys Met Leu Leu Arg Tyr Gly Ala Ser Leu Glu Leu Pro Thr His Gln
            580             585             590

Gly Trp Thr Pro Leu His Leu Ala Ala Tyr Lys Gly His Leu Glu Ile
            595             600             605

Ile His Leu Leu Ala Glu Ser His Ala Asn Met Gly Ala Leu Gly Ala
        610             615             620

Val Asn Trp Thr Pro Leu His Leu Ala Ala Arg His Gly Glu Glu Ala
625             630             635             640

Val Val Ser Ala Leu Leu Gln Cys Gly Ala Asp Pro Asn Ala Ala Glu
                645             650             655

Gln Ser Gly Trp Thr Pro Leu His Leu Ala Val Gln Arg Ser Thr Phe
            660             665             670

Leu Ser Val Ile Asn Leu Leu Glu His His Ala Asn Val His Ala Arg
            675             680             685

Asn Lys Val Gly Trp Thr Pro Ala His Leu Ala Ala Leu Lys Gly Asn
        690             695             700

Thr Ala Ile Leu Lys Val Leu Val Glu Ala Gly Ala Gln Leu Asp Val
705             710             715             720

Gln Asp Gly Val Ser Cys Thr Pro Leu Gln Leu Ala Leu Arg Ser Arg
                725             730             735

Lys Gln Gly Ile Met Ser Phe Leu Glu Gly Lys Glu Pro Ser Val Ala
            740             745             750

Thr Leu Gly Gly Ser Lys Pro Gly Ala Glu Met Glu Ile
            755             760             765
```